US009894340B2

(12) United States Patent
Holub

(10) Patent No.: US 9,894,340 B2
(45) Date of Patent: Feb. 13, 2018

(54) COLOR CALIBRATION OF COLOR IMAGE RENDERING DEVICES

(71) Applicant: RAH COLOR TECHNOLOGIES LLC, Alexandria, VA (US)

(72) Inventor: Richard A. Holub, Alexandria, VA (US)

(73) Assignee: RAH COLOR TECHNOLOGIES LLC, Alexandria, VA (US)

(*) Notice: Subject to any disclaimer, the term of this patent is extended or adjusted under 35 U.S.C. 154(b) by 0 days.

(21) Appl. No.: 15/368,022

(22) Filed: Dec. 2, 2016

(65) Prior Publication Data

US 2017/0085852 A1    Mar. 23, 2017

Related U.S. Application Data

(60) Continuation of application No. 14/933,781, filed on Nov. 5, 2015, now Pat. No. 9,516,288, which is a (Continued)

(51) Int. Cl.
*G09G 5/02* (2006.01)
*H04N 9/73* (2006.01)
(Continued)

(52) U.S. Cl.
CPC ............. *H04N 9/735* (2013.01); *G01J 3/02* (2013.01); *G01J 3/0202* (2013.01); (Continued)

(58) Field of Classification Search
CPC ....... G09G 2320/0693; G09G 2340/06; H04N 9/3182; H04N 13/0246; G06T 7/002
See application file for complete search history.

(56) References Cited

U.S. PATENT DOCUMENTS 2,790,844 A   4/1957 Neugebauer
4,441,120 A   4/1984 Gerritsen
(Continued)

FOREIGN PATENT DOCUMENTS

EP   0 562 973   9/1993
EP   579224      1/1994
(Continued)

OTHER PUBLICATIONS

Apple unveils ColorSync 2.0, PR Newswire, Mar. 28, 1995.
(Continued)

*Primary Examiner* — Hau Nguyen
(74) *Attorney, Agent, or Firm* — Lukacher Law Group; Kenneth J. Lukacher

(57) ABSTRACT

Color calibration of color image rendering devices, such as large color displays, which operate by either projection or emission of images, utilize internal color measurement instrument or external color measurement modules locatable on a wall or speaker. A dual use camera is provided for a portable or laptop computer, or a cellular phone, handset, personal digital assistant or other handheld device with a digital camera, in which one of the camera or a display is movable with respect to the other to enable the camera in a first mode to capture images of the display for enabling calibration of the display, and in a second mode for capturing image other than of the display. The displays may represent rendering devices for enabling virtual proofing in a network, or may be part of stand-alone systems and apparatuses for color calibration. Improved calibration is also provided for sensing and correcting for non-uniformities of rendering devices, such as color displays, printer, presses, or other color image rendering device.

28 Claims, 77 Drawing Sheets

Related U.S. Application Data continuation of application No. 14/161,121, filed on Jan. 22, 2014, now abandoned, which is a division of application No. 12/799,930, filed on May 5, 2010, now Pat. No. 8,638,340, which is a division of application No. 11/216,784, filed on Aug. 31, 2005, now Pat. No. 7,728,845.

(51) Int. Cl.

| | | |
|---|---|---|
| G01J 3/02 | (2006.01) | |
| G01J 3/18 | (2006.01) | |
| G01J 3/28 | (2006.01) | |
| G01J 3/50 | (2006.01) | |
| G03B 27/54 | (2006.01) | |
| H04N 1/60 | (2006.01) | |
| H04N 9/31 | (2006.01) | |
| H04N 9/68 | (2006.01) | |
| H04N 17/02 | (2006.01) | |
| H04N 9/09 | (2006.01) | |
| H04N 17/04 | (2006.01) | |
| G06T 7/80 | (2017.01) | |
| G06T 7/90 | (2017.01) | |
| H04N 9/12 | (2006.01) | |
| G01J 3/46 | (2006.01) | |
| G01N 21/27 | (2006.01) | |
| G09G 3/34 | (2006.01) | |

(52) U.S. Cl.
CPC ........... *G01J 3/0218* (2013.01); *G01J 3/0262* (2013.01); *G01J 3/0264* (2013.01); *G01J 3/0272* (2013.01); *G01J 3/0289* (2013.01); *G01J 3/0291* (2013.01); *G01J 3/18* (2013.01); *G01J 3/28* (2013.01); *G01J 3/50* (2013.01); *G01J 3/506* (2013.01); *G03B 27/547* (2013.01); *G06T 7/80* (2017.01); *G06T 7/90* (2017.01); *G09G 5/02* (2013.01); *H04N 1/6033* (2013.01); *H04N 1/6052* (2013.01); *H04N 9/09* (2013.01); *H04N 9/12* (2013.01); *H04N 9/3182* (2013.01); *H04N 9/3194* (2013.01); *H04N 9/68* (2013.01); *H04N 9/73* (2013.01); *H04N 17/02* (2013.01); *H04N 17/045* (2013.01); *G01J 3/462* (2013.01); *G01J 3/463* (2013.01); *G01J 2003/2866* (2013.01); *G01J 2003/466* (2013.01); *G01N 21/274* (2013.01); *G06T 2207/10024* (2013.01); *G06T 2207/20072* (2013.01); *G09G 3/3413* (2013.01); *G09G 2320/0285* (2013.01); *G09G 2320/0626* (2013.01); *G09G 2320/0666* (2013.01); *G09G 2320/0693* (2013.01); *G09G 2330/021* (2013.01); *G09G 2360/144* (2013.01); *G09G 2360/147* (2013.01)

(56) References Cited

U.S. PATENT DOCUMENTS

| | | |
|---|---|---|
| 4,630,076 A | 12/1986 | Yoshimura |
| 4,635,095 A | 1/1987 | Legrand et al. |
| 4,658,286 A | 4/1987 | Schwartz et al. |
| 4,677,465 A | 6/1987 | Alkofer |
| 4,700,218 A | 10/1987 | Thomsen et al. |
| 4,729,016 A | 3/1988 | Alkofer |
| 4,742,387 A | 5/1988 | Oshima |
| 4,745,465 A | 5/1988 | Kwon |
| 4,823,283 A | 4/1989 | Diehm et al. |
| 4,839,829 A | 6/1989 | Freedman |
| 4,843,573 A | 6/1989 | Taylor et al. |
| 4,939,581 A | 7/1990 | Shalit |
| 4,941,038 A | 7/1990 | Walowit |
| 4,975,862 A | 12/1990 | Keller et al. |
| 4,980,759 A | 12/1990 | Smyth |
| 5,029,183 A | 7/1991 | Tymes |
| 5,040,889 A | 8/1991 | Keane |
| 5,049,791 A | 9/1991 | Kawakami |
| 5,049,986 A | 9/1991 | Aono et al. |
| 5,057,913 A | 10/1991 | Nagata et al. |
| 5,077,600 A | 12/1991 | Ichigaya et al. |
| 5,083,195 A | 1/1992 | Evelin |
| 5,113,355 A | 5/1992 | Nomura |
| 5,115,229 A | 5/1992 | Shalit |
| 5,146,328 A | 9/1992 | Yamasaki et al. |
| 5,177,602 A | 1/1993 | Fujimori |
| 5,181,181 A | 1/1993 | Glynn |
| 5,195,033 A | 3/1993 | Samph et al. |
| 5,200,816 A | 4/1993 | Rose |
| 5,219,036 A | 6/1993 | Schwager et al. |
| 5,220,324 A | 6/1993 | Morita |
| 5,225,900 A | 7/1993 | Wright |
| 5,231,481 A | 7/1993 | Eouzan et al. |
| 5,243,414 A | 9/1993 | Dalrymple et al. |
| 5,253,047 A | 10/1993 | Machishima |
| 5,272,518 A | 12/1993 | Vincent |
| 5,278,641 A | 1/1994 | Sekizawa et al. |
| 5,302,830 A | 4/1994 | Shivanandan |
| 5,309,257 A | 5/1994 | Bonino et al. |
| 5,313,291 A | 5/1994 | Appel et al. |
| 5,319,437 A | 6/1994 | Van Aken et al. |
| 5,333,069 A | 7/1994 | Spence |
| 5,345,315 A | 9/1994 | Shalit |
| 5,349,452 A | 9/1994 | Maeda et al. |
| 5,363,318 A | 11/1994 | McCauley |
| 5,394,204 A | 2/1995 | Shigeta et al. |
| 5,414,538 A | 5/1995 | Eschbach |
| 5,416,890 A | 5/1995 | Beretta |
| 5,426,517 A | 6/1995 | Schwartz |
| 5,428,720 A | 6/1995 | Adams, Jr. |
| 5,432,906 A | 7/1995 | Newman et al. |
| 5,444,556 A | 8/1995 | Ito et al. |
| 5,450,502 A | 9/1995 | Eschbach et al. |
| 5,452,019 A | 9/1995 | Fukuda et al. |
| 5,459,678 A | 10/1995 | Feasey |
| 5,465,111 A | 11/1995 | Fukushima et al. |
| 5,471,313 A | 11/1995 | Thieret et al. |
| 5,479,186 A | 12/1995 | McManus et al. |
| 5,485,284 A | 1/1996 | Shono et al. |
| 5,495,428 A | 2/1996 | Schwartz |
| 5,499,040 A | 3/1996 | McLaughlin et al. |
| 5,510,851 A | 4/1996 | Foley et al. |
| 5,512,961 A | 4/1996 | Cappels, Sr. |
| 5,528,261 A | 6/1996 | Holt et al. |
| 5,532,848 A | 7/1996 | Beretta |
| 5,539,539 A | 7/1996 | Fujimoto et al. |
| 5,544,258 A | 8/1996 | Levien |
| 5,544,356 A | 8/1996 | Robinson et al. |
| 5,554,912 A | 9/1996 | Thayer et al. |
| 5,556,107 A | 9/1996 | Carter |
| 5,561,459 A | 10/1996 | Stokes et al. |
| 5,568,169 A | 10/1996 | Dudek et al. |
| 5,568,192 A | 10/1996 | Hannah |
| 5,602,932 A | 2/1997 | Macdonald et al. |
| 5,604,596 A | 2/1997 | Ukai et al. |
| 5,611,030 A | 3/1997 | Stokes |
| 5,614,948 A | 3/1997 | Hannah |
| 5,625,758 A | 4/1997 | Schneider et al. |
| 5,627,950 A | 5/1997 | Stokes |
| 5,634,092 A | 5/1997 | Stokes |
| 5,668,890 A | 9/1997 | Winkelman |
| 5,694,227 A | 12/1997 | Starkweather |
| 5,731,818 A | 3/1998 | Wan et al. |
| 5,739,809 A | 4/1998 | McLaughlin et al. |
| 5,748,221 A | 5/1998 | Castelli et al. |
| 5,751,965 A | 5/1998 | Mayo et al. |
| 5,754,682 A | 5/1998 | Katoh |
| 5,760,760 A | 6/1998 | Helms |
| 5,767,980 A | 6/1998 | Wang et al. |
| 5,774,225 A | 6/1998 | Goldstein et al. |
| 5,786,803 A | 7/1998 | Hernandez et al. |
| 5,803,570 A | 9/1998 | Chen et al. |

(56) References Cited

U.S. PATENT DOCUMENTS

| | | |
|---|---|---|
| 5,805,213 A | 9/1998 | Spaulding et al. |
| 5,806,081 A | 9/1998 | Swen et al. |
| 5,809,165 A | 9/1998 | Massen |
| 5,809,213 A | 9/1998 | Bhattacharjya |
| 5,812,286 A | 9/1998 | Lin |
| 5,821,917 A | 10/1998 | Cappels |
| 5,821,993 A * | 10/1998 | Robinson ............ H04N 17/002 348/187 |
| 5,828,793 A | 10/1998 | Mann |
| 5,850,472 A * | 12/1998 | Alston .................... G01J 3/10 382/162 |
| 5,867,603 A | 2/1999 | Barnsley et al. |
| 5,881,209 A | 3/1999 | Stokes |
| 5,905,906 A | 5/1999 | Goffinet et al. |
| 5,909,291 A | 6/1999 | Myers et al. |
| 5,978,745 A | 11/1999 | Devine |
| 6,018,361 A | 1/2000 | Fuji et al. |
| 6,043,909 A | 3/2000 | Holub |
| 6,072,546 A | 6/2000 | Nakayabu |
| 6,075,888 A | 6/2000 | Schwartz |
| 6,083,353 A | 7/2000 | Alexander |
| 6,157,735 A | 12/2000 | Holub |
| 6,219,099 B1 | 4/2001 | Johnson et al. |
| 6,246,790 B1 | 6/2001 | Huang et al. |
| 6,310,650 B1 | 10/2001 | Johnson et al. |
| 6,335,983 B1 | 1/2002 | McCarthy et al. |
| 6,337,922 B2 | 1/2002 | Kumada |
| 6,373,531 B1 | 4/2002 | Hidaka et al. |
| 6,373,979 B1 | 4/2002 | Wang |
| 6,381,343 B1 | 4/2002 | Davis et al. |
| 6,430,311 B1 | 8/2002 | Kumada |
| 6,430,312 B1 | 8/2002 | Huang et al. |
| 6,459,425 B1 | 10/2002 | Holub et al. |
| 6,459,436 B1 | 10/2002 | Kumada et al. |
| 6,504,950 B1 | 1/2003 | Murashita et al. |
| 6,522,313 B1 | 2/2003 | Cottone |
| 6,522,778 B1 | 2/2003 | Tamagawa |
| 6,525,772 B2 | 2/2003 | Johnson et al. |
| 6,549,652 B1 | 4/2003 | Persiantsev et al. |
| 6,549,653 B1 | 4/2003 | Osawa et al. |
| 6,549,654 B1 | 4/2003 | Kumada |
| 6,603,879 B2 | 8/2003 | Haikin et al. |
| 6,611,249 B1 | 8/2003 | Evanicky et al. |
| 6,618,076 B1 | 9/2003 | Sukthankar et al. |
| 6,621,923 B1 | 9/2003 | Gennetten |
| 6,654,491 B1 | 11/2003 | Hidaka |
| 6,704,442 B2 | 3/2004 | Haikin et al. |
| 6,750,992 B1 | 6/2004 | Holub |
| 6,784,995 B2 | 8/2004 | Merle et al. |
| 6,867,883 B1 | 3/2005 | Cholewo et al. |
| 6,995,870 B2 | 2/2006 | Holub |
| 7,057,639 B2 | 6/2006 | Spoonhower et al. |
| 7,075,643 B2 | 7/2006 | Holub |
| 7,102,648 B1 | 9/2006 | Holub |
| 7,110,002 B2 | 9/2006 | Wada |
| 7,161,558 B1 | 1/2007 | Eidem et al. |
| 7,280,251 B1 | 10/2007 | Holub |
| 7,286,256 B2 | 10/2007 | Herbert |
| 7,312,897 B2 | 12/2007 | Holub |
| 7,710,433 B2 | 5/2010 | Holub |
| 7,710,560 B2 | 5/2010 | Holub |
| 7,715,052 B2 | 5/2010 | Holub |
| 7,728,845 B2 | 6/2010 | Holub |
| 7,729,008 B2 | 6/2010 | Holub |
| 7,791,761 B2 | 9/2010 | Holub |
| 7,830,546 B2 | 11/2010 | Holub |
| 8,009,175 B2 | 8/2011 | Holub |
| 8,279,236 B2 | 10/2012 | Holub |
| 8,416,444 B2 | 4/2013 | Holub |
| 8,537,357 B2 | 9/2013 | Holub |
| 8,638,340 B2 | 1/2014 | Holub |
| 8,665,289 B2 | 3/2014 | Holub |
| 8,760,704 B2 | 6/2014 | Holub |
| 8,817,314 B2 | 8/2014 | Holub |
| 8,917,394 B2 | 12/2014 | Holub |
| 9,036,209 B2 | 5/2015 | Holub |
| 9,057,645 B2 | 6/2015 | Holub |
| 9,404,802 B2 | 8/2016 | Holub |
| 2003/0046557 A1 | 3/2003 | Miller |
| 2003/0058334 A1 | 3/2003 | Boyden et al. |
| 2004/0095478 A1 | 5/2004 | Takano et al. |
| 2004/0150835 A1 | 8/2004 | Frick et al. |
| 2004/0196252 A1 | 10/2004 | Kim |
| 2005/0151042 A1 | 7/2005 | Watson |

FOREIGN PATENT DOCUMENTS

| | | |
|---|---|---|
| EP | 1 443 775 | 8/2002 |
| JP | 61-292026 | 12/1986 |
| JP | 62-91078 | 4/1987 |
| JP | 4-329066 | 11/1992 |
| JP | H06233226 | 8/1994 |
| JP | 7-17115 | 1/1995 |
| JP | 07-095427 | 4/1995 |
| JP | 7-288704 | 10/1995 |
| JP | 10-173943 | 6/1998 |
| WO | WO 95/31794 | 11/1995 |
| WO | WO 96/00435 | 1/1996 |
| WO | WO 96/01466 | 1/1996 |
| WO | WO 96/01467 | 1/1996 |
| WO | WO 03/043307 A1 | 5/2003 |

OTHER PUBLICATIONS

ColorSync 2.0 White Paper, Apple Computer, Inc., at least as early as 1995.
X-Rite Introduces Monitor Optimizer, Business Wire, Mar. 23, 1995.
X-Rite Introduces ATS Series Auto-Tracking Spectrophotometer at DRUPA, Business Wire, May 5, 1995.
Fraser, B., Getting Color in Sync, MacUser, pp. 74-81, Apr. 1996.
Gretag SPM Family Spectralphotometer Service Manual, Gretag Color Control Systems, Chapters 1-9, Jun. 1993.
Gretag SPM 50, Gretag Color Control Systems, at least as early as 1994.
Gretag SPM 55, Gretag Color Control Systems, at least as early as 1994.
Gretag SPM 60, Gretag Color Control Systems, at least as early as 1994.
Operating Manual Gretag Spectrolino, Gretag Color Control Systems, May 1996.
Spectrolino Color Solutions, GretagMacbeth, May 1997.
Gretag Color Quality V2.0, Gretag AG, Sep. 1996.
Light Source announces Barco Graphics' support of Colortron color prepress solutions, Business Wire, May 10, 1995.
Rothenberg, M., Colortron II: Higher-res, MacWeek GA, vol. 9, No. 40, Oct. 9, 1995.
Light Source and Linotype-Hell to deliver joint solution for managing color, Business Wire, Oct. 26, 1995.
Rothenberg, M., Monaco tones up color management, MacWeek GA, vol. 10, No. 7, Feb. 19, 1996.
Color Solutions Announces New ColorBlind Products and Enhancements for 1996, ColorBlind's New Products Press Release, Color Solutions, Inc., Sep. 27, 1995.
Scitex, Helios and Logo cooperate in color management solutions, Business Wire, Sep. 29, 1995.
Chu, W-I., and Swen, S., ColorSync: Synchronizing the Color Behavior of Your Devices, Institute of Electrical and Electronics Engineers, 41st IEEE Computer Society International Conference, Proceedings of COMPCON'96, pp. 440-444, 1996.
ColorBlind and the ICC Standard, Color Solutions, Inc., at least as early as Nov. 1996.
DTP22 Spectrophotometer RS232 Communications Protocol (OEM Version), Serial Interface Manual, X-Rite, Inc., at least as early as Apr. 17, 1996.
DTP92-10 (Monitor Optimizer), X-Rite, Inc., Dec. 2, 1993.
Logo GmbH: Farbkalibrierung von der Theorie zur Praxis, DruckIndustrie, vol. 5., pp. 5-13, May 1996, with English translation.

(56) References Cited

OTHER PUBLICATIONS

Profile tool—ScreenShot, Logo GmbH Steinfurt, dated May 13, 1995.
Swen, S., ColorSync 2.5—Building a color platform, SPIE vol. 3300, pp. 86-88, 1998.
What's New in ColorSync 2.5, Apple Technical Publications, Apple Computer, Inc., Jul. 17, 1998.
Apple Unveils ColorSync 2.5, PR Newswire, Sep. 29, 1997.
Spectrolino Spectrophotometer, Gretag-Macbeth, Mar. 1998.
Spectrolino, SpectroScan, SpectroScan T Operating Manual, Gretag-Macbeth, Apr. 2000.
Lawler, B., ColorSync, ColorSync Technology Brief, Apple Computer, Inc., 1999.
Advanced Color Imaging Reference, Apple Computer, Inc., 1995.
Defendants' Answer, Affirmative Defenses, and Counterclaims, United States District Court for the Western District of New York, Case 6:10-cv-06710-CJS, Document 9, Filed Apr. 4, 2011, pp. 1-30.
Holub, Richard A. et al., Three-Component Color Representations for Graphic Arts, IS&T Final Program and Advance Printing of Paper Summaries, IS&T's 46th Annual Conference, May 9-14, 1993, pp. 163-165.
Holub, Richard A. et al., Three Component Color Representations for Graphic Arts, Proceedings of the Annual Technical Conference Technical Association of the Graphic Arts, Rochester, NY, 1993, pp. 50-66.
PostScript Language Reference Manual, 2nd Edition, Adobe Systems, Incorporated, 1990, pp. i-vi and 1-764.
Japanese Patent Office Action dated Feb. 14, 2012, Japanese Patent Application No. 2011-074873, translation of Action and Pending Claims.
Apple Computer, Advanced Color Imaging on the Mac OS, Addison-Wesley, Aug. 1995, p. 344.
InterColor Consortium, ICC Profile Format 3.0, Jun. 10, 1994, p. 82.
Murch, G., Management on the Desktop, IS&T and SID's Color Imaging Conference, pp. 95-99, 1993.
Birmy Graphics Corp., PowerRIP 3.1 for Macintosh Manual, Jul. 1995, p. 44.
Asadi, B. et al., QuarkXPress 3.2/3.3 Bible, IDG Books, 1993, p. 694.
Takehara, K., et al., A SAW-Based Spread Spectrum Wireless LAN System, IEEE Second International Symposium on Spread Spectrum Techniques and Applications, Nov. 29, 1992, pp. 175-178.
Starkweather, G., A High Resolution Laser Printer, J. Imaging Technol. 11(6): 300-305, 1985.
Stone, J., et al., Color Gamut Mapping and the Printing of Digital Color Images, ACM Transactions on Graphics 7(4): 249-292, 1988.
Gentile, R., Device Independent Color in PostScript, in SPIE vol. 1913, Human Vision, Visual Processing and Digital Display IV, pp. 419-432, 1993.
Maeda, M. et al., Object Oriented Color Management System, in SPIE vol. 1909, Device Independent Color Imaging and Imaging System Integration, pp. 195-205, 1993.
Tektronix, Inc., Phaser 240 User Manual, p. 202, 1995.
Tektronix, Inc., TekColor(tm), Color Management System, p. 115, 1990.
Canadian Patent Office Action dated May 29, 2012, Canadian Patent Application No. 2,559,350, and Pending Claims.
Graphic Technology—Color Reflection Target for Input Scanner Calibration, American National Standard, Annex B, pp. 18-20, Jun. 1993. (ANSI IT8. Jul. 2, 1993).
International Color Consortium Profile Format, Version 3.01, May 8, 1995.
J. Gordon & R. Holub, on the Use of Linear Transformation for Scanner Calibration, Communications and Comments, Color Research and Application, vol. 18, No. 13, pp. 218-219, Jun. 1993.
W.K. Pratt, Digital Image Processing, New York: Wiley, Chapter 19, pp. 551-559, 1978.
R. Holub, W. Kearsley & C. Pearson, Color Systems Calibration for Graphic Arts: I. Input Devices, Journal of Imaging Technology vol. 14, No. 2, pp. 47-52, Apr. 1988.
R. Holub, W. Kearsley & C. Pearson, Color Systems Calibration for Graphic Art: II. Output Devices, Journal of Imaging Technology, vol. 14, No. 2, pp. 53-60, Apr. 1988.
Abstracts of Awards for Fiscal Year 1995, SBIRP, U.S. Department of Commerce, pp. 46.
Vanhala et al., A General Teleproofing System, Reprinted from: Proceedings of the TAGA Conference, Rochester, New York, pp. 88-99, May 1991.
R. Holub, Colorimetric Aspects of Image Capture, Track III-Image Processing, IS&T's 48th Annual Conference Proceedings, Arlington, VA, pp. 449-451, May 1995.
Ocean Optics, Inc., Price and Data Sheet for Spectrometers & S1000 Miniature Fiber Optics Spectrometer, Mar. 1995.
Roy S. Berns, Ricardo J. Motta, Mark E. Gorzynski, CRT Colorimetry. Part I: Theory and Practice, Color research and application, vol. 18, No. 5, pp. 299-314, Oct. 1993.
Roy S. Berns, Mark E. Gorzynski, Ricardo J. Motta, CRT Colorimetry, Part II: Metrology, Color research and application, vol. 18, No. 5, pp. 315-325, Oct. 1983.
Cowan, W., An Inexpensive Scheme for Calibration of a Colour Monitor in Terms of CIE Standard Coordinates, Computer Graphics, vol. 17, No. 3, pp. 315-321, (1983).
Marszalec, E. et al., On-Line Color Camera Calibration, IEEE, pp. 232-237 (1994).
Marszalec, E. et al., Color Measurements Based on a Color Camera, Proc. SPIE/NEW vol. 3101, Image Processing Techniques and Applications: Algorithms, Methods and Components II, Munich, 170-181 (1997).
Swain, Michael J. et al., Color Indexing, International Journal of Computer Vision, 7:1, 11-32 (1991).
Funt, Brian V. et al., Color Constant Color Indexing, IEEE Transactions on Pattern Analysis and Machine Intelligence, vol. 17, No. 5, pp. 522-529, May 1995.
Radius PressView System User's Manual, Jun. 1995.
Radius PressView 17SR and PressView 21SR User's Manual, Mar. 1995.
Radius ProSense Display Calibrator User's Manual, Jun. 1995.
Wallace, J., Microdischarge devices reach large pixel counts, Optoelectronics World News, Laser Focus World, www.laserfocusworld.com, pp. 13-14, Apr. 2005.
GretagMacbeth AG, Eye-One Beamer, 2004.
Koldenhof Grafimedia Expertise, Rijswijk, the Netherlands, Unrivaled Displays. Breakthrough Colors?, pp. 1-13, 2003.
GretagMacbeth, Eye-One, New Eye-One Color Management System from GretagMacbeth, 2003.
GretagMacbeth, Eye-One Color Management System, Millions of Colors. One Eye-One, 2005.
GretagMacbeth, Eye-One, Color Tools to Ignite Your Imagination, 2004.
Pointer, M., The Gamut of Real Surface Colours, Color Research and Application, vol. 5, No. 3, pp. 145-155, 1980.
Hunt, R., A Model of Colour Vision for Predicting Colour Appearance in Various Viewing Conditions, Color Research and Application, vol. 12, No. 6, pp. 297-314, 1987.
Johnson, T., An Effective Colour Management Architecture for Graphic Arts, TAGA Proceedings, pp. 88-111, 2000.
Johnson, T. et al., The Effects of Gloss and Viewing Flare on Colour Appearance, TAGA Proceedings, pp. 280-301, 2002.
Nussbaum, P. et al., Factors Affecting the Appearance of Print on Opaque Substrates, TAGA Proceedings, pp. 47-62, 2003.
Edge, C., Requirements for Virtual Proofing, TAGA Proceedings, pp. 64-83, 2005.
Jenkins, D. R. et al., Digital imaging colorimeter for fast measurement of chromaticity coordinate and luminance uniformity of displays, Proceedings of SPIE, vol. 4395: Flat Panel Display Technology and Display Metrology, II, F. Kelley, Ed., (2001).
Office Action dated Apr. 30, 2009 with Notice of References Cited for U.S. Appl. No. 11/452,546, filed Jun. 14, 2006.
Holm, J., Tastl, I., McCarthy, A. and Derhak, M., ICC Votable Proposal Submission: Perceptual Intent Reference Medium Color Gamut, International Color Consortium (Feb. 22, 2005).

(56) References Cited

OTHER PUBLICATIONS

Specification ICC.1:Oct. 2004 (Profile version 4.2.0.0) Image technology colour management—Architecture, profile format, and data structure, International Color Consortium, 2004.
Specification ICC.1:Apr. 2001 File Format for Color Profiles, International Color Consortium, 2001.
JEITA CP-3451 Exchangeable image file format for digital still cameras: Exif Version 2.2, Japan Electronics and Information Technology Industries Association, 2002.
Universal Serial Bus Device Class Definition for Video Devices, Revision 1.1, USB Implementers Forum, 2005.
U.S. Appl. No. 60/195,688, Gaido et al., filed Apr. 7, 2000, entitled Remote Press Proof System.
Windows Color System, Evolution in the Microsoft Color Management Ecosystem, Microsoft Corporation, 2005.
Windows Color System and API: An overview, Microsoft Corporation, 2005.
European Search Report and European Search Opinion dated Dec. 4, 2009 from European Patent Application No. EP 06813988, which claims priority to PCT/US2006/033975.
Brown, S. W. et al., 1999, NIST Calibration Facility for Display Colorimeters, Proceedings IS&T/Spie 11th International Symposium, San Jose, CA.
Brown, S. W. et al., 1999, Calibrating Colorimeters for Display Measurements, Information Display, Dec. 1999, pp. 30-34.
Marszalec, E. et al., 1996, Some Aspects of RGB Vision and Its Applications in Industry, Int'l. J. Pattern Recognition and Artificial Intelligence, vol. 10, No. 1, pp. 55-72.
Defendants' Answer to Plaintiffs First Amended Complaint, Affirmative Defenses, and Counterclaims, United States District Court for the Western District of New York, Case 6:10-cv-06710-CJS, Document 11, Filed Apr. 25, 2011, pp. 1-42.
International Color Consortium, ICC Profile Format Specification, Version 3.2, Nov. 20, 1995.
"ColorFlow Custom Color Software ICC," Eastman Kodak Co., 1999.
"ColorFlow ICC Production Tools," Eastman Kodak Co., 1998.
"ColorFlow ICC Profile Tools," Eastman Kodak Co., 2000.
"Kodak ColorFlow ICC Soft Proof," Eastman Kodak Co., 1998.
Office Action on U.S. Appl. No. 13/617,973, dated May 21, 2013, United States Patent and Trademark Office.
W. Press, B. Flannery, S. Teuklosky, & W. Vetterling, Numerical Recipes the Art of Scientific Computing, Cambridge University Press, Chapter 14.3, pp. 509-520, Chapter 5.3, pp. 137-140, Chapter 9.6, pp. 269-273, & Chapter 10.8-10.9, 1986.
How to Create Color Profiles for ColorSync 2.0, Apple Computer, Inc., 1996.
Gretag Color Quality V 2.0, Chapters 2 and 3, Gretag, AG, 1996.
Fairchild, M. et al., Image Color-Appearance Specification Through Extension of CIELAB, Color Research and Application, vol. 18, No. 3, pp. 178-190, Jun. 1993.
Walker, D., Color Management—Three Advanced Topics, IS&T's Third Technical Symposium on Prepress, Proofing, & Printing, pp. 81-85, 1993.
Stokes, M., et al., A Standard Default Color Space for the Internet—sRGB, pp. 1-19, Nov. 5, 1996.

\* cited by examiner

CASE 1: THE MINIMUM INPUT L* IS LESS THAN
MINIMUM OUTPUT L*

———————————————————— L* = 100.0

L*out = L*in

———————— Lclip ————
———— Lpivot ————————  Lmin_out = L* 20.0
————————————————  Lmin_in = L = 10.0

CASE 2: THE MINIMUM INPUT L* IS GREATER THAN
MINIMUM OUTPUT L*

———————————————————— L* = 100.0

L*out = L*in

———————— Lclip ————
———— Lpivot ———————— Lmin_in = L* = 20.0
———————————————— Lmin_out = L* = 10.0

FIG. 14

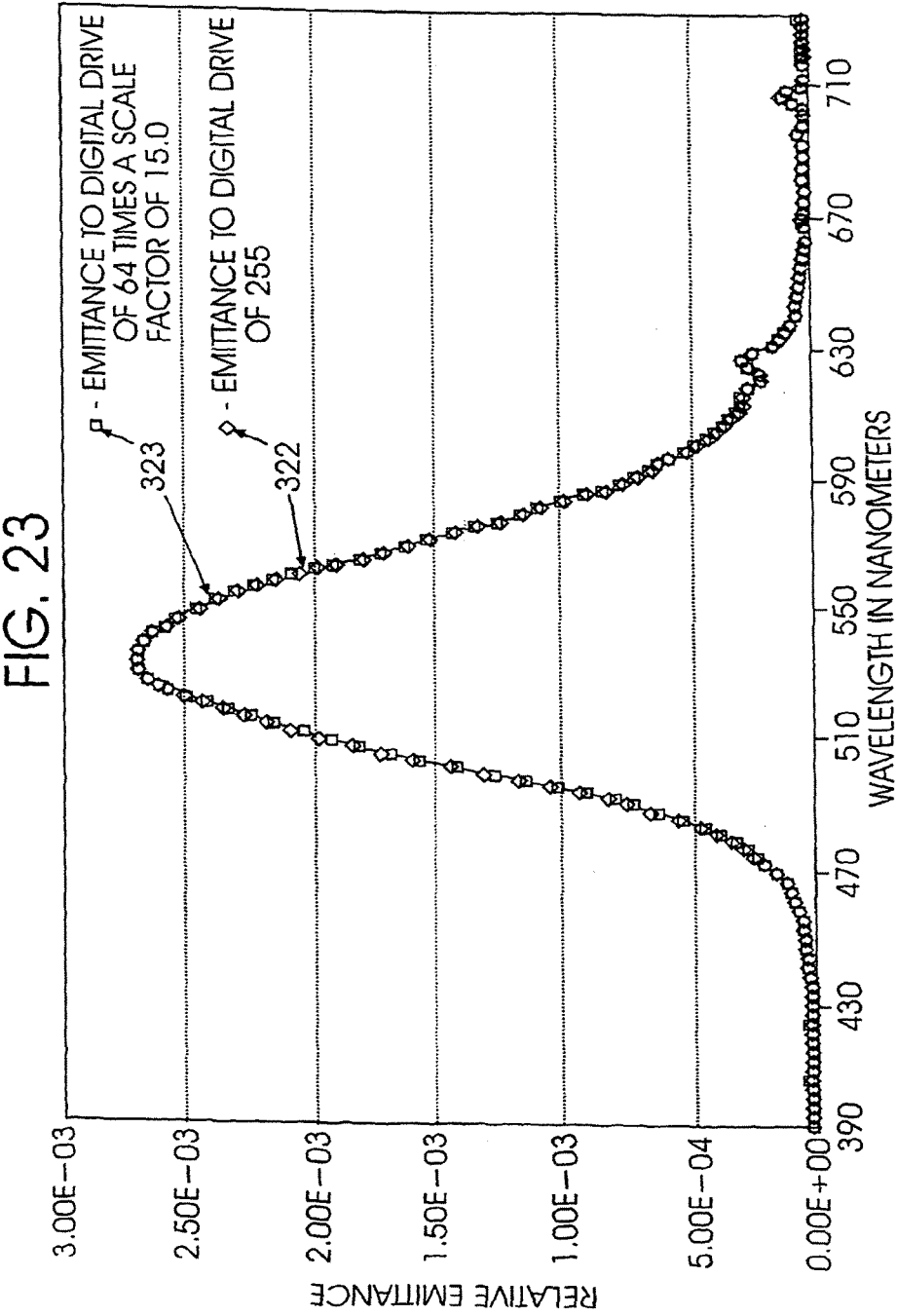

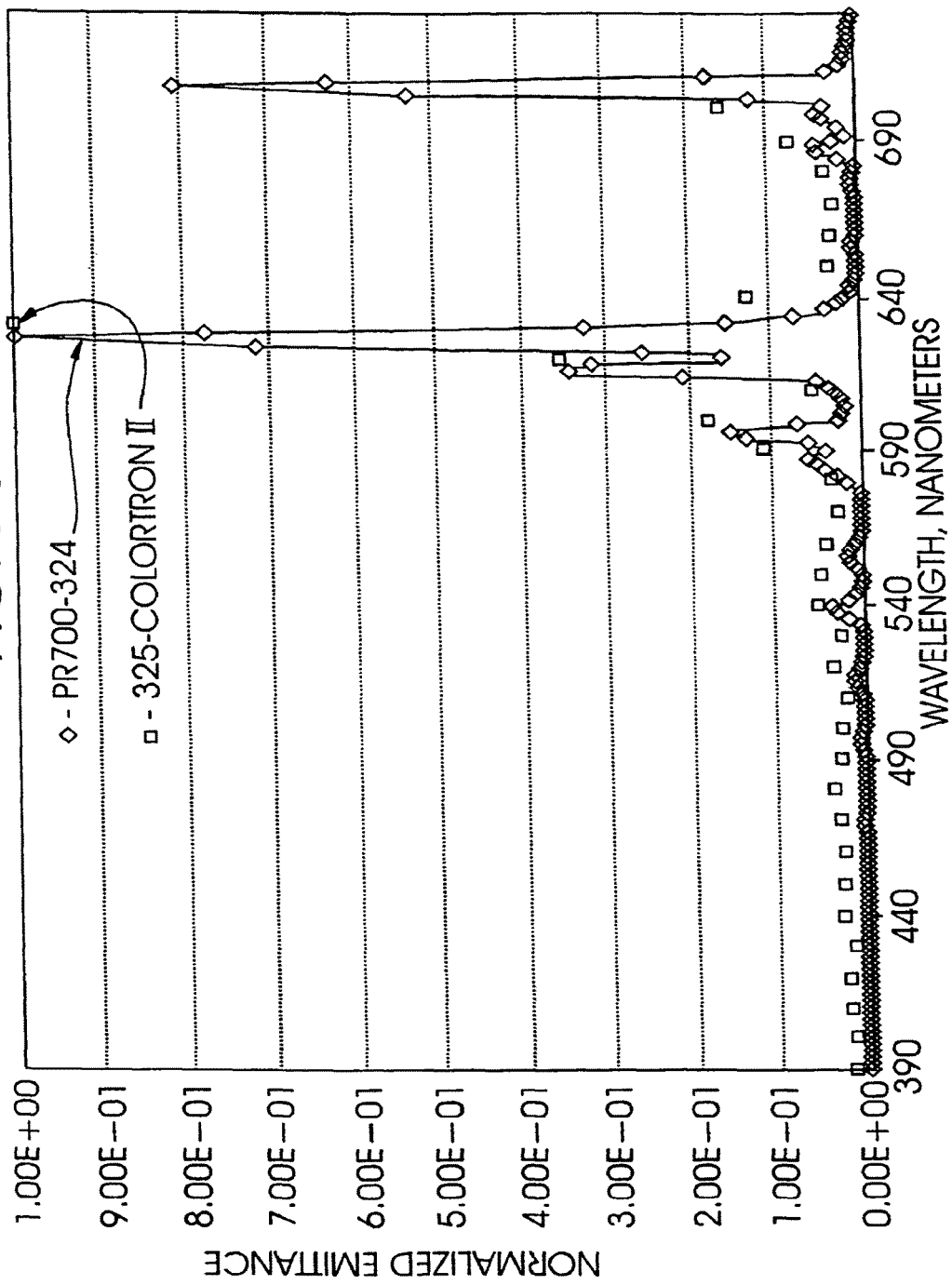

| | |
|---|---|
| D0 | SET OUTPUT-FREQUENCY SCALING TO DIVIDE BY 1. |
| D1 | SET OUTPUT-FREQUENCY SCALING TO DIVIDE BY 2. |
| D2 | SET OUTPUT-FREQUENCY SCALING TO DIVIDE BY 10. |
| D3 | SET OUTPUT-FREQUENCY SCALING TO DIVIDE BY 100. |
| S0 | SET INPUT SENSITIVITY TO 1x. |
| S1 | SET INPUT SENSITIVITY TO 10x. |
| S2 | SET INPUT SENSITIVITY TO 100x. |
| P0 | POWER DOWN SENSOR UNTIL 'S' COMMAND. |
| P1 | POWER DOWN SENSOR UNLESS READING. |
| Tx (0≤x≤FFFF) | SET SAMPLING PERIOD TO (3.2768)(x) MILLISECONDS. |
| R | TAKE READING. |
| E0 | TURN ECHO OFF. |
| E1 | TURN ECHO ON. |
| Q | QUERY VERSION OF SOFTWARE. |

FIG. 29

COLOR CALIBRATION OF COLOR IMAGE RENDERING DEVICES

This application is a continuation of U.S. patent application Ser. No. 14/933,781, filed Nov. 5, 2015, which is a continuation of U.S. patent application Ser. No. 14/161,121, filed Jan. 22, 2014, now abandoned, which is a divisional of U.S. patent application Ser. No. 12/799,930, filed May 5, 2010, now U.S. Pat. No. 8,638,340, which is a divisional of U.S. patent application Ser. No. 11/216,784, filed Aug. 31, 2005, now U.S. Pat. No. 7,728,845. U.S. Pat. Nos. 6,043,909, 6,157,735, 6,459,425, and 6,750,992 are herein incorporated by reference.

FIELD OF THE INVENTION

The present invention relates to systems and apparatuses for color calibration of color image rendering devices, such as large color displays operating by either projection or emission of images, or displays associated with desktop, workstations, laptop, handsets, or handheld computers. The displays of the present invention may represent a rendering device as described in the above-incorporated patents for enabling virtual proofing in a network, or may be part of stand-alone systems and apparatuses for color calibration. In addition to calibration as described in the above incorporated patents, improved calibration is described for sensing and correcting for non-uniformities of rendering devices, such as color displays, printer, presses, or other color image rendering device.

BACKGROUND OF THE INVENTION

Color display calibration is described in U.S. Pat. Nos. 6,043,909, 6,157,735, 6,459,425 and 6,750,992, in which sensor configurations are presented for different display types. One such type of arrangement is suited to a projection display as described, for example, at column 16, lines 31-35, of U.S. Pat. No. 6,043,909. Such sensors were located near the source of projected light and were as close as possible to the line of sight. However, many contemporary displays used in large screen applications, such as home theatre or commercial projectors, may benefit from color calibration to assure color accuracy, and further may represent rendering devices useful for virtual proofing described in the above U.S. patents.

Further, often color display are not uniform over their field of view, and thus areas of such display may be appear brighter than others, and may appear to have different color balance amongst different color channels at different points. Thus, it would also be useful to detect non-uniformities in color displays and correct for such non-uniformity, thereby providing consistency in displayed color. Furthermore, it would be useful if such detection and correction of non-uniformity may be extended to other rendering devices, such as printers and presses.

SUMMARY OF THE INVENTION

It is one object of the present invention to provide color display calibration systems for large screen displays which operate by either projection or non-projection (e.g., self-luminous or LCD).

Another object of the invention is to provide a dual use camera for a portable device in which one of the camera or a display of the portable device is movable with respect to the other to enable the camera in a first mode to capture images of the display for enabling display calibration, and in a second mode for capturing image other than of the display, such as of the user for video teleconferencing or for enabling calibration of other color rendering devices, such as color displays, printers, or presses.

It is a further object of the present invention to detect and correct non-uniformities of color displays and other rendering devices, such as printers and presses.

Briefly described, the present invention embodies a color projection display device for outputting images onto a screen having a color measuring instrument within the housing of the display device, where the color measurement instrument utilizes either the projector's optics, or separate optics for imaging reflected light from the screen. The electronics of the display device provides for calibration of the display utilizing measurement data from the color measurement instrument, and/or provides for virtual proofing with one or more other rendering devices over a network.

When such color measurement instrument is not integrated in such housing, a color measurement module may be provided which is attachable to either the wall or a speaker opposite the screen, which is especially useful in home or commercial theater environments. A control unit, which communicates image data for output by the display device, or the electronics of the display device enables calibration of the display and/or virtual proofing in accordance with color measurement data received from the color measurement module. Such color measurement module may also be utilized for other large screen display devices, such as rear projection color display device or a self-luminous ("emissive") color display, based on technologies, such as LCD, plasma, OLED, and the like, to enable calibration of the display and/or virtual proofing. Methods are provided for manually or automatically focusing and aligning a sensor of the color measuring module with a reference image on the screen, and for detecting and correcting for spatial luminous distortions detected between the reference image and the sensed image.

The present invention also provides automatic color calibration for a portable device with a color display and an attached or built-in color camera. A processor of the portable device calibrates color of the display in accordance with one or more images of the display captured by the camera. One of the camera or the display is movable with respect to the other to enable the camera to capture one or more images of said display to enable calibration, and one of the camera or display being movable with respect to the other to capture images other than of the display. As such the camera of the portable device is a dual use camera, since in a first mode it captures one or more images of the display to enable calibration, and in a second mode captures images other than of the display (such as of the user in the case of video teleconferencing). In the first mode, the camera is automatically aligned with the screen for carrying out color calibration, spatial uniformity correction, and/or virtual proofing by software or program operating on the portable device. The camera may also have a third use of being oriented for imaging another color display of another image display device (e.g., theater display system) to provide color image data representative of the another color display, and one of the processor of the portable device or the another image display device enables calibration (and/or spatial uniformity correction or virtual proofing) of the another color display in accordance with the color image data. Further, such third use of the portable device may be applied to other color rendering devices than color displays, such as printers, presses, and copiers, which output color image data onto a surface, such as media, in which the processor of the portable device or the other color rendering device enables calibration (and/or spatial uniformity correction or virtual proofing) of the color rendering device in accordance with the color image data.

The processor of the portable device calibrates color of the display in accordance with color image data captured by said camera representing color of one or more calibration forms outputted by the processor on the display. The camera may be further capable of capturing images providing information regarding spatial non-uniformity of color reproduction across the screen of the display.

The portable device may be a portable computer, and an arm is provided having a first end attached to the frame of the display and a second end attached to the camera, in which the camera is pivotally mounted at the second end to enable the camera to be oriented in a first mode to capture one or more images of the display to enable calibration, and in a second mode to capture images other than of the display. The portable device may also be a cellular phone or other handset with a built-in camera having an upper portion with the display and a lower portion with the camera. The upper portion is pivotally mounted with respect to the lower portion to enable the upper portion to be pivoted in a first mode to capture one or more images of the display for display calibration, and in a second mode to capture images other than of the display. The portable device may also represent a cellular telephone or handset without any pivotal portions, where its camera is attached to the cellular phone by an arm that is pivotal in one or more dimensions to orient the camera in a first mode to capture one or more images of the display for display calibration, or in a second mode to capture image other than of the display.

In the case of the portable device representing a cellular phone or handset, the camera may also be capable of being oriented to capture an image representative of the amount of ambient illumination, such that the backlight of the display is turned on or off in accordance with the amount of ambient illumination exceeding a threshold, or a gradient function, or turned on or off in accordance with the amount of ambient illumination exceeding a threshold and turned off after an interval expires since last input via the user interface of the cellular phone or handset.

Apparatus, systems and methods are also provided by the present invention for detecting and correcting for spatial non-uniformity of a display screen of large screen display devices, portable or laptop computer, color monitors (e.g., CRT or LCD), or the like, or hardcopy color image rendering devices, such as printers or presses, or smaller portable devices, such as cellular phones, handset, or personal data assistants with a camera. A color measuring instrument, such as an imaging sensor (e.g., CCD) measures rendered flat field images for each of the color channels, and for each measured image determines the pixel coordinate (x,y) that has the lowest fraction (or ratio) Imin/Imax of measured intensity, where Imin and Imax are the measured lowest intensity pixel and highest intensity pixel, respectively, in a channel. Using first the channel and its pixel (x,y) having the lowest fraction overall, all of the other pixels in each of the other channels are reduced in intensity while providing the desired neutral or white balance (i.e., white point) of pixel (x,y). If such intensity reduction in the other channels for pixel (x,y) is greater than Imin/Imax for the measured flat field image for the other channel, than another pixel is selected in such other channels, and then all of the other pixels in each of the channels are reduced in intensity while providing the desired neutral or white balance (i.e., white point) for that pixel. If no such white balance can be determined for that pixel, one pixel is found with or given the correct white balance, and the other pixel coordinates in each channel are each incrementally reduced in intensity in one or more channels until each pixel has a proper neutral balance. The resulting reduction in intensity for each pixel coordinate in each channel are stored in a correction non-uniformities table. Such table is applied to image data prior to being outputted by the rendering device.

An apparatus and method are also provided by the present invention for applying spatial uniformity correction in a production printing context, in which positional dependences of color are accounted for on press sheets. Corrections for positional dependencies of pixels rendered by a press may be modified by one or more of spatial uniformity correction table, a rendering color transformation, or a color-to-color' transformation within the signature of the press (i.e., the relative print densities achievable at a trailing location of an impression as a function of reproduction densities required at a more leading position within the same impression (transfer of ink to paper)).

The apparatuses, systems, and methods described herein may be used in the virtual proof environment described in the above incorporated U.S. patents, but are not limited for use in such environments, and may provide stand-alone calibration of a rendering device by software or program, operative in a control unit or host computer in communication with such rendering device and color measuring instrument, for color calibration of color image rendering systems to assure that color is accurately displayed with respect to rendered images as measured by such color measurement instrument.

BRIEF DESCRIPTION OF THE DRAWINGS

The foregoing and other features, objects, and advantages of the invention will become more apparent from a reading of the following detailed description in connection with the accompanying drawings, in which:

FIG. 14 is an illustration of the construction of a simple gamut operator of the gamut configuration data embodying properties of invertibility and reciprocality;

FIG. 16B is a flow chart of the process for calibrating a rendering device having more than four colorants by adding a neutral auxiliary colorant to a rendering transformation, in which FIGS. 16A and 16B are shown connected;

FIG. 21C is a menu at the second level of hierarchy in the GUI to enable a user to manipulate the process of making color transformations at a rendering device;

FIG. 23 is a graph illustrating the spectrum of the green phosphor emission from a cathode ray tube (CRT) color display;

FIG. 23A is a graph illustrating the spectral emission of a red phosphor emission as recorded by two different models of colorimeters;

FIG. 29 is a table of the command set used by a computer to communicate with the color measurement instrument of FIG. 28;

DETAILED DESCRIPTION OF THE INVENTION

The color calibration of the color video displays, described later in connection with FIGS. 35-38, may be part of a virtual proofing environment described in the incorporated patents. As such, the following describes the system enabling such environment as set forth in the incorporated U.S. Pat. No. 6,459,425.

Figure 1:
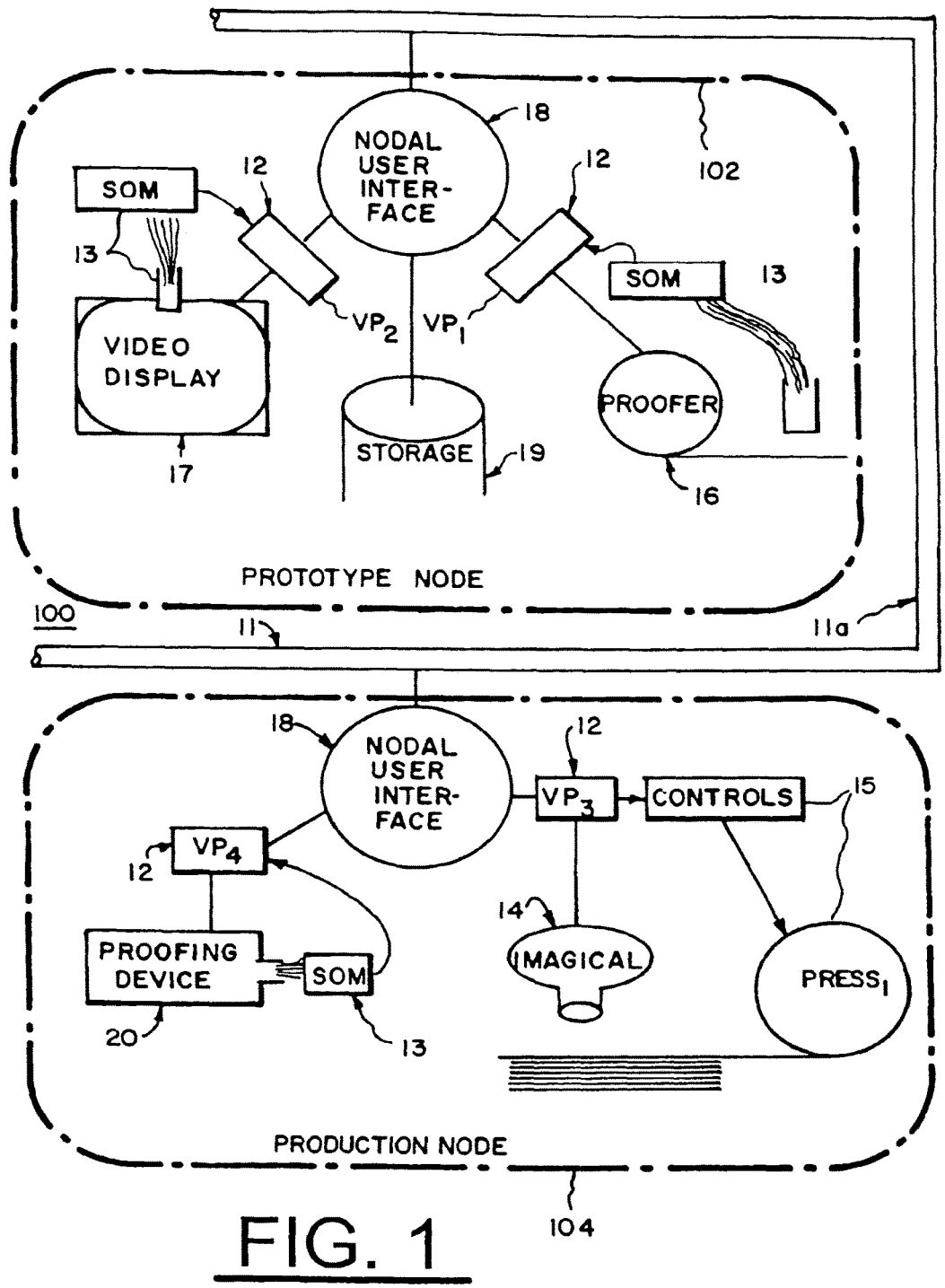
FIG. 1 shows the system in accordance with the present invention.

Referring to FIG. 1, the system 100 of the present invention is shown. System 100 has a network 11 having a pipe 11a through which multiple nodes (or sites) of network 11 can be linked for data flow between nodes. Network 11 may be a telecommunication network, WAN, LAN (with a server) or Internet based. Two types of nodes are present in system 100, prototype nodes 102 and production nodes 104. For purposes of illustration, only a general node of each type is shown in FIG. 1, however there may be multiple nodes of each type in network 11. Network 11 is modifiable to be configured by any one node to connect any two or more nodes in system 100. Each node has a micro-processor based computer, with a network communication device, such as a modem, which is part of a system having a rendering device for producing color reproduction and color measuring instrument (CMI) for measuring the color output of the rendering device. The computer may be a programmable general purpose computer or mainframe computer. Although a computer at a node is preferred, alternatively, the computer may be omitted at a node and the node operated remotely via pipe 11a from another node.

Prototype nodes 102 allow a user to perform pre-publishing functions in system 100, such as proofing (hard or soft), as well as the input of digital color image data. A user may interface with the node through standard interface devices, such as a keyboard or mouse. Rendering devices in system 100 define any type of system or device for presenting a color reproduction in response to digital color signals. The rendering devices of prototype node 102 are proofing devices, such as video screen display device 17 or proofer device 16. Proofing device 16 are hard copy devices, such as analog film-based devices, dye diffusion thermal transfer devices, ink jet printers, xerographic printers, and other similar devices. Video screen display 17 is useful for soft proofing (without a hard copy) and may be a high resolution video projection display for projecting images onto paper substrate(s) to be used in volume reproduction with resolution sufficient to reveal moiré, i.e., halftone frequency beating patterns. Note that proofing devices are typically used to represent the performance of a client, such as a production rendering device described below at production node 104. The CMI associated with each proofing device is referred to as a standard observer meter (SOM) 13 and provides color measurement data from images from the proofing device. SOMs 13 have the capability of measuring color as humans see it using the internationally accepted Standard Observer mentioned earlier, and will be described in more detail later.

One of the pre-publishing functions supported by prototype node 102 is designing page layouts. Accordingly, a user or designer at nodes 102 can input digital color graphical/image data from a storage 19, which may be a hard drive, or from other sources. The color image data may consist of page layouts having images at low and high resolutions, such as RGB. A user at the node can define color preferences for rendering of the color image data, and later modify such preferences. The rendering of the inputted color image data at rendering devices to create soft or hard proofs is discussed later.

Production nodes 104 of network 11 control a production rendering device via the device's control system. Production rendering devices include volume production machinery, such as press 15, which includes gravure presses, offset presses, electrophotographic printing machines, ink jet printers, flexographic presses, and the like. In addition, production nodes 104 may also have one or more rendering devices and SOMs 13 of a prototype node 102, such as proofing devices 20, which allows proofing to occur at a production site. CMIs of node 104 are called imagicals. Like SOMs 13 of prototype nodes 102, imagicals 14 provide color data for images rendered by press 15 in color coordinates of the Standard Observer. Proofing devices at prototype nodes 102 may also be outfitted with imagicals 14 which may incorporate a SOM 13. The differences between SOMs 13 and imagicals 14 will be described later. The main distinctions between production rendering devices and proofing devices are that the proofing devices are typically called upon to represent some other device, referred to herein as a client, such as printing press 15 of a production node 104 and such presses may have interfaces to and mechanisms of control that are different from those of proofers.

At a production rendering device, the circuitry at node 104 differs from node 102 because it interfaces with inking control systems of the production rendering device to maintain its color quality during volume reproduction. This allows control of the actual marking process, including variables such as ink film thickness, toner density, and the like, by supporting on-line colorimetry from a CMI within image areas of printed sheets. Analysis of the CMI data can be used to produce error signals in CIELAB color difference units or in other units suitable for interface to commercially available inking control systems.

The nodes 102 and 104 each provide circuitry, which includes the computer and modem described above, for computation and communication. This circuitry operates responsive to programming of interface and application software stored at the nodes 102 and 104, and received user commands at the nodes. The processes defined by such programming operate system 100. The circuitry perform several functions. First, it accepts measurement data from CMIs and computes color transformation functions to translate between human-perceptible colors of the measurement data into rendering device colorant values. Second, it processes and transmits color graphical/image data from one node or site in a network 11 to another. Third, it can issue reading instructions to CMIs mounted on a rendering device to measure rendered color images, and issue rendering instructions to a rendering device at the node using a stored color transformation. Fourth, the circuitry performs communications in system 100 in accordance with protocols for local or wide area networks, or telecommunications networks based on modem (either direct or mediated by Internet connection—note that Internet connectivity is not limited to modem), satellite link, T1 or similar leased line technologies, ISDN, SMDS and related switched linkages, including Asynchronous Transfer Mode-enabled versions, TCP/IP, token ring, and the like. Fifth, the circuitry implements calibration of rendering devices to a common, human perceptible language of color, such as CIE, defined earlier, by producing and storing color transformation information. Sixth, the circuitry performs verification of the calibration of the rendering device to maintain accuracy of the stored color transformation information. These and other capabilities of the circuitry at a node will become apparent from the below discussion which describe further the processes referred to above.

A feature of the present invention is a data structure operating within system 100 called a Virtual Proof, hereafter called VP 12. The VP data structure is a file structure for storing and transmitting files representing color transformation information between network 11 nodes. The contents of these files is outlined later. The VP is dynamic because it can be revised by nodes to assure the output color (colorants) of a rendering device using data from CMIs. Preferably, the VP does not contain color image data representing page layouts, and is associated with the page layouts. However, it can alternatively have files storing some image data, although being separable from the often bulky high resolution image data representing the page layouts. The VP has components or files shared by the nodes in network 11, and local components or files present only at each node. Shared components are those useful by more than one node in network 11, while local components are particular to information of each individual node's rendering device. Shared components are transmitted by the circuitry of each node to other nodes of network 11 via pipe 11a. Preferably, VP shared components are compact for transmission from node to node in network 11 quickly. These shared VP components include files representing the user color preferences inputted at node 102 or 104, which is needed by each node in calibrating its rendering device. Each rendering device has its own version of a VP stored at its associated node which represents the shared VP components and local components for that particular rendering device. In FIG. 1, $VP_1$ $VP_2$, $VP_3$ and $VP_4$ represent the versions of the virtual proof for each rendering device. The arrows from SOM 13 or imagical 14 represents the measurement data received by the node incorporated into color calibration data, which is stored in a local component of the VP.

The VP provides system 100 with many useful features, which include remote proofing for both intermediate and final approval of color products, conferencing at multiple nodes in the network between users which may have different rendering devices, and distributing color preference data with or without page layout image data. The conferencing mentioned above allows users to negotiate over the colors appearing in page layout and to confer about color corrections. For example, conferencing may use video displays 17 (soft proofs) of the page layouts using remote annotation software, such as imagexpo. Another important feature of the VP is that it is modifiable such that as changes occur at a rendering device, such as in inks or substrates, system 100 can automatically adjust the rendering device's calibration. In addition, adjustments to calibration may be performed on demand by a user. This allows a user to update color preferences, such as color assignments of page layouts being rendered by rendering devices in the network without retransmitting the entirety of the image data.

A feature of system 100 is that it compensates for differences in the gamuts of different devices. As described earlier, a gamut is the subset of humanly perceivable colors that may be captured or rendered by a device. The preceding definition implies that the ideal or limiting gamut is the set of all colors that a normal human can see. It is important to distinguish between receptive and rendering gamuts. The former refers to the gamut of a sensor or camera of a CMI, or human. The latter refers to the colors that an output rendering device is capable of producing in a medium by application of its colorants. Although it may be possible to design a rendering device that may produce all the colors we can see under suitable circumstances, rendering gamuts are generally smaller than the human perceptual gamut due to the properties and limitations of practical reproduction media. For example, the gamut of a color print viewed in reflected light is generally smaller than that of a video display device viewed in controlled illumination which is generally smaller than the gamut available with positive photographic transparencies. All the foregoing rendering gamuts are generally smaller than receptive gamuts.

Figure 3A:
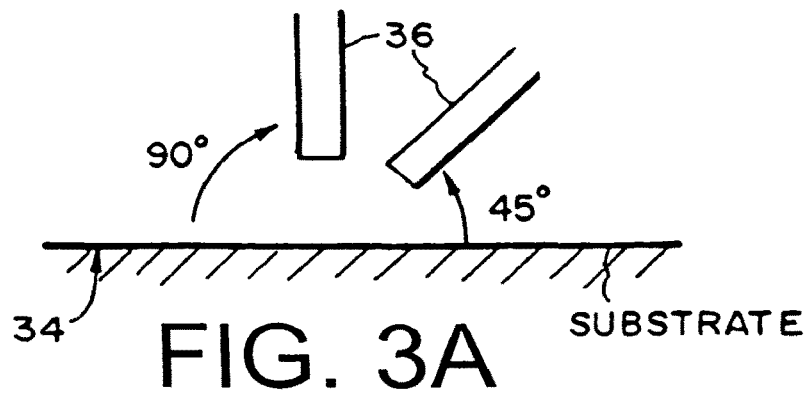
FIG. 3A shows geometries of a color measuring instrument sensor for making non-contact color measurements of reflective substrate.
Figure 2:
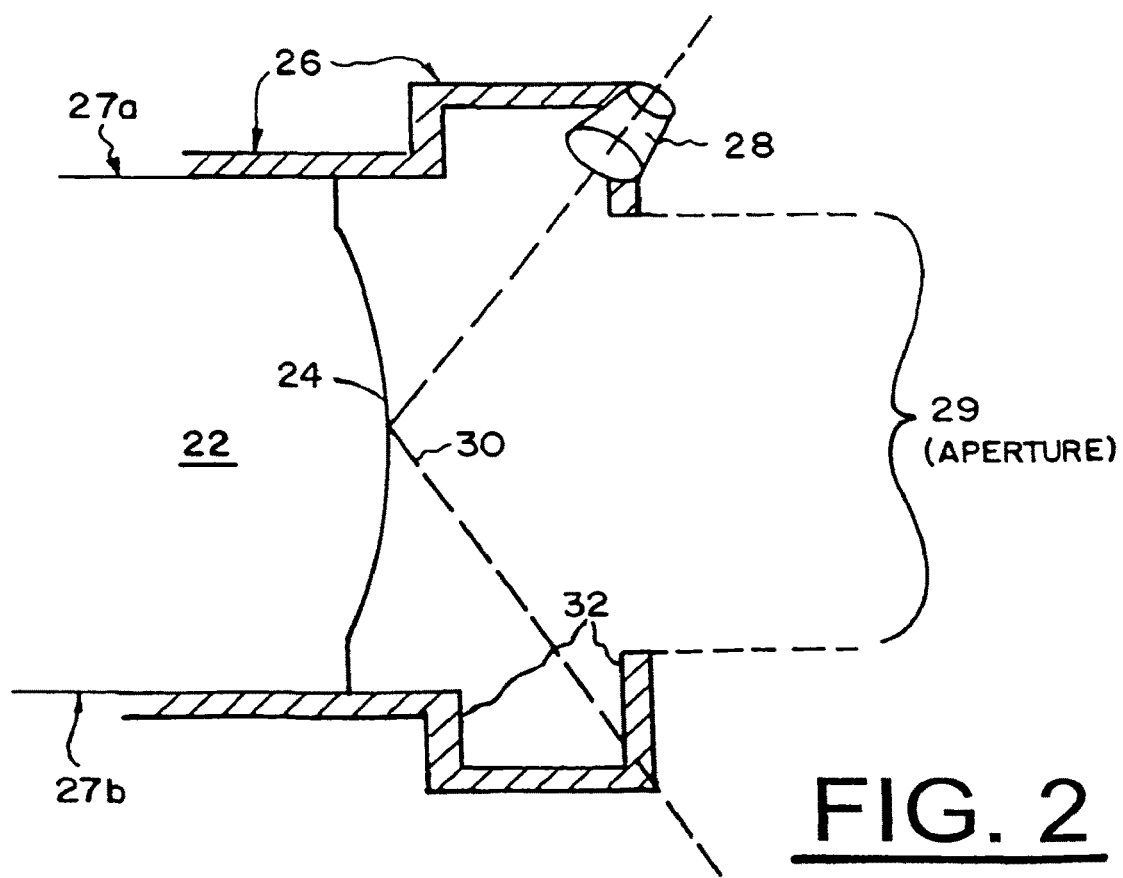
FIG. 2 shows a configuration of a color measuring instrument sensor for a video screen display.

The CMI's of FIGS. 2 and 3A are colorimeters such as discrete (unitary) colorimeters (SOM 13) or imaging colorimeters (imagical 14) which may be used in conjunction with single-channel light-detectors. These colorimeters may be stand-alone units or built-in to a rendering device. As stated earlier, the CMIs are controlled by their associated nodes in system 100 for calibration and verification of rendering devices. SOMs 13 and imagicals 14 are specialized to measure color in different ways. SOMs are suited for measuring a spatially homogeneous patch of color, preferably in a multiplicity of spectral bands. Preferably, at least 15 spectral bands spanning the visible spectrum are sampled, making a SOM more-than-3-channel input device. The transformation from relative spectral energy or reflectance to image colors employs the convolution. An example of a SOM is a unitary colorimeter or a spectrophotometer of a U.S. Pat. No. 5,319,437 issued to Van Aken et al.

However, the distinction between SOMs and imagicals is not intrinsic. A SOM with a sufficiently restricted aperture and area of view and which could perform the spectral integrations sufficiently rapidly and which could scan rasters of image data may qualify as an imagical. Imagicals are suited for multi-scale (i.e., variable resolution) imaging colorimetry, consisting of an array of photosensors, such as CCDs, capable of sensing color, as would the Standard Observer.

SOM 13 is calibrated against a reference standard illumination source whose calibration is traceable to the U. S. National Institute of Standards and Technology or similar organization. The calibration of SOM 13 is generally set by the factory producing the device. SOM 13 should be periodically recalibrated to assure its reliability. Calibration of imagicals will be described later.

Further, SOM 13 may be used in conjunction with an imagical. SOM 13 can provide a check on the calibration of imagical 14 by sampling some of the same colors measured by the imagical and providing reference data to compare against the imagical measurements. Under suitable circumstances the SOM enables a spectral interpretation of what is seen by the imagical so that a spectral illumination function characteristic of viewing can be substituted for that used in measurement as described in connection with FIG. 3B.

Referring to FIGS. 2 and 3A, preferred configurations for sensors for CMIs in system 100 are shown. Because colorimetric accuracy of CMIs and their ease-of-use are desirable, the preferred configuration of CMI device colorimetric sensors is to have them be as unobtrusive as possible to the user. Thus, in the preferred embodiment, CMIs are built-in to the rendering device.

In the case of a conventional video display or monitor, FIG. 2 shows the preferred embodiment for sensor of a CMI. A cowel 26 attaches to a upper chassis 27(a) to frame a faceplate or screen 24 of video display 22 and to shield the display from most ambient illumination. A fiber optic pickup (not shown) coupled to a projection type lens or lens system 28 plugs into cowel 26 in order to measure color of screen 24 without actually touching the screen or requiring placement by the user. Path 30 shows that the line of sight of the lens and fiber optic pickup reflects off faceplate 24 and views the blackened inner surface of a lower cowel 32 attached to lower chassis 27(b) such that it does not see specularly reflected light reflected from faceplate 24. Nonetheless, operation of display 22 is preferably in an environment with subdued illumination.

Preferably the CMI for a display screen is as a unitary colorimeter SOM 13. The unitary colorimeter takes color measurements via lens system 28 when needed in response to instructions from circuitry at a node. Unitary colorimeter SOM 13 can measure relatively small areas of screen 24 using a sensor connected to the fiber optic pickup. This sensor can be a spectral sensor, a 3 or 4 filter colorimeter or a single channel sensor. A spectral sensor must be able to resolve 2 nanometer wavebands across at least the long wave (red) end of the spectrum in order to make an adequate measurement of the red phosphor of conventional CRTs. This could be accomplished with a grating monochromator and linear photodiode array, or linearly variable interference filter and diode array. Scanning the red end of the spectrum may be performed with a narrowly, electronically-tuned, spectrally variable optical filter in order to locate red phosphor peaks exactly. If a 3 or 4 channel filter colorimeter is used, compatibility with system 100 requires that the spectral sensitivity of the arrangement be a linear combination of the human color matching functions with acceptable precision. The video display 22 phosphors change on a slow time scale. Therefore, provided that the primary chromaticities of the display are measured on a regular schedule, the SOM of FIG. 2 may be replaced by a single-channel meter for routine measurements of gamma (the voltage in—photons out characteristic of the device) very accurately for the three channels.

Alternatively, an imagical may be used instead of a unitary colorimeter SOM 13 in FIG. 2. In this case the sensor of the imagical may be centered in a door (not shown) which is attached to cover the aperture 29 of cowel 26 and 32 (the cowel may surround the entire perimeter of the chassis) so that the sensor views faceplate 24 center along a line of sight. Imagical may acquire data needed to flatten the screen, i.e., make it regionally homogeneous in light output or to compensate for interactions among adjacent pixels in complex imagery. However, both of these factors are second-order effects.

It was noted earlier that the preferred embodiment utilizes a video display 17 that projects the image, preferably onto printing paper. In this configuration, the CMI which monitors output is situated near the source of projected light, as close as possible to being on a line of sight. Preferably, a projection video display is capable of resolutions exceeding 1200 lines per inch. In this way, it is possible to simulate rosettes, moires and details of image structure on the hard copy and to show the actual structure of images captured from prints with a CMI equipped with macro optics. To provide high resolution projection, butting together a composite image using several limited-area-displays may be performed. Regardless of type of display 17, the display may use additional primaries in order to extend gamut or better simulate subtractive colorants.

FIG. 3A shows an example of a sensor of a CMI for measuring a substrate 34 (hard proof), such as produced by a proofer device. In the case of a digital proofing device, such as a dye sublimation or ink jet printer, it is desirable to position a dual fiber optic pickup/illuminator 36 arrayed for 45 and 90 degrees measurement geometry near the print head in order to sample recently printed color pixels of substrate 34. Pickup/illuminator 36 have projection-type lenses coupled to both a sensor fiber and a illumination fiber within a light shielding sleeve to implement non-contact measurements and to protect against stray light. Pickup 36 relays light to an analysis module of a CMI in which, preferably, a spectral colorimetric measurement is made. If placement near, the print head is not practical, then placement over the exit path of printed sheets is preferred. This sort of placement is preferred for proofing devices which are page printers, such as electrophotographic or conventional, analog proofers. As was the case with monitors, the use of a single-channel device to monitor linearization is compatible, provided that the nature of the device variation over time is compatible with intermittent, full, colorimetric calibration. For example, it may be sufficient to calibrate a dye sublimation proofer only once for each change of ribbon. Although it is preferred to build the CMI into the proofing device in order to minimize user involvement with the process, system 100 can alternatively require the user to place the printed copy on a X-Y stage equipped with the dual fiber optic pickup/illuminator 36.

At production node 104 of system 100, it is preferred that images rendered from a press are captured as soon as possible after they are printed, i.e., after all the colorants are applied. In this way the data necessary for control are available promptly. Although system 100 may estimate the color-error of printed sheets relative to an aim value, the preferred embodiment applies imaging colorimetry of a CMI to the analysis of the image area. Preferably, there is a spectral component to the CMI measurement such that interactions of the colorants with the stock or printing substrate can be analyzed and it is easier to compute the colors as they will appear under standardized viewing conditions.

Figure 3B:
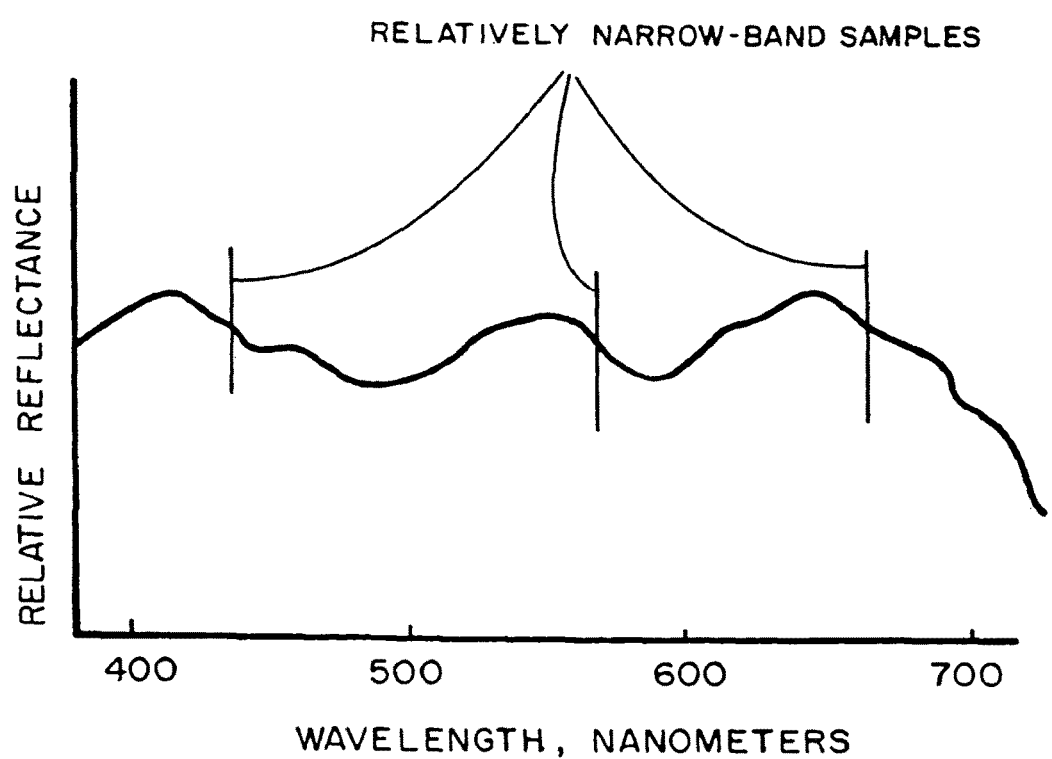
FIG. 3B shows use of a color measurement instrument to estimate a composite spectral function given knowledge of the underlying spectral functions of the colorants being mixed.

Imagical 14 of a production node 104 may employ SpectraCube technology, or cameras using any filtering technology that can simulate Standard Observer response adequately. The preferred embodiment, imagical 14 has one or more cameras, such as solid state area arrays, in which the light can be filtered through at least three wavebands, either simultaneously or sequentially, in conjunction with a unitary type colorimeter which views a determinable region of the image viewed by the camera. This provides for the possibility of a spectral interpretation of each pixel as needed. A spectral interpretation is desirable in order to be able to control color to a criterion of how it will appear under the final viewing illuminant. For example, an on-press camera could be several cameras/sensors, each equipped with a relatively narrow-band filter. The cameras, used in conjunction with a unitary colorimeter, can sample composite spectral curves, as shown in FIG. 3B, in such a way that inference of the total spectral reflectance function is possible. The minimum number of camera channels depends on the number of colorants and the complexity of their spectral absorption curves. The cameras may include an infrared-sensitive camera to differentiate the black contribution to a spectral curve from contributions of non-neutral colorants.

Preferably, imagical 14 is capable of multifocus or variable focus imaging so that larger areas of the image can be viewed at lower resolution or vice versa. Views of small areas at high resolution enable simulation of fine image structure by proofing devices capable of sufficiently high resolution display. It is also preferred that imagical 14 is equipped with anti-aliasing filters since much of the input to the imagical can be expected to be screened or pixilated. Also preferably, the viewing illuminant is controlled to simulate the viewing illuminant during the measurement. This may be achieved using a spectrally-adaptive, electronically tunable filter to match the illumination spectrum of any desired light source.

Ease of use and accuracy requirements indicate that CMIs are calibrated or self calibrating in the preferred embodiment. The preferred embodiment of the unitary device SOM 13 approximates a dual-beam device, such as spectrophotometer of Van Aken et al. cited earlier. The spectrum of light reflected from the unknown sample is compared either simultaneously or successively with the light of the same source reflected from a known reflector. In this way it is possible to separate the spectral contributions of colorants, substrates and illumination sources and to estimate their true functional forms over multiple impressions. This increases the CMI's accuracy. Even with such measuring, however, regular recycling of instruments for factory re-calibration or field recalibration using standardized reflectance forms should be performed. Also, if video display 17 is a self-emissive monitor, the above dual-beam functionality although not useful in computing a difference spectrum, provides a means of evaluating possible drift or need for re-calibration in the instrument.

System 100 operates in accordance with software operating at the nodes, which is preferably based on object oriented coding, a well known programming technique. However, other programming techniques may also be used. The discussion below considers the different input and output devices, e.g., CMIs and rendering devices, as objects. Each object refers to software applications or routines in system 100 which provides input to or accepts output from other applications (or devices).

Figure 4A:
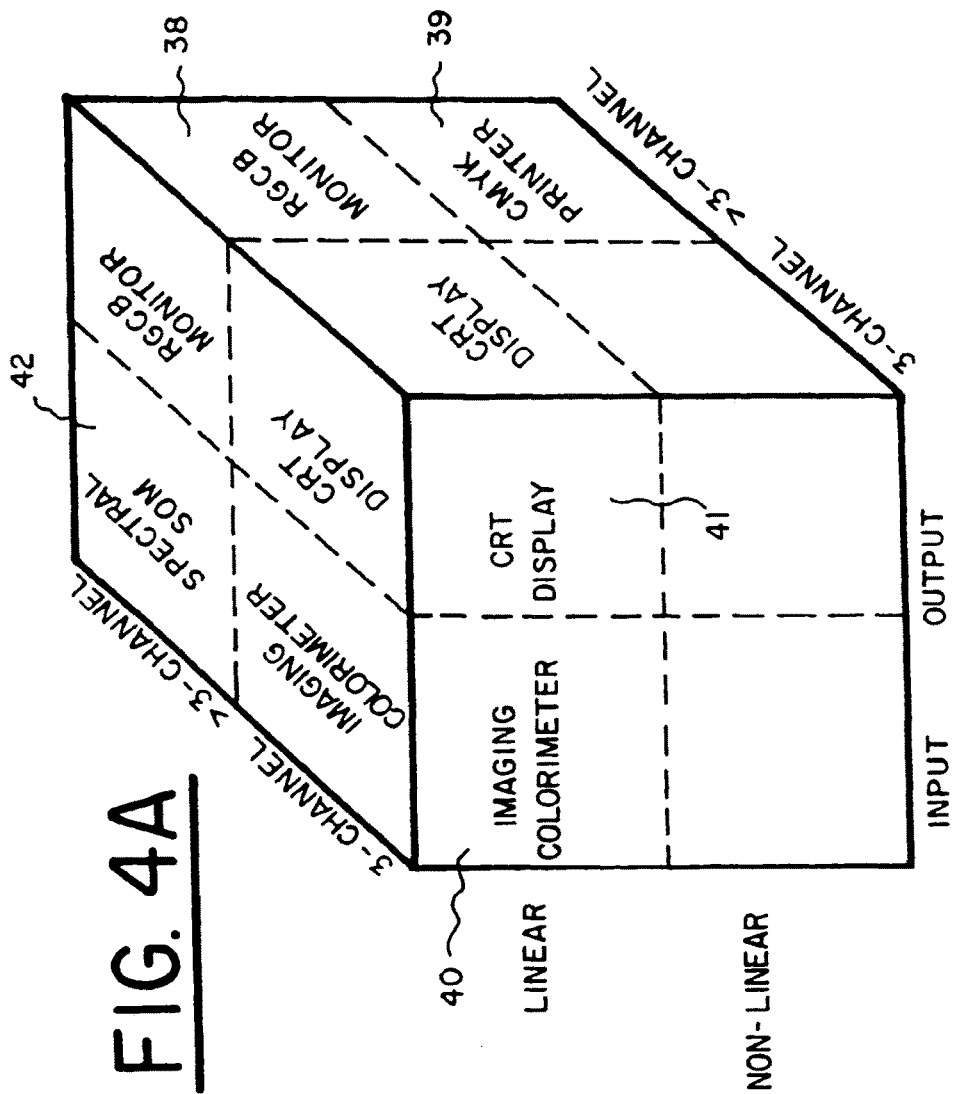
FIG. 4A illustrates the devices of the system separated into device classes inheriting various structures and procedures for color calibration and transformation.

Referring to FIG. 4A, a three-dimensional matrix model of the abstract class device/profile is shown. For example, a device may be instantiated as a linear input device or non-linear output device and derive properties through inheritance. An object created from a certain class is called an instance, and instances inherit the attributes of their class. Inheritance is a functionality of object-oriented coding and provides for grouping objects having common characteristics into a class or subclass. The matrix is extended in a third dimension to include 3-colorant-channel devices and morethan-3-colorant-channel devices. Display devices may have 4 or more colorant channels (for example, Red, Green, Cyan, Blue, indicated by RGCB Monitor 38) in order to enhance gamut or better simulate subtractive color reproduction processes. In other circumstances, a display device may appear to fall into the same class as a CMYK printer 39, which it represents in a soft-proofing/client relationship. The appropriate models and transforms are those associated by inheritance with the subclass into which the new device falls within the general matrix.

A CMYK printer 39 exemplifies the (sub)class output/non-linear/more-than-three-channel. By inheritance, client-proofer relationships are shared by members of subclass output, since the ability to enter into client-proofer relationships can be passed to all members of the subclass by inheritance. Note that the subclass of input devices is distinguished by conservation of gamut among its linear members. Likewise, specific instances of subclass linear inherit an association with linear matrix models of color transformation, whereas non-linear subclass members associate with color transformation by polynomial evaluation, interpolation or other form of non-linear color mixture function. Procedures performing the color transformations are incorporated in the data structures defining the objects, and are discussed later in more detail. More-than-three-channel devices require procedures for rendering with the extra colorants, which is also discussed later in more detail.

Note that the class hierarchy depicted herein supports instantiation of devices of types "scnr" "mntr" and "prtr" as promulgated by the ICC Profile Specification. However, the class hierarchy disclosed herein is considerably more general, flexible and extensible. The properties of flexibility and extensibility are illustrated by the following practical example: a video display ("mntr" in prior art ICC Profile Spec) in system 100 may occupy any of a number of cells within the class structure depending on its physical properties (for example, the number of colorant channels it has) and purpose (stand-alone design workstation or soft proofer representing a four-colorant device.)

The term "linear" herein, when applied to a device, means that linear models of color mixture can successfully be applied to the device. It does not imply that a video display is intrinsically linear. For example, among input devices, linear defines that linear color mixture models can be used to convert from CIE TriStimulus Values to linearized device signals and vice versa. Further note, that one application can be an output device with respect to another. For instance, application software may convert RGB TriStimulus Values into CMYK colorants and occupy the same cell as a CMYK printer 39.

The calibration of devices in system 100 is indicated by the classes of the devices 40, 41, 42 and 39 in FIG. 4A. Calibration herein includes the process of obtaining color transformation data in uniform color space. Once devices at nodes in a configured network 11 of system 100 are calibrated, the colorants produced by nodal rendering devices can then be controlled, however such calibration remains subject to recalibration or verification processes, as described later. There are four classes of devices 40, 41, 42 and 39 which require calibration:

1) imaging colorimeters or imagicals 14 (class input/linear/3-channel);

2) video displays 17 (generally in class output/linear/3-channel);

3) unitary, spectral colorimeters or SOM 13 (class input/linear/more-than-3-channel); and 4) printers or presses (generally in class output/non-linear/more-than-3-channel).

Optionally, non-linear input devices may be used in system 100, but are less preferred. An example of a procedure for calibrating non-linear input devices to a colorimetric standard is described in Appendix B of the American National Standard "Graphic technology—Color reflection target for input scanner calibration" (ANSI IT8.7/2-1993).

In the first class of devices, the calibration of imagicals 14 involves preparing compensation functions for the separable non-linearities of the device's transfer function, which are usually addressed in each color channel individually. These compensation functions may be realized in one-dimensional look-up-tables (LUT), one for each color channel. The compensation functions may be defined in a calibration step in which measurement signals from imagical 14 are generated in response to observation of step wedges of known densities. Next, specifying the constant coefficients of a linear color mixture model expressed as a 3×3 matrix transformation, hereinafter referred to as matrix M, which converts linearized device codes into CIE TriStimulus Values, such as XYZ, or related quantities. Last, the gamut of the input is scaled to fit within the color coordinate scheme in which images are represented. Because inputs to the system are printed copy (proofs and press sheets), gamut scaling is often unnecessary except when the image representation is a space such as calibrated, monitor RGB which may not encompass all the colors of the print. Occasions on which this would most likely be a problem are those involving extra colorants used for "Hi Fi" effects, although limited ranges of conventional printing cyans and yellows are out-of-gamut for some monitors. Preferably, imagicals 14 are self-calibrating to assure the accuracy of their color measurements. The compensation function LUTs, matrix M, and possible gamut scaling data are considered the calibration transforms for each imagical 14.

Figure 4B:
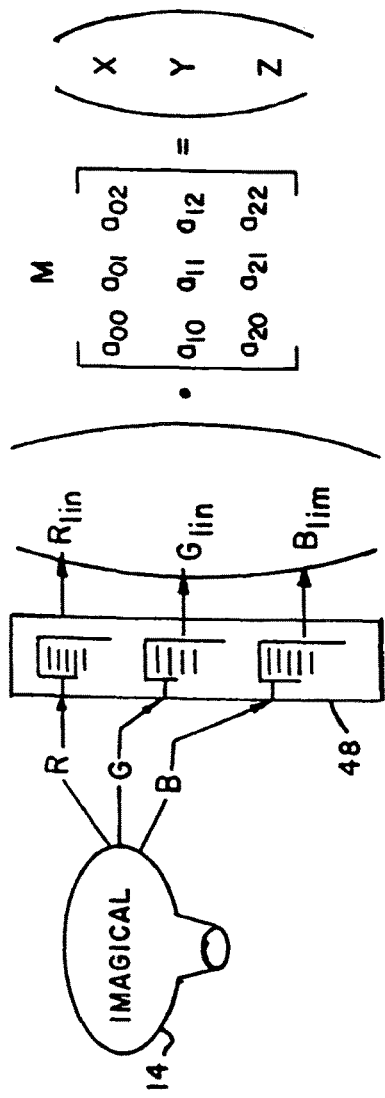
FIG. 4B is a process diagram for color transformation of a class of devices including linear color measuring instruments.

The color transformation in imagicals 14 into uniform color space based on the above calibration is generally shown in FIG. 4B. Imagicals 14 output measurement signals R, G and B, also referred to as device codes. The measurement signals are passed through compensation function LUTs 48 (or interpolation tables) to provide linearized signals $R_{lin}$, $G_{lin}$ and $B_{lin}$, in order to compensate for any non-linearities in the relationship between light intensity sensed by imagical 14 and the device codes. Matrix M then operates on the linearized signals $R_{lin}$, $G_{lin}$ and $B_{lin}$ to provide X, Y, and Z coordinates. Matrix M is shown consisting of the 3×3 coefficients ($a_{00}$-$a_{22}$) defining the linear combinations of $R_{lin}$, $G_{lin}$ and $B_{lin}$, needed to match X, Y and Z, the TriStimulus Values (TSVs) of the CIE Standard Observer. Although not shown in FIG. 4B, gamut scaling is performed after TSVs are converted to Uniform Color Space coordinates such as those of CIELAB. Scaling of an input gamut onto an output gamut in this case is entirely equivalent to processes detailed for rendering devices later in this description.

Calibration of video displays 17 in the second class of devices follows the same steps for imagicals 14 described above, however since video displays 17 are output rendering devices, matrix M and compensation function LUTs are inverted.

Figure 4C:
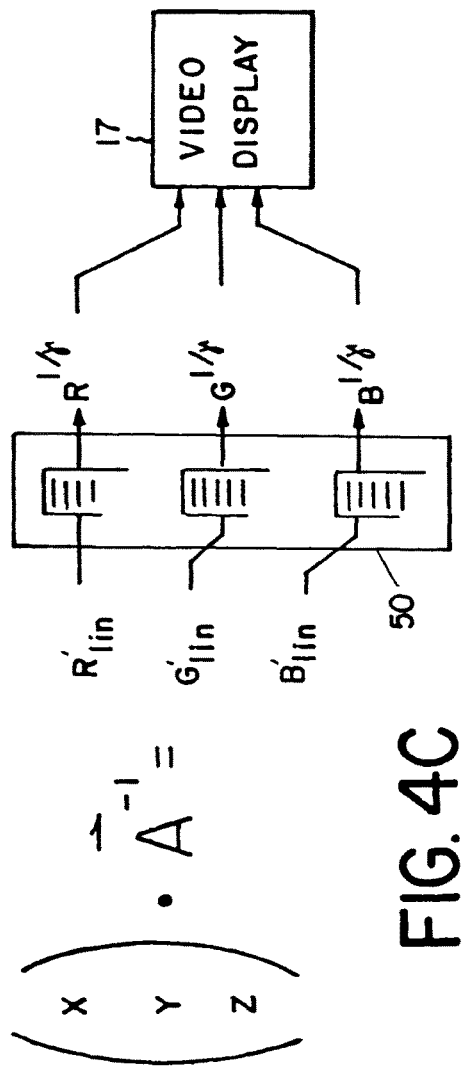
FIG. 4C is a process diagram for color transformation of a class of rendering devices including video-color displays.

Referring to FIG. 4C, device independent color coordinates XYZ are input signals to display 17. Rendering employs the inverse of the operations used for imagical 14. The inverse of the calibration matrix M is called $A^{-1}$ (to emphasize that we are considering numerically different matrices for the two devices) and is used to convert the XYZ input signals to linear device signals $R'_{lin}$, $G'_{lin}$ and $B'_{lin}$. The linear device signals $R'_{lin}$, $G'_{lin}$, and $B'_{lin}$ are postconditioned using the inverse of the compensation function LUTs which define the non-linear relationship between applied signal and luminous output of display 17, a function which is defined and adjusted in a separate, empirical step of calibration. The output from the LUTs are gamma corrected signals $R^{1/\gamma}$, $G^{1/\gamma}$, and $B^{1/\gamma}$ representing the input to display 17. Note that there is no necessary relationship between the matrices $A^{-1}$ and M in FIGS. 4B and 4C. Further, since the LUTs of FIGS. 4B and 4C may be used with various types of transformations in system 100, they are preferably represented by a separate data structure, within the software architecture, which may be combined like building blocks with other structures, such as 3×3 matrix, or multidimensional interpolation table, to form more complex data structures.

As stated earlier video displays 17 generally belong to the subclass output/linear/3-channel in FIG. 4A. However, there are two important exceptions to this: a) when display 17 is used to represent a more-than-3-channel printer, the transforms used to drive the display are non-linear—in other words, a proofing device manifests attributes of its client; and b) when display 17 is used as an accomplice in the creation of computer-generated art, the video display can be considered a linear input device, since new, digital, RGB data are created in the medium and color space of the display. Likewise, calibration for a RGCB Monitor (device 38 of class linear/output/>3-channel) is a simplification of procedures for calibrating the class of non-linear/output/>3-channel devices, which is described below.

In the third class of devices, the calibration of unitary, spectral colorimeters or SOM 13 is set by the factory, as discussed earlier, and thus does not require the preparation of calibration data to provide device independent color coordinates.

Figure 5:
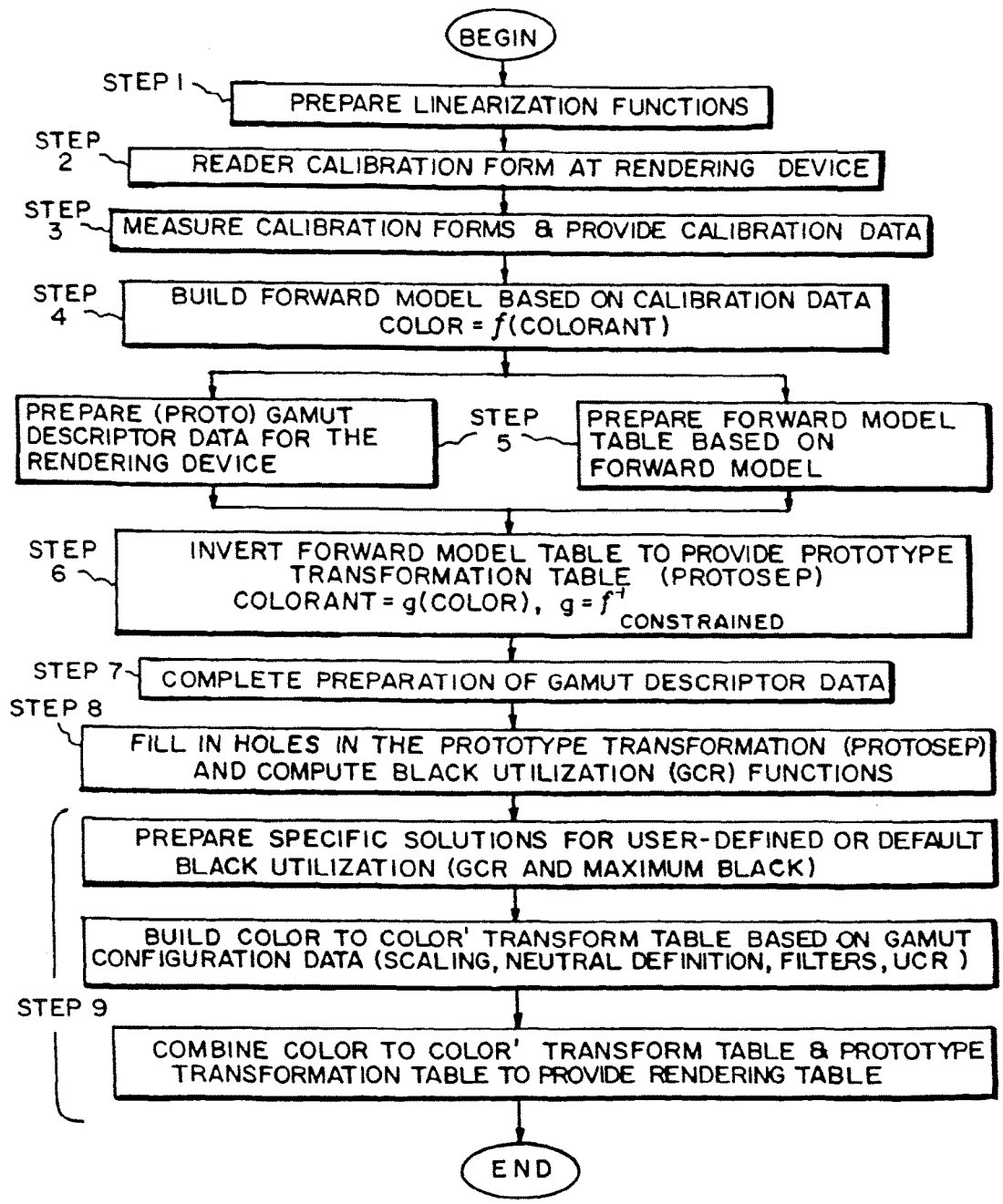
FIG. 5 is a process diagram for calibrating a class of rendering devices including printers and presses at a node in the system of FIG. 1 to provide color transformation information.

Referring to FIG. 5, the process of calibrating the fourth class of devices is shown. It should first be noted that for proofing devices in order to represent one device on another (to proof) it is necessary to have an accurate model of the color reproduction of both devices. It is preferred that the proofing device has a larger gamut than the client and that accurate knowledge of gamut boundaries be derivable from the models of colorant mixture. Because proofing is an issue with output devices, it is necessary to develop rendering transformations that invert the models of colorant mixture and that mix colorants on the proofer in such a way as to match the colors produced by the client as closely as possible. In other words, this should involve respecting the gamut limitations of the client device when rendering on the proofer. In summary, the following four kinds of color transformations are developed in calibration of the fourth class of devices:

1) forward models that enable calculation of the color, in device independent coordinates, of a mixture of colorants;

2) forward model inverses that enable calculation of the amounts of colorants needed to render a desired device independent color coordinate;

3) descriptions of gamuts in terms of boundaries specified in device independent color coordinates; and 4) mappings of colors realizable on one device onto those realizable on another in a common, device independent coordinate system (gamut configuration data).

The above four color transformations are discussed in more detail below. The following is in reference to a hard copy proofing device or proofer, but is applicable to other devices in the fourth class, including high and low volume presses.

Figure 6A:
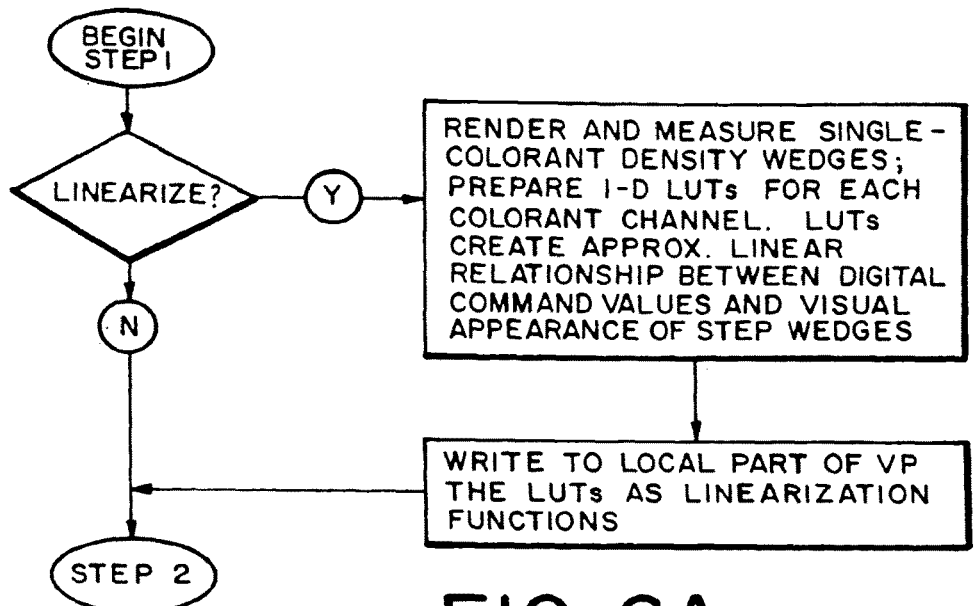
FIG. 6A is a flow chart detailing step 1 in FIG. 5, preparing linearization functions.

Step 1 of FIG. 5 is the process of preparing linearization functions, which is shown in more detail in FIG. 6A. This process establishes a linear relationship between the digital codes sent to the proofer and the output of the proofer, measured in units such as visual print density. Linearization improves the utilization of the available digital resolution and is usually implemented by means of one-dimensional Look Up Tables (LUTs) that map linear digital codes from the nodal computer onto signals that drive the marking engine of the proofer to produce an output that is approximately linear. For example, step wedges printed in C, M, Y and K respectively should produce gradations in measurable visual density that increase linearly as a function of the digital codes commanded by the host.

Usually, linearization involves printing a step wedge on the marking engine without the benefit of the LUT—if data are passed through the LUT, it applies an identity mapping. The color samples of the wedge are analyzed by the CMI associated with the proofer and the measurements are supplied to the nodal processor so that it can compute the transfer function from command codes to print densities. The measured transfer function is compared to the desired one and a function that compensates for the errors in the measured function is prepared—this is what is loaded into the LUT for use in normal image transmission. The LUTs are written to the local part of the VP as linearization functions.

Linearization is not a strict prerequisite for the remaining procedures because a multidimensional color transformation could be designed to accomplish what the one-dimensional LUTs are supposed to do. Thus, linearization of step 1 although preferred in system 100, may optionally be incorporated into other color transformations in FIG. 5. However, it is generally advantageous to exclude as many sources of non-linearity as possible from the transformation function which is specified by the procedures outlined here.

Figure 6B:
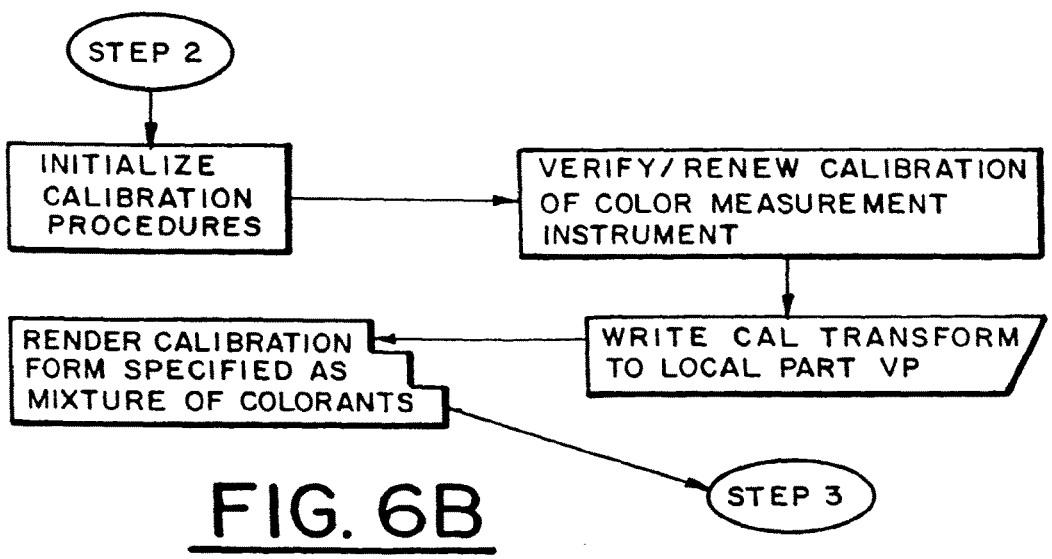
FIG. 6B is a flow chart detailing step 2 in FIG. 5, rendering calibration forms.

Step 2 of FIG. 5 involves verifying or renewing the calibration of the CMI and rendering calibration forms, and is described in the flow chart of FIG. 6B. After initializing calibration procedures, if the CMI associated with the rendering device is an imagical 14, it is calibrated to provide calibration transforms, as described above. Preferably calibration of the CMI is performed automatically in response to instructions from circuitry at the node.

After the CMI associated with the rendering device is calibrated, a calibration form is rendered on the proofer. For example, this form may have the following attributes: 1) a sampling of all combinations of four levels of all of the colorants, 2) inclusion of approximately neutral step wedges, 3) several samples of flesh tones, 4) a number of redundant patches—these are common inkings placed at different locations on the proof to provide information about spatial non-uniformities of the proofing process. It also is useful to include at least short step wedges in each of the colorants and their overlaps, for example, cyan, magenta and yellow as well as blue (cyan+magenta), green (cyan+yellow) and red (magenta+yellow.)

The calibration form described consists of about 300 samples in the case of 4 colorants and can fit on an 8.5×11 inch (21.5×28 cm) sheet with patch sizes of 1 cm on a side. However, generally, the number of patches should be three times the number of polynomial terms fitted to the data (discussed later in step 4, FIG. 8.) Patch sizes are scaleable for compatibility with various CMIs. In addition to the tint samples, the target has markings similar to pin registration marks and demarcated handling zones to facilitate transfer of the target from the proofer to the CMI if the CMI is not incorporated into the proofer. The registration marks indicate clearly where and how to insert the copy in a stand-alone CMI so that the instrument will find the patches where they should be and the handling zones will emphasize to the user that the image area should not be touched. Hard copy proofers may write an identifying number and/or bar code for the device and for the specific proof (including date and time) on the proof.

Alternatively, a device in the fourth class, such as a running press, may be calibrated by analysis of live imagery (rather than a calibration form) digitized by an imagical provided 1) that the images analyzed sample the gamut of the device adequately and 2) that the effects of page adjacency within a signature on color reproduction can be accounted for (for example by reference to stored historical data at the node.) As always, the relevant data for calibration are the known colorant specifications embodied on the printing plate and the colors resulting on the printed sheets.

Figure 7:
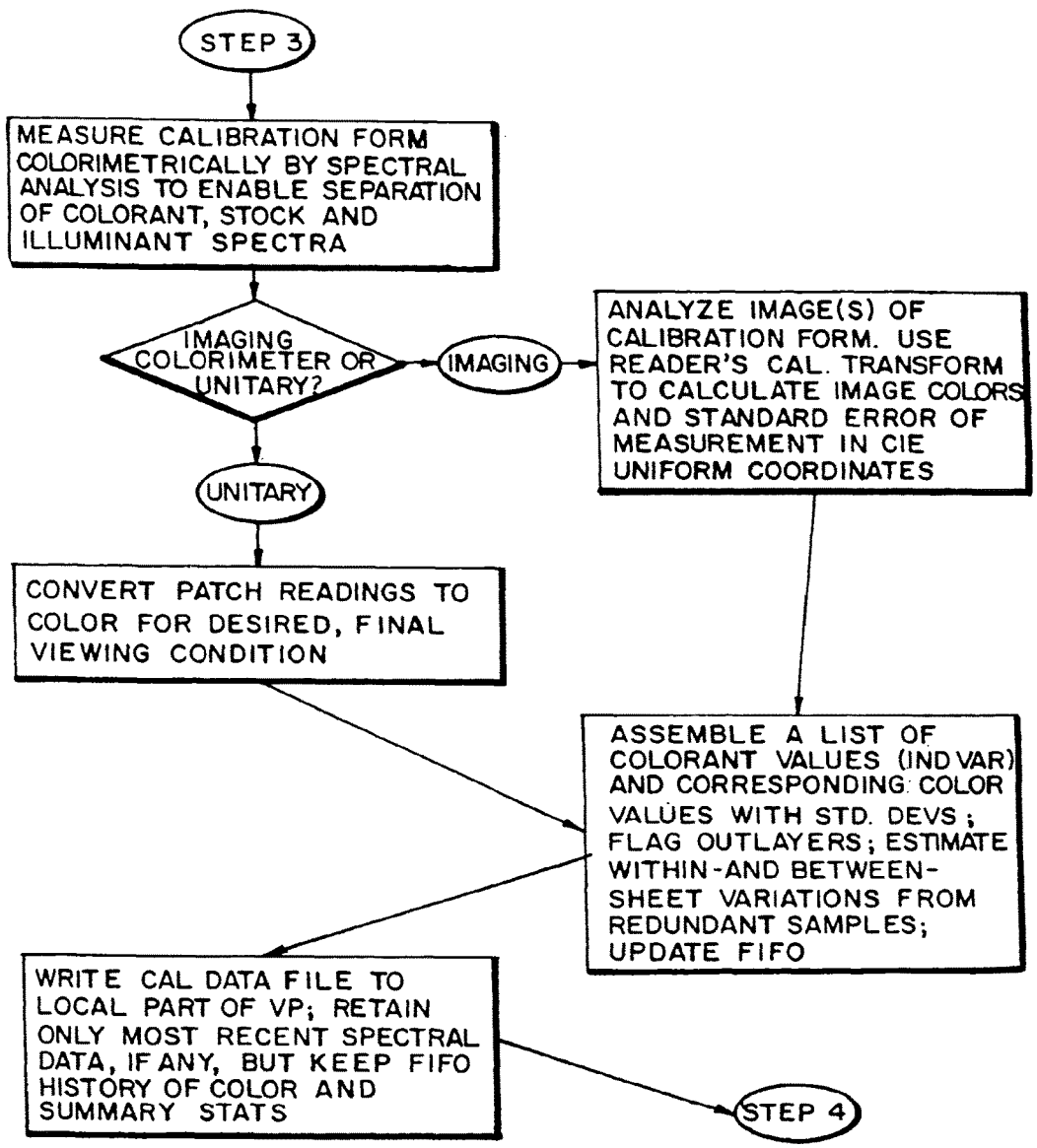
FIG. 7 is a flow chart detailing step 3 in FIG. 5, measuring calibration forms and providing calibration data.

After rendering the calibration form, the form is measured by a CMI and calibration data is provided (Step 3 of FIG. 5). The processes of step 3 are detailed in the flow chart of FIG. 7. As stated earlier, the preferred CMI is a linear colorimeter, such as a imaging or unitary colorimeter, which is capable of providing spectral analysis data which supports illuminant substitution. The CMI should produce several readings of color to the node; if one is an outlyer compared to the others because of a blemish on the copy or some malfunction, then the software at the node excludes it from the averaging for that patch. If no two of the measurements agree, then the patch should be flagged so as to identify it as a problem in subsequent processing. More generally, the number of measurements of each patch is odd to permit voting by the software in the interest of selecting trustworthy measurements.

If imaging of the calibration form is performed by an imaging colorimeter or imagical 14, then the imaging colorimeter analyses the images on the form, and uses its calibration transforms from step 2 to calculate image colors and standard error of measurement in CIE Uniform Coordinates, such as L*, a*, b*. Also the imaging colorimeter provides many sample values of each patch color; regional checks for nonuniformity of color in the sampled area should be performed. However, if imaging of the calibration form is performed by an unitary colorimeter or SOM 13, then the patch readings from the form are converted to color measurements in CIE Uniform Coordinates.

Each patch measurement may include information about sensitivity, integration time, wavelengths sampled, illuminant substitutions, and the like. The series of measurements from each calibration form are accompanied by at least one record of the reference spectrum, although, obviously, reference spectral data will be collected and used on every reading, at least for reflection measurements.

Regardless of the type of CMI, a list of colorant values (the Independent Variables, IVs, to the fitting procedure) to corresponding color values (Dependent Variable) with standard deviation are assembled. On this list of measurements outlyers are flagged. An estimate of sheet variation from redundant sampling is produced.

In addition to multiple measurements within a given sheet, two other means for enhancing the reliability of the data are provided. First, the software supports measurements of multiple sheets and second, an historical record of measurements from a particular proofer or press is preferably maintained at a node. Historical data can be stored more compactly and compared more readily to current data if the measurements are converted from spectral form to colorimetric form. Spectral data of the measurement is stored in a database at the node in terms of color and summary statistics.

Preferably, the database maintains a FIFO history of color and summary statistics from the most recently measured forms. Because step 5 involves least squares error minimization, flagging of outlyers is preferred to reduce the influence of one bad reading. A decision on whether a current reading is legitimate is made by comparing CIE ΔE* values rather than the two spectra. The assembled list with flagged outlyers and standard deviation of each patch measurement is written to a calibration (cal.) data file in the local part of the VP, for later use in building the forward model.

After step 3 is complete, processing continues to step 4 of FIG. 5, building a forward model based on the calibration of step 3. Step 4 is flow charted in FIG. 8. This model will represent color as a function of colorants of the proofer or press. It should first be noted that generic polynomials provide a satisfactory form for models of color generation by colorant mixture on printing devices. However, this does not exclude any other mathematical or physical modeling procedure capable of producing transformation functions of sufficient colorimetric accuracy. Polynomials of relatively low order in each of the colorant variables may be fitted very nearly to within the device variation. In other words, the uncertainty of the model prediction is not much greater than the uncertainty of color rendered in response to a given set of digital codes. Low order implies that the colorant variables are not represented as powers greater than 2 or 3 and that the sum of the powers of the independent variables in a single term of the polynomial is limited to 4. Therefore, if the inks C, for cyan, M, for magenta, Y, for yellow, and K, for black are the independent variables, a valid term could be $C^2MK$, but not $C^2M^2K$. Analytical derivatives are easily computed, which makes them advantageous for model inversion.

A polynomial forward model is fitted to a data set consisting of independent variables of colorant and dependent variables of device independent color coordinates (stored in the calibration data file of the VP) by the method of least squares. A polynomial is a linear combination of each of its terms which are called, mathematically, basis functions at step 82. Without loss of generality, discussion can be simplified by considering functions of two variables, C and M, in which each variable may be raised to a power of up to 2 and the sum of powers may not exceed 4:

$$R=a_{00}+a_{10}C+a_{20}C^2+a_{01}M+a_{11}CM+a_{21}C^2M+a_{02}M^2+a_{12}CM^2+a_{22}C^2M^2$$

$$G=b_{00}+b_{10}C+b_{20}C^2+b_{01}M+b_{11}CM+b_{21}C^2M+b_{02}M^2+b_{12}CM^2+b_{22}C^2M^2$$

$$B=c_{00}+c_{10}c+c_{20}C^2c_{01}M+c_{11}CM+c_{21}C^2M+c_{02}M^2+C_{12}CM^2+c_{22}C^2M^2$$

In the foregoing, color is the vector valued function |RGB| of the variables C and M and the a's, b's and c's are constant coefficients which give the proportions of their corresponding terms to be mixed in forming the linear combination. The purpose of the fitting procedure is to find the set of coefficients which results in the least squared error when comparing the color measured at a given patch with the color calculated by substituting the patch's colorant values into the forward model. The polynomials are untruncated within the constraints on the powers. The DV may also be L*, a*, b* coordinates of CIELAB uniform color space.

Figure 8:
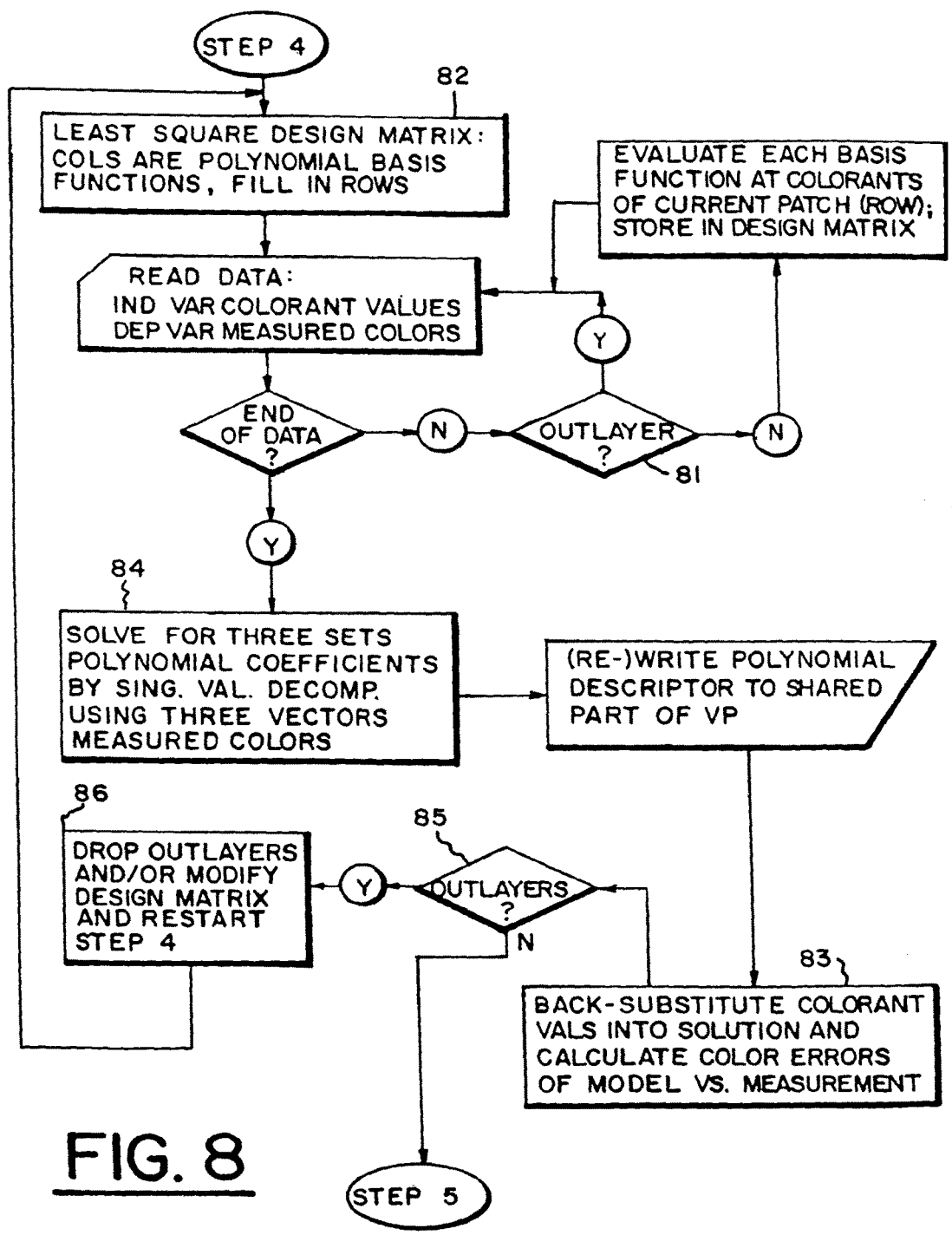
FIG. 8 is a flow chart detailing step 4 in FIG. 5, building a forward model based on the calibration data from step 3 of FIG. 5.

In FIG. 8, the process of building a forward model begins by building a design matrix for the problem (step 82). The design matrix has M columns, one for each basis function, and N rows, one for each patch measurement. The number of rows should exceed the number of columns; practically, the ratio of N to M should be greater than 3 for good results. After reading the cal. data file, each cell in the matrix is filled with the value of the basis function for the column at independent variables (inks) given by the row, divided by the standard deviation of the patch measurements, if available, else by 1 (step 83). Note that the patch measurements themselves do not enter the design matrix. Then use the design matrix and vectors of patch measurements for each of the three, color, dependent variable dimensions to write matrix equations that can be solved for the desired coefficient vectors preferably by Singular Value Decomposition, SVD (step 84).

The numerical methods outlined in the preceding and the following paragraphs are similar to those described by Press, et al. (*Numerical Recipes*, Cambridge University Press, Cambridge, UK, 1986.) Sections 14.3, "General Linear Least Squares," with SVD fitting, and 5.3, "Polynomials and Rational Functions".

The model and its derivatives can be evaluated efficiently by a method of recursive factorization. The method depends on use of polynomial terms as basis functions. However, it permits evaluation of the function with no more than 1 multiplication and 1 addition per polynomial term. Because the independent variables never need to be raised to a power, the demands for precision on the computational machinery are not as great. The principle can be seen most readily in one dimension; the function $y=a_0+a_1x+a_2x^2$ can be factored to yield $a_0+x(a_1+a_2x)$ which evaluates with 2 multiplies and 2 adds. Generalizing this to the two-dimensional function described above:

$$a_{00}+a_{10}C+a_{20}C^2+M(a_{01}+a_{11}C+a_{21}C^2)+M^2(a_{02}+a_{12}C+a_{22}C^2), \text{ or}$$

$$a_{00}+C(a_{10}+a_{20}C)+M[(a_{01}+C(a_{11}+a_{21}C))+(a_{02}+C(a_{12}+a_{22}C))M].$$

How to generalize to three or four dimensions is apparent.

At step 81, the patches that were flagged during measurement as outlyers are excluded from the fitting. The fitting program estimates the variation in the device based on deviations of color in redundant patches and/or measurements of multiple copies. The average error of fit is calculated as the average $\Delta E^*$ (CIE Color Difference Unit) over the set of measurements of patch colors compared to the colors predicted by the fitted polynomial (step 83). This average should not exceed the estimated device variation by more than 1 $\Delta E^*$ unit. When it does, or when the software detects individual patch discrepancies exceeding 4 or 5 $\Delta E$ units, the software flags apparently outlying points (step 85). It then computes trial fittings with outlyers omitted to see if average error can be improved (step 86). It also is informed with a strategy for applying various sets of basis functions in the interest of achieving an acceptable fit. However, the fitting procedure will reject a dataset at step 86 rather than get too involved with it.

Principal Component Analysis, or an equivalent method, may be employed to reduce the number of polynomial terms (complexity of the model) consistent with a given average error criterion. This technique is similar to those described in Johnson and Wichern, Applied Multivariate Statistical Analysis, 3rd ed., Englewood Cliffs, N.J.: Prentice Hall, 1992, ch. 8.

Fitting concludes with writing a final polynomial model descriptor (a data structure and a file) consisting of a header and lists of coefficients. The header includes information such as the identity(ies) of proofs measured, relevant dates and times, the ingredient data files, the form of the polynomial (maximum powers of the independent variables and maximum order of a term) goodness of fit statistics. The polynomial descriptor will be needed later by the polynomial evaluator of the software and is written into the shared portion of the Virtual Proof.

Although this discussion is directed to a 4-colorant printer or press, the polynomial forward model is, potentially, part of a soft proofing transform which enables a video display to represent a client printer. It can be used to compute a colorant$_A$ to colorant$_B$ transformation for what is effectively a CMYK, subtractive-color video display, in that CMYK colorant values are processed through a transformation to produce device-specific RGB for a monitor. This can generalize to use of more-than-four-colorant-printers and more-than-three-colorant displays.

After the polynomial model descriptors are computed, a forward model table (FMT) and prototype gamut descriptor data are prepared (step 5 of FIG. 5). The processes of step 5 are detailed in the flow chart shown in FIG. 9A. As described above, the polynomial based on the model descriptors represents the forward model. The forward model enables us to predict the colors resulting when certain colorant mixtures are asked for on the printer or press. System 100 includes a polynomial evaluator to evaluate this polynomial either in hardware circuitry or software at the node. Referring to FIG. 9B, a topology of operators is shown (multipliers 86 and adders 87) to implement the polynomial evaluator for the two-colorant case, cyan (c) and magenta (m). Each operator receives two inputs. Inputs (operands) designated by two numerals are the constant coefficients and inputs designated by C 89 or M 90 stand for the independent variables, amounts of colorant. For instance, 21 88 denotes the coefficient which corresponds to the second power of C times M. In order to evaluate a function of three variables, 3 of the units shown in FIG. 9B are needed. Four variables require 27 such units for an untruncated polynomial. In a hardware realization of the evaluator, it is preferable to retain the generality of the polynomial form and zero poly terms (or their coefficients) that are missing due to truncation. If 27 units are too many for a cost-effective device, then the calculation may be staged and the successive stages pipelined through a subset of the 27 units, albeit at some cost in control logic and speed. Given the opportunities for parallelism in a hardware implementation, the preferred embodiment benefits by a chip to transform ink values to colors at video rates. Such a chip may be a component of nodal circuitry encompassing a graphics accelerator to drive a video display device for soft proofing at the node. It accelerates the generation of color separation transformations because evaluation of the colorant to color model is a major factor in that computation. It also accelerates the evaluation of color separation transformations in situations where the data of the inverse, color-to-colorant conversion can be fitted by polynomials with a sufficiently small average error of fit. Data for fitting can be the addresses and entries of an interpolation table of sufficient size, as discussed below.

Figure 9A:
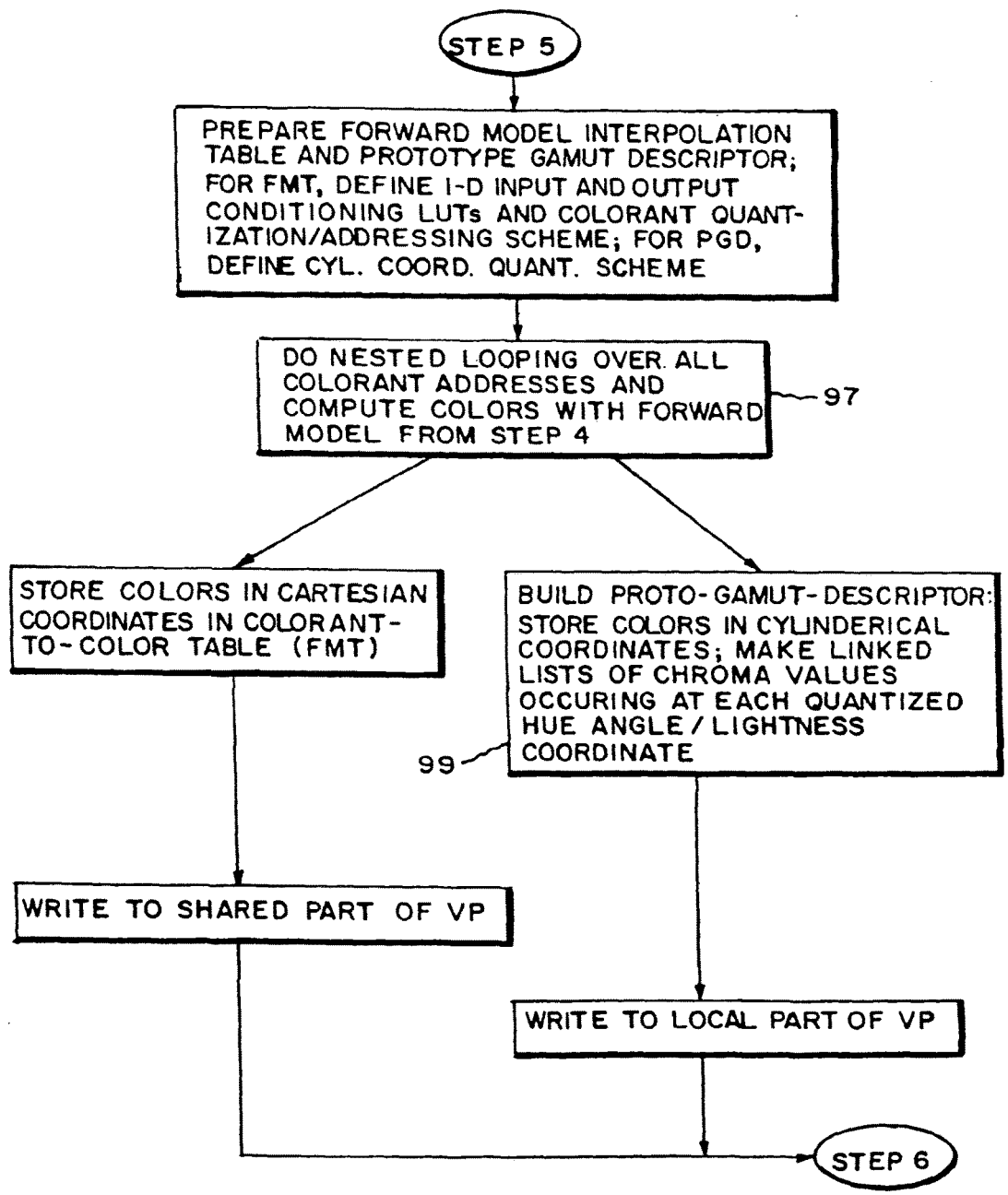
FIG. 9A is a flow chart detailing step 5 in FIG. 5, preparing gamut descriptor data for the rendering device and preparing a forward model table based on the forward model from step 4 in FIG. 5.
Figure 9B:
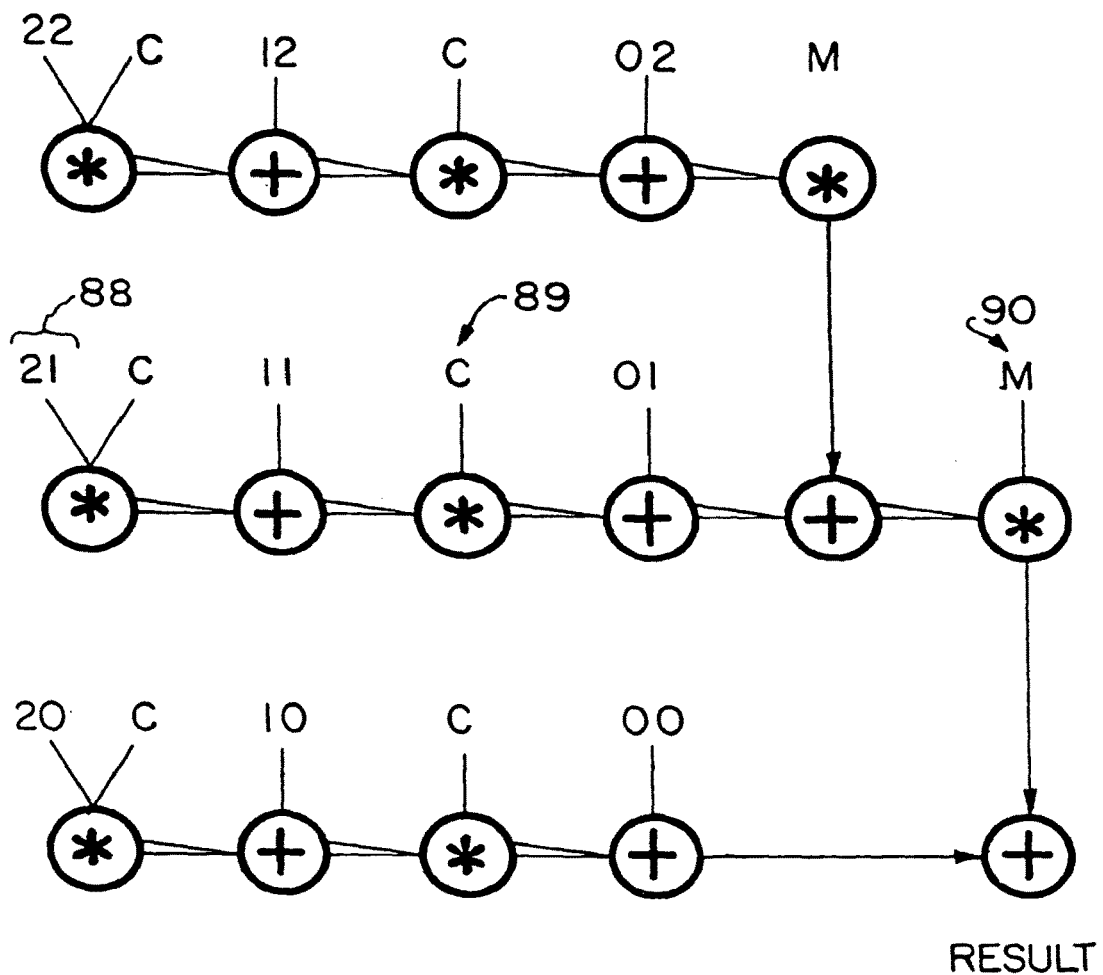
FIG. 9B is an illustration of the operators and operands evaluating the polynomial function of the forward model in the case of two independent (colorant) variables, C and M.
Figure 9C:
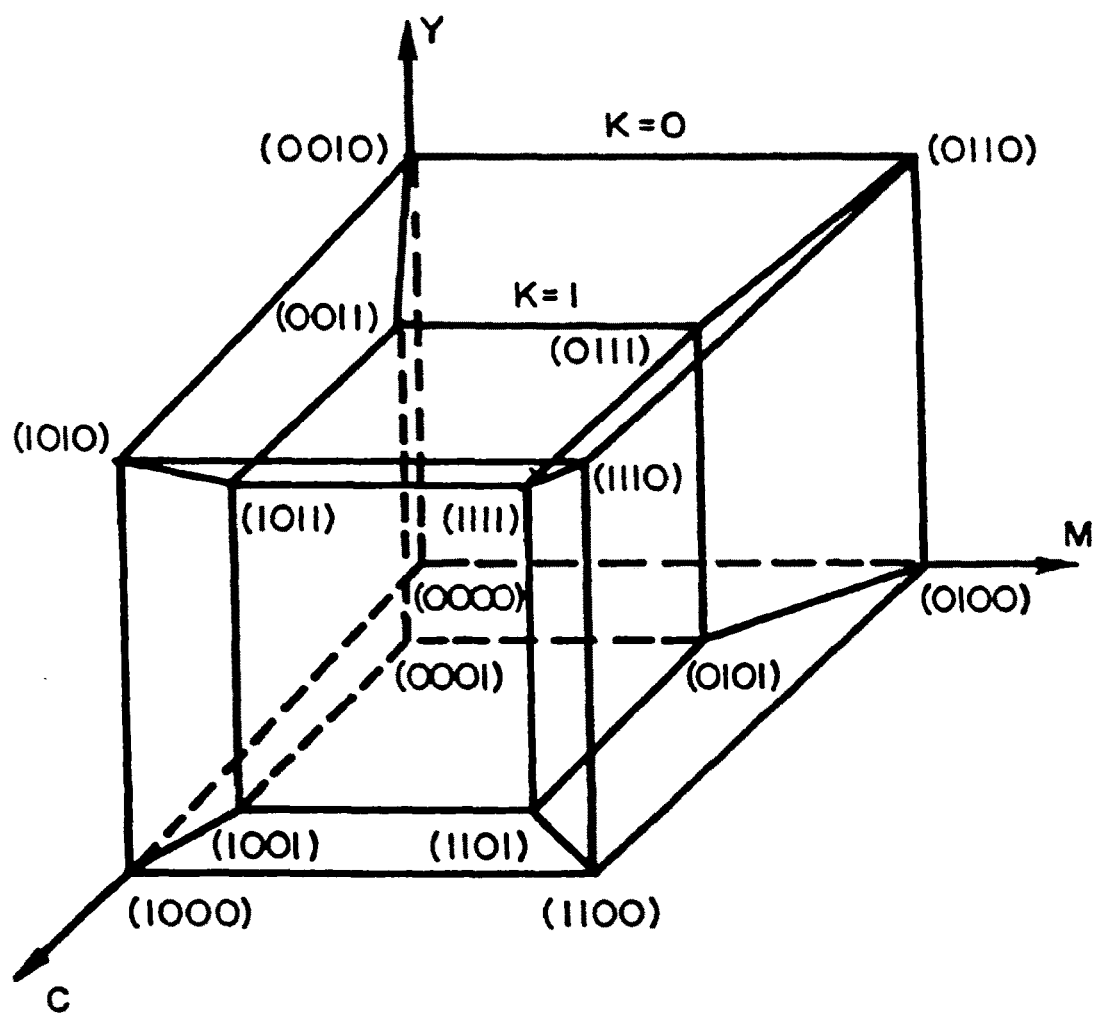
FIG. 9C depicts a hypercube in the coordinates of the Cyan, Magenta, Yellow and Black colorants in which all colors producible with a CMYK printer are contained within the hypercube.

The FMT stores the results of the polynomial evaluator in a data structure and colorant quantization/addressing scheme shown in the CMYK hypercube of FIG. 9C, which contains the entire gamut of colors reproducible by a CMYK printer. The hypercube may be subdivided into a FMT having 17 points (16 intervals) per colorant dimension for sufficient accuracy. However, the software architecture supports more or less, within the constraint that the numbers of grid points per dimension satisfy the equation $2^n+1$, where n is integer. Depending on the requirements of the rendering applications and equipment, a software switch controls whether the tables are written in pixel interleaved (each address of a single table holds the values of all dependent variables) or frame interleaved format. In the latter case, three M-dimensional tables are prepared, where M is the number of colorants. Each "cell" of a table has an M-dimensional address and contains a color coordinate computed by evaluation of the forward model at step 97 of FIG. 9A. At step 97 nested looping over all colorant addresses is performed and computed colors from the forward model are stored at each address. Thus, each model evaluation yields three color coordinates each of which is deposited in a cell corresponding to the M colorants which produce it in the appropriate table. Colors of inkings in the midst of a hypercuboid are estimated by interpolation.

Figure 9D:
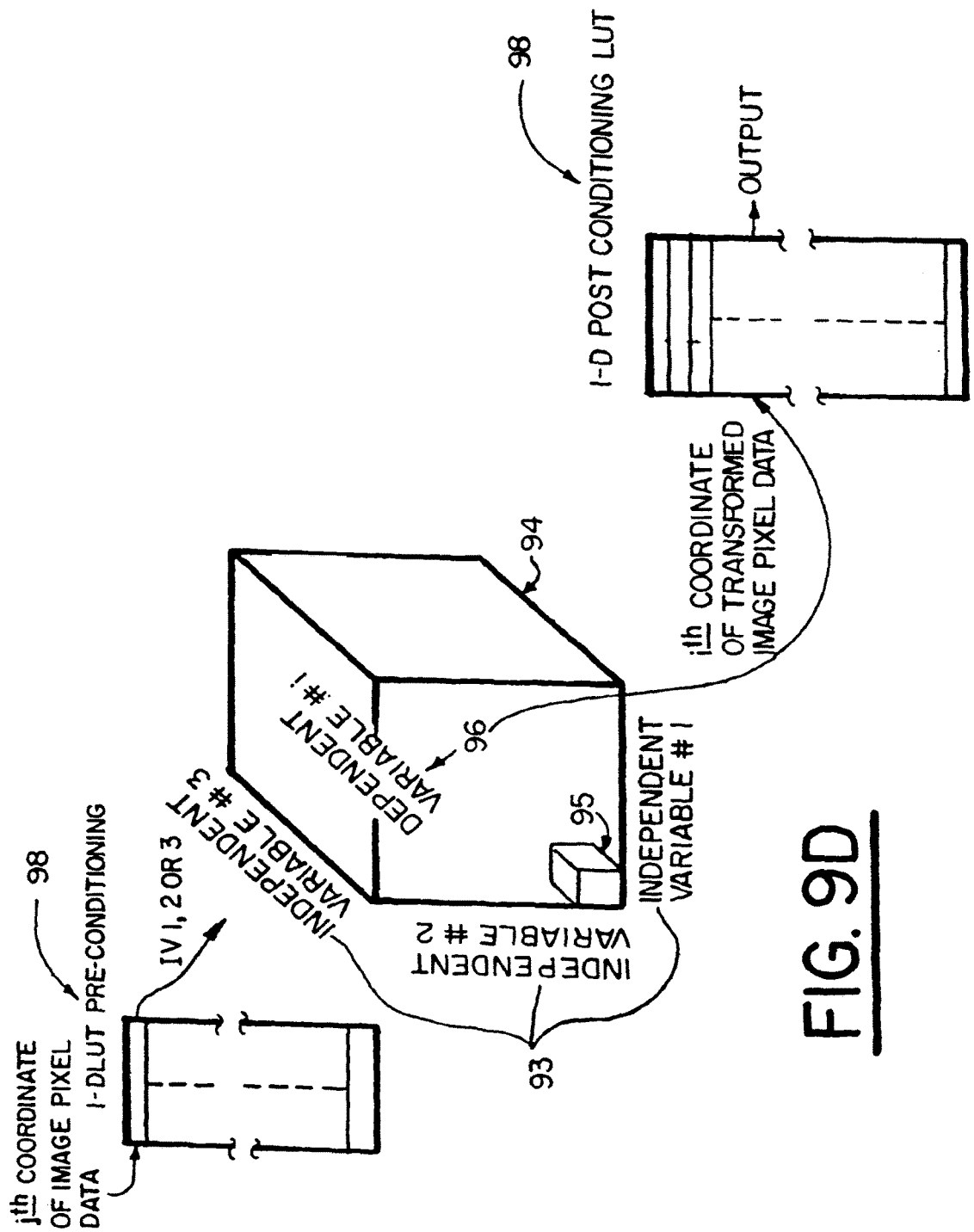
FIG. 9D is an illustration of a data structure for interpolation in 3 dimensions which may use either pre- or post-conditioning look-up tables.

Referring now to FIG. 9D, each of the M channels of input to the FMT may be provided with preconditioning LUT for each of the Independent Variables and each output channel may be processed through a 1-dimensional post-conditioning LUT. Interpolation is preferably performed by linear interpolation in the nodal circuitry or software.

The data structure in FIG. 9D accommodates the preconditioning of j address variables by j 1-dimensional transformations which may be implemented as look-up tables with or without interpolation 98. The preconditioning transformation may pass one or more of the j inputs Independent Variables (IVs) through to the multidimensional transform unaltered (identity transformation) or may apply a functional mapping such as a logarithmic conversion. The multidimensional transform 94 has j input variables and i outputs. The preferred implementation of the transformation is by interpolation in a sparse table of function values or by evaluation, in hardware, of a set of polynomials fitted to the tabular values (where fitting can be done with sufficient accuracy.) In FIG. 9D, a 3-dimensional IV 93 is applied to the multi-dimensional transform 94. Multidimensional transform 94 consists of many smaller cuboids 95 whose corner points are the sparsely sampled values of the N at which values of one (or more) of the dimensions of the dependent variable, DV, 96 are stored. The IV provides addresses and the DV contents. The subcuboid 95 is shown at the origin of the addressing scheme. Interpolation is used to estimate values of the DV occurring at value of the N which are between corner points.

The data structure of FIG. 9D also accommodates the post-conditioning of the i output variables (DVs) of the transformation by i 1-dimensional transformations which may be implemented as look-up tables with or without interpolation 98. One of the transforming functions which may be included in the post-conditioning is the linearization function optionally produced by step 1 of FIG. 5.

The purposes of the 1-dimensional pre- and post-conditioning functions include improving the extent to which the relationship between variables input to and output from the multidimensional transformation 94 is approximated by whatever interpolation function is employed in evaluating the transformation. Therefore, the form of the functions should be known from preliminary studies of the device and the pre- and post-conditioning transforms must be in place during calculations of Steps 2 through 9 if they are to be used at all. For example, a linearization function which may be defined in step 1 should be used in rendering the calibration target in step 2.

Figure 9E:
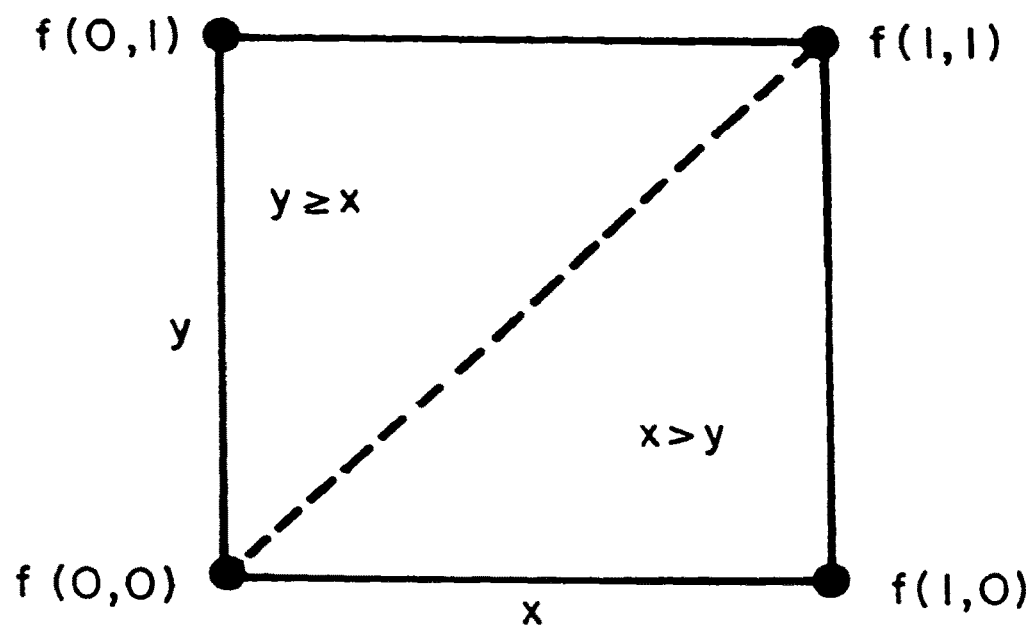
FIG. 9E is a graphical illustration of linear interpolator in two dimensions.

A linear interpolation formula for two dimensions which generalizes to higher dimensions with a simple, proportional scaling in the number of operations is described in Gallagher, "Finite element analysis: Fundamentals," Englewood Cliffs, N.J., Prentice Hall, pp. 229-240, 1975. For example, given a cell in a two-dimensional array of sparsely sampled points as shown in FIG. 9E, the interpolated value of a function f(x,y) at a point (x,y) interior to the cell may be calculated as the weighted average of the endpoints in the direction of the longer of the components x or y plus the weighted average of the endpoints in the direction of the second longest component. In other words, order the distances of the point with respect to the axes of the cell and then sum the fractional distances along those ordered dimensions. Written as an equation:

for $y<x, f(x,y)=f(0,0)+x*(f(1,0)-f(0,0))+y*(f(1,1)-f(1,0))$, and for $x>=y, f(x,y)=f(0,0)+y*(f(0,1)-f(0,0))+x*(f(1,1)-f(0,1))$.

FIG. 9A also flowcharts the preparation of the prototype gamut descriptor (GD) data. As colorant addresses are converted into colors to populate the FMT (step 97), the colors are also converted into cylindrical coordinates of CIE hue angle, chroma and lightness. Hue angle and lightness are quantized to become addresses into a 2-D gamut descriptor, preferably dimensioned at least 128×128 for adequate resolution (step 99). The Chroma component of the color is not quantized, but is stored in linked lists of Chroma values associated with each hue angle, lightness coordinate. The finished gamut descriptor data is prepared from the prototype GD data later at step 7 of FIG. 5, and consists only of surface chroma values for each coordinate. Therefore, the prototype is not a shared file and is written to the local portion of the VP, while the FMT is written to the shareable portion.

Next, at step 6 of FIG. 5, the FMT is inverted into a prototype transformation table, also called Proto SEP table. Rendering image at a rendering device requires this inversion step, i.e., finding the colorant mixtures to realize a desired color which may be given in device independent coordinates or in the color coordinate system of some other device (such as the CMYK monitor mentioned above.) Due to the complexity of the problem, it is generally not feasible to perform forward model inversion in real time as imagery is rendered. Practical approaches rely on interpolation in a sparse matrix of inverse function values. However, offering interactive control over key aspects of the separation transformation (also called SEP) implies that at least some parts of the calculation occur nearly in real time. Because inversion of the forward model involves evaluating it, potentially numerous times, acceptable performance requires a very rapid means of evaluating the forward model. One method involves design of specialized hardware for polynomial evaluation. When specialized hardware is unavailable, software performance can be significantly enhanced via the same strategy as used for speeding rendering transformations: interpolate in a sparse table of forward model values, in particular in the FMT.

The proto SEP represents a color to colorant transformation with color coordinates as inputs and inkings as outputs. For illustration purposes, we will consider the case in which color coordinates are expressed in CIELAB units, L*, a* and b*. In order to build a sparse table of inverse function values for the proto SEP, the following addressing scheme is defined. If address variables, or inputs, are represented at 8-bit resolution, the span of the table in each dimension is 0-255 ($2^8$) digital levels. Continuous perceptual dimensions are mapped onto those levels so as to satisfy two criteria: a) the entirety of the input and output gamuts of interest must be represented, and b) adjacent digital levels are not perceptually distinguishable. Input and output gamuts will be detailed later; briefly, an input gamut is that of a device or application which supplies images (in this case for separation) and an output gamut is that of a device or application which receives the image—in this case for rendering. With the above addressing scheme, a prototype separation table is computed. The following outlines the general process for building the proto SEP table.

For each grid point, or address, of the table, the amounts of the colorants needed to produce the input color are found. There are N tables, one for each of N colorants, assuming frame interleaved formatting. First, a starting point of the correct inking is speculated. Calculate its color by the forward model and compare the calculated color to the desired, address color. Save the color error, modify the inking, recalculate the color and see if the error is reduced. The forward model is also employed to calculate the partial derivatives of color with respect to ink. The resulting matrix, shown in the equation below, yields the direction of the movement in color occasioned by the change in colorants. The partials of color error with respect to each of the colorants indicate whether movement is in the correct direction. If negative, this indicates movement in the correct direction along that ink zero; then store each of the inkings in their respective tables.

$$\begin{matrix} da^* \\ db^* \\ dL^* \end{matrix} = \begin{matrix} |\delta a^*/\delta C, \delta a^*/\delta M, \delta a^*/\delta Y, \delta a^*/\delta K| \\ |\delta b^*/\delta C, \delta b^*/\delta M, \delta b^*/\delta Y, \delta b^*/\delta K| \\ |\delta L^*/\delta C, \delta L^*/\delta M, \delta L^*/\delta Y, \delta L^*/\delta K| \end{matrix} \cdot \begin{matrix} dC \\ dM \\ dY \\ dK \end{matrix}$$

The foregoing paragraph gives a simplified explanation of the algorithm embodied in procedures which use Newton's Method for finding roots ("Newton-Raphson") or one of many optimization methods for searching out "best" solutions in linear (e.g., the Simplex method of linear programming) or non-linear multidimensional spaces. The algorithm can also be implemented with neural networks, fuzzy logic or with the aid of content addressable memory. A neural network can be trained on the results of repeated evaluations of a mathematical model. Further, neural networks may also be utilized to perform any of the color transformations of FIG. 5, e.g., building the forward model or rendering transform table. Color transformation with neural networks is described, for example, in U.S. Pat. No. 5,200,816. Newton's method is applied to find the root of an error function, i.e., the solution is at the point at which the derivative of the error function goes to zero. Strictly, Newton's method is only applicable in situations where a solution is known to exist. Therefore, although it is an efficient procedure, it is supplemented by other optimization methods, such as "Simulated Annealing." (The model inversion technique described above is similar to those in Press, et al. sections 9.6, 10.8 and 10.9, respectively, already cited.)

Optimization methods can produce a useful result when no exact solution exists, as in the case when the desired color is unprintable by (or out of the gamut of) the device. The optimization is driven by an error function which is minimized, typically by using downhill, or gradient search procedures. In the case of Newton's Method, one of the colorant variables (in the four colorant case) must be fixed in order to find an exact solution; otherwise, there are infinitely many solutions. Usually, black is fixed. The algorithm for model inversion uses supporting search procedures in case the primary technique fails to converge to a solution.

Figure 10A:
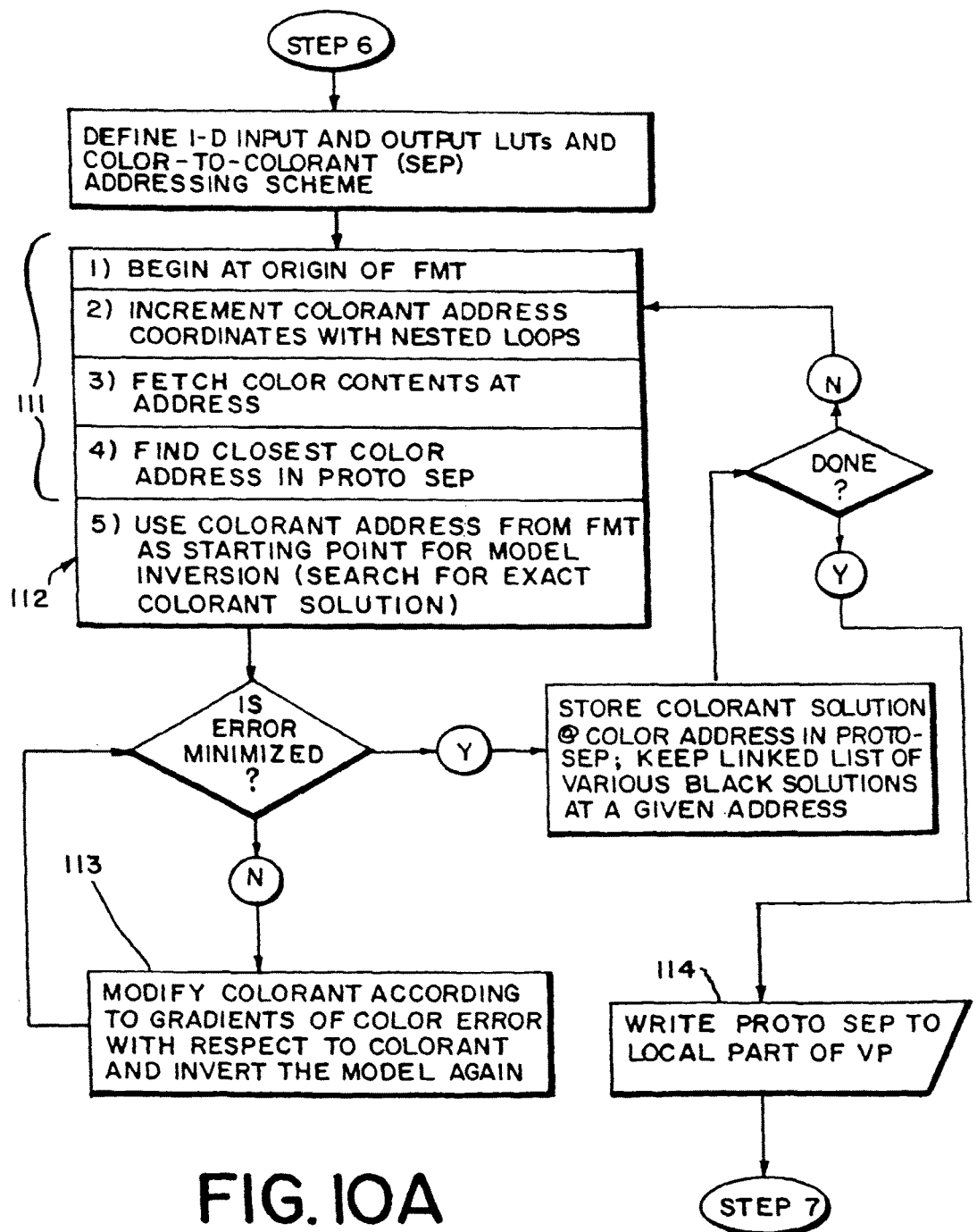
FIG. 10A is a flow chart detailing step 6 in FIG. 5, inverting the forward model table to provide a prototype transformation table.
Figure 10B:
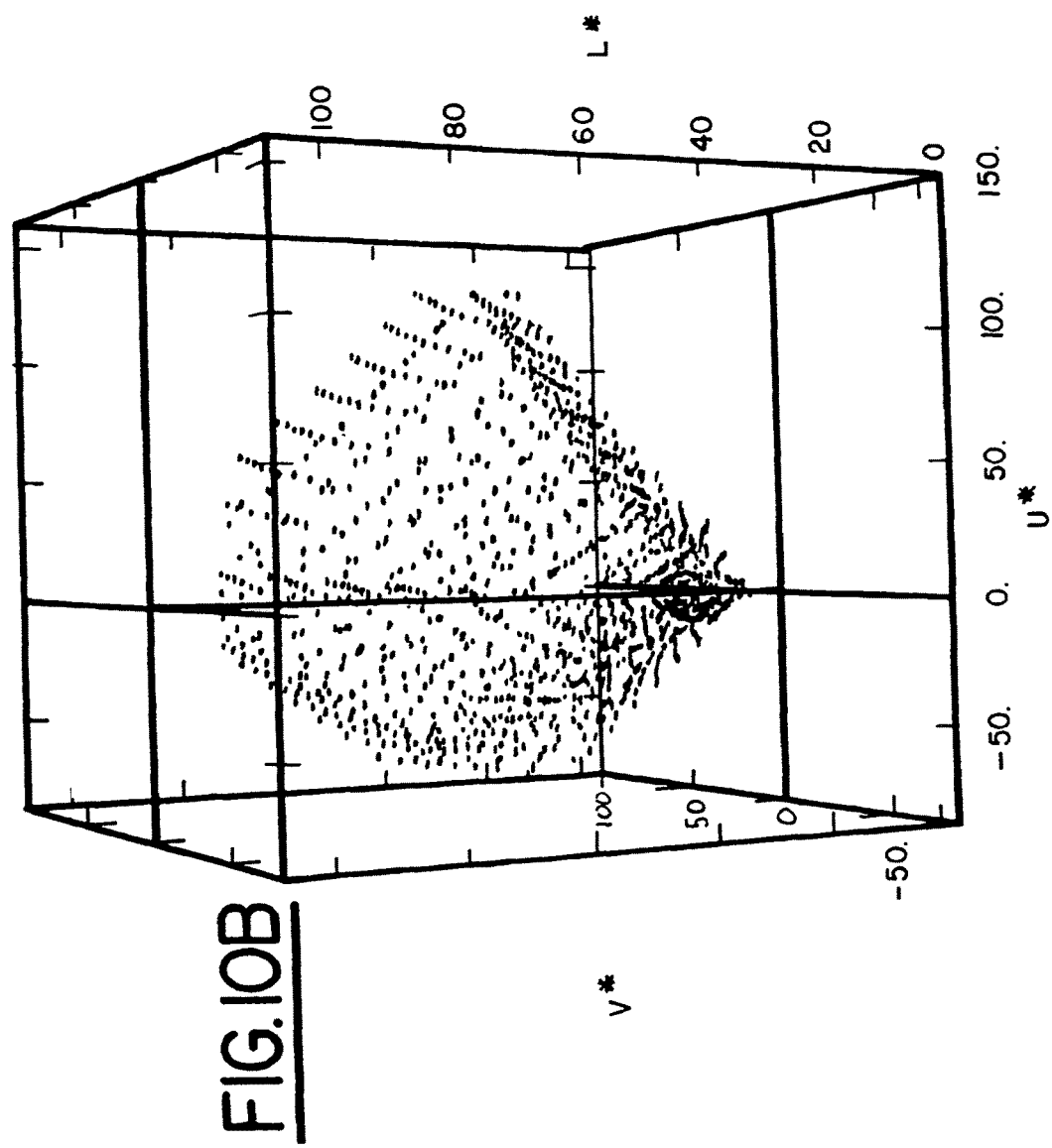
FIG. 10B is an example of the hypercube of FIG. 9C where the colorant values are transformed into device independent color coordinates.

The foregoing, simplified account overlooks the possibility that the gradient surface on the way to the solution has local minima in it which thwart the search procedure. This risk is minimized by the present inventors' technique of using the FMT to provide starting points which are very close to the solution. The above process for building the proto SEP Table is applied in system 100 as shown in the flow chart of step 6 in FIG. 10A. For each color entry in the FMT, find the closest color address in the prototype separation table (step 111). Then use the colorant address of the forward model table as the starting point in a search for a more exact ink solution at that color address of the proto SEP (step 112). The search and the addressing of the interpolation table can be in the cylindrical coordinates of hue, chroma and lightness or in the Cartesian coordinates L*, a* and b*. In the preferred embodiment, the forward model table has at most 17×17×17 84K grid points and the prototype separation table has at most 33×33×33~=35K grid points many of which will not be within the gamut of the printer and some of which may not be physically realizable, i.e., within human perceptual gamut. (This is the case because the gamut of a set of colorants is not likely to have a cuboidal shape suitable for representation in computer memory when it is converted from device coordinates to the coordinates of the color addressing scheme, as illustrated in FIG. 10B.) Therefore, there is a favorable ratio of starting points to solutions.

An important advantage of keying off the FMT is that most searches are guaranteed to be for printable colors. For colors near the gamut surface, Newton Raphson may fail because there is not an exact solution such that an optimization procedure is required. The search routine may use either the interpolative approximation to the polynomial (the FMT) for speed in a software-bound system or the full-blown polynomial for greater precision. In either case, the derivatives are easily calculable and the iterative searching procedures driven by gradients of color error (step 113).

The result of step 6 is a prototype color to colorant transformation (proto SEP) table in which virtually all printable addresses contain one or more solutions. Because of the favorable ratio of starting points to required solutions, many addresses will have solutions based on differing amounts of the neutral (black) colorant. The multiple black solutions are very useful in preparing to perform Gray Component Replacement and are stored in linked lists at the appropriate addresses of the proto SEP, which is stored in the local portion of the VP (step 114). At this stage there are two ingredients of a final rendering transformation in need of refinement: the prototype gamut descriptor and the proto SEP.

An example of the results of step 6 is shown in FIG. 10B, in which coordinates which are plotted within a cuboidal structure suitable for representing the perceptually uniform color space coordinates. Addresses having data are shown by black crosses. If the cube were subdivided into numerous cuboids so as to create an interpolation table, as described in FIG. 9D, it is clear that many of the cuboids would not correspond to colors that are realizable on the device. The coordinates of the perceptually uniform space are L*, u* and v* from the CIE's CIELUV color space in the example.

Figure 11:
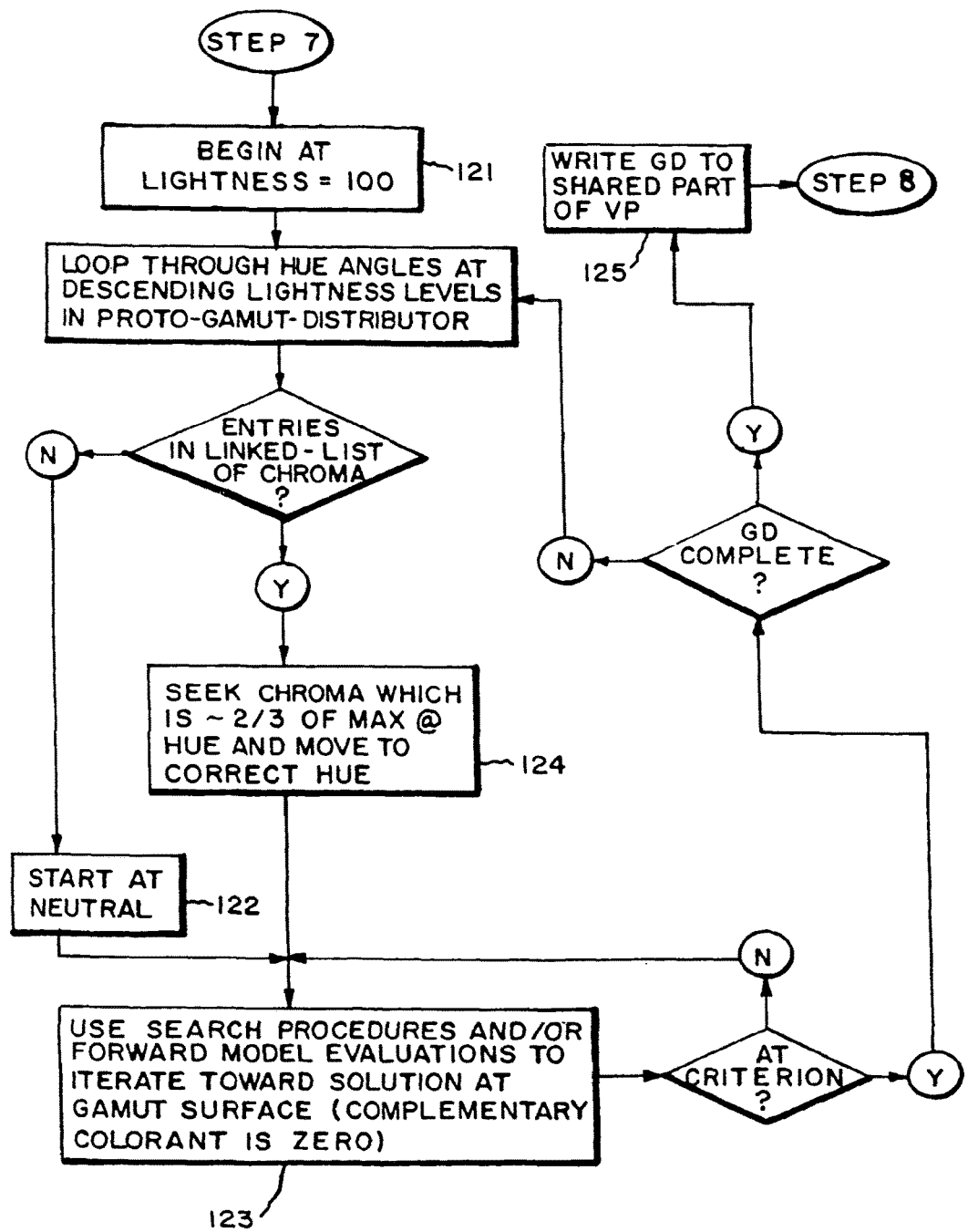
FIG. 11 is a flow chart detailing step 7 of FIG. 5, finishing the gamut descriptor data.

After step 6, the prototype GD data of step 5 is refined into finished GD data at step 7 of FIG. 5. Step 7 processes are shown in the flow chart of FIG. 11. System 100 needs a favorable ratio of FMT entries to proto GD addresses; therefore, most of the addresses get one or more solutions. Relatively few of these are surface Chroma points. The objective of step 7 is to use proto GD data as starting points for an iterative motion toward the gamut boundary using search and model inversion techniques described previously. Gamut surfaces often manifest cusps, points and concave outward surfaces. Therefore, quantization of the descriptor must be at fairly high resolution (128×128 or more is preferred) and initiation of searches for a surface point from other surface points of different hue angle is often unfruitful. Because it is known what colorant mix (i.e., little or no colorant) is appropriate at the highlight white point of the gamut, it is best to begin refinement there, using solutions at higher luminances as aids at lower luminances (step 121).

At least one of the colorants must be zero at the gamut surface. Therefore, the strategy is to start near the desired hue angle from well within the gamut, move onto the desired hue angle and then drive outward until one of the non-neutral colorants goes to zero (step 123). It is often possible to zero the colorant that is expected to go to zero to hasten search procedures (such as Newton Raphson) which require constrained iterations. Starting points are usually available from a linked list stored in the proto GD; that failing, one may be had from a neighboring hue angle, lightness cell, or, that failing, by setting out from neutral in the desired hue direction (step 122). If polynomial evaluation hardware is available, it can accelerate on-the-fly calculation of surface points by forward model evaluation. Given a hue angle and lightness, the device coordinates bounding a small patch of the gamut surface are identified and colorant mixtures within the patch processed through the forward model until the maximum chroma at the hue/lightness coordinate is produced (step 124). In situations where it is necessary to fall back to methods involving model inversion, the hardware assist continues to be valuable because searching involves numerous evaluations of the polynomial and its derivatives, which are also polynomials. Once a refined gamut descriptor has been completed, it is written to the shareable portion of the VP (step 125).

Figure 12:
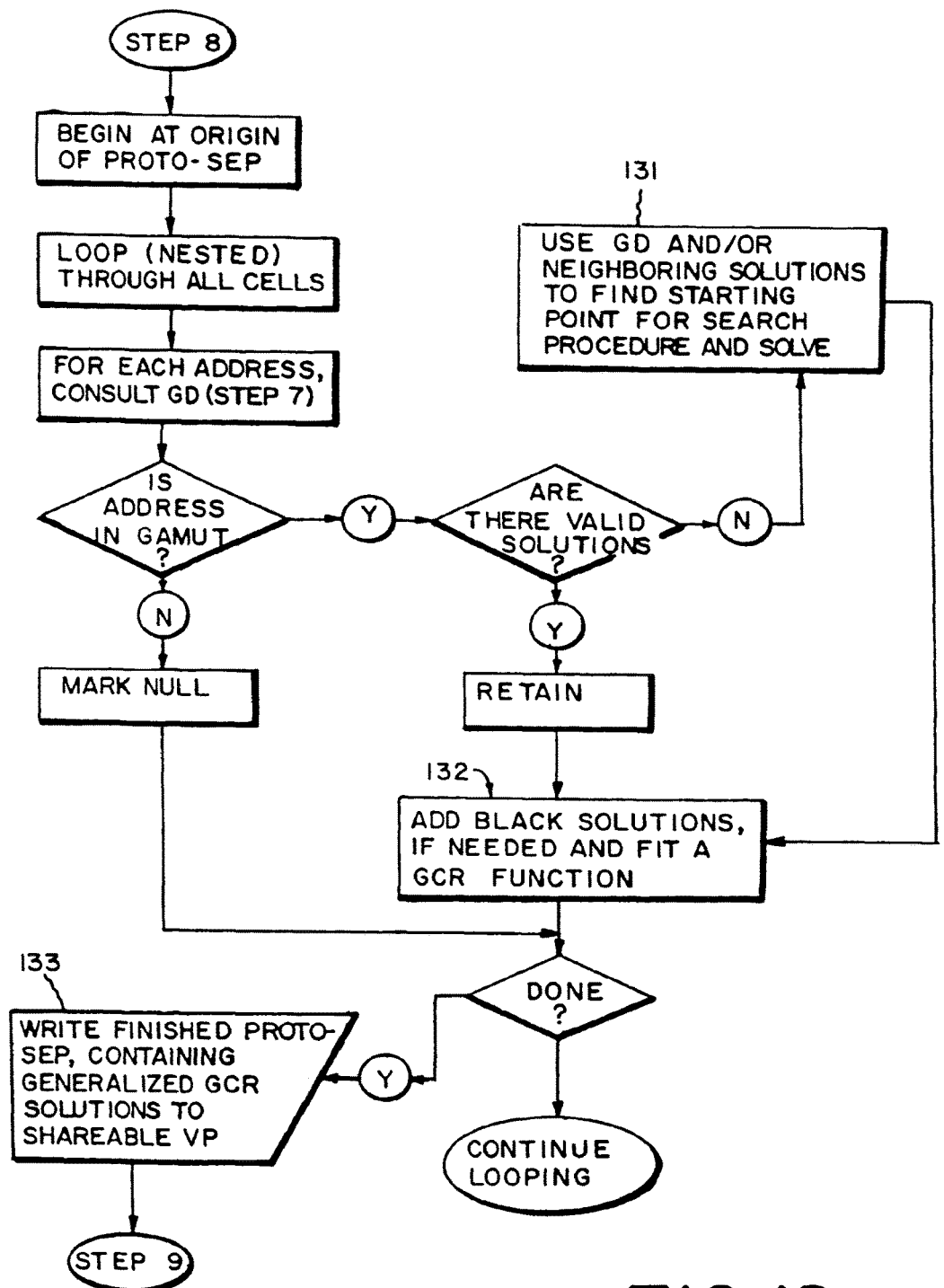
FIG. 12 is a flow chart detailing step 8 of FIG. 5, filling in any missing entries of prototype transformation table, computing black utilization (GCR) functions for all colors of the table having multiple black solutions and marking unprintable colors NULL.

Referring to FIG. 12, a flow chart of the processes in Step 8 of FIG. 5 is shown, filling in any holes which may exist in the Prototype Transformation and computing functions that summarize the trade-off (Gray Component Replacement, GCR) between neutral and non-neutral colorants at each color address. A "hole" is a color address which is printable but for which no inking solution has yet been found. The resulting proto SEP table is called a generalized color-to-colorant table because it does not provide solutions for a specific amount of black. Step 8 has two goals. First, it seeks solutions for any colors interior to the gamut which have none (step 131) and writes NULL into all unprintable addresses. The mapping of unprintable colors to within gamut occurs later in step 9 in response to gamut configuration data, which the user may select using the GUI screen of FIG. 21F, which is described later. Second, it stores at each address the means to exchange neutral for non-neutral colorants (Gray Component Replacement.) The preferred process is to store several solutions which can be interpolated amongst using LaGrangian, Spline or generic polynomial interpolating functions (step 132). The exact specification of black utilization is incorporated later in step 9, which also may be selected by the user via the GUI screen of FIG. 21E, which is also described later. The finished prototype color to colorant (proto-SEP) transformation table is written to the shareable portion of the VP (step 133).

Step 9 of FIG. 5 includes the following processes:
1) Converting colorants of the proto-SEP transformation table based on black utilization information specified in the black color data;
2) Building Color to Color' Transform Table based on gamut configuration data, e.g., gamut scaling, neutral definition or gamut filter(s); and
3) Combining Color to Color' Transform Table with a transformation table containing specific GCR solutions to provide a rendering table.

The black color data and gamut configuration data may be set to defaults or selected by the user as color preferences, as described in more detail later.

Figure 13:
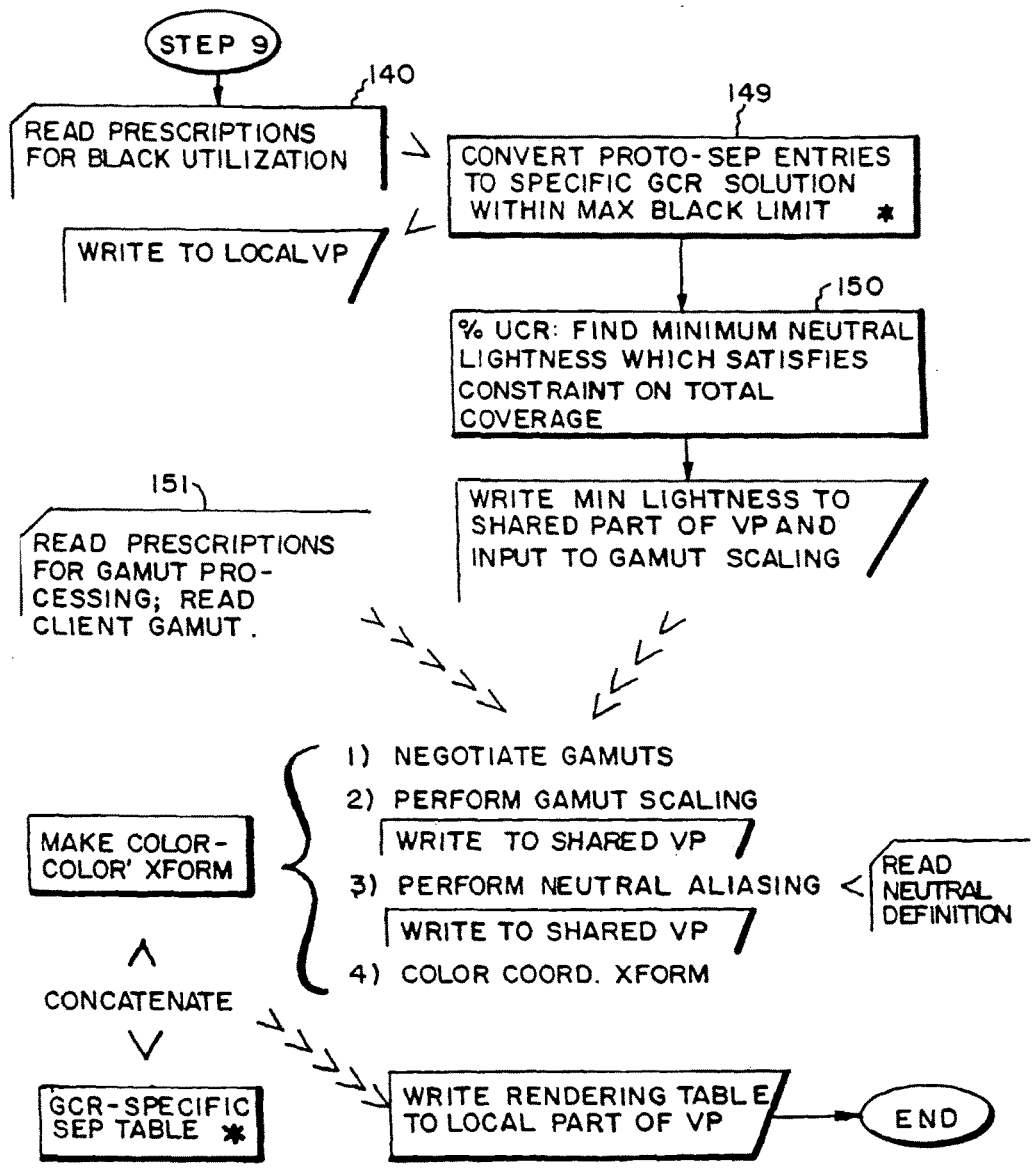
FIG. 13 is a flow chart detailing step 9 of FIG. 5 which includes: converting colorants of prototype transformation table based on black color data; building color to color' transform table based on gamut configuration data; and combining the color to color' transformation table and the converted prototype transformation table to provide a rendering table.

Referring to FIG. 13, the processes of step 9 are flow charted. Although step 9 is operative of four-colorant rendering devices, more-than-four colorant devices may also be provided with a rendering table as will be explained in discussion of FIGS. 16A and 16B. First, the finished proto SEP table (generalized color-to-colorant) and the black utilization data are read (step 140). The latter include Gray Component Replacement, % Under Color Removal (% UCR or UCR, a term referring to a limitation on total colorant application or Total Area Coverage, TAC) and possible constraints on the maximum amount of black or neutral colorant to be used; all three together are referred to herein as "black utilization."

The prescriptions for black utilization come from one or more of the following sources: a) local or system-wide defaults, b) broadcast of custom functions and limit values from a "boss node" configured in network 11 and c) values defined through a user interface which may be applied locally or transmitted and shared. Note that modifications of black utilization do not have colorimetric effects. For example, compensating increases in neutral colorant by decreases in non-neutral colorants in GCR does not change the color noticeably. Fields in the VP control selection of the source of prescriptions for black utilization under particular rendering circumstances. A user may select the black utilization in the Graphic User Interface of the model software, which is described later in connection with FIG. 21E. The black utilization data, which includes % UCR, maximum black, and the GCR function or black solution, are stored in the shared part of the VP.

The first step in preparing a rendering transformation, then, is to convert the data on GCR stored at each printable address into a particular black solution by referring to the curve giving % GCR as a function of density while observing the maximum black constraint (step 149). Thus, the entries in the proto-SEP transformation table are converted based on a specific GCR solution within a maximum black limit. The converted proto-SEP table is stored in the local part of the VP. The second step is to find the maximum neutral density at which the total area coverage limitation is satisfied, i.e., % UCR (step 150). This is done by moving up the neutral, or CIE Lightness, axis through the quantization scheme from the minimum printable Lightness, examining colorant solutions, until one is found that is within the limit. The minimum Lightness so identified is stored for use in the gamut scaling process to be discussed presently. Although it is conceivable to store min Lightness values as a function of color, rather than simply as a function of Lightness, for purposes of gamut scaling, this is usually an unwarranted complexity.

In order to convert the GCR-specific result of the foregoing methodology into a rendering transformation, it must be "married" with a "conditioning" transformation. The latter is a color-to-color' conversion expressible as an interpolation table of the format presented earlier. (Note that any transformation that is evaluated by interpolation and that can be fitted with acceptable color accuracy by a polynomial may be performed by suitable hardware for polynomial evaluation.) It serves the multiple purposes of scaling unprintable colors of the addressing scheme onto printable values, "aliasing" the color definition of neutral to accommodate user requirements (FIG. 21E, 270) and effecting conversions among color addressing variables.

An example of the latter is the conversion from Cartesian CIELAB addressing to "Calibrated RGB" addressing which is useful if the image data that will be processed through a rendering transformation are represented as RGB. It will be described later that Conditioning Transformations (CTs) play an important role in verification and device control. A CT is often the result of the "concatenation" of several individual, conditioning transformations serving the purposes just identified. The applications of transform concatenation include: 1) the method whereby a separation table with many NULL entries is made useful for rendering by concatenation with a conditioning transform which performs gamut scaling with considerable savings in transform-generation time and 2) feedback control of the color transformation process as will be detailed later.

In order to minimize cumulative interpolation errors, intermediate color to color' transforms may be stored and/or evaluated at high precision. Wherever possible, exact conversions of table entries should be utilized. For example, once all the mappings of CIELAB color to CIELAB color' have been compiled, the conditioning table entries for a color coordinate conversion from CIELAB to "calibrated RGB," for example, may be computed using analytical expressions.

Note that system 100 does not preclude importation (as described in discussion of User Interface) of standardly formatted color transformations ("profiles") prepared by applications other than the Virtual Proofing application. Accordingly, the rendering transformation may incorporate user preferences indicated through a transformation-editing tool (called a "profile editor" by some Application Software Packages.)

A key purpose of the conditioning transformation is gamut scaling, described below. It is important to elaborate this point: If the target device for the rendering transformation is a proofer, then the output gamut to which colors are scaled may be that of its client. The relevant, conditioning data for all devices on the network resides in the Virtual Proof. If the client's gamut fits entirely within the proofer's, then substitution of client for proofer gamuts is used to render a representation of how imagery will appear on the client. The display and negotiation of compromises to be made when the client's gamut does not fit entirely within the proofer's is discussed in conjunction with FIG. 21F, below. Note that, in addition to accommodating a client's gamut, successful proofing may require other mappings. For instance, tone scale remappings to compensate for differences in overall luminance levels between video displays and reflection media may be performed. Likewise, "chromatic adaptation" transformations to compensate for changes in illumination, viewing conditions, etc. may also be implemented by means of data structures or tables of what are called "conditioning" or color-to-color' transforms (output color transforms) herein.

Elaboration of the concept of color "aliasing," presented above is also appropriate: Neutrals are conventionally defined in terms of colorant in industry; elements of the default neutral scale which appears in FIG. 21E (step 270) generally do not have common chromaticity coordinates up and down the Lightness axis. In order to map colorimetrically neutral addresses onto the desired mixtures of colorants, it is necessary to convert the colorimetric addresses to the colors of the "colorant neutrals"—a process herein referred to as "aliasing" because one color address masquerades as another. The term has a different usage, familiar to signal processing, when used herein in connection with imaging colorimetry.

Specifically, the processes involved in making a color-to-color' transform (numbered 1 to 4 in FIG. 13) are as follows: (Recall that the goal is to be sure that only printable address colors are applied to the GCR-specific SEP table in the course of making a Rendering Table. Normally, $color_{out} = color_{in}$ at the outset. More detailed discussion of input gamuts, output gamuts and gamut operators follows. The sequence of the processes is important.)

1) Negotiate gamuts: In preparing a rendering transform to enable a proofing device to represent a printing press the color addressing of the color-to-color' table may be defined by the input gamut—in terms of the color image data. The range of colors represented in the table is limited by the extreme image values in the three dimensions of Uniform Color Coordinates. Because the quantization scheme is regular (cuboidal) there will be color addresses which do not occur in the image data (recall FIG. 10B.) These may be ignored, or mapped approximately onto the surface of the image's gamut. In place of the image's gamut, a general representation of the gamut of the original medium of the image may be used.

This method is preferred, for instance, to using the gamut of the press as the input gamut because so doing would require conversion of bulky image data into coordinates that are all within the press's gamut. An objective of system 100 is to provide means of interpreting image data in various ways without creating a multiplicity of versions of that data. An exception would occur if image data specifically from a press sheet were required to evaluate image structure due to screening, etc. as part of the proofing process.

The output gamut may be the lesser of the client's (printing press) AND proofer's gamuts, where "AND" connotes the Boolean operator whose output is the "least common gamut." This may be derived using gamut filters, as discussed later. In this negotiation, the proofer's gamut may be constrained to be that available within the Total Area Coverage (% UCR) limitation applicable to the press at the user's discretion. Other interactive tools may be used to control the definition of the output gamut subject to the ultimate restriction of what can be rendered on the proofing device within the default or selected % UCR constraint, if applicable. (Of course a video display proofer's gamut is not intrinsically subject to a UCR constraint.)

2) Perform gamut scaling: Using gamut operators to be discussed later, map color values to color' and store the color' values at the color addresses in the table.

3) Perform neutral aliasing: In each lightness plane, the color of the conventionally neutral inking (FIG. 21E, 270) is offset from the neutral color coordinate $a^*=b^*=0$ by an amount $a^*, b^*$. In order to map image neutrals to this offset color, the color' values in the conditioning table should be shifted in such a way that an address of 0,0 maps to a color' value of $a^*, b^*$. The function which performs the shift may be designed so that the amount of the shift decreases with distance from neutral.

4) Transform Color Coordinates (if necessary): The reason for this and a method of implementation were suggested previously, namely, it is preferred to perform gamut operations in Uniform Color Coordinates, but the image data may be represented in a color notation such as "calibrated RGB" so that a rendering table must be addressable by RGB coordinates. Because exact mathematical equations generally govern the relationship between Uniform CIE color and calibrated RGB, each color' value in the conditioning table is converted to RGB by means of the equations.

The Color-Color' Transform (XForm) is produced by the above steps and then concatenated with the GCR-specific SEP table. The result is a rendering table for transforming the color of input color image data into colorant data for the rendering device, which is stored in the local part of the VP.

The following discussion is related to providing gamut mapping data of the gamut configuration data. Color addresses that are not printable must be mapped onto printable ones. In the present application, the output gamut is that of the proofer of interest or the printer it represents. However, the input gamut is not fixed by the architecture or software design because it may vary and have a profound effect on the rendering of out-of-gamut and nearly-out-of-gamut colors. This is the case because the outermost, or limiting, colors vary greatly among possible input gamuts. Input gamuts that warrant distinctive processing include:

1) Other proofing devices include both hardcopy and video display devices (VDDs). Hardcopy devices are likely to have gamuts that are fairly similar, requiring only minor relative adjustments. Self-luminescent, additive-color devices such as video displays have very differently shaped gamuts from reflection devices so that the best mapping from input to output as a function of color will be unlike that for a reflection device. Computer-generated images originate in applications which are likely to exploit the gamut of a video device. Many retouching and page assembly applications use the RGB coordinate system of the monitor to store and manipulate images because it facilitates display on the VDD and interactivity. In this case, the input gamut is often that of the VDD, even if the image was originally scanned in from film.

2) Printing presses will usually have smaller gamuts than the proofing devices that represent them, restricting what is to be used of the available proofing gamut. If printed images are captured by an imaging colorimeter as part of calibration or verification so as to constitute the image data, the input gamut may be better approximated by the rendering gamut of the printer than the receptive gamut of the colorimeter.

3) Electronic or digital cameras will usually have much greater gamuts than any output device, necessitating a very significant restriction on what portions of the input gamut can be printed. Note, however, that the maximum gamut of a linear camera encompasses many colors that are not commonly found in natural photographic scenes. Accordingly, it may be preferable to design mapping functions for this class of device that are based on the scenery as well as ones based on device capabilities.

4) In conventional photography, the scene is first captured on film before being captured digitally. The relevant input gamut is the rendering gamut of film.

5) Regardless of the input medium and its gamut, there may be image-specific imperatives. For instance, a very "high-key" image, consisting almost entirely of highlights, lace, pastels, etc. may not make extensive use of the available gamut of a color reversal film. The best gamut mapping for this particular image is not the generic one for film.

The gamut mapping data is provided by a gamut operator which is a function which maps an input color to an output color. The process of constructing the gamut operator is shown in FIG. 14. It is a common practice to "clip" the input gamut to the output. In other words, all colors outside the output gamut are mapped onto its surface. This may be done in such a way as to preserve hue, saturation (Chroma) or Lightness or a weighted combination of the three. System 100 can work with such operators and supports access to them through the "Rendering Intents" function in the GUI, as shown latter in FIG. 21F. However, invertibility, reciprocality and smoothness are preferred properties of gamut operators, especially when processing and transforming image data.

Invertibility is an important property of the function because it insures that no information is lost except that due to quantization error. Reciprocality means that a mapping of input color to output color may involve either a compression or reciprocal expansion of the gamut, depending on which gamut is larger. Smoothness, or continuity of the first derivative, reduces the risk of noticeable transitions ("jaggies") in images which are due to gamut scaling. A simple exemplar of an invertible, reciprocal operator is illustrated in FIG. 14. It is presented to demonstrate and clarify key concepts and then an operator which is also smooth is explained. A mapping of Psychometric Lightness, L*, is shown, however, the same operator is applicable to CIE Chroma, C*, as well. It is assumed that hue is to be preserved in the mapping; a separate tool is supported within the GUI to gamut operations later shown in FIG. 21F, for situations in which users want to modify hues. FIG. 14 depicts the two cases of reciprocality, one in which the dynamic range of the input device must be compressed in order to fit the output gamut and the other in which input lightnesses can be expanded to fill the larger dynamic range of the output device. The operator introduced below is able to handle both cases without explicit user intervention, although operator override is also supported through the GUI of FIG. 21F.

Define $L_{pivot}$ as the greater ("lighter") of the minimum input and output L* values.

$$L_{pivot} = \max(L_{min\_in}, L_{min\_out})$$

where the minimum input lightness may, for example, be the L* value of the darkest color that can be reproduced on a positive reversal film and the minimum output lightness the L* value of the darkest color printable on a reflection medium. $L_{pivot}$ is denoted in FIG. 14A by a plain dashed line.

For lightnesses higher than $L_{clip}$, the gamut operator maps input to output lightnesses identically as indicated by the equation in the open space below the maximum L* of 100. A "cushion" is put between $L_{pivot}$ and $L_{clip}$ in order to insure that the mapping is invertible:

$$L_{clip} = L_{pivot} + (L^*_{max} - L_{pivot}) * \text{cushion}.$$

0.1 is a reasonable value for cushion, chosen so as to reduce the risk of losing information due to quantization error to an acceptable level. In the limit in which cushion=1, the entire range of input L* values is scaled uniformly, or linearly, onto the range of output L* values.

In either case 1 or 2, all lightnesses between $L_{clip}$ and $L_{min\_in}$ are scaled onto the range of lightnesses between $L_{clip}$ and whether the scaling represents a compression or an expansion. A piecewise-linear scaling function is illustrated below for simplicity. Note that all L values refer to CIE Psychometric Lightness in these equations whether they appear with a * or not.

If $(L^*_{in} > L_{clip})$ then $$L^*_{out} = L^*_{in}$$

Else $$L^*_{out} = L_{clip} - [(L_{clip} - L^*_{in})/(L_{clip} - L_{min\_in})^* (L_{clip} - L_{min\_out})].$$

The concept can be extended by adding the property of smoothness described earlier. The operator is based on a continuously differentiable function such as sine on the interval 0 to π/2, which generally resembles the piecewise linear function described above in shape but has no slope discontinuity. A table (Table I) of values of the function is given below; the first column is a series of angles in radians, X, from 0 to π/2 (90), the second, the sine of the angle, Y, and the third the fraction Y/X. If we set Y/X=(1−cushion), we can control the "hardness" or abruptness of the gamut-mapping implemented by the operator stated below the table in for the case of cushion~=0.1. For speed, the various evaluations implied may be implemented by interpolation in look-up tables. The operator described does not enable a purely proportional scaling (cushion=1.) The latter is not generally desirable but is available to users through the gamut options of the GUI in FIG. 21F.

TABLE I

| Angle, x (rad) | sin(x) | sin(x)/x | | |
|---|---|---|---|---|
| 0.0000 | 0.0000 | * | | |
| 0.0873 | 0.0872 | 0.9987 | | |
| 0.1745 | 0.1737 | 0.9949 | | |
| 0.2618 | 0.2588 | 0.9886 | | |
| 0.3491 | 0.3420 | 0.9798 | | |
| 0.4363 | 0.4226 | 0.9686 | | |
| 0.5236 | 0.5000 | 0.9549 | | |
| 0.6109 | 0.5736 | 0.9390 | | |
| 0.6981 | 0.6428 | 0.9207 | | |
| 0.7854 | 0.7071 | 0.9003 | <------ "cushion" | 0.10 |
| 0.8727 | 0.7660 | 0.8778 | | |
| 0.9599 | 0.8191 | 0.8533 | | |
| 1.0472 | 0.8660 | 0.8270 | | |
| 1.1344 | 0.9063 | 0.7989 | | |

If $L^*_{min\_in} < L^*_{min\_out}$)

$$0.707^*((100-L_{out})/(100-L_{min\_out})) = \sin[0.785^*((100-L_{in})/(100-L_{min\_in}))]$$

Else $$0.785^*((100-L_{out})(100-L_{min\_out})) = \arcsin[0.707^* ((100-L_{in})/(100-L_{min\_in}))]$$

The operators presented above rely on gamut descriptors to find the limiting colors of the input gamut that must be mapped into the output gamut. Once corresponding surface points in the two gamuts have been identified, the scaling function is used to prepare the conditioning transformation.

In summary, input gamuts can be very different from output gamuts. They often have a larger range of luminances (or dynamic range) such that it is preferable to perform a scaling in Lightness before working on Chroma or saturation. Secondly, scaling of Chroma is performed along lines of constant hue. Compensation for imperfections in the CIE models (embodied in CIELAB and CIELUV) of hue constancy or for elective changes in hue are handled separately. An example of elective changes is the need to map highly saturated yellows from film input to highly saturated print yellows by way of a change of hue angle. Modifications of hue can be accomplished through the conditioning transformation by color aliasing.

Figure 15A:
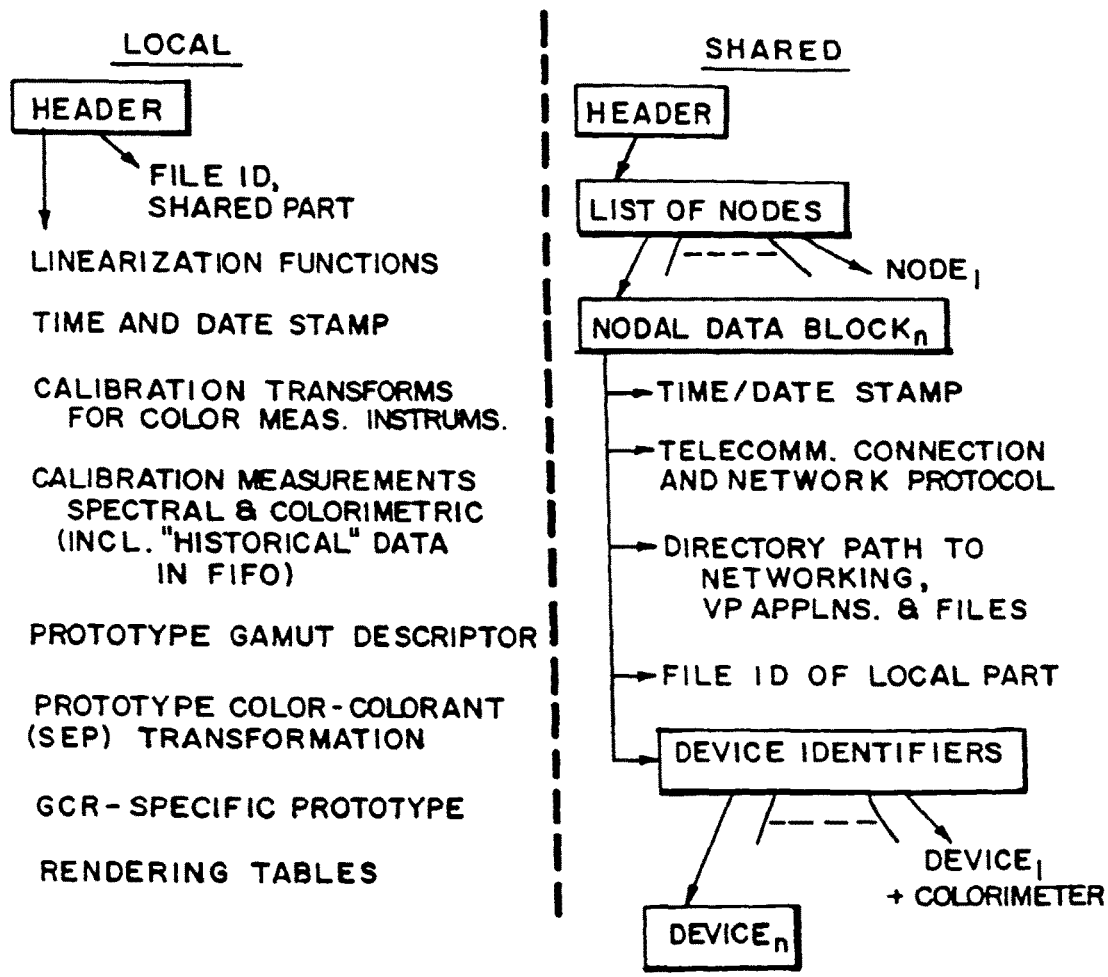
FIGS. 15A and 15B show the constituents of local and shareable components in the data structure of the Virtual Proof.
Figure 15B:
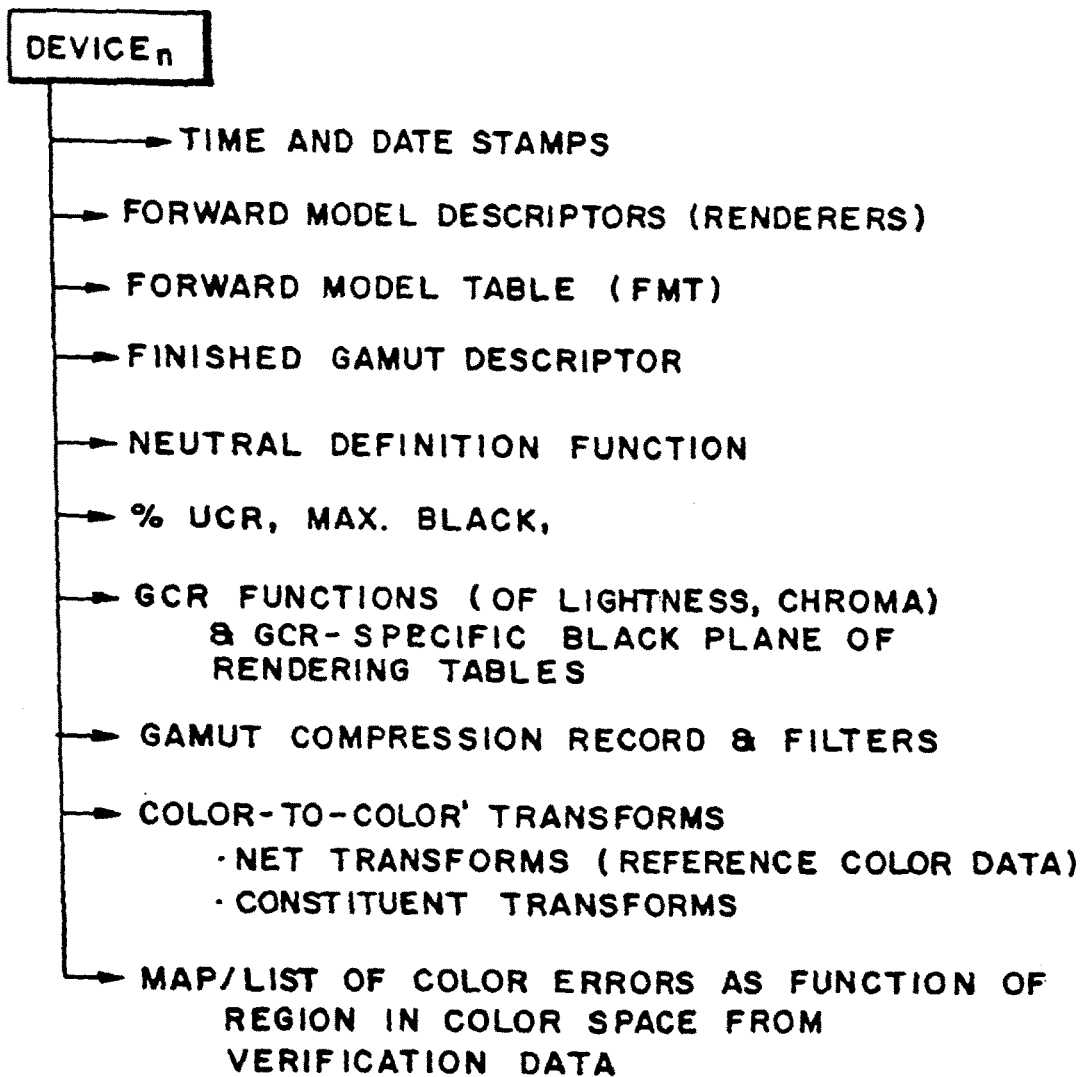

Referring now to FIGS. 15A and 15B, the shareable and local components described above in the VP are shown. In the interest of compact messages, not all shareable data need be transmitted in each transaction involving Virtual Proof. To the application software which administers the Graphical User Interface Software, both operating at a node, the VP is a set of data structures based around the classes Node and Device/Transform. The data structures map onto a general file structure which is not bound to a particular operating system, computer platform or processor. Object-oriented conventions of data-hiding are employed in the software to insure the integrity of transformations which are manipulated at a node. Accordingly, the VP files which store the data and transformations have local and shared components, as stated earlier; shared components consist of data which are read-only to all nodes except the one assigned responsibility for the data. During initialization in preparation for virtual proofing described in connection with FIG. 18, participating nodes insure that appropriate data are written to the relevant nodal fields within the shared file system.

The VP enables revision of color aspects of page/image data up to and even during rendering. An important aspect of revisability is the customization of data for rendering on particular devices. An equally important property of revisability is that page/image data need not be altered directly; rather they are "interpreted" in various ways through the medium of the VP. This eliminates the need to maintain multiple, large versions of page/image data at a particular node or to move one or more versions around the network repeatedly as a result of re-interpretation. Therefore, although the VP allows for image specificity and linking, preferably it is not bound into page/image files. The structure of the VP is similar to that of the Tagged Image File Format (an example is described in "TIFF™ Revision 6.0", Jun. 3, 1992, Aldus Corp., Seattle Wash., pp. 13-16).

Figure 15C:
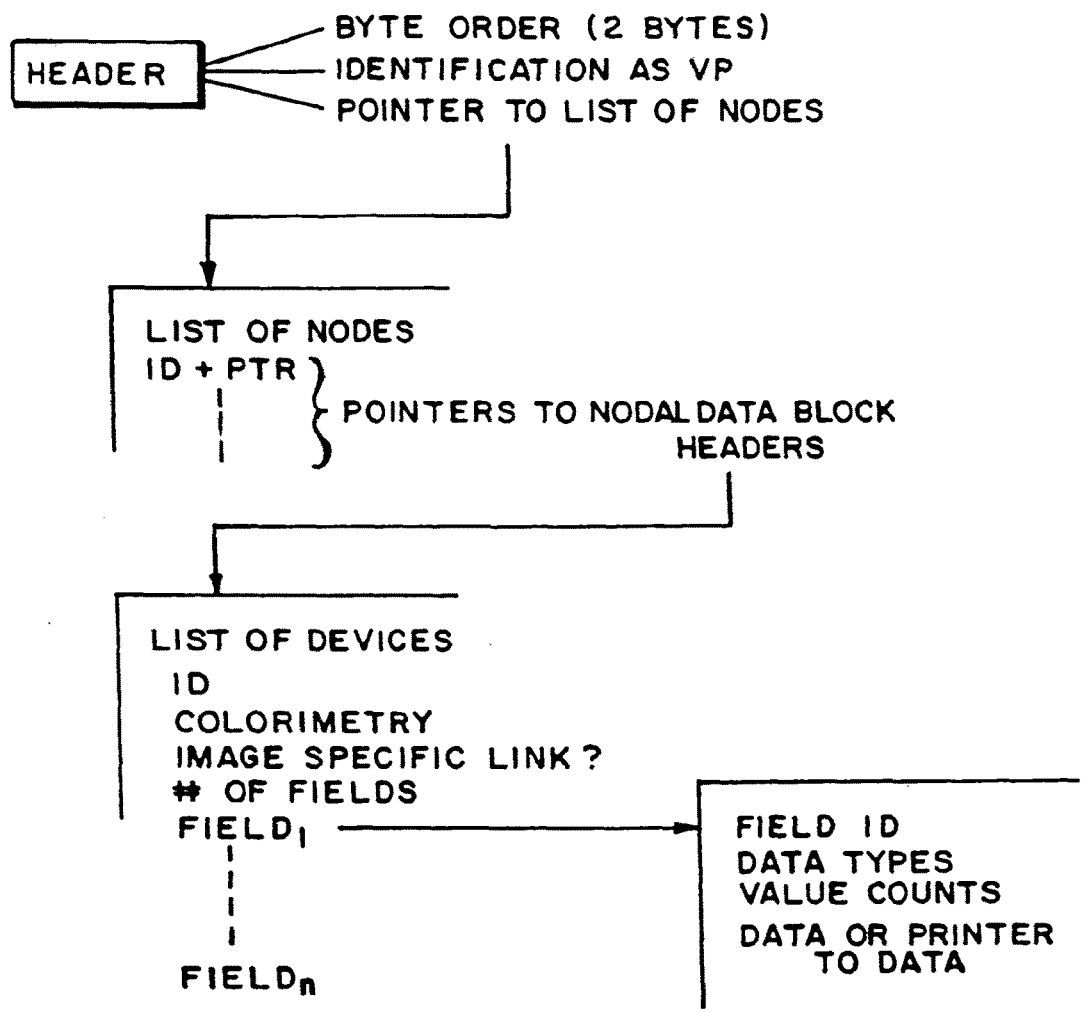
FIG. 15C is an example of a tagged file format for the shared components of the Virtual Proof of FIGS. 15A and 15B.

An example of the tagged or linked list file format for the shared parts of the VP is shown in FIG. 15C. The tags are referred to as Field IDs (bottom right of FIG. 15C.) It is possible for a given device to be present in a VP file more than once, specialized to represent images for different input gamuts or black utilization, etc.

Figure 16A:
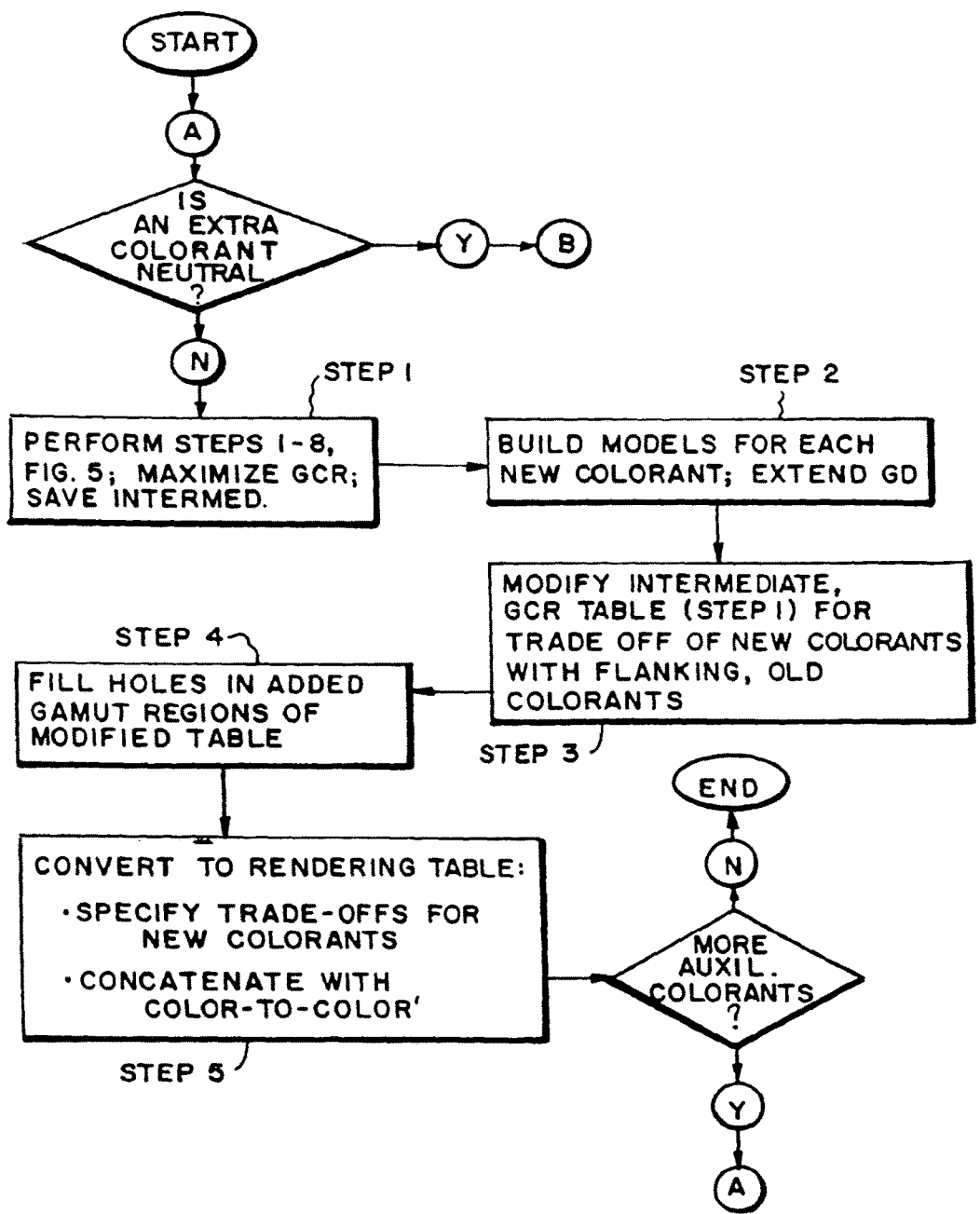
FIG. 16A is a flow chart of the process for calibrating a rendering device having more than four colorants by adding non-neutral auxiliary colorants to a rendering transformation.
Figure 16B:
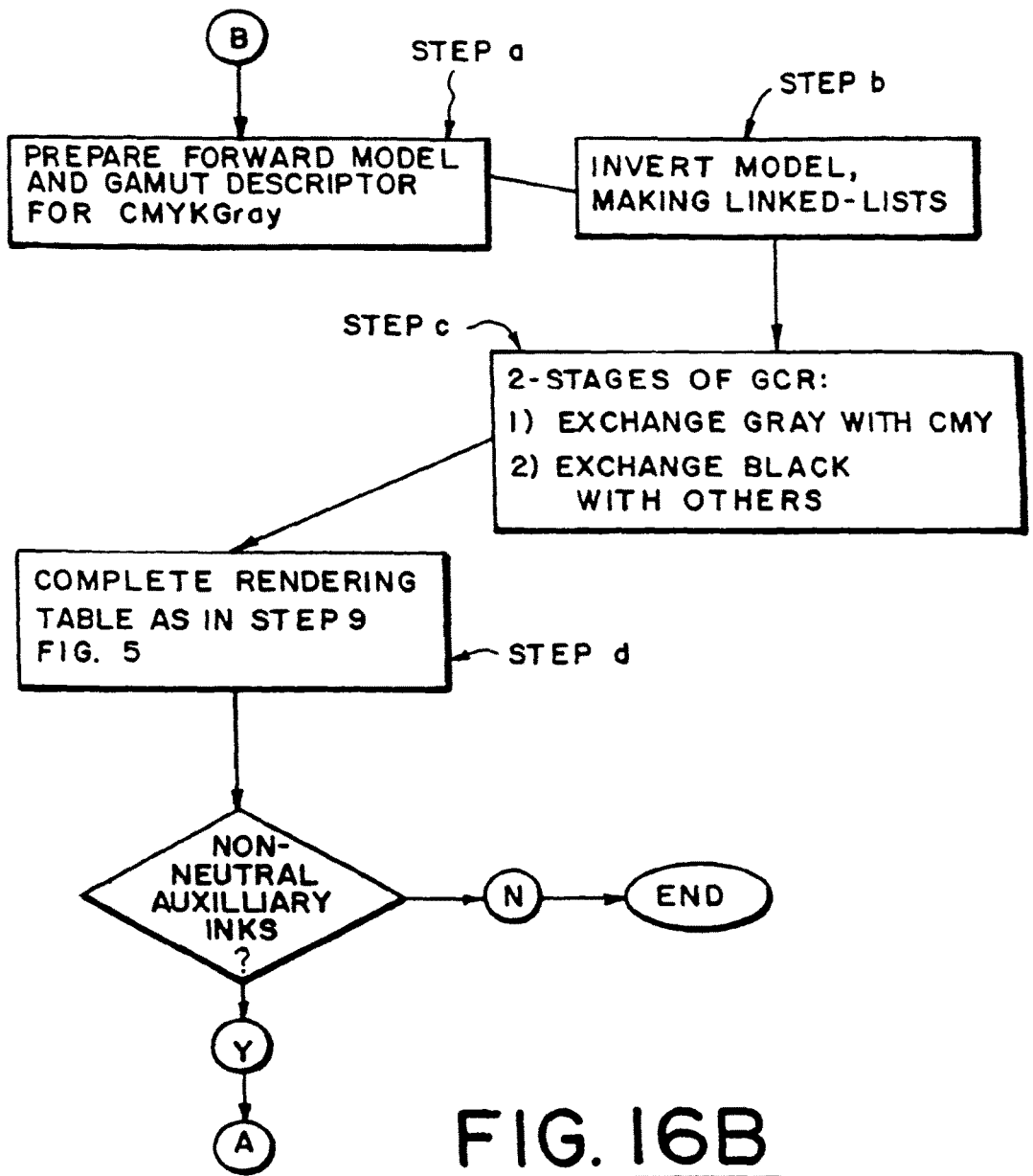

System 100 may incorporate rendering devices at nodes having more than four colorants. The processes for performing color to colorant conversions for more than four colorants is shown in FIGS. 16A and 16B, which are connected at circled letters A and B. In FIG. 16A, after starting, if the extra colorant is neutral, then proceeding continues to the start of FIG. 16B. Otherwise the following steps for adding additional non-neutral colorants (e.g., Red, Green and Blue) are performed:

Step 1) Proceed as for 4 inks through to the stage of gamut scaling. Use the Black Utilization tool which enables % GCR to depend on Chroma, to push towards maximum Black (2-colors+Black, with the complementary color pushed toward zero) solutions. Save this as an intermediate table. This intermediate is the equivalent of a GCR-specific SEP table.

Step 2) Build a model for converting C, M Blue and K (black or N) to color and omitting the colorant complementary to the "auxiliary," in this case, Yellow. Make a Forward Model Table and use the model to extend the original gamut descriptor prepared in (a). Do likewise for C, Y, Green and K and M, Y, Red and K. Note that the general rule is to add additional colorants one at a time, grouping each with the colorants which flank it in hue angle. Make FMTs for each new model for each auxiliary colorant and re-refine the Gamut Descriptor. Note, however, that the multiple models are used to refine only one GD.

Step 3) Modify the proto-rendering table (only one of these is maintained): Within the C, M, Blue, K gamut, there are not multiple solutions with different amounts of black at a given color; however, there are many solutions trading off CM vs. Blue. Store linked lists of these solutions at relevant color addresses in the intermediate table. Do likewise for CYGreenK and MYRedK.

Step 4) Treat the intermediate table as a "prototype table" in the 4-colorant case. Perfect it by making sure that all printable addresses in the new color regions of the table have at least one solution ("fill the holes.")

Step 5) Once the intermediate table has been reprocessed for all non-neutral auxiliary colorants, convert to a rendering table by performing the analog of GCR in the three new regions of the table. Check total area coverage, re-scale gamut and complete as for four inks (Step 9, FIG. 5.)

The foregoing procedure does not estimate the full gamut available; for example, the gamut at the hue angle of cyan is increased by the availability of blue and green. In other words, the BCGN gamut (where N stands for Neutral, or black) is not considered in the foregoing. Overprints of Blue and Green are likely to be substantially dark, compared to cyan. Therefore, the additional colors available in this gamut are not, in general, very numerous and need not be computed. However, in those cases in which the lost colors are important, the procedure outlined above is extended to include auxiliary gamuts centered on the standard subtractive primaries (C, M and Y) rather than on the additional colorants (R, G and B.) The result is overlapping auxiliary gamuts. By default, the decision regarding which of the overlapping auxiliary gamuts to search for a solution chooses the gamut centered on the ink of closest hue angle. There is nothing in the procedure which prevents its extension to even more colorants, which may be added in a recursive fashion. However, practical applications involving the overprinting of more than 7 (or 8, in the case of an extra neutral) colorants are very unlikely.

After the above steps are complete, if more colorants need to be added, processing branches to the circle A at the start of FIG. 16A, otherwise the process for adding additional colorants is complete. In the case of addition of auxiliary colorants which does not involve overprinting more than 3 or 4 colorants at a time (as in the case of multiple, "custom" colorants that might be used in package printing) the colorants are treated as separate sets according the procedures outlined previously.

If the process branched to FIG. 16B (to circle B), then the following steps for adding an approximately neutral colorant, such as gray, are performed: If additional non-neutral colorants are also to be added, add them according the procedure outlined in FIG. 16A above.

Step a) Prepare a colorant to color transformation for the 5-colorant set CMYKGray. Evaluate this model either with polynomial hardware or with a 9×9×9×9×9 interpolation table having about 60,000 five-dimensional cells. The simple linear interpolator is preferred and is particularly appropriate to this situation because the complexity of calculations scales linearly with the dimensionality of the interpolation space. As usual, make a Gamut Descriptor in tandem with building FMT.

Step b) Invert the model as in the 4-colorant case, fixing black and gray; build up linked lists of alternative solutions for a given color.

Step c) Proceed as in the 4-colorant case. When inverting the model, use only CMY and Gray wherever possible (i.e., fix black at zero), adding black only as necessary to achieve density. There are two stages of GCR. In the first, black is held to a minimum and gray is exchanged with C, M and Y. In the second, black may be exchanged, optionally, with gray and small amounts of the other colorants, as needed to keep the color constant. In the second stage, an error minimization routine is needed; Newton-Raphson is not appropriate.

Step d) UCR, preparation of a conditioning transformation, and so on as in the 4-colorant case, follow the second stage of GCR. Complete the rendering table, except for addition of auxiliary, non-neutral colorants.

After the above steps a-d, if additional non-neutral colorants are also to be added, processing branches to circled A in FIG. 16A, otherwise the process for adding additional colorants ends.

Figure 17:
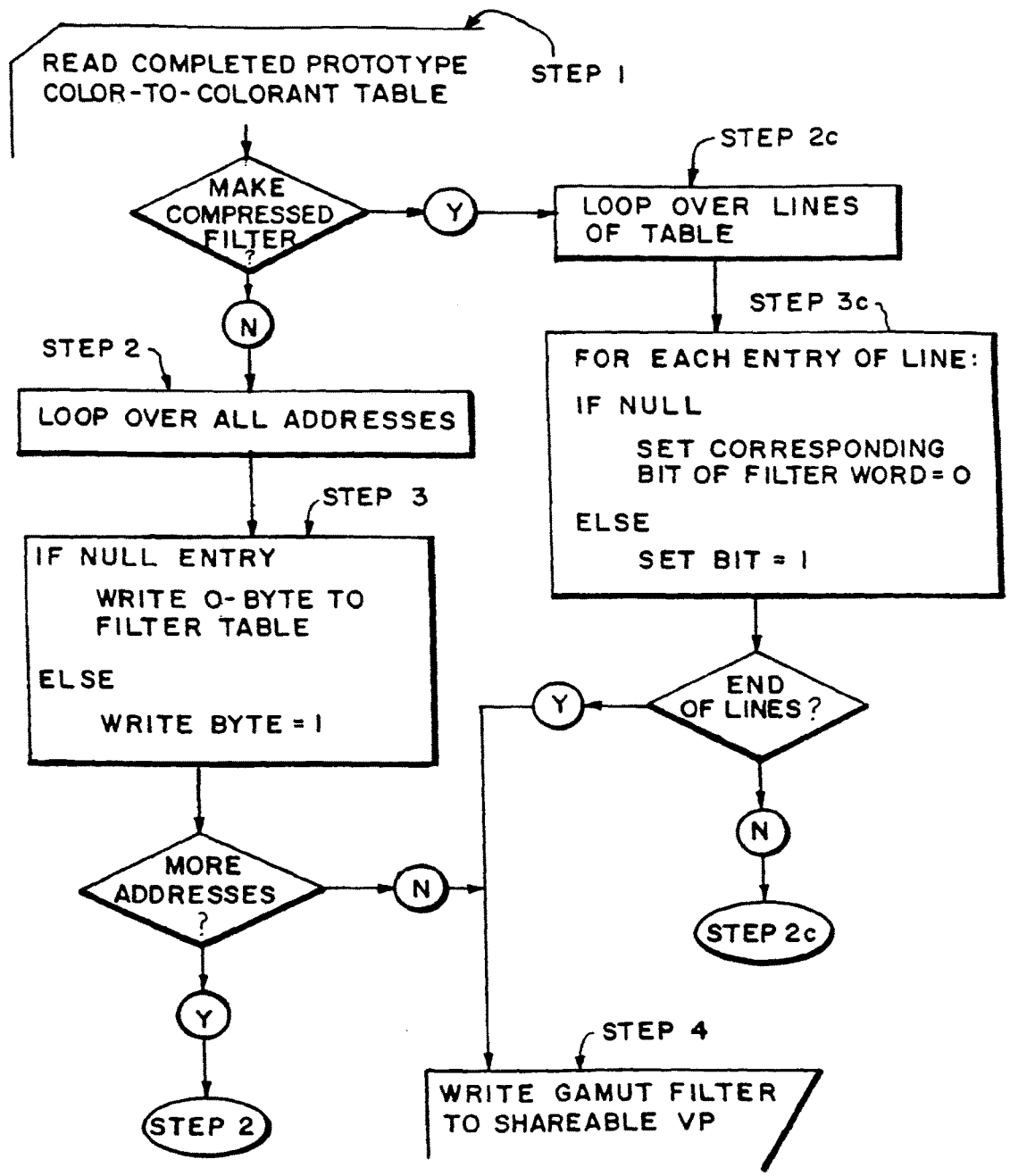
FIG. 17 is a flow chart showing the process for preparing a gamut filter, a data structure which facilitates the comparison of gamuts of two or more rendering devices.

Referring to FIG. 17, the process for building a gamut filter is shown. The finished prototype color to colorant table, filled with NULL cells and specific GCR solutions, is one manifestation of a device's gamut. It can be converted into a very useful filter in which each cell gets an indicator bit, 0 if the cell is NULL and 1 otherwise. The filters of two or more devices can be used to enhance visualizations.

Many graphics cards for driving video displays provide an alpha channel or overlay plane enabling the visualization of translucent graphical information on top of a displayed image. The results of performing Boolean operations on combinations of gamut filters for multiple devices may be converted into color-coded or pseudocolor overlay information to reveal things such as which image pixels are in gamut for one device but not another. With this tool, the intersection of the gamuts (the "Least Common Gamut") of five presses can readily be compared with each press's gamut in turn on common imagery, in support of a decision about what to use as a common criterion for color reproduction across the network.

Semi-transparent overlays are generally not possible for hard-copy devices without extensive image processing. In the case of a printer, a monochrome version of the image may be prepared and printed, overlaid with colored speckles indicating regions of overlap of multiple gamuts. The "overlay" is actually constituted by redefining subsets of the pixels in the image which belong to a certain gamut category as a particular speckle color. The foregoing method involves making a modified copy of the color image data with reference to the gamut filter.

An alternative, and preferred, method provided by the invention for readily identifying gamut overlaps is to filter the color-to-color' transform or actual rendering table. This may be done by leaving the contents of "in" addresses as they were while modifying the color or colorant contents of one or more varieties of "out" addresses to contain white or black or other identifying color. Different identifying colors may code different regions of intersection, overlap or disjointedness of the gamuts of several devices. When one or more channels of the (original) color image data are rendered through the "filtered rendering table," colors in the image which are out of gamut are mapped to one of the identifying colors and the resulting print reveals gamut limitations of various devices with respect to the imagery itself. An additional advantage of this method is that it is effective even when some of the colors under consideration are out of gamut for local proofing devices.

Another method of visualization available with the filters is to look at slices through Boolean combinations of the filters for two or more devices. Finished proto SEP tables are not generally useful other than in the preparation of rendering tables for a particular device; therefore, they are kept local. The filters are written to the shared portion of the VP. More specifically, in FIG. 17 a flowchart of the process of making a gamut filter in either a compressed form, in which a single bit is 0 or 1 to denote NULL or "in-gamut," or in a form in which each color's status is coded with a byte equal to 0 or 1 is illustrated. In the compressed case, a computer word may be used to represent a row or line of the prototype color-to-colorant table with each bit packed in the word representing one color address. After reading the proto-table (step 1), the steps of making the compressed filter include 2c) looping over the lines of the table, 3c) setting or resetting the bits of a word depending on printability and 4) finally writing the filter to shareable VP. The steps for making a byte table are completely analogous, except that a byte is devoted to each color address.

The two basic processes of calibration and verification (monitoring) rely on instrumentation and interact to produce the rendering transform which embodies the VP and can interpret color image data.

Figure 18A:
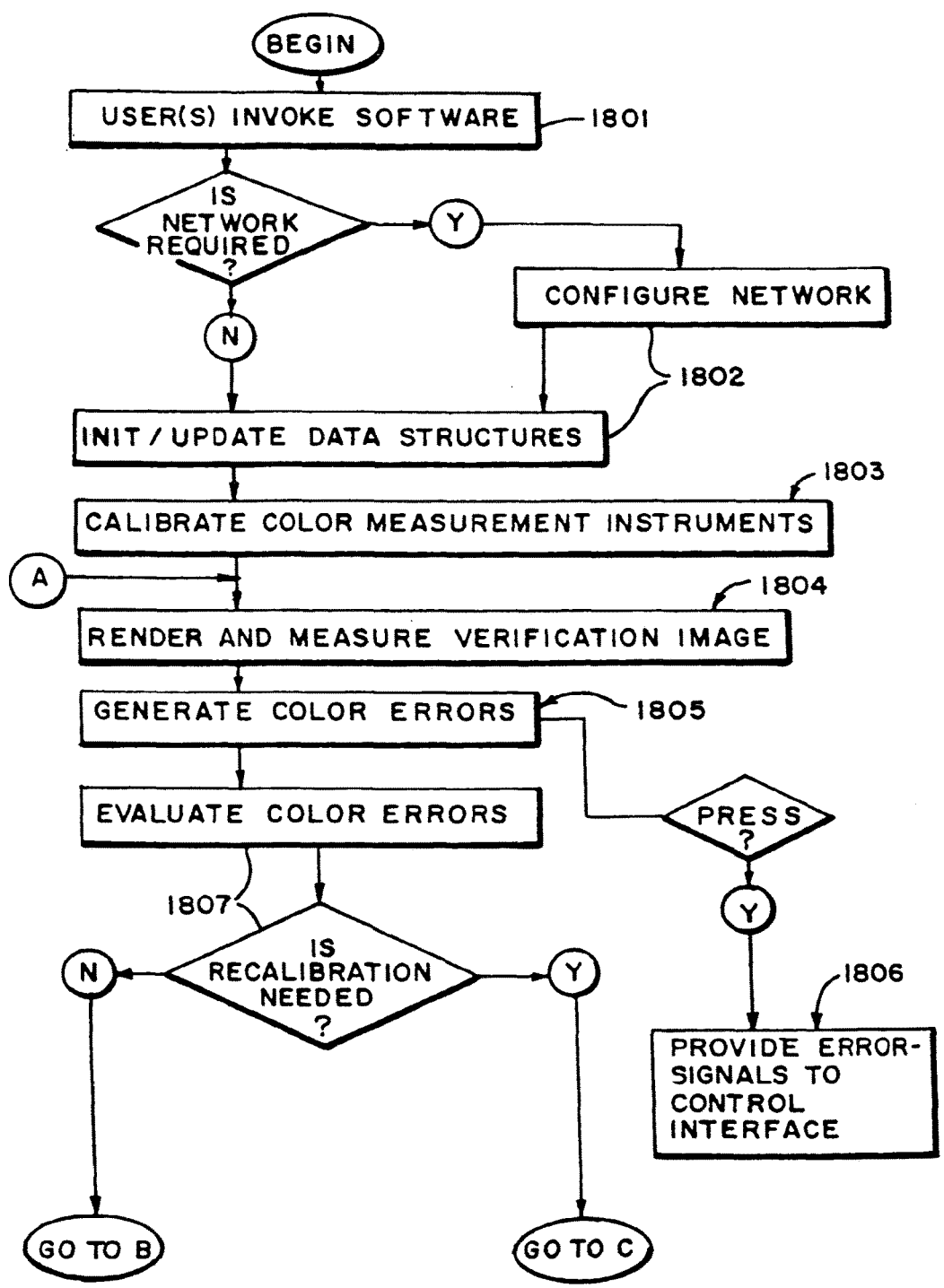
FIGS. 18A and 18B are a flow chart for virtual proofing using the system of the present invention.
Figure 18B:
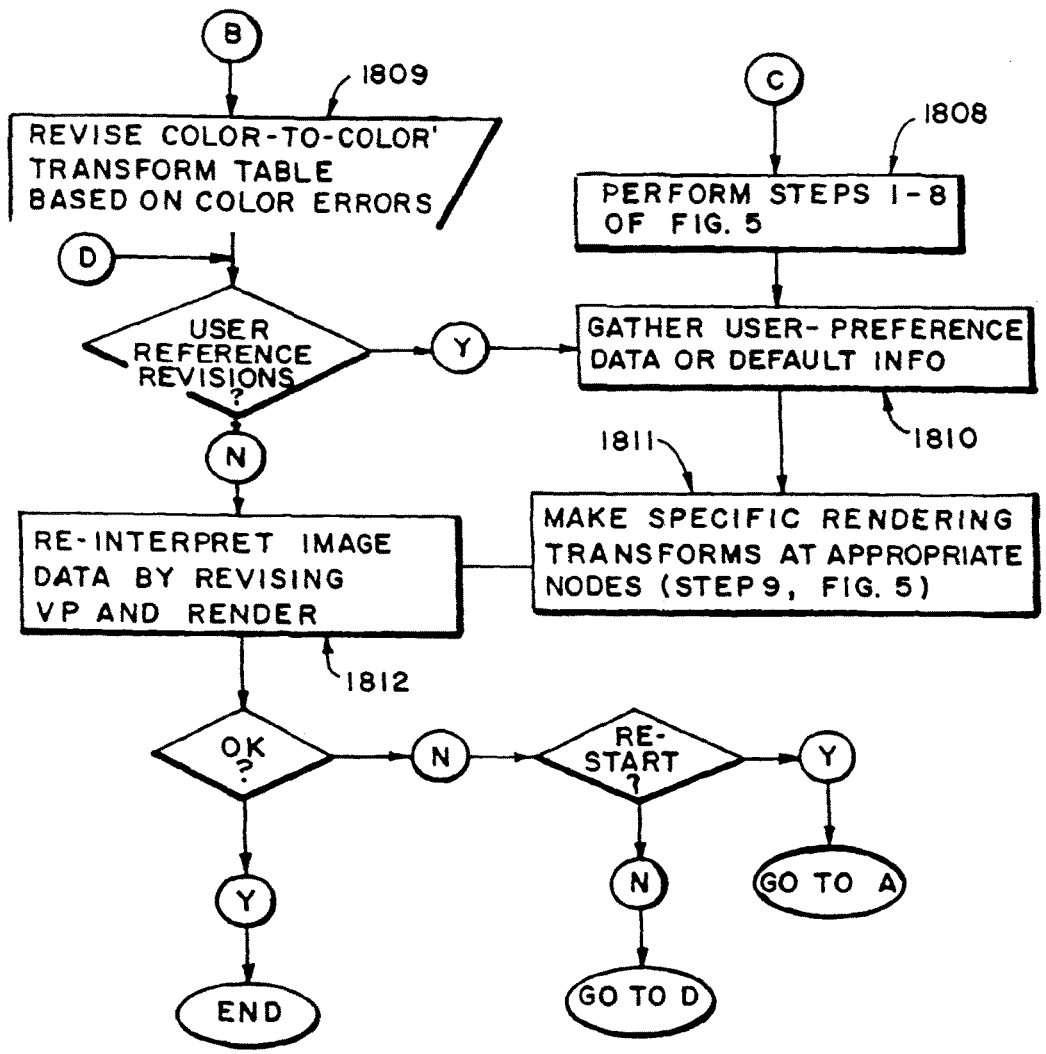

Referring now to FIGS. 18A-B, a flow chart of the program operating at nodes 102 and 104 for virtual proofing in system 100 is shown. These figures are connected at circled letters A-D. At the top of FIG. 18A, one or more users invoke the application software 1801; a single user can run the program in order to revise the Virtual Proof as it relates to the local node, or to other nodes which are accessible. Often, multiple users run the program simultaneously to negotiate the VP. Network readiness is established by making sure that the relevant, participating nodes all share current data 1802. CMI's are put through (preferably automatic) calibration checks 1803. Next, verification of device calibration is attempted by rendering and analyzing color 1804. The details of this step depend on the nature of the device and of the color measurement instrument; if the device is a press, particularly one with fixed information on the plate, the verification is most likely to involve "live" imagery rather than a predefined cal/verification form or target such as one consisting of tint blocks. The color error data 1805 produced by verification are supplied to the press controls, if appropriate 1806, as well as to the program to support decisions about whether color variations can be compensated by modification of existing rendering transforms of the VP or whether recalibration of the device is required 1807.

If re-calibration is called for, the program branches to C, atop FIG. 18B, where systematic calibration after FIG. 5 is undertaken 1808. Else, the program branches to B, atop FIG. 18B, to revise the color-to-color' transform 1809 based on the processing of the color error data, which is detailed later in FIGS. 19 and 20. Next, the need for User-preference revisions is assessed at D. If YES, then gather User preference data 1810 and re-specify rendering transforms 1811 as in Step 9, FIG. 5. If NO, then revise VP for a new interpretation of image data and render 1812. If results are satisfactory, conclude. Else, either recalibrate at A or revise preferences at D, depending on the nature of the diagnostics.

Verification is a feature of system 100 used in virtual proofing, described above, and color quality control of production rendering devices. The reason for verification is that the use of system 100 for remote proofing and distributed control of color must engender confidence in users that a proof produced at one location looks substantially the same as one produced in another location, provided that the colors attainable by the devices are not very different. Once rendering devices are calibrated and such calibration is verified to each user, virtual proofing can be performed by the users at the rendering devices. In production control, such verification provides the user reports as to status of the color quality.

During verification of production rendering devices, on-press analysis of printed image area may be used in control of the production process and for accumulation of historical data on color reproduction performance. Historical data may be used in a statistical profile of the manufacturing run which serves as a means of verifying the device calibration. It is also used to inform and update the virtual proof, enabling better representation of the production equipment by a proofing device. With a sufficient accumulation of historical information, it is even possible to model and predict the effects of neighboring pages in a signature on the color in the page of interest to an advertiser.

Once a device has been calibrated, the color transformations thus can be one of the mechanisms of control. In a control loop, colors produced by the device are compared to desired values and mechanisms affecting colorant application are modulated to reduce the discrepancy between measured and desired values. Control implies continuous feedback and iterative adjustment over many printing impressions, whereas proofing devices are usually one off. Nevertheless, proofing devices vary with time and periodic recalibration is a means of control.

One feature of system 100 is to provide the User with information about the color accuracy of the proof. It has been noted that the invention is compatible with two kinds of instrumentation, unitary colorimeters (SOMs 13) capable of measuring homogeneous samples and imaging colorimeters (imagicals 14) capable of sensing many pixels of complex image data simultaneously. In the following discussion, differences in verification procedures for the two kinds of instrument are considered.

Calibration is best carried out with a specialized form which is known to explore the entire gamut of the device. The rendered form can be measured by either type of instrument. In verification, the requirements of sampling the entire gamut are not as stringent; the interest is often in knowing how well the reproduction of all the colors in a particular image is performed, even if the image samples only a part of the device gamut.

Figure 19:
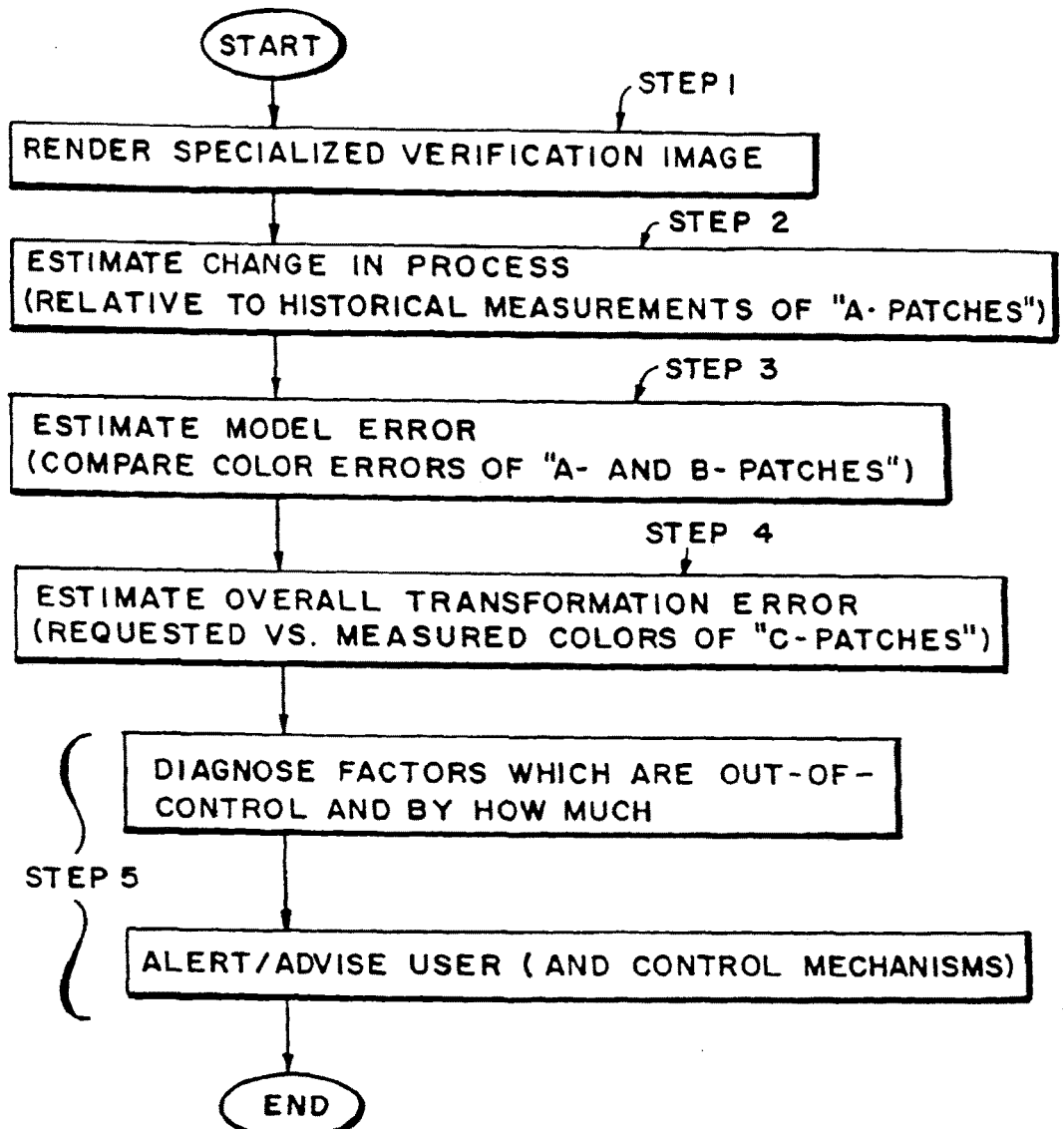
FIG. 19 is a flow chart of the verification procedures employed to estimate process variations based on measurements of color errors.

Referring to FIG. 19, steps 1804-1807 of FIG. 18A are shown. A specialized verification image is analyzed either with a SOM 13 or an imagical 14 according to the following procedures:

Step 1: Render an image consisting of homogeneous samples ("patches") of three types: a) patches whose nominal colorant specifications match those of patches in the original calibration, b) patches whose nominal specs are different and c) patches specified as color. The original calibration procedure (see FIG. 8) produced statistical estimates of within-sheet and between-sheet color differences or process variation. User-defined requirements for accuracy are expressed in terms of standard deviations (or like quantity) within the process variation to define confidence limits for the process. Three kinds of color error derived from verification procedures are used to control the process and are referred to the confidence interval in order to decide if recalibration is necessary.

Step 2: New measurements of type "a" patches (preceding paragraph) are compared to historical values to estimate change in the process; a thorough sampling of color space is useful because it is possible that change is not uniform with color. Step 3: Model predictions of the colors of patches of types "a" and "b" are compared to measurements to yield estimates of the maximum and average values of color error for the forward model. Step 4: Comparisons of the requested colors of patches of type "c" to those obtained (measured) are used to estimate the overall error (due to change of the process, model error, model inversion error, interpolation and quantization errors, when relevant.) Step 5: If color errors assessed in this way exceed the confidence limits, the User(s) are advised that the system needs recalibration and corrective actions may also be taken, such as modification of conditioning transforms, depending on the severity of the problem. If the device is a press, color error data is furnished to the press control system (subject to User intervention) which does its best to bring the press as close to criterion as possible.

The advantage of specialized imagery is that suitably chosen patches provide more information than may be available from imaging colorimetry of images with arbitrary color content. This can guarantee that the entire gamut is adequately sampled and can provide differentiated information about sources of error. However, imaging colorimetry of the reproduction during or shortly after rendering is often the least obtrusive way of verifying that forward models and rendering transformations are current, especially when a volume production device is the object.

Because, as was noted above, the variations in color need not be uniform throughout the gamut of the device, the data structure is segmented into clusters of contiguous cells in order to identify the most frequent colors in the various regions of the gamut. Thus, system 100 herein samples color errors throughout the image. The processing checks to make sure that the frequency it is reporting for a cluster of cells is a peak, not a slope from a neighboring cluster.

In order to improve the reliability with which corresponding peaks in different histograms can be resolved, methods of image processing such as accumulation of counts from multiple images (averaging), bandpass filtering and thresholding are employed. Then regions of the histograms are cross-correlated. Cross-correlation is a technique discussed in many texts of signal and image processing, in which two functions are convolved without reflection of one of the two. It is similar to techniques in the literature of W. K. Pratt, Digital Image Processing, NY: Wiley, 1978, ch. 19, pp. 551-558. A "cross-correlogram" reveals the offsets of one histogram with respect to another in three-space.

The color offsets of the peaks are expressed as color errors. These are made available for numerical printout as well as for visualization. In the latter, the user may choose to view a monochrome version of the image overlaid with translucent color vectors showing the direction and magnitude of color-errors, or may choose to view a simulation of the error in a split screen, full color rendering of two versions of the image data showing what the error can be expected to look like.

For clarity, an equivalent procedure for cross-correlation can be outlined as follows: 1) subdivide the histograms into blocks and "window" them appropriately, 2) calculate Fourier Transforms of the histograms, 3) multiply one by the complex conjugate of the other, 4) Inverse Fourier Transform the product from 3 and 5) locate the maximum value to find the shift in the subregion of color space represented by the block.

For the simplest level of control, the inverse of the color errors may be used to prepare a conditioning transformation which then modifies the rendering transformation employed in making another proof. For more sophisticated, on-line control, the data are used to compute error gradients of the sort described earlier and used by optimization and error minimization algorithms. Results are fed to the control processor of a press or used to modify the rendering transform as a control mechanism for a press (or press-plate) which does not use a press bearing fixed information.

Figure 20:
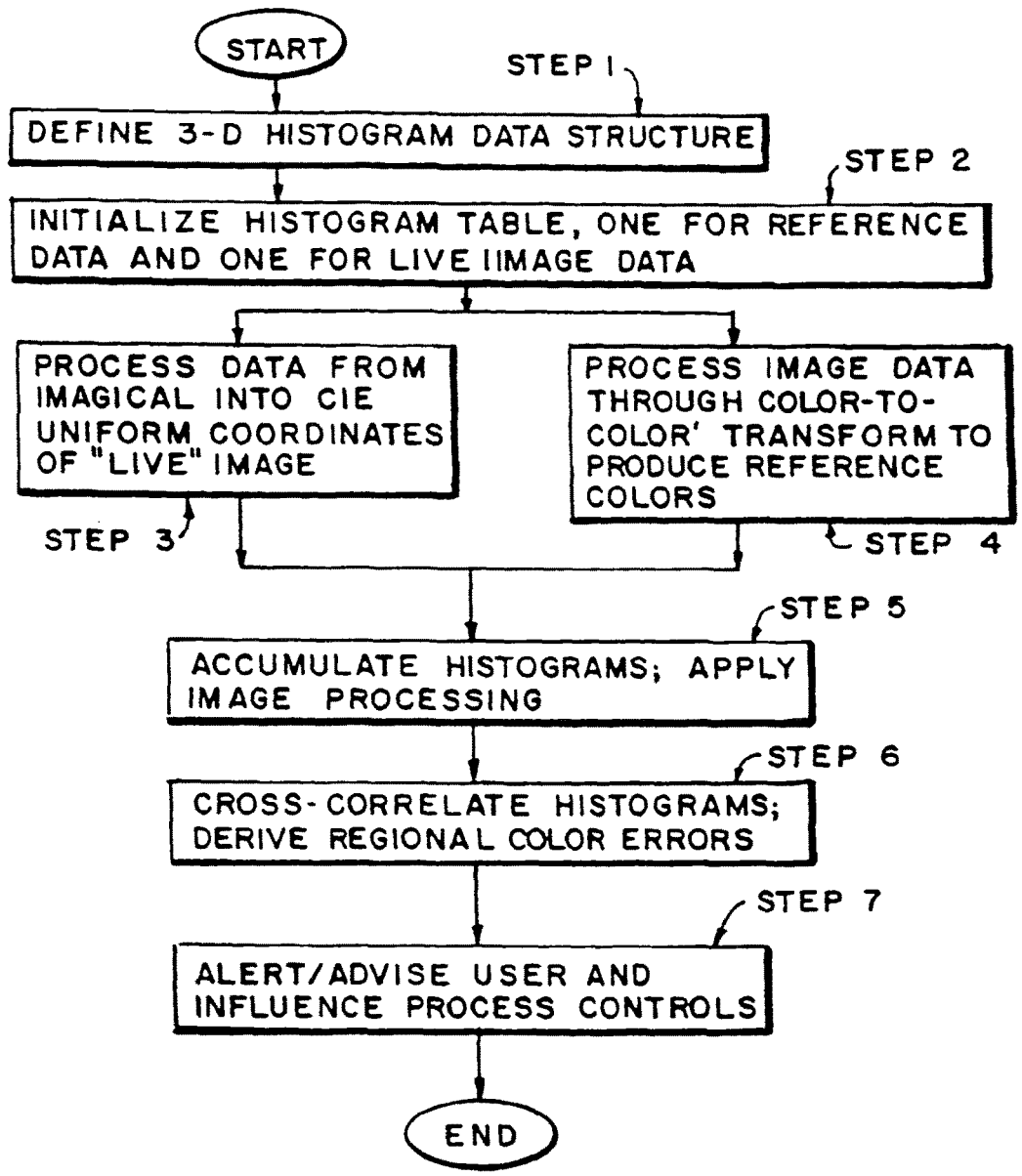
FIG. 20 is a flow chart of the process of preparing a three-dimensional color histogram of color image data in providing a resolution-independent analysis of color error relative to a criterion.

The goal is to determine errors in color reproduction in a resolution-independent way. This is shown in reference to FIG. 20, illustrating processes 1804-1807 in FIG. 18A when an imagical 14 is verifying using live image data. In step 1 of FIG. 20, the histogram is defined. Generally, it is a data structure addressed similarly to the Conditioning Transform (color-to-color' table) described earlier, although the range of colors represented in each dimension of the structure is adaptive and may depend on the imagery. In step 2, the 3-D arrays to hold accumulated histogram data are allocated in memory and initialized; one array is needed for "live" image data and the other for reference data. At step 3, capture of "live" image data occurs. Optical low-pass filtering may precede image capture, preferably by a solid state electronic sensor, in order to reduce aliasing in signal processing. The electronic, pixel data are converted into CIE coordinates, and, simultaneously, a histogram of the relative frequency of occurrence of colors in the image is stored. As mentioned earlier, the data structure may be segmented into clusters of contiguous cells in order to identify the most frequent colors in the various regions of the gamut.

In part 4 of the process, the image data (not that captured by the imagical, but the "original," image data) are processed through the color-to-color' transform to produce Reference Color Data which are accumulated in a histogram structure. It is important to recognize what the requested (or "reference") colors are. They are the colors (preferably in CIE Uniform coordinates) which are the final outputs of all the color-to-color' conditioning transforms (usually exclusive of color-coordinate transforms) and thus represent the interpretation of the image data negotiated by the Users.

In steps 5 and 6, as described above, the program checks to make sure that the frequency it is reporting for a cluster of cells is a peak, not a slope from a neighboring cluster. Accumulation of counts from multiple images (averaging), bandpass filtering of histograms, thresholding, autocorrelation and other operations of image processing are used to improve reliability and the ability to resolve peaks and match corresponding peaks in different histograms. Ordered lists of peaks are prepared and written to the shareable portion of the VP. The lists are compared and corresponding peaks identified. The color offsets of the peaks are expressed as color errors. In step 7, color error data are made available to User/Operator and control systems.

Referring to FIGS. 21A-21F, a Graphical User Interface (GUI) to the application software is shown. The GUI is part of the software operating at the nodes in network 11 for conveying the workings of system 100 at a high-level to the user. The user-interface has reusable software components (i.e., objects) that can be configured by users in a point-and-click interface to suit their workflow using established visual programming techniques. The GUI has three functions: 1) Network (configure and access resources), 2) Define (Transformation) and 3) Apply (Transformation.) All three interact. For instance, verification functions fit logically within Apply Transformation but must be able to feed back corrective prescriptions to Define Transformation which provides a superstructure for modules concerned with calibration and modeling. Therefore, both Define and Apply need access to Color Measurement modules, whether they make use of imaging or non-imaging instruments. "Network" is responsible for coordinating network protocols and polling remote nodes. Part of this function includes the identification of color measurement capabilities of a node. Another part is to insure that a user's mapping of software configuration onto his workflow is realizable. Loading the appropriate color measurement device drivers is as crucial as choosing and initializing the correct communications protocol and proofer device drivers. Therefore, Color Measurement coexists with modules for administering network protocols, building device models, building color transformations and implementing the transformations for the conversion of color images.

For the purposes of this discussion, assume that the application is stand alone. Today, Graphical User Interfaces can be prepared via automatic code generation based upon re-usable components in most of the windowing environments on the market. The depictions of menus and attributes of the User Interface in what follows are not meant to restrict the scope of the invention and are kept simple for clarity.

Figure 21A:
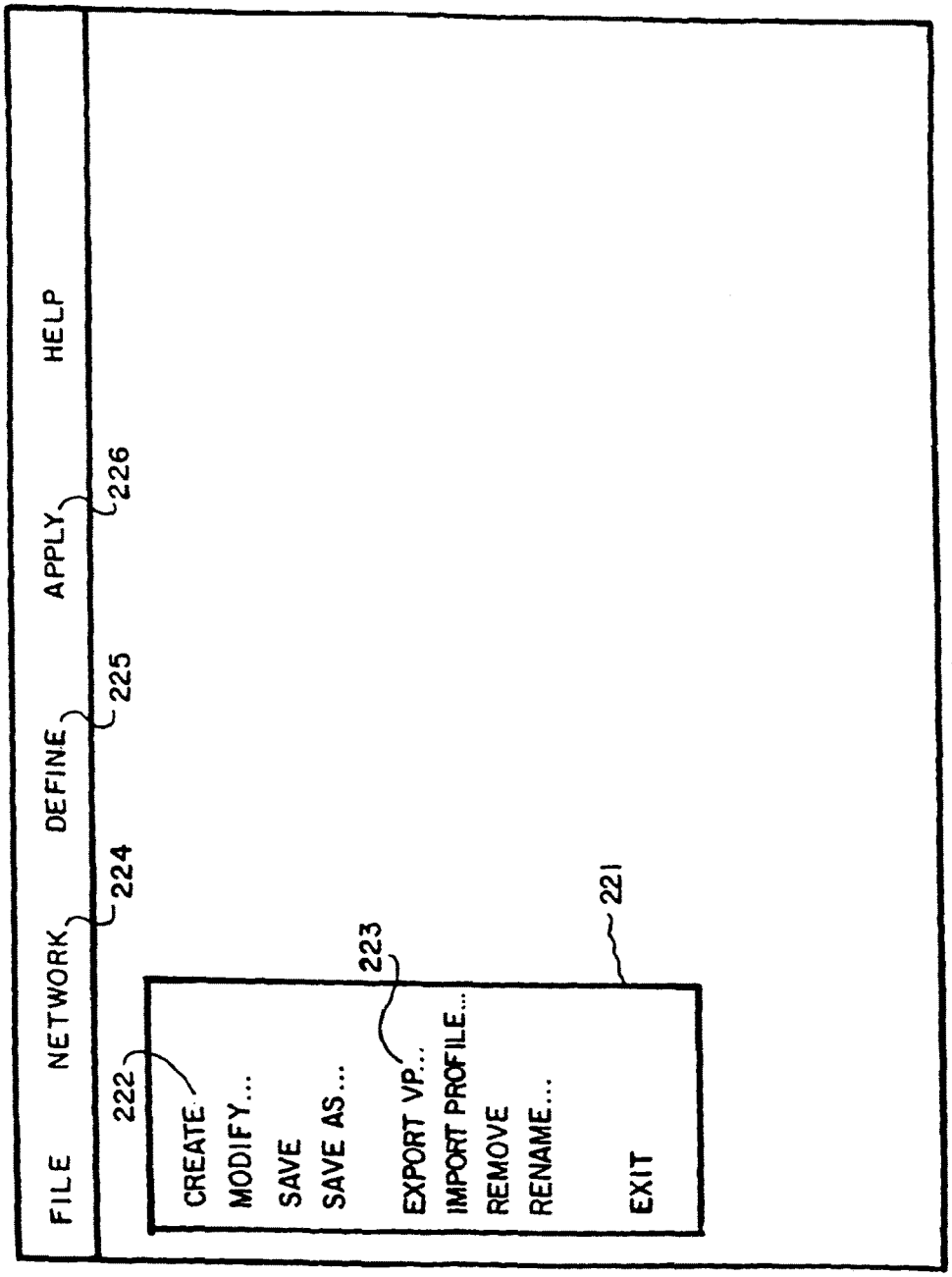
FIG. 21A is a menu of the Graphical User Interface (GUI) to the application software to enable configuration of the network of nodes, remote conferencing and proofing and oversight of the processes involved in calibrating devices in the systems of FIG. 1.

Referring to FIG. 21A, a first level hierarchy screen is shown allowing a user to enable configuration of network 11 nodes, remote conferencing, and user oversight of processes in system 100. Upon invocation, the application introduces itself and offers a typical menu bar with five choices (command names), File, Network, Define, Apply and Help. Clicking File opens a pull-down menu whose selections are like those indicated by 221 in the FIG. Clicking on Create 222 initializes file creation machinery and opens the Network tableau (FIG. 21B) in a mode of readiness to design a virtual proofing network. Export VP (Virtual Proof) 223 offers the option of converting color transformational components of the Virtual Proof into standardized file formats such as International Color Consortium Profiles, Adobe Photoshop color conversion tables, PostScript Color Rendering Dictionaries, TIFF or TIFFIT. A possibility of importing standardized color transformation files is also provided. Other menu items under File are conventional.

The Network heading 224 opens a tableau concerned with membership in the virtual proofing network, the physical and logical connections among nodes and the equipment at the nodes and its capabilities. The Define heading 225 provides means of calibrating (characterizing) devices, enabling customized assemblies of procedures to be applied to appropriate target combinations of devices and color measurement instrumentation. The Apply heading 226 covers display of imagery rendered through the virtual proof and provides tools for verifying and reporting on the accuracy of color transformations, customizing those transformations, conferencing, comparing various versions of the proof and establishing contact with other applications performing like functions. The Main menu offers Help and each of the Network, Define and Apply menus offer Tutorial interaction.

Figure 21B:
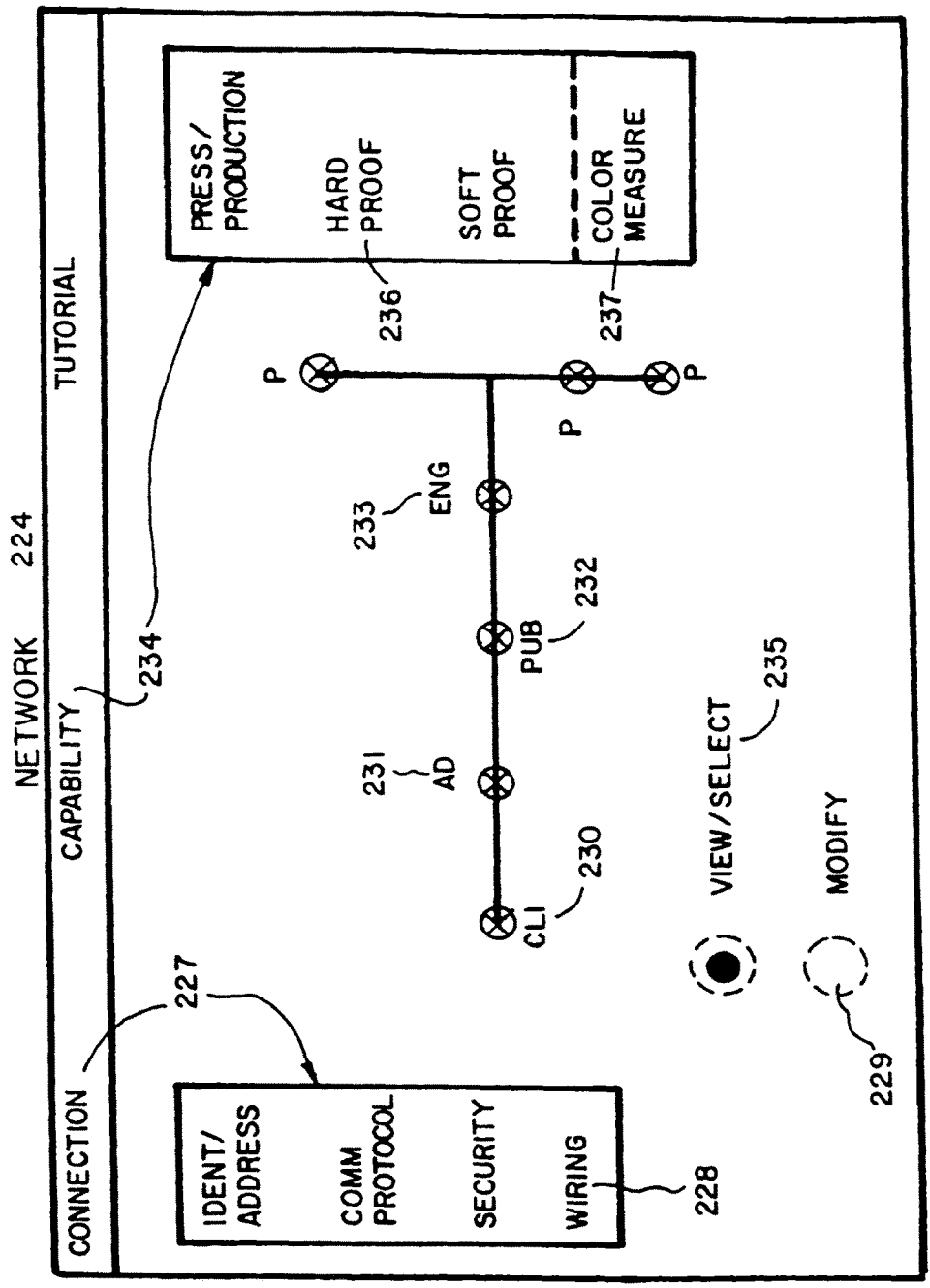
FIG. 21B is a menu at the second level of hierarchy in the GUI to provide access to tools for configuring the network connections and communications protocols.
Figure 2I:
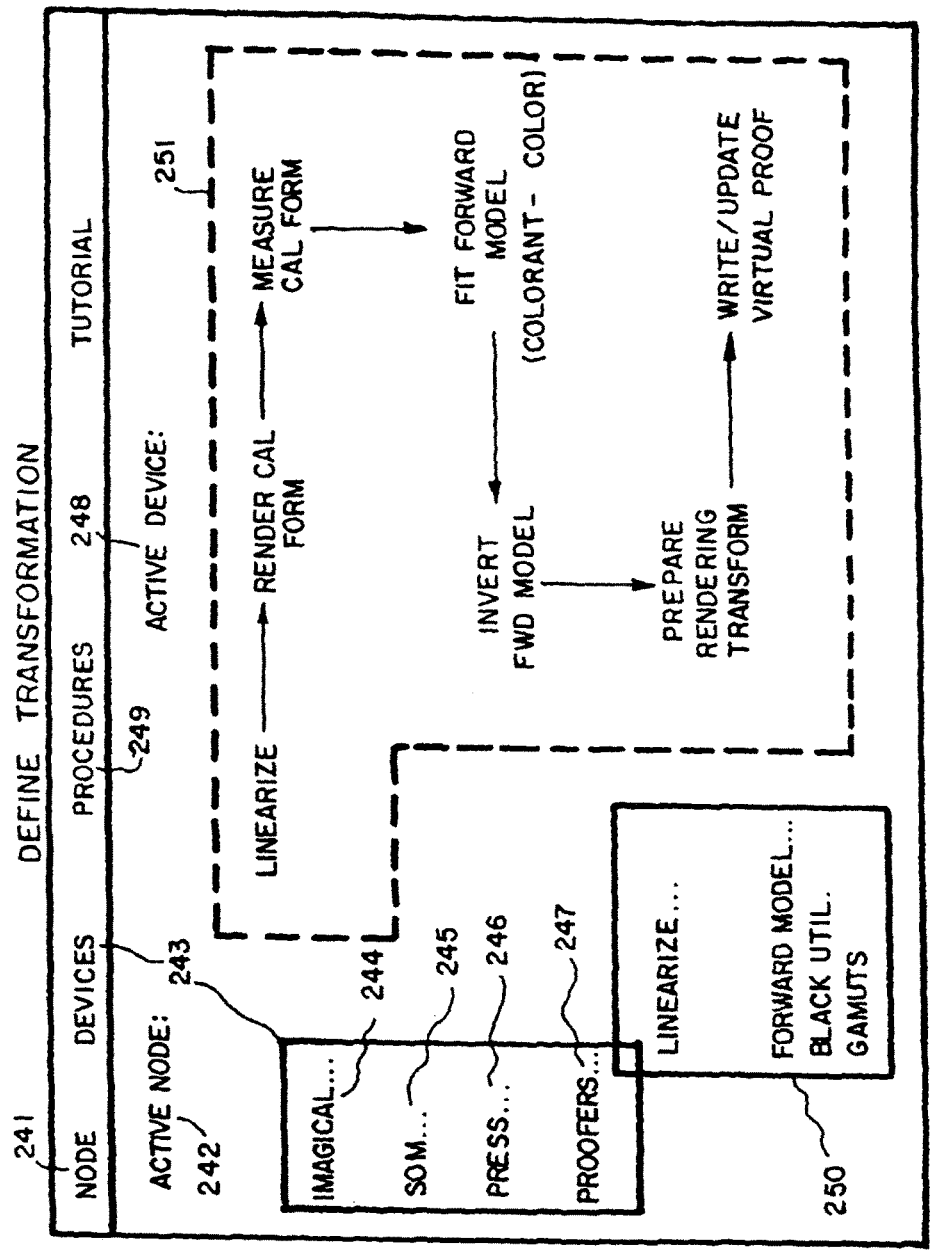

Clicking on Network in the Main menu opens a tableau of FIG. 21B, which is concerned with Connections and Capabilities. Clicking Connection 227 reveals a sidebar concerned with tools and attributes of network 11 connections. For example, during creation (see FIG. 1), it is possible to pick up a wire by way of the "wiring" entry of the sidebar 228 and move it into the field as part of assembling a network model that can be written to a file and can direct proofing commerce. Double clicking on the wire reveals information about the connection or permits editing of the information when the "Modify" radio button 229 is activated. Error notices are generated when the software drivers required to implement the model are not available or when the hardware they require is not present. The present invention is not wedded to particular current (e.g., modem, ISDN, T1, satellite, SMDS) or anticipated (ATM) telecommunications technologies, nor to particular networking protocols. Nodes can be defined, given addresses, security, etc. and can be equipped with proofing devices in a manner similar to the design of connections. The summary of the network's connections and of nodal capabilities is shared through the Virtual Proofs tagged file format described earlier which is kept current at all sites.

In the center of FIG. 21B is an example network topology. It resembles the network of FIG. 1, where "cli" 230 refers to a possible client (e.g., advertiser) member, "ad" 231 an ad agency, "pub" 232 a publisher, "eng" 233 an engraver and the Ps are printers. The links between the nodes are created and modified through the wiring 228 functionality of "Connection" mentioned above. Clicking "Capability" reveals a sidebar 234 concerned with devices and their associated instrumentation for color calibration and verification. An example of the use of the menu is as follows: I am a user at an ad agency who wants to establish a remote proofing conference regarding a page of advertising with a publisher and printer. I bring up the relevant network using "Modify . . . " in FIG. 21A, push the radio button for view/select 235 in FIG. 21B, and click on the "pub" node 232. This creates a connection between the ad and pub nodes if one can be made and initiates a process of updating virtual proof files at either end of the link. Then I click on hard proof 236 and color measure 237. This utilizes the updated VP information to show me what hard copy proofer(s) are available and how they are calibrated and/or verified. Then I follow a similar sequence of actions with respect to a P node. The initiation of display and conferencing about color image data is done via the Apply menu of FIG. 21D.

To pursue the example of the preceding paragraph, suppose that I find that the hard copy proofer at node "pub" has not been calibrated recently. A study of the information about the device in the updated Virtual Proof reveals whether re-calibration or verification procedures can be carried out without operator intervention at that site. From one site or the other, the Define (Transformation) menu of FIG. 21C provides access to the tools and procedures for calibrating while the Apply (Transformation) menu (FIG. 21D) supports verification. A node can be activated in the Network menu and then a device at the node singled out for calibration within Define.

Clicking on "Node" 241 in the bar atop the Define menu of FIG. 21C opens a pull down providing access to other nodes without requiring a return to the Network menu. Which node is active is indicated at the upper left of the menu 242. Clicking on "Devices" 243 opens a pull-down which lists classes of devices; clicking on a member of that list displays an inventory of devices of that class present at the active node. Selecting a device in this list is the first step in the process of calibration and causes the device to be identified as active 248 at the top of the menu. The classes of devices of particular interest in the invention are imaging colorimeters or imagicals 14 ("imagicals," 244), unitary colorimeters (SOMs 13, capable of measuring discrete tint samples, 245), presses 246 and proofers 247 of hard and soft copy varieties. Clicking on "Procedures" 249 reveals a pull down listing calibration modules 250 such as linearization, Forward Model Generation, etc.

Procedures appropriate to the device can be dragged and dropped into the open field at the center of the menu and linked by connecting arrows. The controlling application software monitors the selections, performs error-checking (with notification and invocation of tutorial material) and links together the modules needed to perform the task if possible. FIG. 21C shows a flowchart for complete calibration of a rendering device encircled by a dotted line 251. In the case of some proofing devices, such as Cathode Ray Tube displays and Dye Sublimation printers, it may be sufficient to perform complete calibration only infrequently. In particular, it is usually adequate to re-compensate for the gamma function of a monitor (a process which falls under "linearization") on a regular basis. Because phosphor chromaticities change very gradually, re-determination of the color mixing functions of the calibration need not be performed as frequently. Therefore, a user may activate the CRT device at his node and specify only linearization in preparation for a proofing conference. Alternatively, the present invention covers the equipment of monitors with devices that can participate in continual verification and recalibration.

The "Apply" Transformation menu (FIG. 21D) provides access to the database of pages and images that are the subject of remote proofing through the "Page/Image" 256 selection in the menu bar. Clicking here displays a shared file structure. Although the (generally) bulky color image data file of interest need not be present in local storage 19 of FIG. 1 at all nodes where proofing is to occur, it is generally desirable to make a local copy so that rendering across the network is not necessary. However, one of the purposes of the Virtual Proof is to make multiple transfers of the bulky data unnecessary. The "Node" 257 and "Devices" 258 elements of the menu bar have effects that are entirely analogous to those in the "Define" menu of FIG. 21C. More than one device at a node can be made active in support of a mode in which interactive annotation and conferencing via the medium of a soft proof on a video display is employed to negotiate changes in a hardcopy, remote proof that is taken to be representative of the ultimate client device.

Figure 21D:
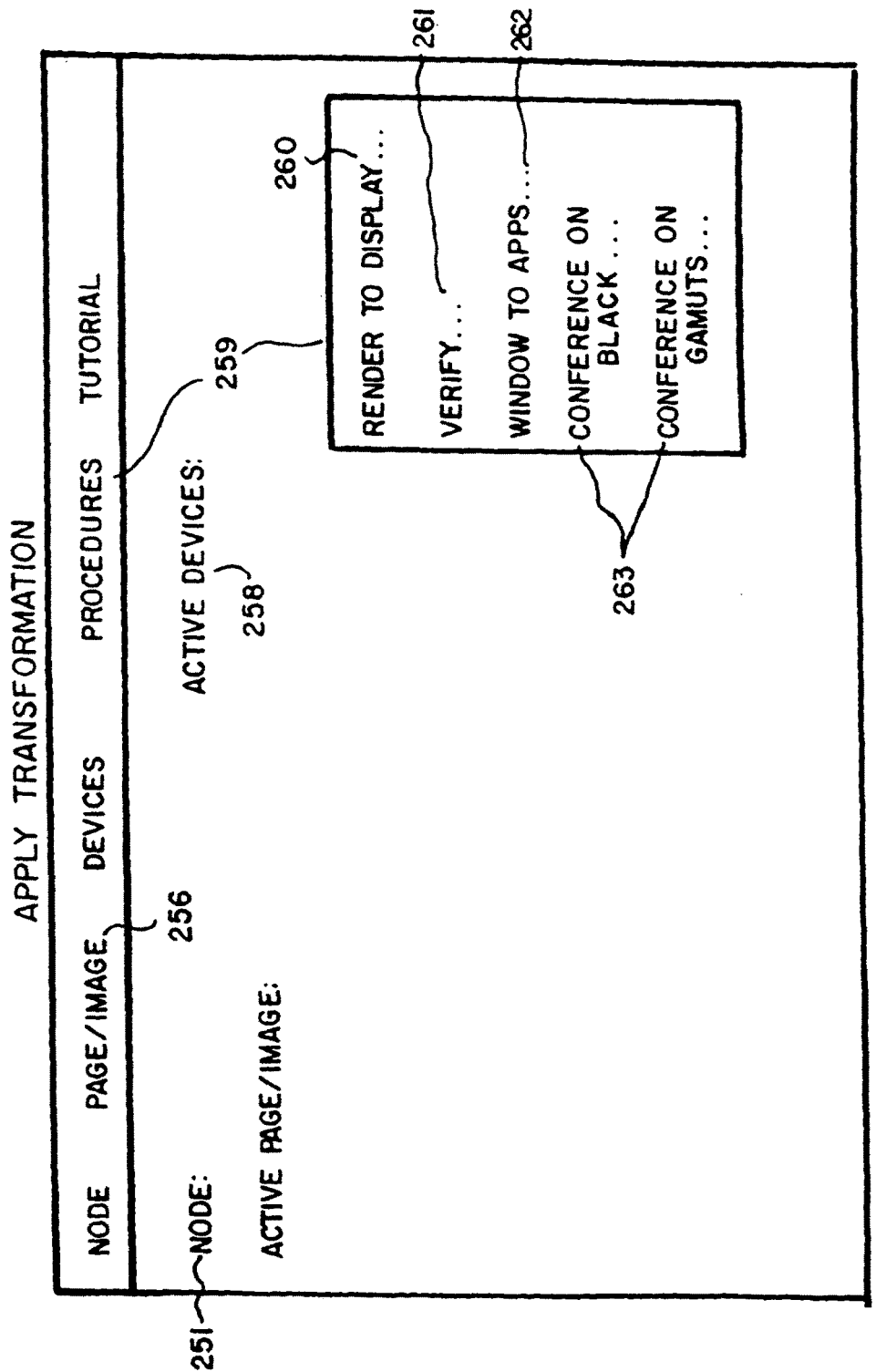
FIG. 21D is a menu at the second level of hierarchy in the GUI to enable a user to oversee the process of using color transformations at a rendering device.

Clicking on "Procedures" 259 in the Apply menu bar of FIG. 21D reveals a pull down that includes functions such as "Render to display . . . " 260, "Verify . . . " 261 and "Window . . . " 262 to external applications. Rendering supports display, either within the Apply window or on a separate, dedicated video display, of imagery a) as the designer imagined it, to the extent that the proofer is capable of showing it, b) as a client device, such as a press, can reproduce it and c) as another proofer is capable of representing the press, including indications of gamut mismatches superimposed on the imagery and location of errors identified by the verification process. To further the example, the virtual proof may mediate a rendering of an image as it appears or will appear on press. If the node includes an imaging colorimeter, then an image of the proof can be captured and analyzed in order to provide verification of how well the proofer represents the client. Without verification, digital proofing and remote proofing for color approval are not really useful.

The Apply menu provides a Window 262 through which to "plug-in" to or to "Xtend" applications such as Adobe Photoshop or Quark Xpress. It also provides the platform for incorporating remote, interactive annotation of the sort provided by Group Logic's imagexpo, reviewed earlier. Imagexpo focuses on marking up images with a virtual grease pencil, a concept that is extended in the present invention to remote conferencing concerning gamut scaling, black utilization and other aspects of the definition of rendering transforms. Aspects of rendering such as black utilization 263 (or gamut operations) can be harmonized across the production network by sharing/exchanging black designs through the virtual proof file structure and mechanism.

Figure 21E:
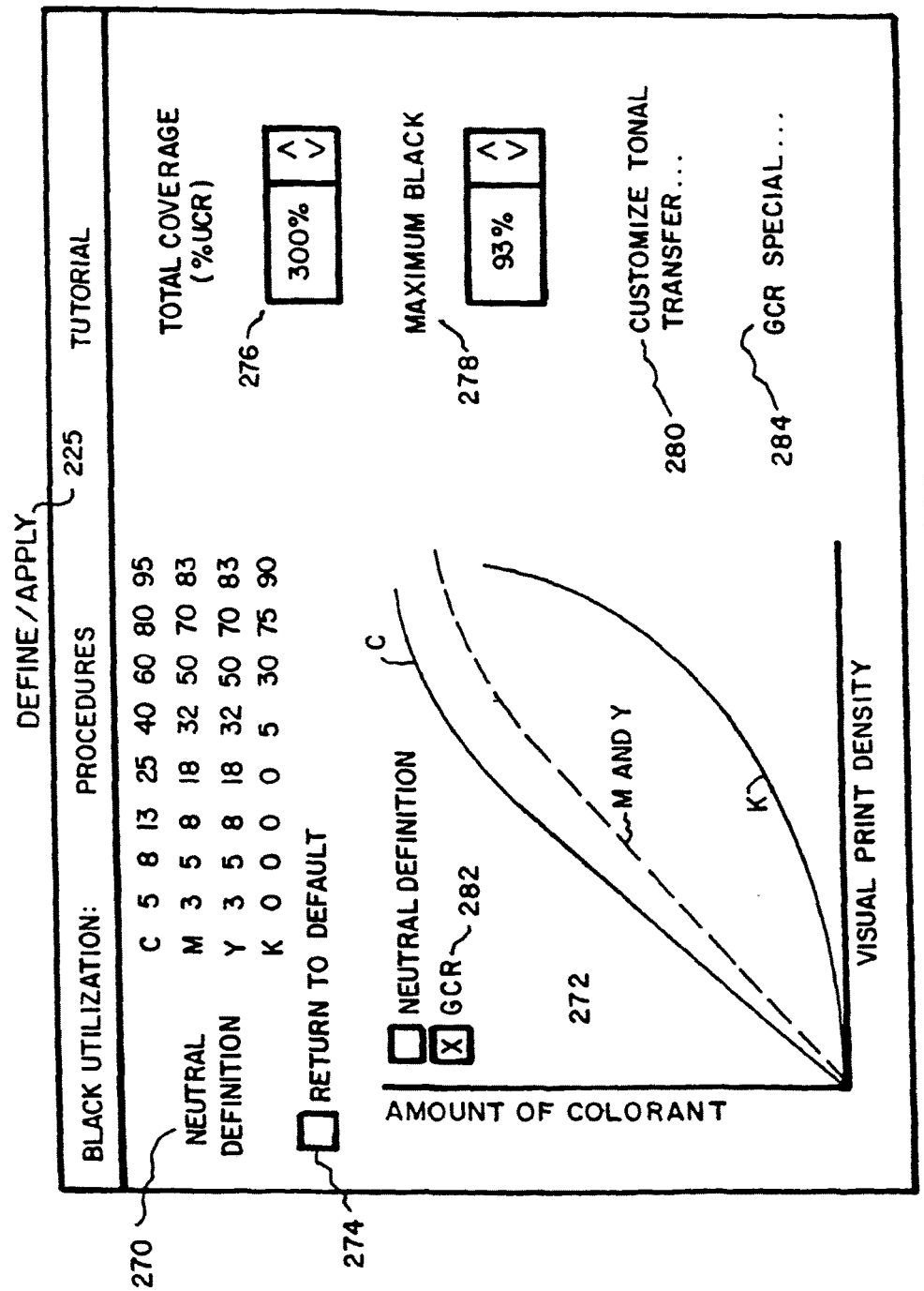
FIG. 21E is a menu at the third level of hierarchy of the GUI which depicts the User interface to black utilization tools in providing black color data, and to neutral colorant definitions.
Figure 21F:
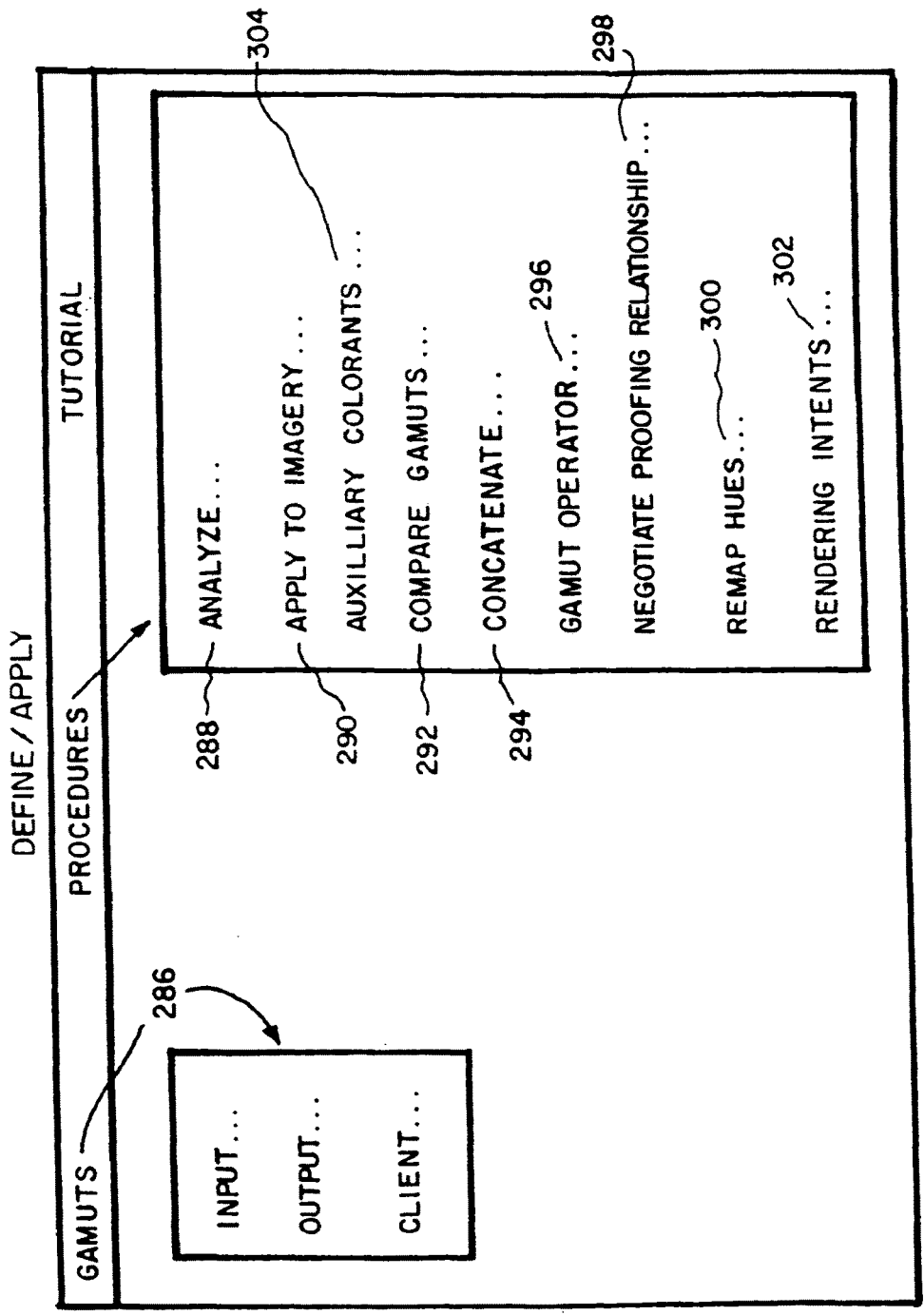
FIG. 21F is a menu at the third level of hierarchy of the GUI which depicts the User interface to gamut processing at a rendering device in the network.

Menus supporting interactive design and selection of user preference data are shown in FIGS. 21E and 21F. A User-Interface to support interactive determination of black utilization is depicted in FIG. 21E. It may be invoked from either Define or Apply menus. At the top right 270 is shown a panel of colorant specifications which are to be considered neutral in color. Users may redefine entries in the panel by clicking and keying or by modifying curves in the graph below 272 provided the graph is toggled to neutral definition rather than GCR. In the neutral definition mode the user may move points on any of the colorant functions; the points are splined together and changes in the graph are reciprocal with changes in the panel. A "return to default" switch 274 provides an easy way to get out of trouble. At the upper right 276, 278, variable readout switches enable definition of maximum colorant coverage and maximum black. At the bottom right 280, "Customize Tonal Transfer" opens the door to user modification of one or more of the 1-dimensional output postconditioning LUTs which are part of the color to colorant transformation. The application warns sternly that the specification of transfer curves which did not prevail during calibration will void the calibration; however, there are situations in which knowledgeable users can make effective use of the flexibility afforded by this function.

When the Graph is switched 282 to GCR mode, the user can control only the shape of the neutral colorant curve; because GCR is colorimetric, the non-neutral curves respond compensatorily to changes in black. The relationship of the curve specified in the graph to the amount of black chosen for a solution at a particular entry in the separation table is as follows: The function shown in the graph represents amounts of the colorants which produce given neutral densities. At each density, there is a range of possible black solutions from minimum to maximum. At the minimum, black is zero or one or more of the non-neutral colorants is maxed out; at the maximum, black is at its limit and/or one or more non-neutral colorants are at their minimum. In this invention, the % GCR is the percentage of the difference between min and max black chosen for a solution. By industry convention, a constant % GCR is seldom desired for all Lightness (density) levels. Therefore, the black curve in the graph defines the % GCR desired as a function of density. Although it is conceivable to make GCR a function of hue angle and Chroma as well as of Lightness, this is usually an unwarranted complexity with one exception: It is useful to graduate GCR with Chroma when preparing transformations for more-than-four colorants as discussed earlier. This need is addressed through the "GCR special . . . " submenu 284 offered at the bottom right of FIG. 21E.

FIG. 21F depicts a GUI screen to gamut operations. Clicking on "Gamuts" reveals a pull-down 286 which provides access to lists of input, output and client gamuts; the latter two are both output gamuts, but a client gamut is known to the system as one that is to be represented on another device. It is possible to drag and drop members from the different types into the field of the menu and to link them with various procedures, as was the case in FIG. 21C. Procedures applicable to the gamuts include: 1) Analyze 288 which displays information on how a particular conditioning transformation was put together (e.g., was it a concatenation of gamut scaling and color aliasing operations?—which ones?) and on gamut compression records, a constituent of the VP which stores key variables of a gamut scaling, such as minimum Lightness, cushion value, functional form, etc. 2) Apply to Imagery 290 enables display of imagery mediated by transformations configured in this or related menus on some device. 3) Compare Gamuts 292 enables visualization, in several forms, of the relationship between the gamuts of two or more devices—this functionality is elaborated in a following paragraph. 4) Concatenate 294 does not apply solely to gamut operations; it links nested or sequential transformations into implicit, net transformations. 5) Gamut Operator 296 provides a graphical display of an operator; this is a different representation of the information available from Analyze 288. 6) Negotiate Proofing Relationship 298 works closely with Compare Gamuts 292; it enables users to make decisions based on information provided by Compare, such as whether to use the Least Common Gamut as the aim point for a network of volume production devices. 7) Remap Hues 300 provides the separable hue adjustment functionality described earlier. 8) Rendering intents 302 is a mechanism for providing users with generic gamut scaling options for accomplishing things like obtaining the most saturated rendering on paper of color originally created in a business graphics application on a video display. Compare Gamuts 292 allows a user to invoke and control the use of gamut filters, which were described earlier in connection with FIG. 17.

System 100 supports the coordination of color control in multisite production in several forms. Because the virtual proof encompasses records of the states of calibration of network devices independent of the color data, application software can define a criterion for reproduction across the network in one of several ways. Based on the states and capabilities of network devices, a criterion may be selected which all devices can satisfy, such as a least common gamut (LCG). LCG defines the aim point for production and the control system strives to minimize the color error with respect to it. Alternatively, users may select one device as the criterion and all others are driven by the controls to match it as closely as possible. Optionally, users may choose to disqualify one or more rendering devices on the network because it/they cannot match the criterion closely enough or due to failures of verification.

Figure 22:
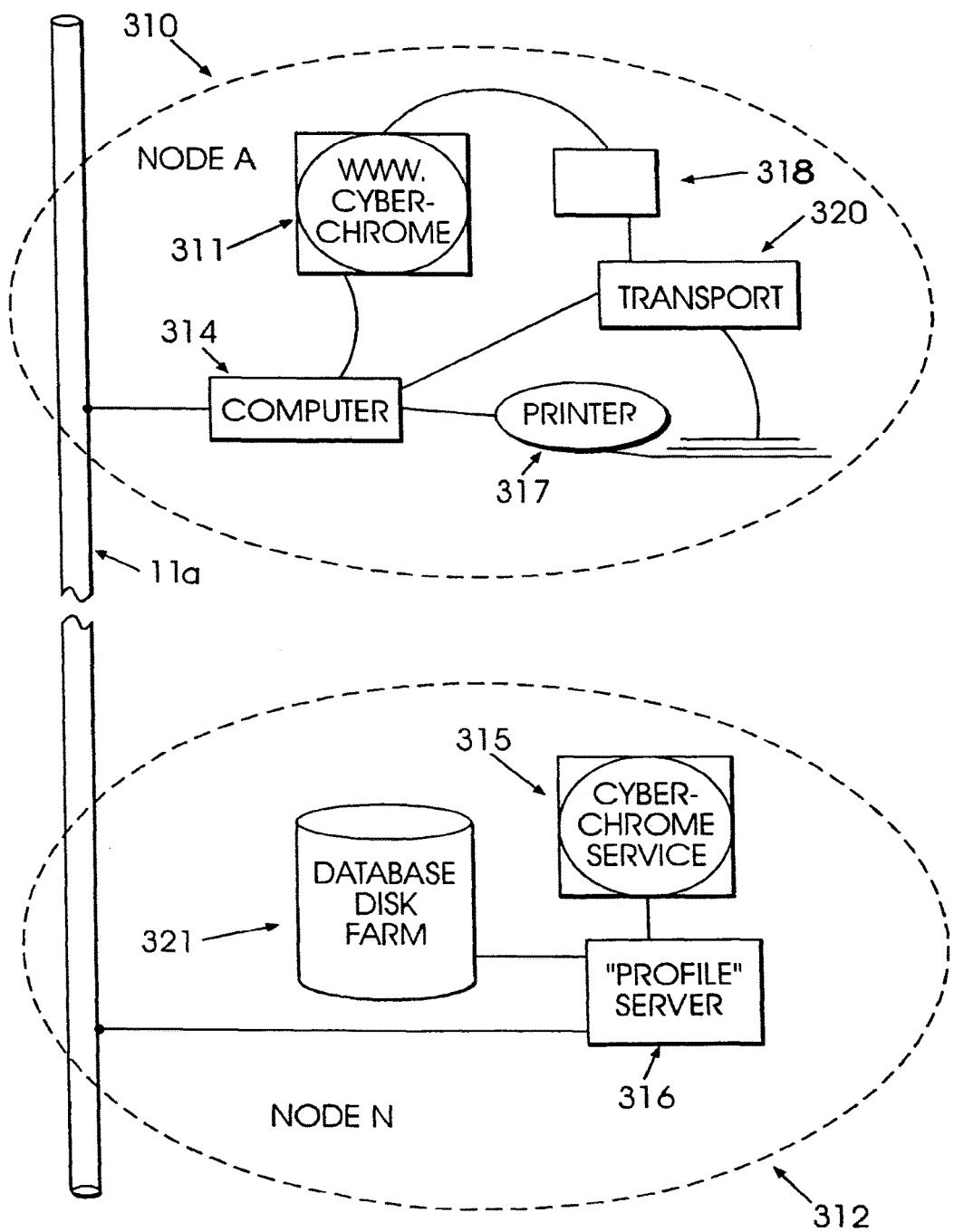
FIG. 22 is a block diagram of an example of the system of FIG. 1.

Referring to FIG. 22, an example of system 100 (FIG. 1) is shown having two nodes of the network. Node N may possess high performance computing processor(s) and, optionally, extensive electronic storage facilities. Node N may also have output devices of various types along with color measurement instrumentation for the calibration of those devices and it may be connected to more than one networks for Virtual Proofing.

In addition to participating in one or more networks for Virtual Proofing, Node N may assist other nodes by computing transformation functions. It may also function as a diagnostic and service center for the networks it supports.

Node A 310 includes components similar to nodes 102 or 104 (FIG. 1) and is linked to other nodes by network link 11*a*. The communication between Node A and Node N is enabled via the Internet or World Wide Web, for example, to a web site service "cyberchrome" 315 at Node N 312. This communication is illustrated by the screen of the video display device 311 being labeled "www.cyberchome". Node A 310 has a computer 314 such as a personal computer or workstation in accordance with application software providing Virtual Proofing as described earlier. Node A 310 need not have a computer other than the processors embedded in the proofing devices or color measurement instrumentation.

In this case, the Virtual Proof for Node A are coordinated by another computer system, such as the computer server 316 at Node N (called hereinafter the profile server), as described earlier in connection with FIG. 1.

Printer 317 is shown for Node A, but not for Node N. A color measurement instrument (CMI) 318 is provided as a module for calibration of the printer. CMI 318 includes a sensor, lamp, reference and control unit (which may itself be of modular design) and a transport mechanism 320 for transporting hard copy of a calibration or verification sheet rendered by printer 317 so that the sheet may be read by the CMI with a minimum of user effort or involvement. Reflection or transmission measurements are facilitated by the transport mechanism 320 for such a sheet, bearing a matrix or array of color samples, which is actuated by click of computer mouse or, preferably, by insertion of the sheet in the transport mechanism. The transport mechanism may be integrated with the printer 317 in which the optical pickup component of the sensor is mounted to move in tandem with the marking head of the device and transport of the copy may be performed by the mechanism of the printer, such as when the printer is an ink jet printer. In either case, the optical pickup link their devices to a control unit for the CMI by fiber optic or by electrical wire link.

The profile server 316 at Node N 312 may consist of a multiprocessor or locally networked array of processors or high performance workstation processor whose performance may be enhanced by special-purpose hardware. The exact architecture (such as RISC or CISC, MIMD or SIMD) is not critical, but needs to provide the capacity to compute quickly color transformation mappings, gamut operations, etc., as described earlier. Any of the processors in the network may have this capability or none may. However, the more responsive the network is in development and modification of Virtual Proof constituents, the more useful it can be. Disk storage or memory 321 (similar to storage 19 in FIG. 1) represents centralized storage of current and historical constituents, which may be shared by one or more nodes on the network. The profile server further provides a database which stores calibration data for rendering devices of the network, such as color profiles (inter-device color translation files), or data needed to generate such profiles. The calibration data produced for each rendering device in the network was described earlier.

Referring to FIGS. 23-32, the calibration of video color monitors or displays shown in FIGS. 1 and 2 will be further described. Video displays play an increasingly important role in color communication. They are used to simulate three-dimensional rendering in synthetic image creation, as such they function as linear, 3-channel, input devices, and are also used ubiquitously in interactive image editing. Further, video displays can be used as soft-proofing devices, thereby providing a video proofer. In the latter application, it is desired to portray an image on a video proofer as it will be rendered on a hard copy device. Although it is not usually possible to match the spatial resolution of hard copy with a soft proof, it is possible to forecast color reproduction.

Although the following describes color calibration of cathode ray tube (CRT) displays, it can also be applied to any video display technology, such as Digital Light Processing (based on Texas Instruments Digital Micromirror Device), flat plasma panels, Liquid Crystal Display panels, etc. The foregoing technologies may be used in front or rear projection applications. An embodiment in which a front projection device is used to project high resolution imagery onto production paper stock was described earlier.

Video displays are highly complicated image reproduction devices, featuring ample adjacency effects (interactions among neighboring pixels, where a neighbor may be spatially removed at some distance.) However, satisfactory results may be obtained by ignoring complex spatial effects and modeling three, separable variables simply: 1) color mixture, 2) gamma or the intensity-voltage relationship and 3) the dependence of luminous output at a pixel on where it is on the screen, independent of its interactions with the level of activity of other pixels.

All video displays behave as light sources and those suited to accurate color reproduction conform to linear rules of color mixture. In other words, they observe, to a reasonable approximation, the principle of superposition. This means that the light measured when all three channels are driven to specified levels equals the sum of the light measured when each is driven separately to the specified level. Also, the spectral emission curve (indicating light output as a function of the wavelength of the light) changes by a constant scale factor as the driving voltage changes.

The last point is illustrated for green phosphor emission in FIG. 23. The emission spectrum is a property of the phosphor and is normally invariant during the useful life of the CRT. The graph shows the activity in the green channel, as a function of wavelength, when driven full scale at digital level 255, denoted by numeral 322, compared with 15 times the activity in response to digital level 64, denoted by numeral 323. The fact that the two curves superimpose means that they differ by a factor which does not depend on wavelength—a linear property important for color mixture. However, the scale factors are not linear with digital drive levels, a manifestation of non-linear gamma in the device. The derivation of color mixing transformation matrices capable of translating RGB device codes for a particular monitor into XYZ TriStimulus Values or vice versa is described, for example, in Holub, Kearsley and Pearson, "Color Systems Calibration for Graphic Arts. II: Output Devices," J. Imag. Technol., Vol. 14, pp. 53-60, April 1988, and in R. Berns et al., "CRT Colorimetry, Part I Theory and Practices, Part II Metrology," Color Research and Application, Vol. 18, Part I pp. 299-314 and Part II pp. 315-325, October 1993.

It has been observed that the spectral emission functions of CRT phosphors do not change over significant periods of time. This means that for a large class of displays, the data needed for color mixture modeling can be measured once, preferably at the factory, and relied on for most of the useful life of the monitor. Phosphor spectra and/or chromaticities measured at the factory may be stored in Read Only Memory (ROM) in the display, they may be written on a disk and shipped with the monitor or, preferably, they may be stored in association with the monitor's serial number in a "Cyberchrome" database at Node N 312 of FIG. 22. It is preferable if spectral data are captured and stored. In the database, they can be made accessible to networks for Virtual Proofing via restricted, keyed access, using typical encryption and security schemes for the Internet.

The balance of Red, Green and Blue channels does vary continually, often requiring adjustment at least daily. RGB balance determines the white point. Key variables subject to change in the R, G and B channels are the bias and gain. The bias, or offset, determines the activity in the channel at very low levels of input from the host computer system, while the gain determines the rate of increase in activity as digital drive increases and the maximum output. Bias and gain controls usually interact within a color channel, but should not interact between channels if the superposition condition is to be satisfied. The gamma of a channel is the slope of the relationship giving log light intensity, usually in units of CIE Luminance, or Y, and log digital drive supplied by the host computer system. In order to maintain a given white balance and overall stability of tone and color reproduction, it is necessary to regulate the bias and gain in the three channels. Consistency of gamma is the main determinant of tone reproduction, while white point stability depends on the balance of activity in the three channels.

Ambient illumination refers to light that reflects off the faceplate (or screen) of the display and whose sources are in the surrounding environment. Light so reflected adds to light emitted by the display. A viewer may not be able to distinguish the sources. At low to moderate levels, ambient illumination affects mostly the dark point of the display causing a loss of perceptible shadow detail and, possibly, a change in shadow colors. In effect, gamma (and tone reproduction) are modified, along with gray balance in the shadows. Generally, it is preferable to detect and alert to the presence of ambient contamination so that users can control it than to incorporate ambient influences into the calibration.

The foregoing several paragraphs are meant to set the stage for discussion of monitor calibration in the color imaging system of the present invention.

It is often very difficult to build a good colorimeter, as discussed in the article by R. Holub, "Colorimetry for the Masses?" Pre magazine, May/June, 1995, for video displays. Accurate, repeatable ones are expensive; for example, one marketed by Graseby Optronics sells for around $6000, currently, and a fine instrument by LMT costs considerably more. FIG. 23A shows a comparison between measurement of spectral emission of a red phosphor of EBU type by a PhotoResearch PR700 Spectroradiometer 324 and a Colortron II 325. The plots make clear that an instrument capable of resolving 2 nanometer increments can resolve the complex peaks in the phosphor's spectrum while Colortron cannot. Colortron is a low-resolution, serial spectro as discussed in the earlier cited article "Colorimetry for the Masses?". Calculations of TriStimulus Values and chromaticities based on the two spectra reveal significant errors in the estimation of red chromaticity with Colortron II.

The foregoing analysis suggests that, for phosphor-based displays, at least, continual colorimetry is not required to maintain good calibration. Thus, maintenance of gamma and white balance and monitoring of ambient influences is all that should be required for a phosphor-based display. Such maintenance is described later is connection with FIG. 32.

Figure 24:
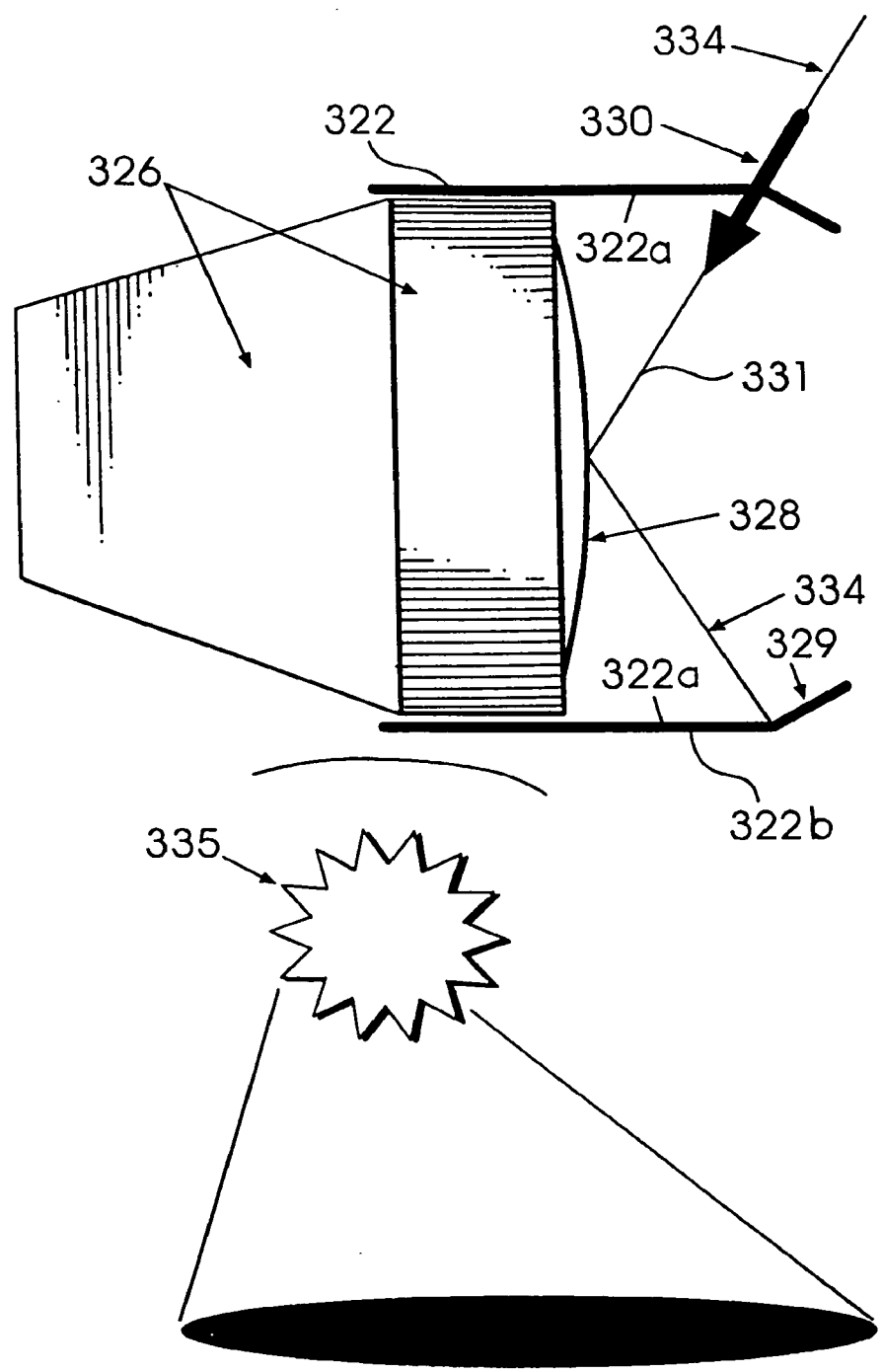
FIG. 24 is a block diagram of the configuration of a color measuring instrument for a video screen display which is similar to FIG. 2.

FIG. 24 shows a configuration of color display 326 (i.e., CRT), cowel and color measurement instrument, as generally shown in FIG. 2, that enables very accurate, inexpensive and automatic maintenance of CRT display calibration. Additional features of this configuration will become apparent from the following discussion of FIGS. 24, 24A, 24B, 24C and 24D.

The cowel 322 is circumferential and helps to shield the faceplate 328 from stray light coming from any direction, including the desktop on which the display 326 may be located. Cowel 322 is black-coated on inner faces 322a to absorb light. The cowel 322 forms a light trap 329 for the embedded sensor 330 coupled to the cowel. A small lamp 335 is located beneath the lower flange 322b of the cowel. Lamp 335 illuminates the desktop without influencing the display significantly in circumstances when overall room illumination is kept low for good viewing.

A sensor 330, often referred to herein as an electro-optical pickup, is lodged in the cowel. It views approximate screen center, denoted by line 331, (however other areas of the screen may be viewed) collecting and focusing light onto the sensor. The line of sight 334 reflects off the screen 328 and into the light trap 329 formed by the lower flange of the cowel, so that specularly reflected light will not enter the sensor. It permits unattended calibration, possibly during screen-saver cycles or at other times when the operating system of the computer at a node is not scheduling activities which would compete with calibration. Because the sensor 330 is perched in the cowel 332, it does not require user involvement to be affixed to the screen, it leaves no saliva or other residue on the faceplate, it does not contribute to desktop clutter and it is well positioned to monitor ambient illumination influences.

Figure 24A:
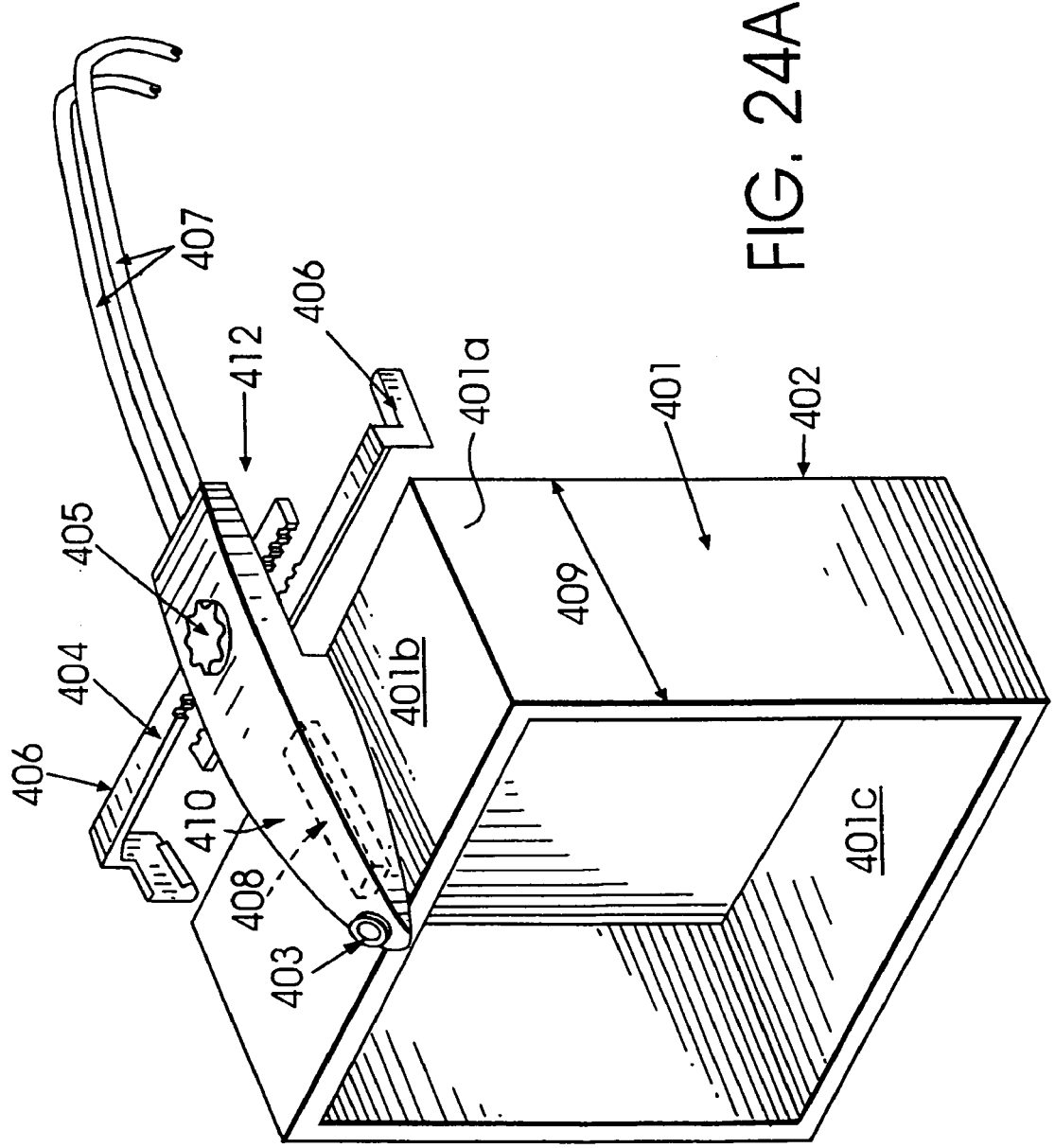
FIG. 24A is a perspective view showing an example of an assembly for mounting a color measuring instrument to a video screen display.
Figure 24B:
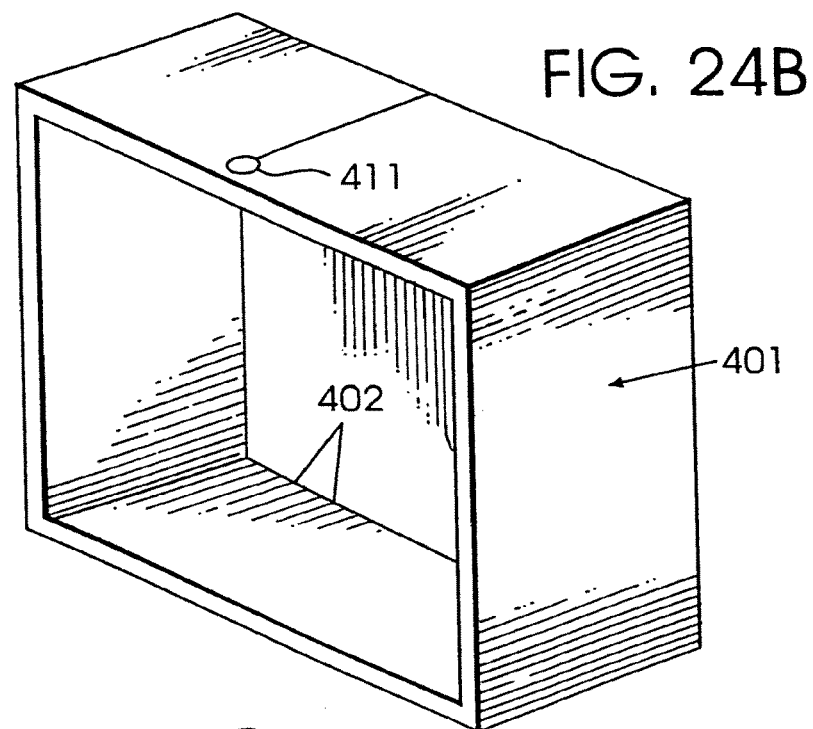
FIGS. 24B, 24C and 24D are perspective view of the cowel, arm member, and one of the brackets, respectively, of FIG. 24A.
Figure 24C:
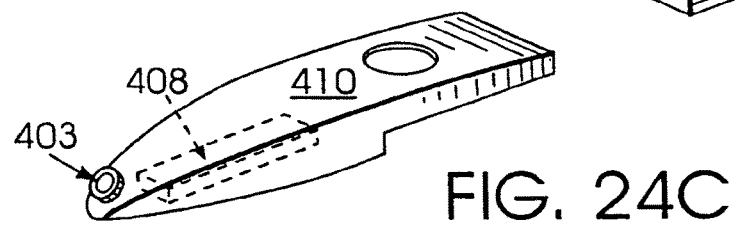
Figure 24D:
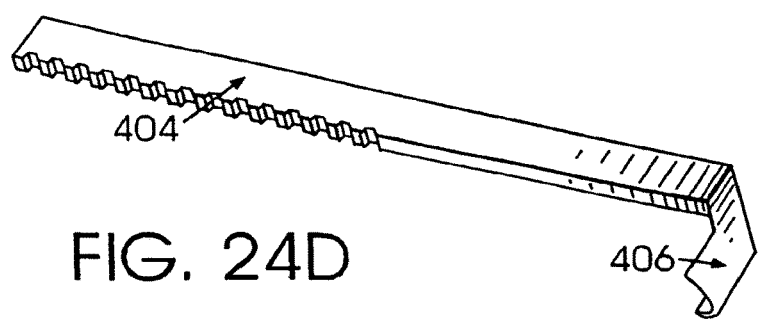

FIG. 24A shows an example of the assembly of cowel and sensor for a color monitor, wherein the circumferential cowel 401, arm member 410, and one of the brackets 404 of FIG. 24A are separately shown in FIGS. 24B, 24C, and 24D, respectively. To satisfy the goal of adapting the cowel to monitors of different size and make, the circumferential cowel 401 is a separable part which can be sized apropos of 17, 20, 21 or 24 inch or other size monitors. It can be made of any material, but preferably is of light weight plastic. The rear edge 402 of the cowel 401 rests against that part of the plastic monitor cover which frames the faceplate of a typical monitor. This has two advantages: First, it provides relief to the mechanism 412 which suspends and supports the circumferential flange 401a of the cowel 401 because a significant component of the force of support is into the front of the monitor chassis. Second, the upper flange 401b of the cowel 401 will support the electro-optical pickup head at socket 403 at a correct and predictable angle of view of the screen.

The mechanism 412 for supporting circumferential cowel 401 on the monitor includes a rack and pinion adjustment mechanism having an extending arm member 410 with a knob and gear 405 to allow adjustment of two brackets 404 having teeth which engage opposite sides of the gear 405. The brackets 404 have ends 406 which attach to the top right and left corners of the monitor's chassis. In other words, adjustment of the knob causes two foam feet at either end 406 of the brackets to move in and out so as to control their pressure against the sides of the chassis. In other words, the sliding bracket rests atop the monitor's chassis and is held in place by an adjustable press fit to the sides of the chassis. It, in turn, provides additional support to the circumferential flange 401a. Arm member 410 connects the brackets 404 to the circumferential flange 401, such as by screws coupling arm member 410 and upper flange 401(b) together. Alternatively, the knob and gear 405 could be replaced by a friction-fitted tube sliding within a sleeve. Cables 407 represents wires being led from the electro-optic components in socket 403 back to an interface such as Universal Serial Bus, of the computer 314 coupled to the monitor 311 (FIG. 22). However, it could also represent an alternate means of attachment, if it were made adjustable front to back of the monitor's chassis. The arm member 410 rests partially on the circumferential flange 401 at upper flange 401(b) and provides a housing for the electronics (circuitry) 408 associated with the electro-optic unit which plugs in at socket 403.

The depth, denoted by numeral 409 of the circumferential flange 401a is the distance from its outermost edge along a perpendicular to the point at which it rests against the monitor's chassis. Due to contouring of the chassis or the cowel (in the interests of a good fit to the chassis or of aesthetics) the depth may vary around the circumference. We have chosen, for example, a depth of 8 inches, on average, to effect a trade off between two factors: the degree of shielding of the viewing area of the screen from environmental stray light (ambient), and the desirability of enabling more than one user an unimpeded view of the screen at one time. At 8 inches, it should be possible for 2 or 3 people seated in front to see the full screen and for 2 or 3 people standing behind them also to see. However, the particulars cited here are not meant to limit the generality of the invention.

Many users like to conduct soft proofing under circumstances in which the hard copy proof may be available for comparison to the soft proof visualized on the monitor. Under said circumstances, it is important to control the viewing conditions of the hard copy. A viewing hood such as the SoftView™ made by Graphic Technologies, Inc. is often used for this purpose. However, it is also important to insure that the viewing hood doesn't contribute to stray light and that it is positioned to facilitate soft- and hard-proof comparisons.

Figure 25:
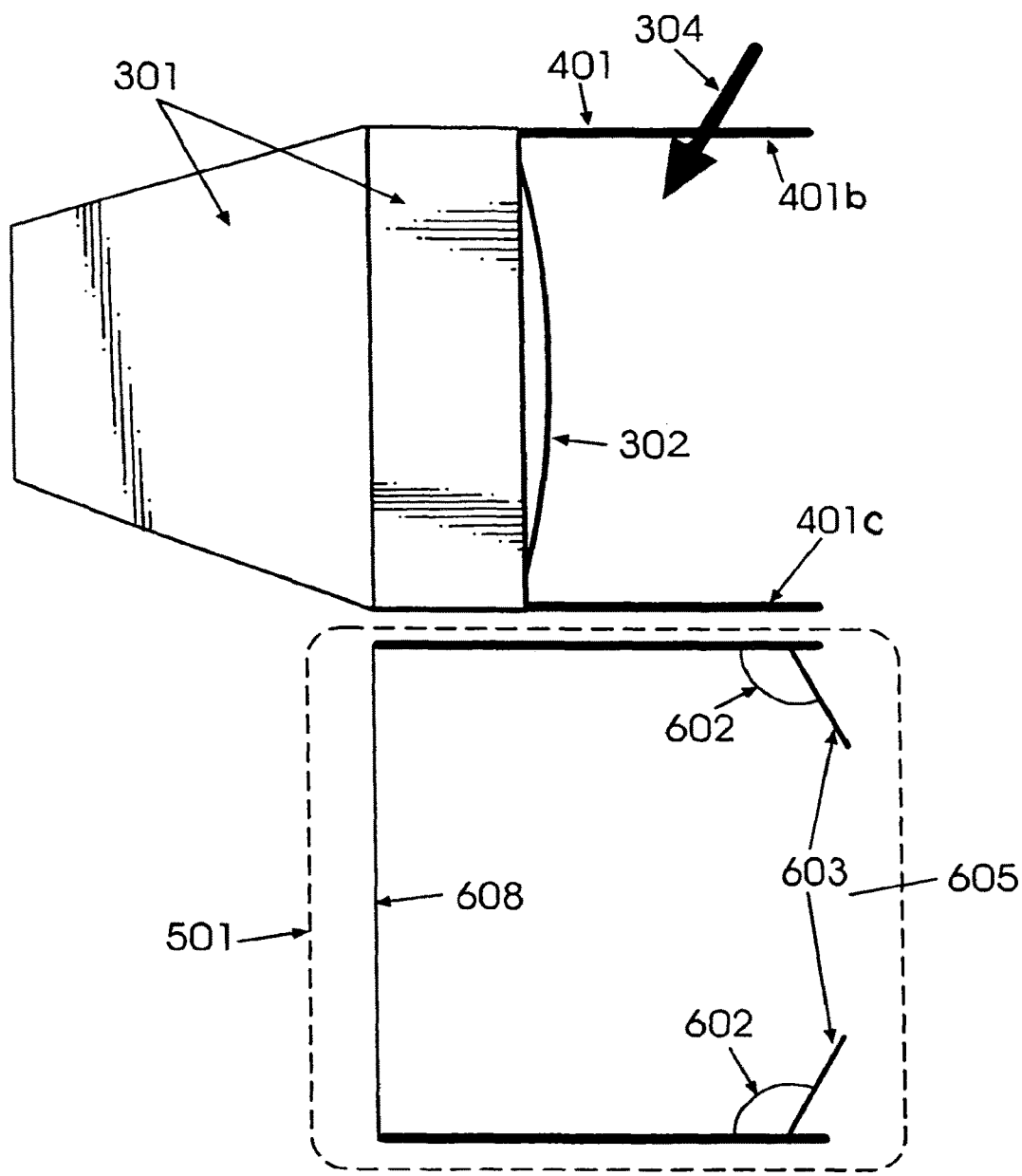
FIG. 25 is a block diagram of the configuration of a color measuring instrument for a video screen display of FIG. 24 which includes a viewing box.

Accordingly, the viewing box (or reflection viewer or hood) 501 shown in FIG. 25 may optionally be provided at Node A 310 (FIG. 22) which is integrated with the cowel 401. FIG. 25 shows an arrangement in which the video display is raised up on a pedestal with viewing box positioned below, so that the top side of the box is contiguous with the bottom flange 401c of the cowel. One side of the box has an opening 605 opposite the back wall 608 of the box upon which media is locatable. Other arrangements are possible, for example, some workspace arrangements may call for situating viewing hood and monitor side-by-side, i.e., integrated to the right or left side of the cowel, and oriented at an angle so as to optimize viewing at relatively short range.

Figure 26:
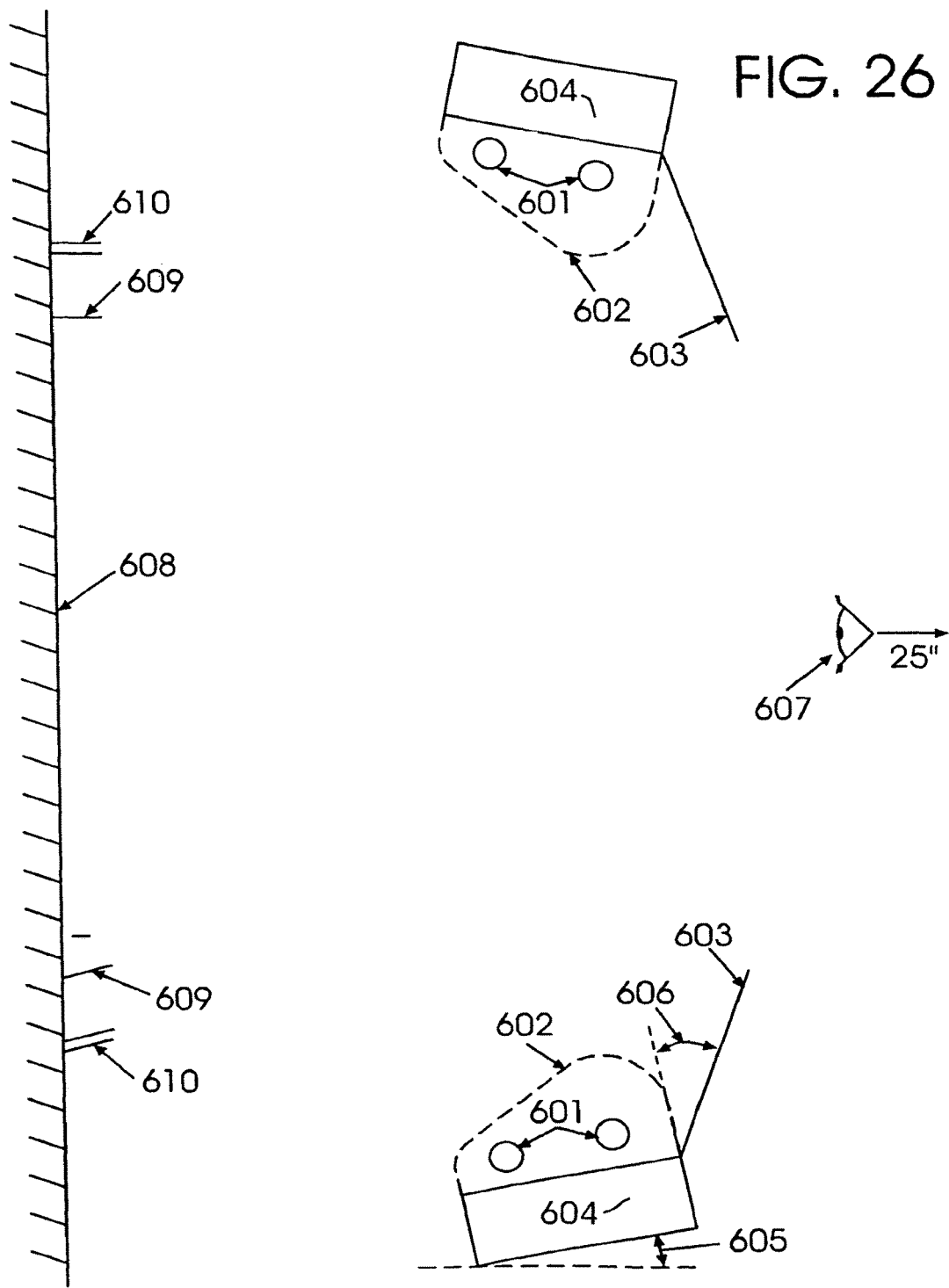
FIG. 26 is a block diagram showing the viewing box of FIG. 25 in further detail.

FIG. 26 is a scale drawing, showing the configuration of light sources 601, lenses 602 and reflectors 603 in the viewing box 501, whose size should be adequate to accommodate at least a two-page spread in publication terms (11×17 inches.) At top and bottom (or left and right) are ballasts 604 which can accept one or two (depending on required illumination levels) Daylight 5000-simulating fluorescent lamps. D5000 is mentioned merely because it is a standard illuminant in certain industries; in other industries, the choice might be different. Approximately pear-shaped plastic lenses serve to diffuse and disperse the light. The lenses should be frosted or waffled (rippled lenticularly) so as to enhance diffusion of light and should not greatly change the color temperature of the fluorescent light.

Any direct sighting of the lamps/diffusers by the viewer 501 (in normal use) is prevented by reflectors 603 which are aluminized or chromed on the side facing inward toward the copy so as to reflect and further disperse the light. The configuration depicted has been shown to result in very uniform, diffuse illumination over the area of at least a two page spread. Angles 605 and 606 are approximately 14° and 34°, respectively. An eye 607 is depicted on a line of sight which should extend at least 25 inches back from the rear viewing surface 608 of the viewing box. The single lines 609 and double lines 610 indicate the extent of the illuminated back wall of the viewer which can be seen from distances of 40 inches and 30 inches, respectively.

The above discussed assembly is preferably equipped with a dimmer. This, along with the choice of number of fluorescent tubes, allows critical control of the brightness levels within the viewing box. Brightness should be made as similar to that of a full-field white on the video display as possible. An additional option for the viewing box 501 is the installation, in the back wall 608, of a light box able to accommodate 8×10 or smaller color transparencies, as is provided in other conventional viewing hoods used in industry.

As explained previously, the primary chromaticities of phosphor-based displays are very constant over time. Therefore, the sensor coupled to cowel 332 (FIG. 24) or 401 (FIG. 24A) should be a simple, calibrated luminance meter, called hereinafter lumeter, sufficient to maintain white balance and gamma and to detect significant increases in ambient illumination over the norm.

However, display technologies which rely on light sources, such as LCD or DMD as defined earlier, may experience drift in primary chromaticities as the external light source ages. It is common for front or rear projection displays based on liquid crystals or digital micromirrors to employ metal halide lamps or xenon arcs. The spectral distribution of the former certainly changes with time and that of the latter may under some circumstances. In these cases, adequate control of color balance requires ongoing colorimetry, such as provided by a spectral based CMI. Even with CRTs, there are occasions in which adequate calibration or re-calibration may involve a color-capable device. For instance, it may be desirable to retrofit a CRT which was not calibrated at the factory with the invention in order to confer its benefits on a user. Accordingly, several types of electro-optic modules are described below, from a Lumeter to a spectral device.

Figure 27:
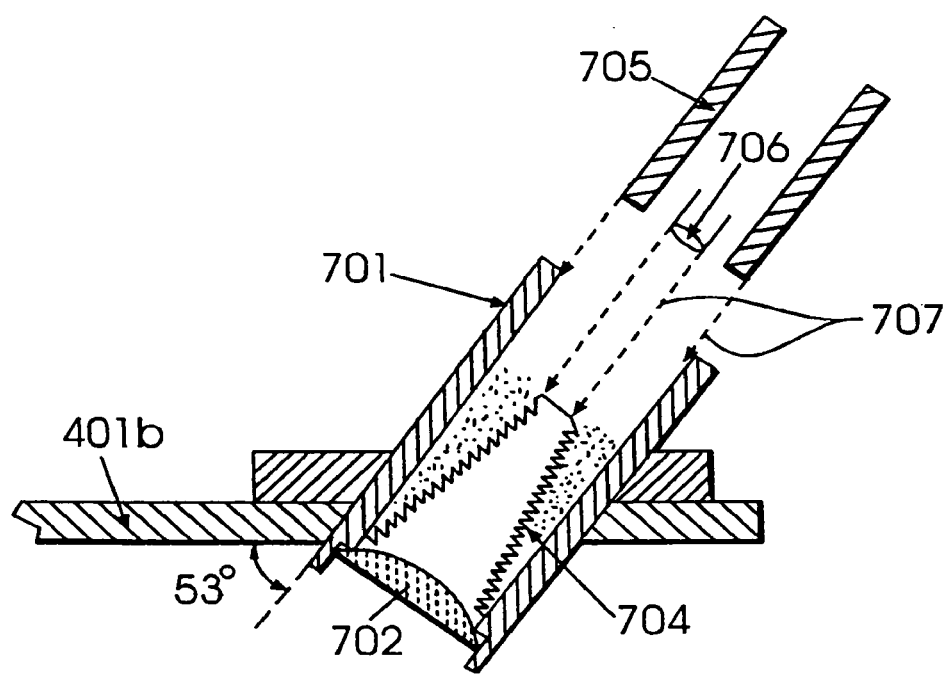
FIG. 27 is a block diagram of part of the sensor of the color measurement instrument located in the cowel of the assembly of FIG. 24A.

Referring to FIG. 27, a cross-section of part of the sensor integrated with the upper flange 401*b* of the cowel in socket 403 (FIG. 24A) is shown having a housing 701 including optics. On the assumption that the center of the outer edge of the upper flange is 7.5 to 8 inches from the chassis and that the flat surface of the flange is perpendicular to the faceplate, the center of the hole bored for the lens tube is 6 inches out. The bore is cocked at an angle of 53° to the flat surface of the flange so as to look at the approximate center of a nominal 21 inch screen. For example, the length of socket 403 may be 2 inches, and 1 inch in diameter.

The lens 702, shown in cross section in the tube, is a commercial grade condenser, plano-convex with diameter of about 20 mm and focal length of about 25.4 mm. It actually forms an image of what is at screen center about 36 mm behind the lens, presumably due to the diffuse and divergent nature of the light source. The inner surface of housing 701 should be very light absorbent. It should be painted flat black, or, preferably, outfitted with a conical baffle 704 with porous black inner surface. The above numerical values of components in FIG. 27 are exemplary, and other values may be used. In particular, a 53° angle is not quite as desirable as 45°, but the important consideration is that the line of sight reflected off the center of the faceplate intersect the black trap formed by the bottom flange of the cowel, as shown in FIG. 23. The black trap shields the sensor from light rays specularly reflected off the faceplate of the monitor.

FIG. 27 also shows an inner tube 705 which slides into the outer lens tube on tracks 707. It is used to bring either a photodiode array or a fiber optic 706 up to the focal plane behind the lens. The photodiode array is employed in the simple lumeter while the fiber optic pickup is used with a spectrograph. In the lumeter, it is desirable not to position the sensor exactly in the focal plane so as to induce a little blurring over the sensor. In the case of the spectrograph, the fiber optic should be chosen to have an acceptance angle which is as compatible as possible with lens 702 and with the spectrograph to which it is coupled.

Separate tubes may be used for the lumeter and the spectrograph. The former could employ a non-achromatic plastic lens whereas the latter benefits from a glass achromat. The two kinds of tube should mate with the flange interchangeably.

Figure 28:
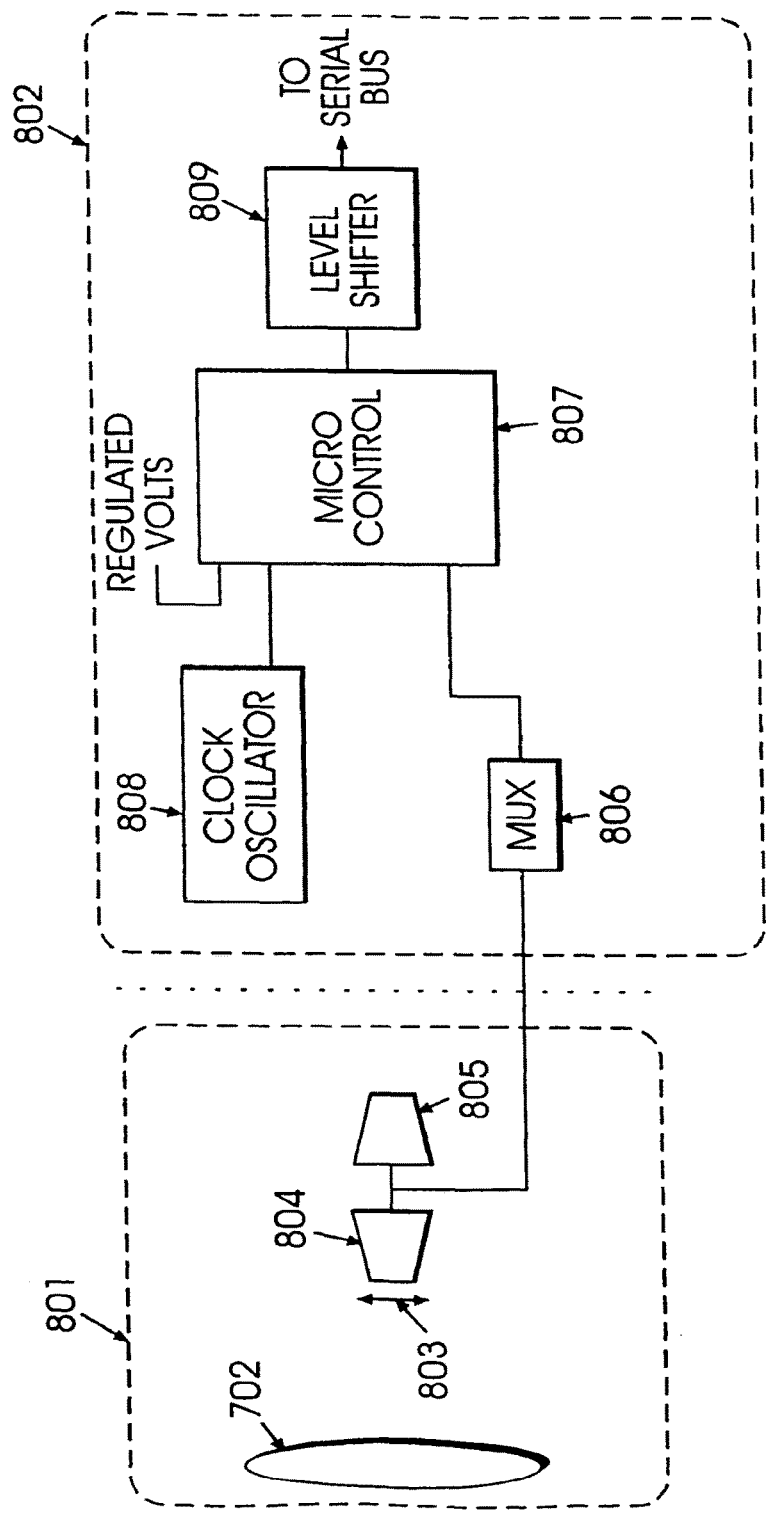
FIG. 28 is a block diagram of the color measurement instrument with the sensor of FIG. 27 and control circuitry.

Referring to FIG. 28, a block diagram of the lumeter is shown with control circuitry. The lumeter includes two parts which may be combined or separate from each other, an electro-optic pickup head 801 and the control and interface electronics circuitry (controller) 802. The electro-optic pickup head 801 includes a lens 702 which converges light onto sensor 804 through spectrally selective filter 803 which must, at the least, attenuate Infrared radiation greatly. Another sensor 805 is an optional sensor identical to sensor 804 except that it is thoroughly light-baffled (i.e., protected from receiving any light).

Sensor 804 may be a photodiode array incorporated in a TSL 230, the programmable member of Texas Instruments' Light-to-Frequency converter (LTFC) family. The device integrates photosensors with an amplification stage and a current to frequency output stage which interfaces directly to a counter on a microcontroller. The lumeter described is very desirable because of the high levels of sensitivity, repeatability and low parts count.

Because its output is a pulse train, the TSL 23X device can be coupled to the control electronics 802 by a lead of up to several feet. Therefore, the device may be fitted into the inner tube with ample baffling and positioned near focal plane. Wires are lead back to the circuit board containing the control electronics. In this way, the electro-optical pickup head 801 can be very compact. As stated earlier, the control electronics 802 may be located in a housing or cavity 408 (FIG. 24A) in arm member 410 connecting the brackets 404 to the circumferential flange. Such control electronics may also be located in a separate circuit enclosure.

Circuitry 802 consists of the control and interface electronics, including a microcontroller 807 having an on-board hardware counter whose overflows are counted in software. This enables long light integration times. A multiplexer 806 of circuitry 802 selects between the two sensors 804 and 805 when both are available, while timing is controlled by a clock oscillator 808. A level shifter 809 provides an interface for adjusting the output of the microcontroller for RS232, RS422, or other communication protocol, such interface may be a USB (Universal Serial Bus) interface.

The lumeter operates by cumulating pulses from the '23X Light-to-Frequency Converter (LTFC) so as to perform A/D conversion by integration. It is best to use some means to ascertain the refresh frequency of the display and to set the integration time to be an integral multiple of the refresh period. One means is to read back the refresh frequency from the processor in the display. Another is to measure it with the lumeter, taking advantage of Fast Fourier Transform algorithms and techniques, such as described, for example, in application notes published by Texas Instruments for the TSL 23X. However, it is also acceptable to set an integration time such that errors due to incomplete refresh cycles are small. An integration time of 5 seconds satisfies this criterion for a 75 Hz refresh rate.

FIG. 29 shows a basic command set used by the host computer to communicate with the lumeter. For example, the series of ascii strings "<E1>" "<P0>" "<D0>" "<S2>" "<T5F5>" is used to initialize the lumeter for data collection, where the ascii strings are enclosed in quotation marks. The effects are to turn on echoing from the lumeter back to the host, to power up the sensor so that it stays "awake" once a sensitivity command is issued, to program frequency division to a factor of 1, to set sensitivity to 100, i.e., use all available photosensors, and to set the integration time to 5 seconds However, in production, it is preferable for most applications to use a non-programmable version of the LTFC such as the TSL 235.

Figure 30:
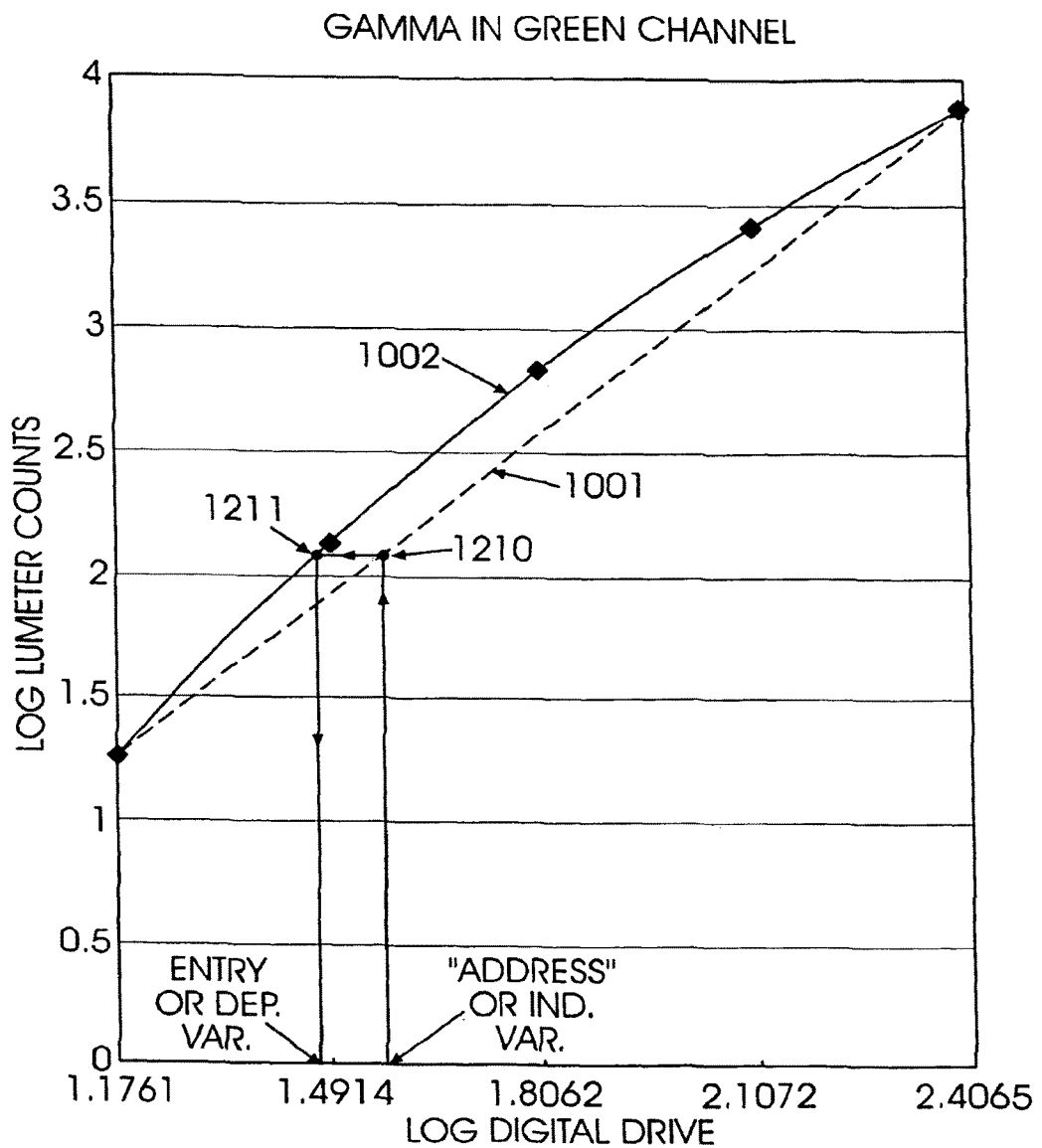
FIG. 30 is a graph of the gamma of the green color channel of the color measurement instrument of FIG. 28.

Intensity/Voltage data collected with a reference spectro-radiometer (a PhotoResearch PR700) and with a lumeter are assembled in Table I below. These are the data needed to calculate gamma. Data are presented for several conditions which test the generality and robustness of the design. FIG. 30 exemplifies the summary data analysis. The actual points 1002 come from the fourth and fifth columns of the second data set, namely full screen green at 23° C. ambient temperature. The values of gamma quoted in what follows are the slopes of straight lines such as 1001.

TABLE I

Measurement of Intensity/Voltage Characteristic for Several Conditions

| Digital Code | Lumeter Counts | PR700 Luminance | Log Digital | Log Lumeter | Log Luminance |
|---|---|---|---|---|---|
| Measured for 6" by 6" square centered in screen, green channel | | | | | |
| 15 | 10 | 0.0398 | 1.1761 | 1 | −1.3997 |
| 31 | 65 | 0.3408 | 1.4914 | 1.8129 | −0.4675 |
| 64 | 350 | 2.191 | 1.8062 | 2.5441 | 0.3406 |
| 128 | 1349 | 9.552 | 2.1072 | 3.13 | 0.9801 |
| 255(max) | 4503 | 33.73 | 2.4065 | 3.6535 | 1.528 |
| Measured from full screen, green channel, room temperature of 23 C. | | | | | |
| 15 | 18 | 0.0397 | 1.1761 | 1.2553 | −1.4008 |
| 31 | 132 | 0.3532 | 1.4914 | 2.1206 | −0.452 |
| 64 | 699 | 2.185 | 1.8062 | 2.8445 | 0.3395 |
| 128 | 2627 | 9.401 | 2.1072 | 3.4195 | 0.9732 |
| 255(max) | 8537 | 32.63 | 2.4065 | 3.9313 | 1.5136 |
| Measured from full screen, green channel, room temperature of 30 C. | | | | | |
| 15 | 23 | 0.0495 | 1.1761 | 1.3617 | −1.3057 |
| 31 | 144 | 0.3883 | 1.4914 | 2.1584 | −0.4108 |
| 64 | 732 | 2.311 | 1.8062 | 2.8645 | 0.3638 |
| 128 | 2696 | 9.642 | 2.1072 | 3.4307 | 0.9842 |
| 255(max) | 8656 | 33.05 | 2.4065 | 3.9373 | 1.5192 |

Gammas calculated in the manner of FIG. 30 for the various conditions are:
 a) for the Lumeter, 2.15, 2.17 and 2.08 for the 6×6 square at 23 C, full field at 23 C and full field at 30 C, and
 b) for the PR700, 2.37, 2.36 and 2.29 for the same conditions, respectively.

Lumeter-derived gammas are a fixed percentage of PR700 values, indicating a robust calibration strategy and good immunity from field size. Both instruments appear to have good temperature compensation; however, there is about a 5% loss of gamma at the higher temperature. This is due to increase in dark current at the higher temperature. For applications in which higher temperatures may be encountered and accuracy to better than 1% is desired, a second, light-baffled sensor (805 in FIG. 28) should be added. Adding a temperature-sensing detector is less expensive than shuttering the system, however a shutter for sensor 804 could alternatively be used. Because sensor 805 is baffled, its readings indicate the dark current which can be calibrated against temperature. Background temperature readings can be taken with long integration cycles to insure accuracy when the instrument is not being used for video display calibration.

The gammas discussed above are not identical to those of a true luminance meter because the lumeter does not have the photopic sensitivity function. However, it is preferable to save the spectral emission characteristics of each phosphor channel, as noted earlier, and to measure the spectral sensitivity function of each lumeter as part of the calibration process. In that way, it will be possible to calculate exactly the relations between true luminosity data and lumeter responses for any phosphor set and any actual lumeter. This is done by convolving (with a shift parameter of zero) the spectral emission function with the human sensitivity function and with the lumeter's spectral sensitivity. In this we are helped by the linear scaling of spectral emission with drive voltage. However, if spectral data on phosphors is not available, very good calibrations will be possible based upon generic data.

The lumeter provides reproducible results from day to day, and is at least as stable as typical reference light sources, given a suitable choice of spectral filtering and a stable lens material. Therefore, the only aspect of self-calibration which is of concern is the monitoring of temperature-dependent dark signal. This is accommodated in the invention so that the lumeter is self-calibrating, automatic and non-contact, as will be described later below.

Figure 31:
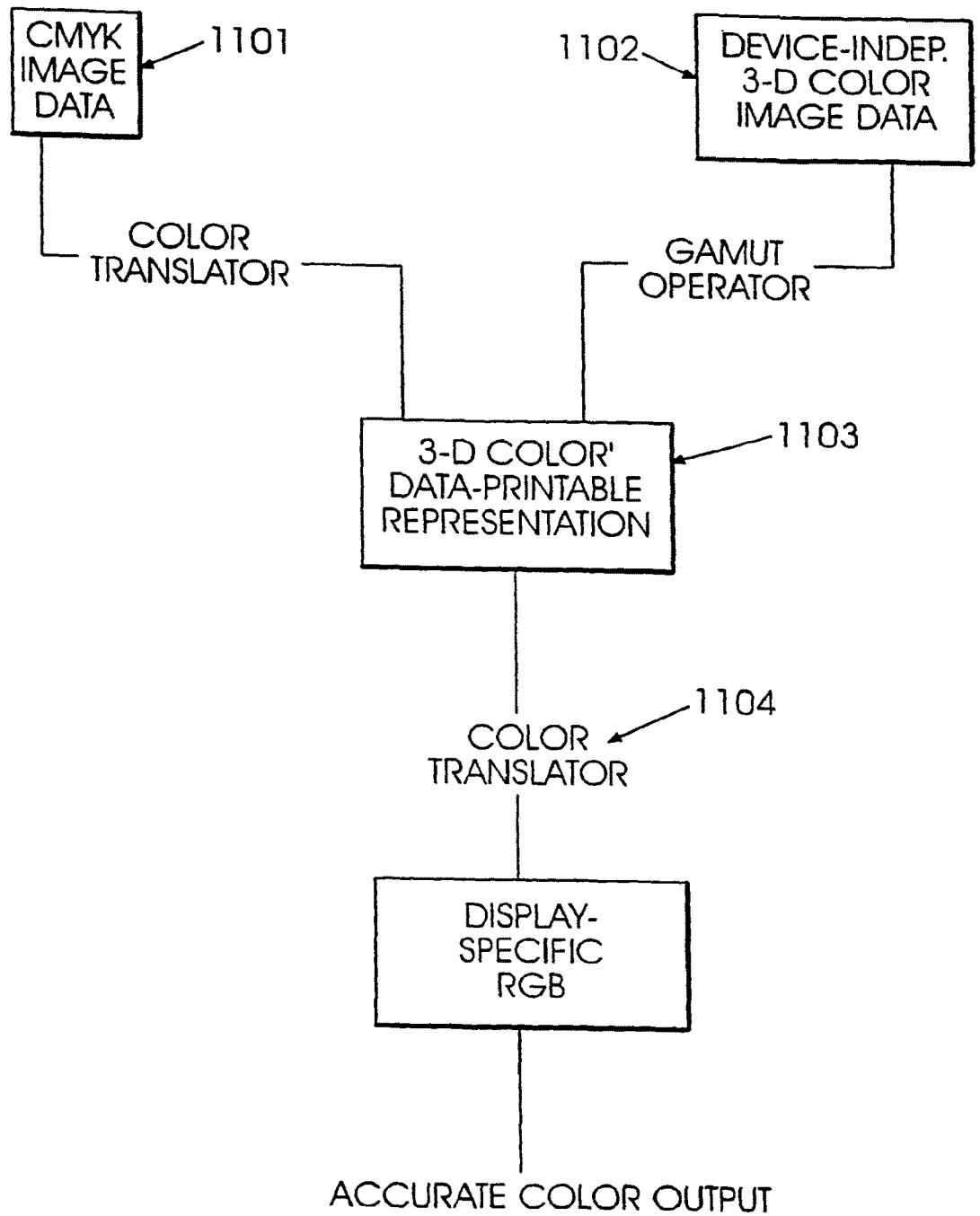
FIG. 31 is a high level flow chart showing the operation of the system in accordance with the present invention for soft proofing to a color display.

Referring to FIG. 31, the high level operation of the system for soft-proofing is shown. Users want to be able to edit or retouch image data while seeing the images they are preparing on the video display as they will appear on hard copy to the greatest degree possible, such as described, for example, in the article by Holub, et. al., J. Imag. Technol., Vol. 14, p. 53. Automatic device calibration at a single installation or coordinated among multiple nodes is provided by the above discussed lumeter and cowel assembly.

Data generally come from one of two sources in a soft-proofing application, CMYK data 1101, or as 3-dimensional color data 1102, usually in a device-independent coordinate system such as CIELAB or calibrated RGB. The first step is to get the data into the form of 3-D color' data 1103, where color' means that all the colors are printable. Since CMYK data are printable by definition, they need only be translated to suitable 3-D coordinates, as described earlier in connection with FIG. 4A. To effect the conversion for data that start out in a device-independent notation, they must be processed through a gamut operator. The latter is based upon gamut descriptors derived from models of the CMYK and display devices which was also described earlier.

Finally, the 3-D color' data must be translated into display-specific RGB signals. The result is accurate color output. Literal colorimetric reproduction on the video display may not be possible, such as described in the article by Holub, et al., op. cit.) The color translator 1104 may involve processing beyond that needed to convert device-independent color' data into calibrated RGB for the particular display. However, the latter conversion is a critical part of the translator, and the concern in this discussion is to show how it is formed or updated automatically.

Figure 32:
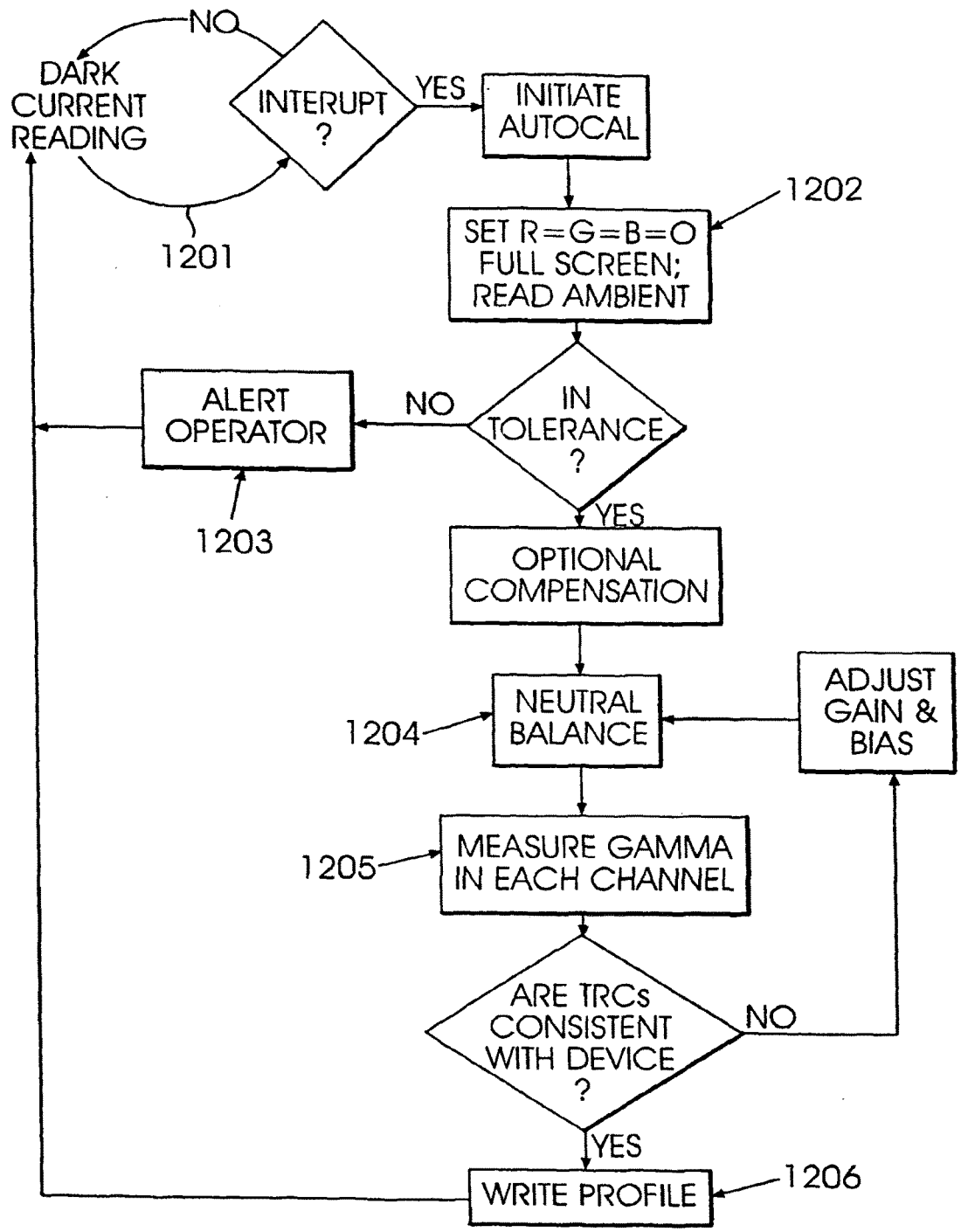
FIG. 32 is a flow chart for the process of maintaining a color display in calibration.

Referring to FIG. 32, a flowchart of the procedures for using the lumeter to set up a video display for soft-proofing and for remote proofing. It assumes that the color mixture component of the device characterization problem has been dealt with. For simplicity, assume that the chromaticity data derived from factory measurements of the display's R, G and B channels are combined with data about the desired white point to form a 3×3 matrix. The color translator 1104 then consists of a stage which converts 3-D color' data into XYZ TriStimulus Values, if necessary, which are then converted into linear RGB by the matrix. Resulting R, G and B values are processed through Tone Reproduction Curves ("TRCs" in the parlance of the International Color Consortium's Profile Format Specification.)

Whatever the sequence of processing steps implicit in a color translator, they will only be effective if the parameters of processing correspond to the actual state of the device. In other words, the chromaticities used to compute the matrix must be those of the device, the three channels must be balanced to the correct white point and the TRCs must compensate for the non-linear gamma of the device. Insuring that the device is in a targeted state called calibration is the object of FIG. 32.

State 1201 shows the Lumeter in an initial state of periodic dark signal reading. This state may be interrupted by initiative of an operator or on cue from the operating system as described earlier. An autocalibration cycle begins by darkening the screen 1202 and measuring the sum of light emitted by the screen (the dark emittance) and reflected off the screen by environmental sources not baffled by the cowel. Call the sum dark light.

One of the shareable components of the Virtual Proof is a default or negotiated tolerance for dark light. If this is exceeded, credible soft proofing at a given node and collaborative proofing between remote nodes may not be possible. The device driver for the lumeter should flag the event 1203. During a prolonged period of system inactivity, it may raise the flag repeatedly; when an operator returns to use the system, however, he/she should be advised that an unattended calibration cycle was not possible. There are two main ways of recovery: a) restore dark light to an acceptable level (operator action), such as adjusting the amount of ambient light reflected from the screen, or b) use a more complicated model of color mixture, if possible, which includes the effects of the dark light.

It should be noted that the lumeter cannot discern the color of dark light. The latter may be important in some applications, either because of fairly high levels of dark light or due to a need for very critical color judgments. When measurement of the color of dark light is necessary, replace the lumeter with a spectrograph, as described later in connection with FIG. 33.

Once the question of dark light is resolved, neutral balance 1204 is established. The aim white point is used in a computation of the relative activity levels needed in R, G and B channels to achieve the target at highlight and in the shadow. First the gains of the amplifiers within the color display which control electron density as a function of external drive are adjusted in each channel until a criterion balance is realized. This establishes highlight white. Next, the biases of those same amplifiers is adjusted until the appropriate balance is realized in the shadows. This is likely to upset the highlight balance. Therefore, several iterations may be needed to balance both highlight and shadow.

Under the simplest model of color mixture, the computation of relative activity levels proceeds as follows: From the factory-supplied calibration data, we have a 3×3 matrix of chromaticities, a column of x,y, z for Red, a column for Green and a column for Blue. The inverse of the foregoing matrix is dotted (a matrix inner product is formed) with the vector of white chromaticity values to yield a vector of weights. When the first weight is multiplied by each entry in the first column of the original matrix, the second weight by each entry in the second column, and so on, an RGB to XYZ matrix results. In particular, the second row of said matrix holds the Y TSV, or luminance value, that should prevail in each channel at the aim white point. The lumeter can be calibrated as described earlier, in connection with FIG. 30, to measure the luminance values so that the system software can decide what changes of gain or bias are needed. The foregoing description is meant only to clarify how the lumeter is used, not to restrict the scope of the invention to this model of color mixture.

Next, the gamma is measured in each channel 1205 by commanding a series of digital levels and measuring the result. If these need to have very specific values, but do not, then it is necessary to re-adjust gain and bias and re-iterate over neutral balance. If the gammas are critical, then the gammas should be adjusted to be close to the target value before neutral balancing. If the gammas merely need to be within a given range, then the TRCs in the profile can be adjusted to reflect the real state of the device once the values are within the desired range. On completion, the profile is updated 1206 and the Lumeter can return to sedentary (standby) mode 1201.

The adjustment of the TRC is accomplished as follows, referring to FIG. 30 If the aim value of output for a given command (this is the address in the TRC lookup table or the independent variable) is 1210, then enter tables of aim and measured values as a function of digital command level to find that level which produces the aim value 1211 among the measured data. That level becomes the entry or dependent value in the TRC LUT. In the interests of avoiding quantization artifacts, it is preferable to use precision greater than that afforded by 8-bit-in/8-bit-out LUTs.

For most video display technologies, with the possible exception of those which rely on microfilters to provide wavelength selection (e.g., LCDs), the problem of color differences in different regions of a nominally uniform color field can be separated from the aspects of device modeling that involve color mixture and gamma. For example, methods for flattening the screen are described in U.S. Pat. No. 5,510,851. The sensor and cowel assembly of FIGS. 23 and 24 can provide an automatic means of measuring non-uniformity of the display. An inexpensive, black & white, solid state camera, fitted with a wide field lens, may be located and centered in a door assembly in cowel 401 which can cover the opening 411 in the cowel 401 (FIG. 24B.) It is preferable to eliminate the effects of environmental light on spatial homogeneity measurements. The camera should view slightly defocused full-field screen in the interest of anti-aliasing, one color channel at a time. The digitized images are then analyzed for non-uniformities and corrections computed and applied, such as described in the above cited patent U.S. Pat. No. 5,510,851, or preferably as described below in connection with FIGS. 40-42, and 43A-43B. The distortion function of the wide-field lens should be measured and factored into the calculation of correction factors, as should differential sensitivity across the sensor array.

The following will describe color measure instruments utilizing spectrographs compatible with high resolution measurement of phosphor emissions from color monitors, i.e., CRTs to provide non-contact measurement, self-calibration, and push-button operation. The term push-button operation refers to the capability of a user automatically initiating color calibration, or that such color calibration is initiated automatically by a computer coupled to the monitor. As stated earlier in connection with FIG. 27, the sensor of the lumeter can be separate from the control and interface electronics. Sensor of the lumeter could also be a fiber optic pickup, with collecting optics, that could be coupled to a spectrograph. Therefore, the arrangement for spectral monitor calibration is non-contact and automatic once the sensor is fitted in the circumferential cowel.

Self-calibration of a spectral instrument involves insuring that readings are associated with the correct wavelengths and have the proper relative or absolute amplitudes. Unless damaged electrically or by radiation, solid state sensors tend to be very stable over time, more so than most lamps. For this reason, reference detectors are conventionally used against which standard lamps can be calibrated. Temporal variations in a source are best dealt with, in reflection or transmission measurements, by a dual beam technique, wherein the light source is reflected (or transmitted) off known and unknown objects either simultaneously or successively, depending on the temporal stability of the source. The spectral properties of the unknown object are inferred from the ratio of its spectrum with that of the known object.

A pulsed xenon source has many advantages for reflection and transmission spectroscopy. It emits strongly in the short visible waves where silicon detectors are less sensitive. It has a very stereotypical array of impulsive spectral lines across the visible spectrum which are very useful for wavelength calibration of spectral sensors. However, output is not stable from flash to flash making them best suited to dual beam designs.

Figure 33:
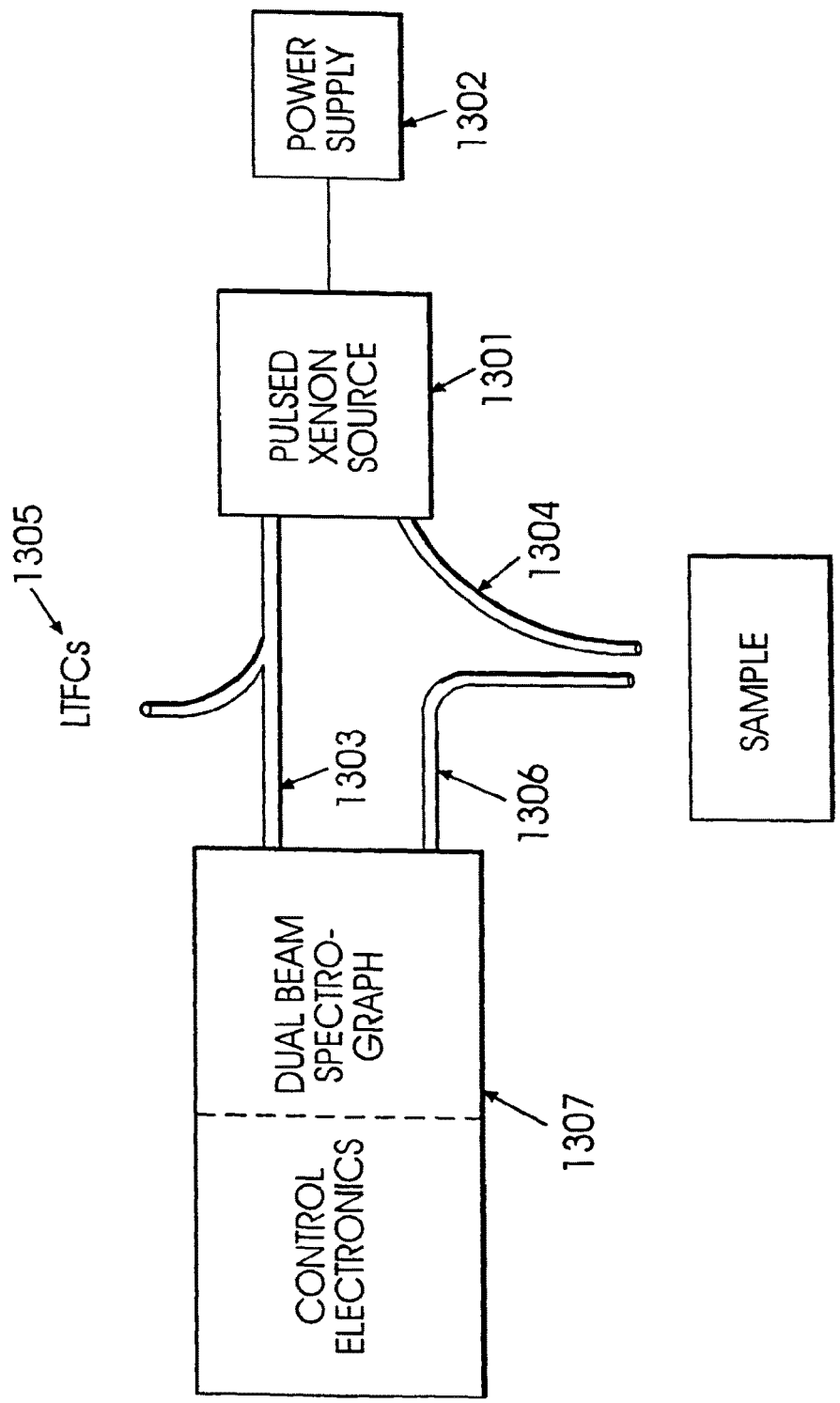
FIG. 33 is a block diagram of a color measurement instrument in accordance with the present invention utilizing a dual beam spectrograph.

Referring to FIG. 33, a block diagram of a color measurement instrument is shown utilizing a spectrograph. Source 1301 shows a pulsed xenon lamp tethered over a short distance to its power supply 1302. Source 1310 may be Xenon modules, such as manufactured by EG&G of Salem, Mass. Two fiber optic taps are taken, tap 1303 to the reference input of the dual beam spectroscope 1307 and tap 1304 to illuminate the reflection sample. Tap 1303 is bifurcated so that light is also taken to an assembly 1305 consisting of at least two Light-to-Frequency Converters (LTFCs) whose purpose will be described presently. Pickup 1306 is a fiber optic pickup which can accept light reflected or transmitted from a sample. Alternatively, it can be placed in the sensor assembly shown in FIG. 27, for use in spectral monitor calibration. Although the fiber optics are employed for flexibility, they must not be flexed during use and the components of the assembly that are linked by fibers must bear a fixed relationship to one another. The term fiber optic tap refers to one or more fiber optic cables.

The LTFCs in assembly 1305 serve two purposes. By monitoring their output in the dark, the temperature of the assembly can be estimated as we have seen earlier. However, they are also used as reference detectors. Each receives light through a different, spectrally-selective filter. For example, two LTFC's may be used, one tuned to a particular peak in the short wave region of xenon output and the other tuned to a peak in a longer wave region. In this way, they serve as a check on the consistency of the sensitivity of the reference sensor in the spectrograph at a given temperature. They also aid in estimating the dark current in the reference line camera. In summary, they contribute to checking amplitude calibration of the spectrograph, which may be controlled by the control electronics of the spectrograph. As noted earlier, the pulsed xenon spectrum provides very predictably placed peaks for use in wavelength autocalibration. The two aspects of calibration discussed here need not be done simultaneously in the case of monitor measurements; it is enough that they have been done recently. Thus, the signals from the LTFC sensors can be used to provide information for automatically checking the calibration of the spectrograph.

Referring back to FIG. 3A, the color measurement instrument of FIG. 33 may also be used for reflection color measurement from a hard copy sample, or media. The fiber optic probes 36 disposed over the paper sample were given a 45/90 geometry. This geometry works well, especially when the illuminating fiber oriented at 45° has a tip of oval shape such that the light spot formed is approximately circular with diameter 3-5 mm and uniformly illuminated. However, the foregoing geometry may not be suited to tight quarters. Two other configurations also produce very good results, even when the illuminating and detecting fiber probes have nearly the same orientation (typically near vertical) with respect to the copy. One configuration includes a polarizer placed over the tip of the illuminator fiber optic and a polarizer that is crossed, with respect to the first, is placed over the detector fiber optic. Specular pickup is severely attenuated, provided that crossing is almost perfect. Alternatively, a diffuser may be placed over the illuminator fiber optic; in this case, the end of the fiber should be several millimeters behind the diffuser. This is easier to setup than the polarizers, but may produce a larger illuminated spot than is desired in some circumstances. In each of the above configurations, all measurements are non-contact. Therefore, they do not disturb the copy sample being measured. The configuration we describe does not require significant baffling of extraneous light due to the very considerable (in a brief interval) output of pulsed xenon.

The preferred spectrographic design for simultaneous, dual beam work is one described by J. T. Brownrigg ("Design and Performance of a Miniature Dual Beam Diode-Array Spectrometer," Spectroscopy, Vol. 10, pp. 39-44, November/December '95) and manufactured by American Holographic (Fitchburg, Mass.) as the MD-5. For applications in which the spectrograph and related modules are embedded in a printer, such as an ink jet plotter with a single, mobile head the design discussed in the article has satisfactory spectral resolution. Other spectrographs providing comparable performance may alternatively be used.

However, for applications in which the unit (the color measurement instrument of FIG. 33) is installed in a pen-plotter-like assembly for measurements of specialized calibration forms and occasionally removed for monitor duty, a modified design is needed to achieve adequate spectral resolution. In it, the optical bench is lengthened and a grating with superior dispersion and focusing properties is used and the system must be aligned to optimize focus in the long wave region of the spectrum.

The pen-plotter assembly transports the paper or copy automatically when a pressure switch senses its presence. The paper/copy is transported through automatically while the pen scans the paper perpendicularly to the direction of the advance. The fiber optics described above replace the pen and scans the copy perpendicularly to the direction of paper advance. Hence, we have a non-contact measurement by an instrument that is fully self-calibrating and provides push-button simplicity. This configuration could easily subserve the color measurements needed in support of soft-proofing as discussed in connection with FIG. 31 and earlier in this description. If one or more instruments of the kind described were available in a network for virtual proofing, they might be shared for hard-copy or, when needed, for monitor calibration.

A less sophisticated calibrator may be used for inexpensive print devices. For "low end" devices, the strategy of choice is to make stock profiles available for identified lots of inks or toners, through the Cyberchrome Service (FIG. 22) and then to use the calibrator to make sure that the devices conform as much as possible to a setup consistent with the assumptions used in making the profile. This would entail, at a minimum, ensuring that the Tone Reproduction Curves (TRC) for each channel in the printer conformed to specification.

Optionally, it would ensure that the image area of the device is flat, i.e., an uniform image reproduces uniformly across and down the page. This would require techniques analogous to those described in the art for flattening video displays, and referred to earlier in this description. In essence, at each point on the page, the TRCs are adjusted to match the least commonly achievable TRC and some sort of interpolation is employed to feather the corrections applied to contiguous blocks on the page for which TRC corrections were computed. A useful instrument for measuring the non-uniformities and initial TRCs for the different color channels is a monochrome scanner such as the PaperPort, marketed by Visioneer of Palo Alto, Calif. This is an advance over Bonino's patent (U.S. Pat. No. 5,309,257) in two respects: a) distribution of colorant-lot-specific profiles and b) flattening the page. Each of these have considerable impact on the color reproduction of any device, especially less expensive ones.

Figure 34:
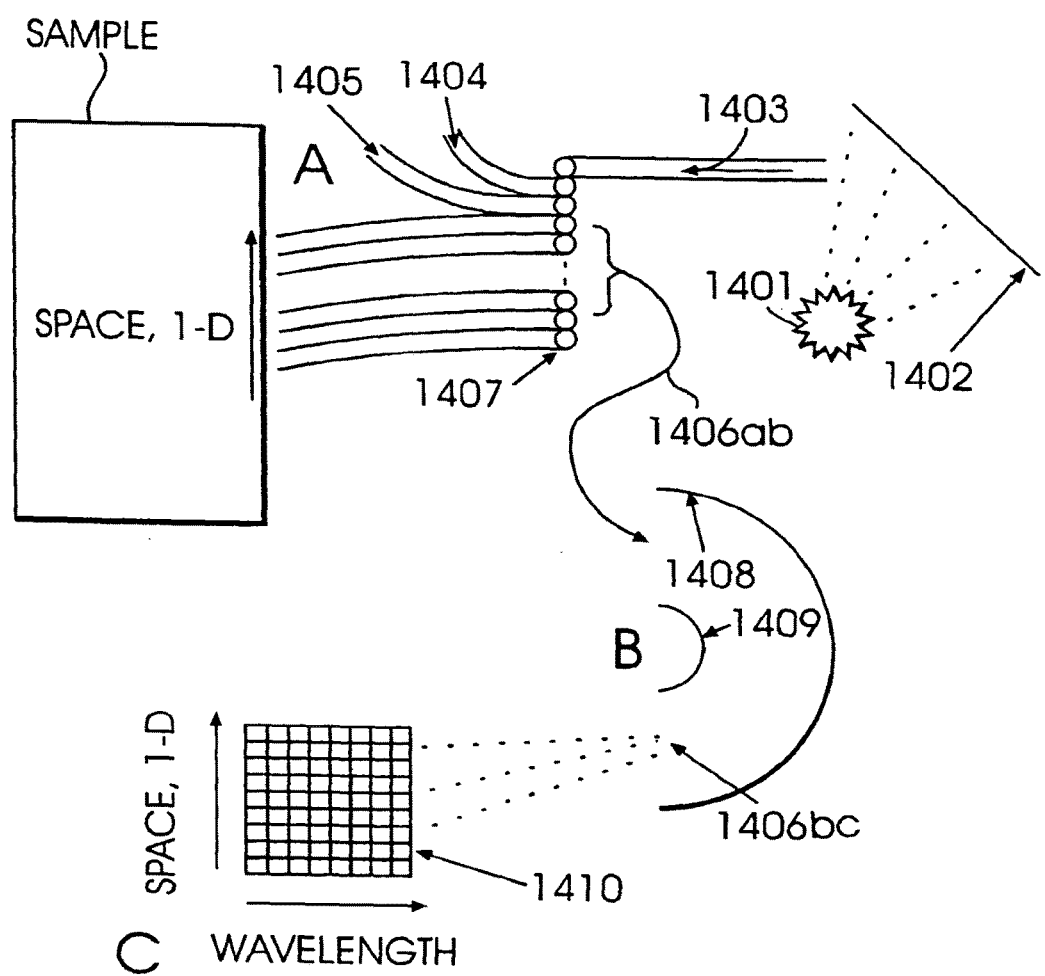
FIG. 34 is a block diagram of the a color measurement instrument in accordance with the present invention utilizing a concentric spectrograph.

Referring to FIG. 34, a block diagram of a color measurement instrument utilizing a concentric spectrograph is shown for providing spectral imaging colorimeter. Such a color measurement instrument is preferably used for page printers, such as a xerographic press. Concentric spectrographs are described by L. Mertz, Applied Optics, Vol. 16, pp. 3122-3124, December 1977, and are manufactured by American Holographic (Fitchburg, Mass.) and Instruments SA (Edison, N.J.) Source 1401 is an illumination source. By virtue of the spectral analysis, the interpretation of object colors can be independent of the source, opening the possibility of simulating the appearance of a product, for a customer, under various viewing conditions.

Reflector 1402 is a conventional reflector and pickup 1403 a fiber optic pickup which collects light from the reference reflector for conveyance to the spectrograph. Light from the reference reflector is shown on the sample object. Light reflected from the sample object is formed on a row (streak) of pixels indicated by fibers 1407. Fibers 1407 can be a row of fiber optic bundles, or samples (pixels) of the image formed by a lens instead (A.) Collection of reference light by 1403 enables a dual beam operation in which the influence of the source illuminant can be extracted from each pixel. Fiber 1404 is a fiber which sees a black trap and is used to generate reference dark current on the array. Fiber 1405 is a fiber (or generally, an input) which transmits light from a source used for wavelength calibration, such as source providing light of known wavelength(s).

Surface 1408 is the reflecting surface of a concave mirror whose center of curvature is shared with convex holographic grating surface 1409; this is a simplified depiction of a concentric spectrograph (B.) Rays 1406$_{ab}$ and 1406$_{bc}$ show the flow of image rays to imaged pixels at the entrance slit of the spectrograph and hence to the sensor array 1410, on which one dimension encodes wavelength and the other distance in space along the imaged streak (C.) In other words, the concentric spectrograph outputs spectra spatially related to points along the line of light provided to the spectrograph. Thus, the wavelengths of each spectrum related to light received from each of fibers 1403, 1404, and 1405 can provide calibration reference information for automatically calibrating the spectrograph.

The spatial resolution of a practical implementation is such that anti-aliasing filters, described earlier, are required. Conventional compression algorithms must be applied to the spectral data to make it sufficiently compact for storage. Where data need to be captured at high spatial resolution, a separate line camera with approximate photopic sensitivity should be used to capture the gray scale information of the image, while the chromatic information is coded at lower resolution by the concentric spectrograph. The approach lends itself to multi-resolution encoding of images as practiced in a number of commercial imaging architectures such as Kodak's PhotoCD and the FlashPix. When used as a digital camera, the sensor arrays must be translated across the plane of the subject. When applied to on-press measurement of color across the web, the arrays are stationary and the web moves. Thus, the transport mechanism 320 (FIG. 22) for a physical copy and associated light-collecting optics should constitute a module distinct from the module which attaches to video display and from the module containing sensor(s) and control electronics. Light-collecting modules may be connected to the control module by fiber optic links.

As a spectral, imaging colorimeter, the capture device will require the speed and image quality insured by a concentric optical design along with anti-aliasing software or optical design and with facilities (hardware and/or software) for compressing and manipulating spectral data and for hierarchical, multi-resolution image storage compatible with conventional image data protocol, such as Flash Pix.

Although the above description relates to the printing and publishing industry, it is also applicable to other industries, such as textile printing. Further, in packaging and related industries, more than four colorants may be used in circumstances in which no more than four colorants overlap within a given region of the page. The system can accommodate this by applying the herein methods to separate regions of the page.

Figure 35:
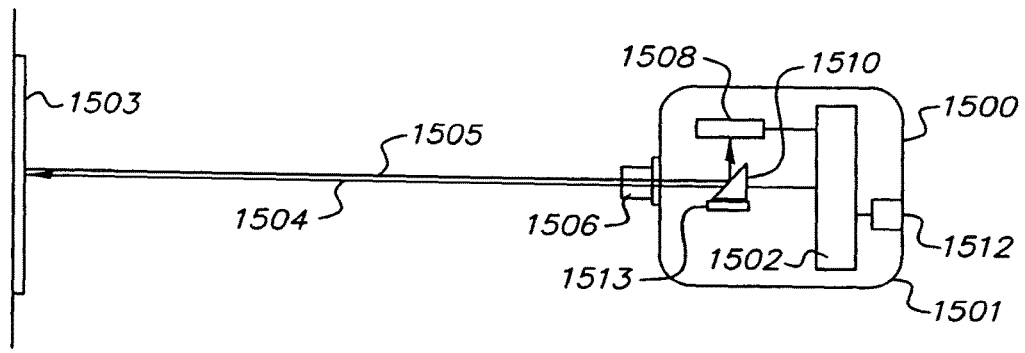
FIG. 35 is a block diagram of a front projection display device with color calibration in accordance with the present invention in which projection optics project upon a surface and the same optics are used to receive reflected light from the surface onto a color sensor.

Video projection is described earlier in that a video display 17 (FIG. 1) can project an image, and a CMI that monitors the output is situated near the source of projected light, as close as possible to being on a line of sight. Referring now to FIG. 35, such a color display is shown in more detail in the case of a front projection color display 1500 (also referred to as a color projector). This display represents one of the rendering devices described above that may be used in virtual proofing with one or more other rendering devices.

Projection color video display 1500 has a housing 1501 having electronics 1502 which projects light 1504, via projection optics 1506, onto a surface 1503, such as a screen. A color measuring sensor 1508 is provided in housing 1501, and a beam splitter or partially-silvered mirror 1510 deflects light 1505 onto the sensor 1508 that is reflected back from the surface and collected by projection optics 1506. Light 1504 which reconstructs an aerial image on surface 1503 is produced by electro-optics of electronics 1502 from image data. As such electronics 1502 may be typical of digital electronics, such as a microprocessor-based system, for optically producing such images, and projection optics 1506 (illustrated as a lens; may be one or more lenses providing focus and/or zoom control) for mediating the image reconstruction which is typical of projection optics used in front color projector devices. For example, transduction of digital image data to time- and space-varying signals for projection may be implemented by digital light processing by digital micromirror devices, such as available from Texas Instruments, Inc. However, any other projection rendering technology may also be used.

Some of the projected light deflected by beam splitter 1510 falls into a light trap 1513, such as a light absorbing block, and is wasted. Reflected light 1505 from surface 1503 follows a path through optics 1506 and is deflected by beam splitter 1510 onto sensor 1508. Sensor 1508 may be either of an imaging type or a spatially-integrating type and either color or monochrome. "Monochrome" has a single- rather than multi-channel sensor in terms of the number of wavebands of light distinctly apprehended by the sensor. Thus, optics 1506 employed for variable focus in the projection system of projector 1500 is also utilized to collect light for the sensor 1508 integrated in housing 1501 of the projector.

Additional optical elements comprising lenses, filters, etc., may be positioned in path 1510 to 1508 as needed.

The image data provided to electronics 1502 may be provided digitally, through an interface 1512 from a computer (e.g., image data prepared by a presentations software package) or from a network. However, data derived from analog television signals, for example, are not excluded. Data may also be high definition digital video, or of other typical digital video formats. The types of networks providing data include broadcast television, Internet, cable or any known information-carrying medium with adequate bandwidth. They may also include Virtual Proofing networks. The image data may be "read-out" for projection by a digital micromirror device, or reproduction by any technology subserving similar functionality, such as Cathode Ray Tube technology or self-luminescent flat panel technologies employing liquid crystals, plasma or OLED (Organic Light Emitting Diodes) whether used for projection or otherwise. Flexible displays, "e-paper" and prints (hard copy prepared by printers or presses) are also relevant rendering devices/media. Alternatively, or in addition to, interface 1512, an optical drive may be provided, such as DVD, CDROM, or other optical storage device, which may be directly accessible to the electronics 1502 of the projector 1500.

Optionally, another sensor, or fiber optic pickup routed to such a sensor, may be placed at the location occupied by light trap 1513 en lieu of such light trap. The purpose of the sensor would be to monitor the overall level and/or spectral composition of the projector's luminous source. Sensors providing this functionality include the CMI's of FIGS. 2, 3A, and 3B described earlier as colorimeters, such as discrete (unitary) colorimeters (SOM 13) or imaging colorimeters (imagical 14) which may be used in conjunction with single-channel light-detectors. The sensor may also have one of optical filters, fiber optics, or wavelength separating element (e.g., grating, prism, or monochromator) through which reflected light is received from the screen. Also, the spectrograph of FIG. 33 may be used, or the sensors described in U.S. application Ser. No. 09/832,553. As such, the sensor may be a spectral sensor having wavelength resolution adequate to achieve Nyquist sampling of the luminous source, two or more light detectors tuned to different, narrow regions of the spectrum or two or more light detectors with broad, overlapping, non-identical spectral sensitivities. The choice of sensor and strategy for monitoring the projector's luminous source depend on the optical and physical properties of the source and design trade-offs having to do with cost, required accuracy, "footprint" or space considerations within the projector housing. Under suitable circumstances, the sensor at 1508 may double as the source monitor by receiving light routed through fiber optics from the location of light trap 1513.

For example, if the projector 1500 employs Texas Instruments' Digital Light Processing (Micro-Mirror Device) technology in conjunction with a metal halide light source, it may be advantageous to monitor the lamp's output before it is filtered into Red, Green and Blue channels for carrying the information of the corresponding channels of digital color image data. In this case, it may not be desirable to position the sensor or fiber optic pickup at the location of light trap 1513, where rapidly varying filtered light would likely be present. Monitoring the lamp directly may provide opportunities for control instead of, or in addition to, those available by monitoring at location of the sensor 1508, where light reflected from the display surface is sensed.

Luminous source monitoring is also advantageous for non-projection displays, and as such, the above-described considerations apply to light sources used in LCD and other flat-panel display technologies. Variations in the source can occasion changes in the system's white point and/or overall luminous output, which can be compensated for by revising color transformations employed by the digital display controller as described herein and in the patents incorporated by reference herein. Where continual calibration/monitoring is needed or desired, a sensor 1508 should be selected with sufficiently rapid response time that single frames of calibration images can be interspersed by the display controller and synchronously captured by the sensor.

Figure 36:
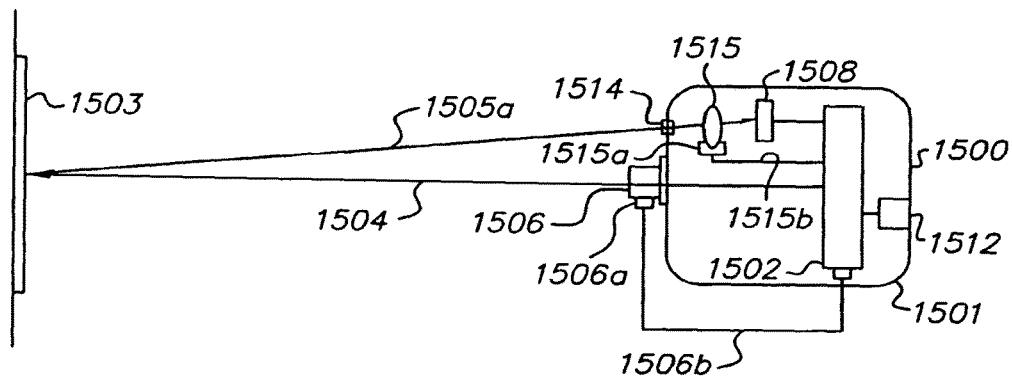
FIG. 36 is a block diagram similar to FIG. 35 in which different optics than the projection optics receive reflected light onto the color sensor.

Another embodiment of the color projector 1500 is shown in FIG. 36. This embodiment is the same as that shown in FIG. 35, but without both beam splitter 1510 and the use of optics 1506 to collect reflected light. In this embodiment reflected light 1505a from screen 1503 returns through an aperture 1514 in housing 1501 to sensor 1508 via optics 1515. Optics 1515 is illustrated as a lens, and may be a single lens or a lens system enabling variable focus (with or without zoom) for imaging light 1505a onto sensor 1508. Aperture 1514 may be open or have a transparent window (e.g., plate).

It is advantageous, although not necessary, to have the sensor 1508 assembly incorporated in the projector 1500 close to the "line of sight" of the projection housing's assembly because it facilitates making focusing adjustments in tandem. The projection lens assembly may be adjusted for variable projection distances by an autofocus mechanism based on technologies routinely employed in cameras. Alternatively, a manual adjustment may be provided wherein the projection assembly is grasped and twisted (as with camera lenses) or a knob operates on a rack and pinion (as in traditional "carousel" projectors) and the foregoing adjustment is communicated to the sensor assembly through suitable gearing. In either automatic or manual cases, implementation of the controls for focusing light onto the sensor benefit by coordination with the projection focus mechanism, and appropriate settings may be calibrated at the factory. For example, electronics 1502 may control the focus setting of optics 1506 and 1515, such as by actuators/motors 1506a and 1515a, respectively, via signal along connections or lines 1506b and 1515b, respectively, for moving one or more optical elements of such optics. In this manner, when projector focus (or zoom if provided) is changed for optics 1506 by electronics 1502 (or manually by the user) via signals to drive actuator/motor 1506a, a proportional change is made to actuator/motors 1515a, such that when optics 1506 is focused (and aligned via zoom) onto surface 1503 the optics 1515 image of the reflected light from surface (or a portion thereof) onto sensor 1508 is in focus. In another advantageous embodiment, the sensor system employs imaging electronics and the system performs the role of auto-focusing the projection display, as described later below in connection with FIG. 38A.

In addition to projecting images in accordance with image data, electronics 1502 of FIGS. 35 and 36 enables color calibration as described earlier for virtual proofing in which one or more reference images are projected on the surface 1503 by the electronics 1502 and are measured by sensor 1508. The sensor 1508 provides to the electronics 1502 color measurement data representative of reflected light from the surface. The projector 1500 is interfaced to a computer system at a node, similar to such color displays described earlier, to control reproduction of displayed images on screen 1503, whereby the electronics of the projector provides color measurement data from its sensor 1508 as needed in performing calibration and/or virtual proofing.

Alternatively, the computer system may be omitted at a node and the projector 1500 operated remotely via pipe 11a from another node. Optionally, a separate computer system is not utilized, and electronics 1502 provide the functionality of such computer system to enable color calibration and virtual proofing, whereby interface 1512 provides a network communication device to other sites along a network.

The projector 1500 may also provide stand-alone calibration by programming the microprocessor of electronics 1502 to project images in accordance with reference images stored in memory of the electronics 1502, utilize its sensor 1508 to provide color measurement data in device independent units, and then generate color error data by comparing measured data with the color data of the reference images. A color transform is created (or modified) in accordance with the color error data, such that the image data to be projected is transformed such that projected colors onto surface 1503 match the color of the reference images. The color transform may be for example, a look-up-table or color curve, for the color channels. Projector 1500 of FIGS. 35 and 36 may represent a home, commercial, or digital color theater projector.

Although it is preferred, especially for projection-type displays, it is not necessary to have the sensor 1508 assembly incorporated in the projector because the light emitted by the display screen is generally divergent or diffuse, such that there is not a narrowly defined angle of collection. This can be understood intuitively from the fact that users are able to see what is on the screens with fairly wide latitude with respect to viewing angle. However, the further off-axis the sensor is, the greater the need for luminous distortion corrections, particularly if the sensor is an imaging sensor.

Figure 37:
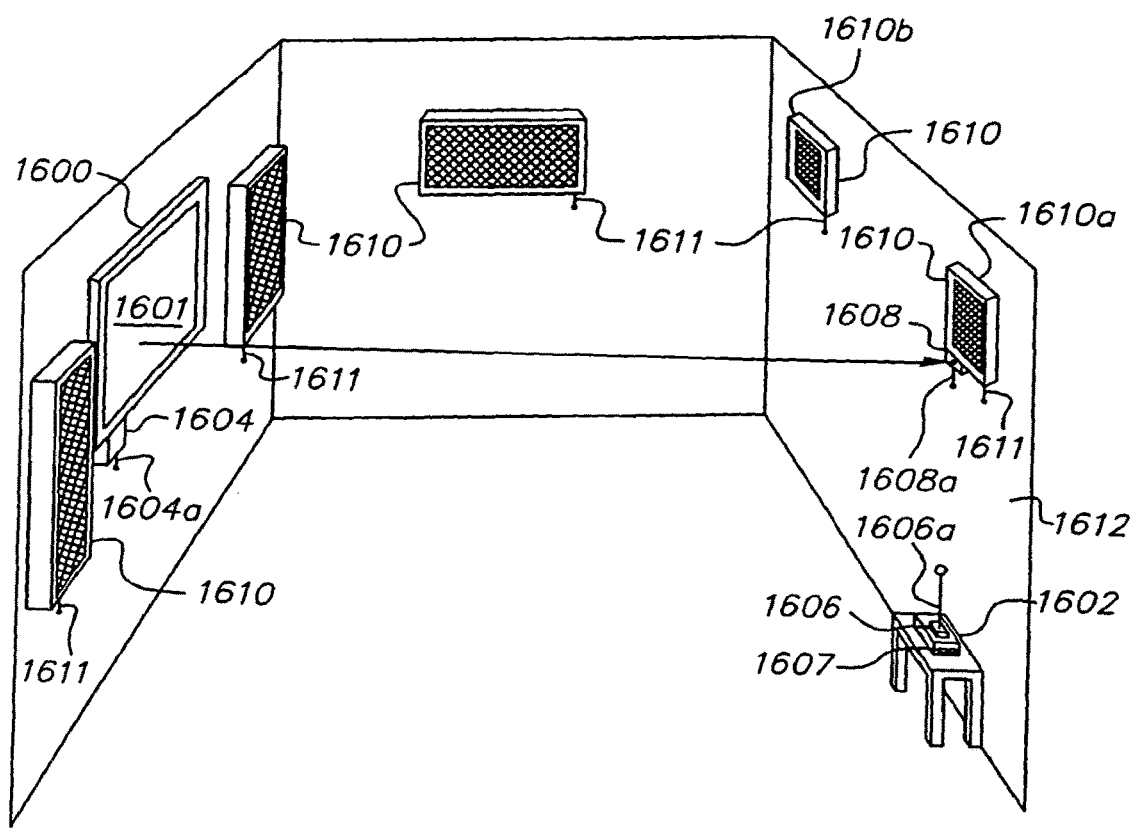
FIG. 37 is perspective view of a home theatre system in a room having a flat panel display and multiple speakers about the walls of the room in which a color measuring module is attached or integrated with a speaker of the home theatre system to provide color calibration of the flat panel display.

Although an arm member may be attached to the top or side of a large area display of a "home theatre" system in order to support a sensor or light pickup disposed to have a suitable view of the screen, users may prefer another arrangement as shown in FIG. 37. A display 1600 having a screen 1601 is connected to a television receiver and digital control unit 1602. Display 1600 may be a typical self-luminous display, such as an LCD color display with a large flat panel screen 1601 which may be mounted on a wall, as shown, or located on a base or stand. Wireless communication between the electronics of the display 1600 and the control unit 1602 is provided by their respective wireless interfaces 1604 and 1606 having respective antennas 1604a and 1606a. Display 1600 and/or interface 1604 have electronics enabling communication with control unit 1602. The control unit 1602 also wirelessly (e.g., RF or IR) communicates with relatively low-bandwidth peripherals, such as a calibration sensor ("CMI") module 1608 having antenna 1608a, and signals via interface 1606 to speakers 1610 situated in the room. Each speaker 1610 has electronics providing a wireless interface to receive signals from their antenna 1611 representing audio to be outputted by their speakers, and such speakers may be wall mounted as shown, or may have self-supporting cabinet, base, or stand. The digital control unit 1602 also has other interfaces 1607 providing one or more ports to devices, such as a cable TV input, a "game box," a "cable" or other type of modem (a modem may also be integral to unit 1602) a satellite dish, a wired or wireless LAN connection to one or more computers (a network interface card or equivalent may also be integral to unit 1602) either directly or through a hub and router arrangement and the like. Among interfaces 1607 is at least one for user interaction (joystick, remote control unit, etc.) supported by an operating program. Indeed, control unit 1602 may be a general purpose or personal computer with user-interfacing devices, such as keyboard and mouse and other typical peripherals. The control unit 1602 enables stand-alone calibration of display 1600, such as described earlier in connection with FIGS. 35 and 36, or represents a rendering device for virtual proofing with other rendering devices. Optionally, the control unit 1602 and display 1600 may be without their respective wireless interface and instead be connected by cable or wires and/or optical fibers in which the control unit may be situated in proximity to display 1600. Control unit 1602 also may be wired to speakers 1610 and also CMI 1608.

It is common to mount one or more of the speakers 1610, such as speakers 1610a and 1610b, on an opposite wall 1612, directed toward the screen 1601 at an angle not too far away from the normal to the screen 1601 surface, as shown in FIG. 37. The CMI module 1608 may be incorporated with speaker 1610a. Alternatively, a stand-a-lone CMI module 1608 can be mounted directly on the wall 1612 or other structure on the wall, such as may be useful when a speaker is not present to properly position the CMI module to view an angle at or near normal to screen 1601.

The sensor-to-screen configuration of FIG. 37 may also be used with rear-projection display instead of a self-luminous display 1600. The rear-projection display may be a typical rear projection display having electronics programmed for communication with control unit 1602 to enable stand-alone-calibration as described earlier in connection with FIGS. 35 and 36, and virtual proofing described earlier. If the rear-projection display, or display 1600, has microprocessor-based electronics which can support the operation of control unit 1602, the control unit 1602 may optionally be removed and its functionality provided with such electronics.

Figure 37A:
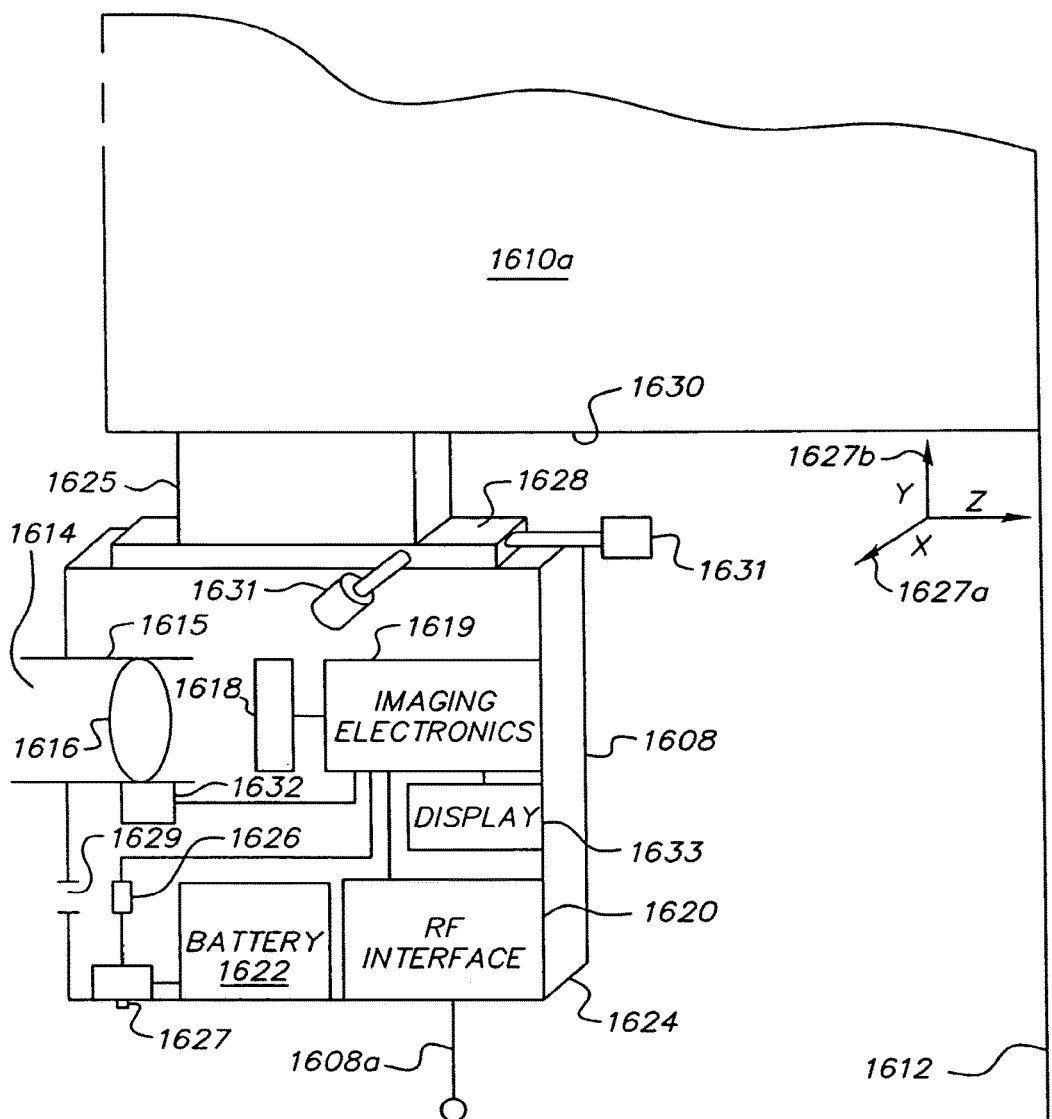
FIG. 37A is a block diagram of the color measuring module of FIG. 37.

A block diagram of CMI 1608 is shown in FIG. 37A having an aperture 1614 with a tube or cylinder 1615 in which is fixed a lens or lens system 1616 for imaging onto a sensor 1618 (such as a photodiode or CCD). The sensor 1618 is controlled by imaging electronics 1619 which receives color measurement data from sensor 1618 which may be outputted to control unit 1602 via RF interface 1620. Imaging electronics may represent a microprocessor-based device with memory which can carry out programs such as operating in response to commands from control unit 1602, or circuitry for enabling data from sensor 1618 to be formatted for transmission via interface 1620 to the control unit 1602. A replaceable battery 1622 provides power to the components within the housing 1624 of the CMI 1608.

In order to insure that the CMI 1608 senses the screen 1601, and not other areas, the CMI module may be equipped with a laser diode 1626 which may be activated by push-button 1627 or by programmed command from control unit 1602 to electronics 1619 via RF interface 1620. The laser diode 1626 provides an aiming beam through aperture 1629 onto screen 1601. An x-y stage 1628 is coupled by a mounting member 1625 which attached to the outer surface 1630 of speaker 1610a, such attachment may be by screw(s). The x-y stage may be similar to that used in optical microscopes. The CMI module 1608 orientation is adjustable in two dimensions (a "left-right" dimension of adjustment is suggested by in the x direction 1627a, and "up-down" dimension is along the y direction 1627b) until the aiming laser beam aligns with a centered spot, annulus or "bull's eye" of an alignment image illuminated on the display screen 1601 by control unit 1602 allowing for a small offset due to the fact that the laser pointer is not centered with respect to the optic axis of the sensor 1618. This may be performed manually by the user rotating one or both x and y adjustment screws 1631 of stage 1628 until alignment with feature(s) of the alignment image on screen 1601 is achieved. To adjust the angular position of CMI module 1608 to view a screen, member 1625 is mounted (by screws or bolts) to surface 1603 to provide the desired angular view (line of sight) of barrel 1615 to the screen. Angular adjustment mechanisms may also be provided, such as by coupling mounting member 1625 to a ball rotatable in a socket mounted to surface 1603 (or vice versa), or using a hinge to couple mounting member 1625 to surface 1603 to pivot the CMI module, in which once at the desired angular position a set screw locks the ball or hinge in place. Optionally, instead of laser diode and aperture 1629 the imaging electronics may control movements of stage 1628 until it detects the features of the image of the alignment image on sensor 1618.

Although critical focus will not be necessary, the lens system 1616 may need a z-axis adjustment for varying the focus, such as provided by actuator or motor 1632 having a gear engaging an outer thread along cylinder 1616 to move the tube, and its lens system therein, along the z-direction. However actuator 1632 may be removed, and several different fixed-focus calibration sensor modules may be made available; in this case, the installer/maintainer of the home theatre system would choose the appropriate one of module 1608 having the proper fixed focus distance, which may be aligned when mounted on speaker 1610a and tested at the time of installation. Variable focus may be provided in the ways mentioned above, namely adapting autofocus technology commonly used in cameras or manual focus of the sort used in cameras or projectors. In the case of manual, variable focus, it will be necessary either to provide a viewfinder, or to mark the barrel of the adjustment cylinder 1615 extending outside housing 1624 with distances between the module and display screen 1601 (or to screen 1701 of FIG. 37B). A lock down should be provided to prevent the cylinder 1616 from moving once proper focus is obtained. An optional display 1633 is shown for enabling electronics to output the captured image from sensor 1618, similarly to that of a digital camera, to enable a user to determine when focus is achieved. In addition, a sensor 1618 may be an imaging sensor (e.g., CCD) which may be operated in coordination with the control unit 1602 electronics to seek optimum focus and correct alignment as was described earlier. Display 1633 need not be built-in, but may be available to an installer or user through interface to a hand-held device, as discussed later.

Among the steady improvements in flat panel technology is included a reduction in the degree of directionality of the screens. (In some applications, directionality is desired, but theatre applications are not among them.) In other words, variations in luminance and/or color with the extent of off-axis viewing have diminished. Nevertheless, in a situation in which a speaker/CMI combination is mounted in a position that is at a substantial angle from the normal to the screen, it may be necessary to correct calibration readings for a directional effect. It may be possible to do this automatically, based on stored correction factors, if the calibration sensor of the CMI 1608 is an imaging device, capable (with software) of estimating the angle of regard (see below.) Otherwise, an approximate correction of readings may be used toward those that would be obtained along a normal based on the angle of regard programmed at the time of system installation, and consistent with either on-site calibration or values derived from factory calibration for different angles of regard.

The CMI module 1608 may be battery-powered as described above. Alternatively, power may be provided through a wire connection, possibly associated with an assembly for a speaker, or to an AC adapter to a power outlet in the room. Wireless communication by the control unit 1602 (FIG. 37) to other components may utilize a communication protocol, such as Bluetooth.

Figure 37B:
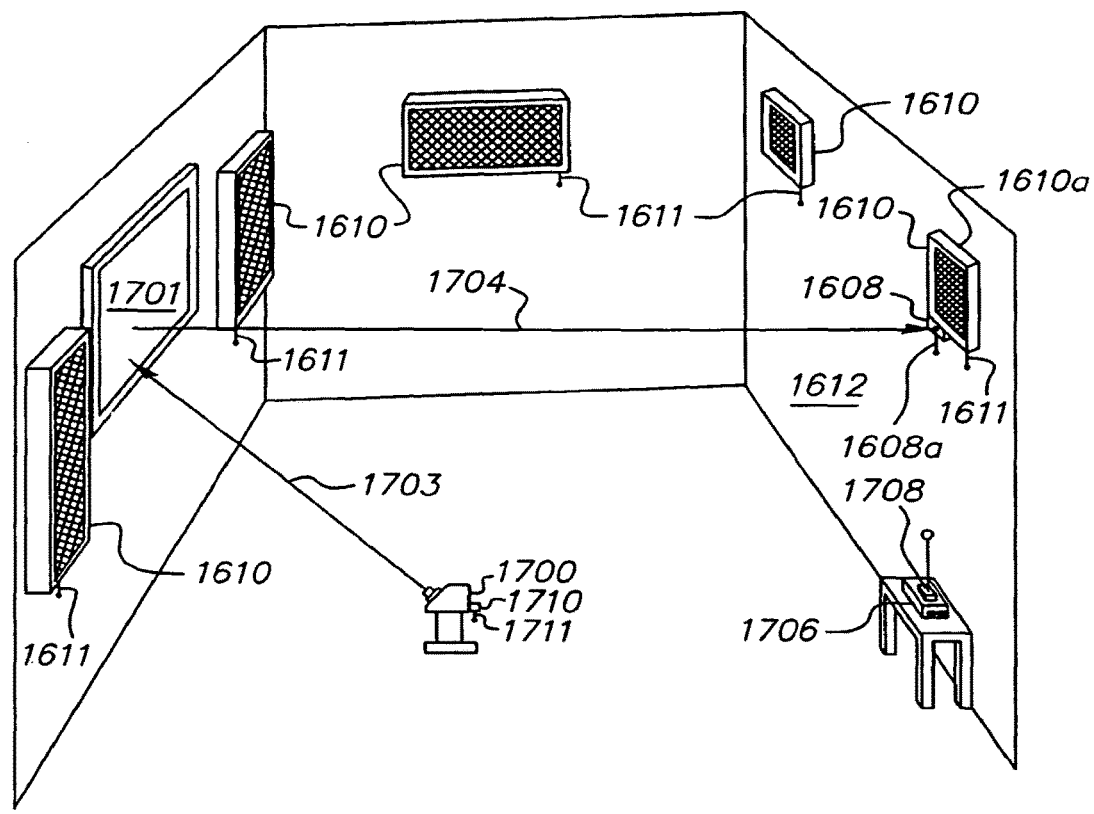
FIG. 37B is similar to FIG. 37 with a front color projection display device and a color measuring module attached or integrated with a speaker to provide color calibration of the projection display device.

The sensor-to-screen configuration described for FIG. 37 may also be employed for front-projection display systems. Accordingly, another embodiment of front color projector is illustrated in FIG. 37B showing a projector 1700 projecting images onto the surface of a screen 1701, as indicated by arrow 1703. As in FIG. 37, the sensor 1608 may be mounted to speaker 1610a, or to wall 1612. The sensor 1608 receives reflected light from the screen 1701, as indicated by arrow 1704. The control unit 1706 may be the same as control unit 1602, and able to communicate, via its wireless interface 1708, to projector 1700, via the wireless interface 1710 and antenna 1711 of the projector. The controller 1706 provides image data to projector 1700, wirelessly, and also enables calibration and virtual proofing of the projector similar to that described earlier for projector 1500 of FIGS. 35-36. The controller 1706 may have a network interface device for enabling virtual proofing with sites along a network, or the controller may provide stand-alone color calibration for the projector 1700. Optionally, the controller 1706 may be removed, and the operation of the controller provided within projector 1700 by the projector's microprocessor-based electronics. If desired, wires (or fiber cables) rather than wireless interfaces and antenna may be used for enabling communication between control unit 1706 and other components in FIG. 37 or 37B.

Placement of the CMI 1608 as shown in FIGS. 37 and 37B at a distance from a screen may also be used in theaters, in which the CMI is located along the theater wall near the wall opening through which a digital color theater projector projects light on a screen. Such digital theater projector may be calibrated for color similar to the front display projector 1700. Purveyors of streaming video or movies-on-demand may reasonably and advantageously require a level of image and color fidelity at commercial installations where their products are viewed.

The foregoing considerations apply as well to a camera system that may be employed to measure or verify uniformity of luminance and/or color across the rendering surface. In this case, an imaging sensor is substituted for a "spot" sensor. Focus is more important in this case, although the anti-aliasing effects of some degree of defocus may nonetheless be advantageous. Technologies mentioned in earlier disclosures may also be used for said purpose.

Since the sensor's "line of sight" may not be along a normal to the screen surface in FIGS. 35, 36, 37, and 37B, it may be necessary to estimate the angle of regard and to correct for distortions introduced by the lens system and the angle of regard in software, possibly with specialized hardware assist. Correction for such distortion is described, for example, in bibliographies compiled by Azriel Rosenfeld on image interpretation in the literature on computer vision, see http://iris.usc.eduNision-Notes/rosenfeld/contents.html. Furthermore, once the angle of regard has been calculated, as described below, it is possible to employ directionality corrections automatically.

Figure 38:
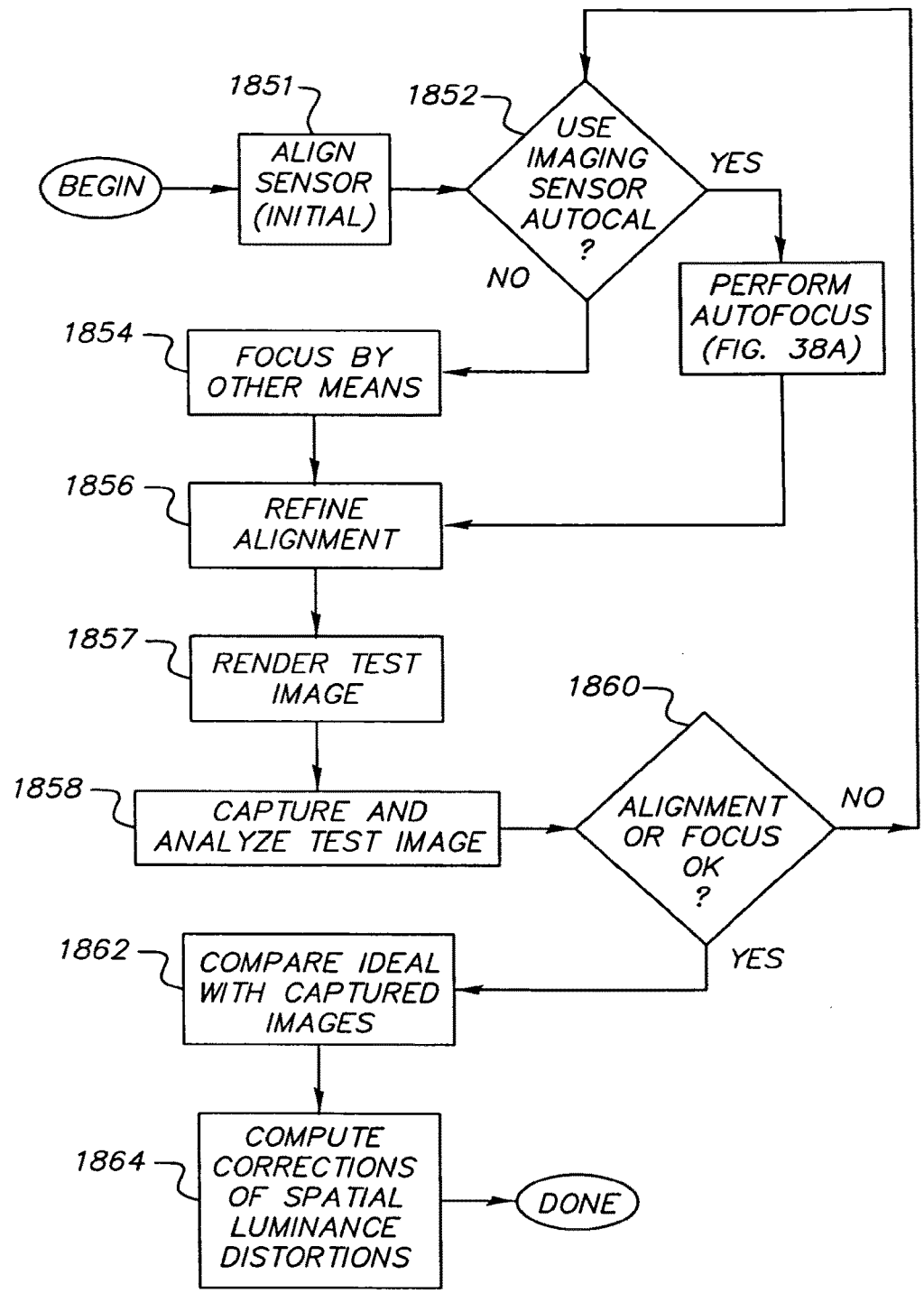
FIG. 38 is a flow chart for the process of focusing and aligning the color measure module of FIGS. 37, 37A, and 37B and determining a spatial luminance distortion function.
Figure 38A:
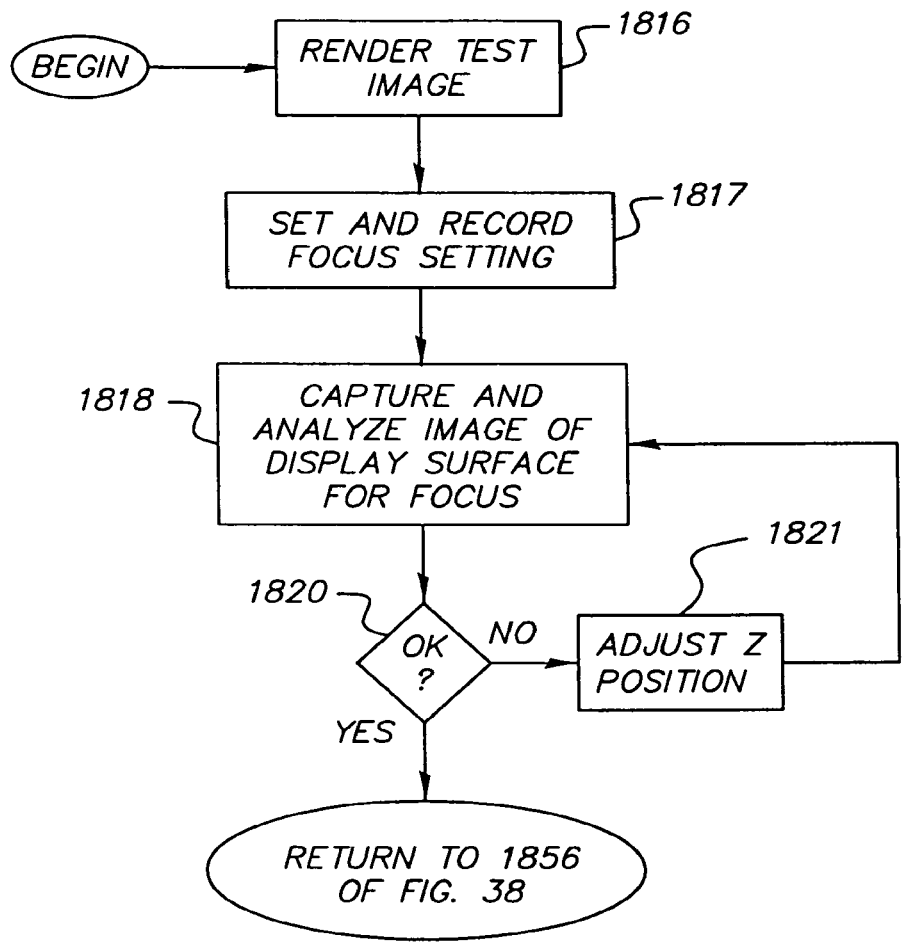
FIG. 38A is a flow chart of the Perform Autofocus block of FIG. 38.

Referring to FIGS. 38 and 38A, a flow chart is shown of the process for aligning the CMI module 1608 of FIGS. 37, 37A and 37B with the display surface and then correcting for spatial luminous distortion. The CMI module 1608 (FIG. 37A) is initially aligned when the module is first mounted onto the frame of the speaker 1610*a* or mounted on the opposite wall of a room facing the display surface (step 1851). Next, if the imaging sensor 1618 (e.g., CCD) is not used for autocalibration (step 1852), then the lens system 1616 is focused such as by manual rotation of cylinder 1615 (FIG. 37A) using distance marks on the cylinder or, optionally, using viewfinder display 1633 (step 1854). If imaging sensor 1618 is used for autofocusing (step 1852), then the process shown in FIG. 38A takes place.

In FIG. 38A, an alignment image is rendered (step 1816), and then the electronics 1619 sets and records the focus setting for the lens system 1616 (step 1817). For example, the focus setting may be set by initializing the actuator 1632 with respect to the cylinder 1615 at a known origin position, such as by a stop along the outside of the cylinder which stops movement of the actuator when the cylinder is in its full in or out position. The electronics 1619 then provides one or more drive (analog/digital) step signals which move the actuator 1632 to one of different focal positions, where each step (forward or back) changes the focus by a known distance. When step 1817 is first performed, the electronics may set the focus setting to about half of the focal range. Next, the image of the display surface 1601 or 1701 is captured by sensor 1618 at that focus setting and then analyzed by programming in the electronics 1619 for whether the image was in focus on sensor 1618 (step 1818). For example, the pixels may be analyzed for edges of objects to determine when focus is proper. If OK, the lens system 1616 is properly focused (step 1820), otherwise the electronics 1619 determines the direction of movement along the z-axis for moving cylinder 1615 and moves lens system 1616 by preset distance(s) stored in memory of electronics 1619 accordingly (step 1821), and repeats step 1818. Such z-axis movement is described earlier in connection with actuator 1632 of FIG. 37A. Once focus is OK (or within a predetermined tolerance) at step 1820, the process continued to step 1856 of FIG. 38.

At step 1856, alignment is checked and refined, if necessary, by use of one or more of: (i) the optional aiming beam of laser diode 1626 (FIG. 37A); (ii) electronics 1619 providing an overlay upon the images on display 1633 of an outline of the feature(s) and the user (or installer) manually adjusting stage 1628 in one or more dimensions to align the features imaged with the overlay (also the angle of view may be adjusted, if an angular adjustment mechanism is present); or (iii) electronics automatically detecting if the captured image has certain pixels or pixel regions aligned with the imaged features and if not, moving stage 1628 in one or more dimensions until such alignment is achieved. Alternatively, the control unit may provide automatic detection and alignment by sending commands to the electronics of the CMI module to move stage 1628 in one or more dimensions. At step 1857, the control unit 1602 or 1706, operating in a test and setup mode, displays a spatial calibration pattern stored in its memory, such as one or more square outline figures at high contrast. The CMI module, having been aligned and focused at 1851-1856, captures the test pattern (step 1858). The data may be verified to see if they reveal misalignment or lack of focus (i.e., checking if pixels or pixel regions align with one or more features of the pattern, and measuring pixel width of edges), then a comparison is made of "ideal" image from memory and the captured image as to difference in pixel value in one or more color channels (step 1862). Although only one spatial calibration pattern is described, steps 1857-1862 may be performed using a number of spatial calibration patterns.

Preferably, the actual luminance profile represented by the "ideal" (possibly for each color channel) of the displayed pattern has been measured as part of a factory calibration, if not for each individual screen, then at least generically for a group of devices. From the comparison, the program of the control unit determines at step 1864 the spatial luminance distortions and prepares corrections that will be applied in subsequent calibrations and procedures. Correction functions may be plural in the foregoing if data are collected for each color channel of the rendering device. If depth of field is not adequate to focus the entire test image, focus should be optimized for the center of the imager's field. The imager can be re-focused, as necessary, in order to verify that corrections properly handle the periphery of the display surface.

Use of an imaging sensor 1618 for measuring non-uniformity of the rendering surface was described earlier by use of an imagical to acquire data to flatten the screen, i.e., make it regionally homogeneous in light output or to compensate for interactions among adjacent pixels in complex imagery, and then later in describing color differences in different regions of a nominally uniform color field for a video display screen, for measuring non-video display, and computing corrected Tone Reproduction Curves (TRC's).

Figure 39:
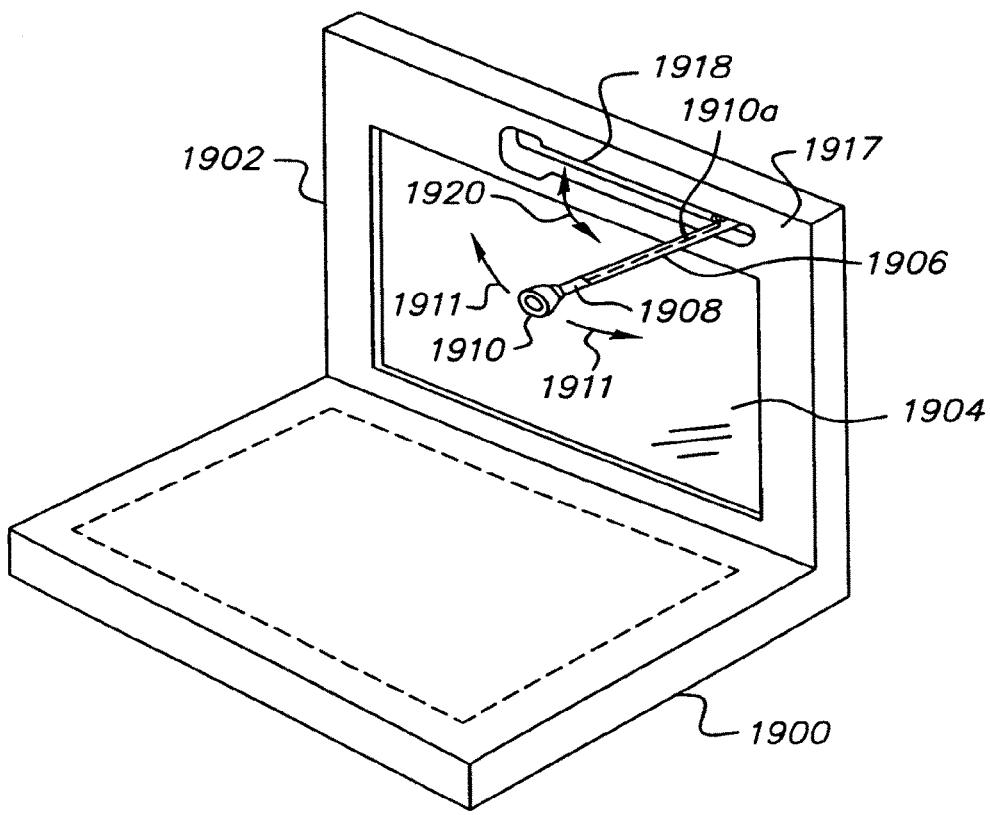
FIG. 39 is a perspective view of a portable, laptop, or notebook computer with an embedded, pivotable arm for mounting a camera capable of supporting both teleconferencing and calibration functionalities.
Figure 39A:
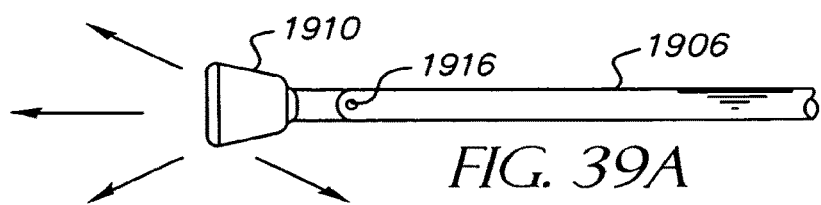
FIGS. 39A and 39B are top and side views, respectively, of the camera of FIG. 39.
Figure 39B:
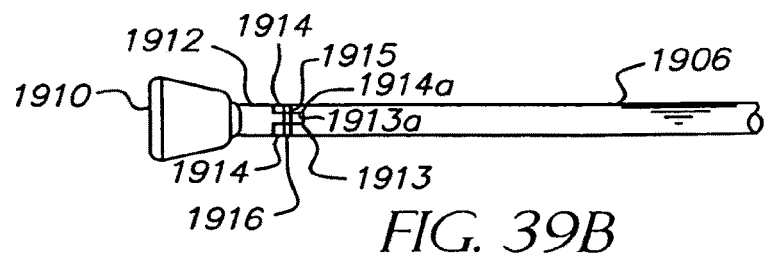

Referring to FIG. 39, an imaging sensor is shown useable with conventional computer (including notebook or portable) video monitors which may also be used as a camera for capturing images of the user. An opened portable, laptop or notebook computer 1900 has a display portion 1902 with a screen 1904 and arm member 1906. The arm member 1906 is shown in FIG. 39 pivoted to the open position and at the end of the arm member is a pivot joint 1908 for mounting a camera 1910. The camera may pivot as indicated by arrows 1911 along joint 1908. The joint is shown in more detail in FIGS. 39A and 39B, in which camera 1910 is coupled by a shaft 1912, which may be part of the camera. The end 1913 of the shaft is shaped to be received between two flanges 1914 extending from the end of arm member 1906. An opening 1915 (shown in dashed lines) extends through flanges 1914 and shaft end 1913, and a pin 1916 is received through opening 1915 to pivotally mount shaft 1912 to arm member 1906. End 1913 is rotatable about pin 1916 in the socket formed between flanges 1914. The other end 1917 of arm member 1906 forms a pin that is pivotally mounted in a grooved slot at one end of a recess 1918 in the top of display portion 1902, such that the arm member can pivot to a full open position (as shown in FIG. 39) or can pivot to a closed position within recess 1918, which is shaped to received the arm member and camera 1910 when the camera is not in use. Arrow 1920 indicates the pivoting of arm member 1906 and camera 1910 from open and closed positions. Other mechanisms for pivotally mounting arm member 1906 to both computer 1900 and camera 1910 may also be used.

Camera 1910 is preferably a small color CCD-based camera of the sort which has been adapted to clip onto the frame of display portion 1902 and used for video conferencing. The camera 1910 can send digital signals to computer 1900, via a cable, to a port of camera 1910, where camera 1910 provides output signals using communication protocol for such port. For example the port may be a USB port using USB communication protocol, or other port or interface (e.g., card) and conventional communication protocol may be used to enable communication between camera 1910 and computer 1900. Preferably, such connection to the computer is via a cable 1910*a* to camera 1910 extending through or along the outside of arm member 1906, as shown in FIG. 39, by a dashed line along member 1906.

Camera 1910 is modified (possibly involving an adjustment of the focal distance for the camera) to attach and pivot about on an arm member 1906 from the frame surrounding the display surface. If display portion 1902 is too thin to accommodate the camera in recess 1918, then camera 1910 can be provided separately to snap into pivot joint 1908 of arm 1906, being held in position by engagement of one or the other detent/button combinations described below. Alternatively, shaft 1912 and a bore in the camera 1910 may each be threaded to enable joining them.

The camera 1910 may be pivoted to "see" the user, such as in a video teleconferencing application, and may be pivoted to face the screen 1904 and thus "see" the screen in a calibration application. Thus the camera has "dual use." Detents are provided on surface 1913*a* of shaft end 1913 and engage one or more buttons along surface 1914*a* of one or both of flanges 1914 as it pivots and thereby temporarily fixes the rotational position of the camera 1910 when rotated by the user. Alternatively, the detents may be provided along surface 1914*a* and button(s) along surface 1913*a*. When the arm member 1906 is in the open position, and the camera is fully rotated to its last detent position to point the camera to the screen, the camera's optics are automatically aligned with the part of the screen to be used for calibration of the color of the screen and/or virtual proofing with other rendering device(s), as described above. Sense switches may be associated with detent positions capable of signaling via a cable or wire 1910*a* to computer 1900 which "dual use" mode is currently actionable.

The dual-use camera 1910 may require a bi-focal adjustment with dual, manual detents capable of securing the focus optics of the camera in position for teleconferencing or calibration applications. As above, corrections for various spatial distortions of the image are applied before measurement non-uniformities are processed for making "field-flattening" compensations. The arm member 1906 need not be embedded in the frame surrounding the screen as shown in FIG. 39, but may be an attachment.

While an imaging sensor is very useful in detecting spatial non-uniformities of luminance and/or color across the display surface, it may lack the sensitivity required to distinguish low light levels in a careful calibration of display gamma or tone reproduction characteristics. It is advantageous to compensate for reduced sensitivity, at least partially, by forfeiting spatial resolution in favor of increased sensitivity and integrating light responses over many pixels when accurate low-light measurements are important. In the foregoing situation, uniformity correction should be made at relatively high luminance on the display, followed by spatially integrated low-light measurements.

Instrumental embodiments and methods described herein are adaptable to hand-held and miniaturized display devices, including cellular telephones, personal digital assistants and the like. Display technology may produce very high resolution, compact arrays of micropixels capable of conveying all the information of conventionally-sized computer screens, especially if viewed by the user through a magnifier. Many cellular phones are equipped with cameras, some of which are capable of transmitting a series of images as a video data stream. Often, speaker phone functionality is included. Many cameras are capable of autofocus and of imaging at relatively close range. However, the cameras are not generally positioned in the handset in such a way as to enable imaging of the handset display, and such handsets are used in environments where the user has little control over environmental (ambient) conditions, including illumination. In the following, several structural and functional improvements are described that increase the range of applications of handset cameras.

Figure 39C:
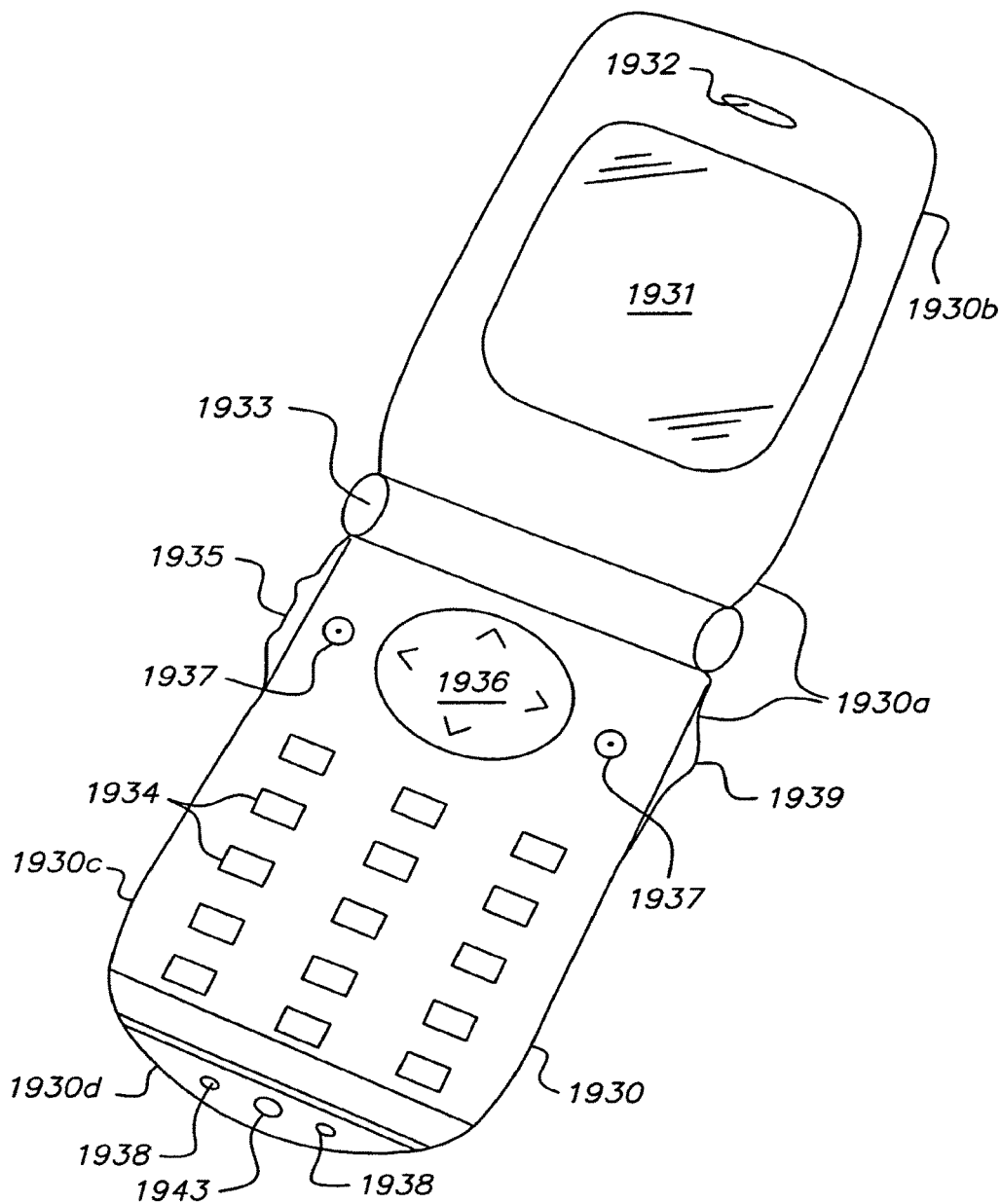
FIG. 39C is a plan view of a portable device of a cellular phone having a built-in color camera utilizing color calibration in accordance with the present invention.
Figure 39D:
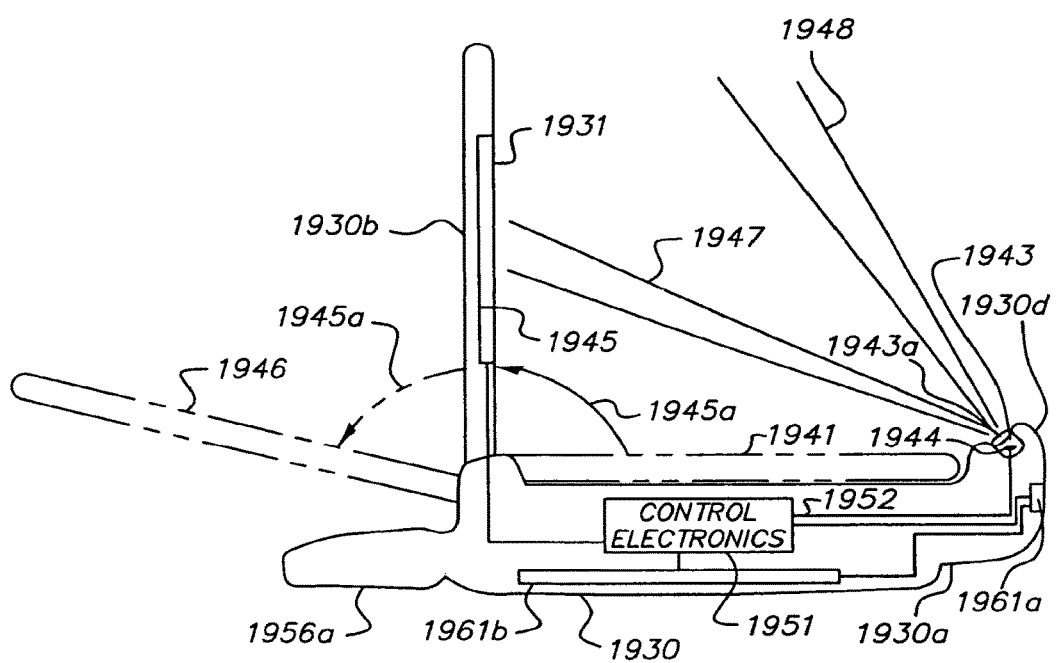
FIG. 39D is a side view of the portable device of FIG. 39C.

FIGS. 39C and 39D illustrate a handset device 1930 having a housing 1930*a* with upper and lower housing portion 1930*b* and 1930*c*, respectively. Upper housing portion 1930*b* is pivotally attached by a joint 1933 to enable rotation to either a closed position or various open positions with respect to lower housing portion 1930*c*. For purposes of illustration, handset device 1930 is illustrated as a typical cellular phone with a display screen 1931 (e.g., a color LCD screen) and a speaker 1932 along upper housing portion 1930*b*. Along lower housing portion 1930*c* is a keypad 1934, a rocker switch 1935 for speaker volume control, one or more microphones 1938, and a joystick-like control 1936. With the handset in an open position, the control 1936 is used for navigating through menus presented on the display screen 1931 to provide a user interface enabling the user to make menu selections by interacting with options shown on screen display 1931, as typical of a cellular phone. Button switches 1937 may be present for use in conjunction with control 1936 in the user interface, as also typical of a cellular phone.

At least one switch or trigger 1939 along housing 1930 operates a camera 1943 which is disposed in an extension 1930*d* of lower housing portion 1930*c*. The camera 1943 has a sensor element 1944, such as a color CCD array, and a lens system (one or more lenses) 1943*a* through which the sensor element captures images. Lens system 1943*a* may optionally have movable actuators to move two or more lenses to provide focus and/or zoom, typical of a portable digital camera. Optionally, a flash may also be present in extension 1930*d* for adding illumination if needed to capture images. The upper housing portion 1930*b* is pivotable along joint 1930 to multiple detented positions 1941, 1945, and 1946 with respect to lower housing portion 1930*c*, as illustrated by arrows 1945*a*, where the default position (like a closed book) is illustrated by the dashed lines and fully open by dash and dot lines. Camera 1943 may be a miniature, digital camera of the type commonly used in handsets. The camera is connected to control electronics 1951 of the handset along link 1952, which may be an extension of an internal bus of the control unit or a variety of high-speed serial bus interface (e.g., Firewire, Universal Serial Bus, etc.). In the former case, memory-mapped i/o, direct memory access, etc., are typical functionalities. However, any connectivity of sufficient bandwidth may be used. A connector 1961*a* along housing 1930 enables external charging of a rechargeable battery 1961*b* for supplying power to control electronics 1951 and other components requiring power for operation, as typical of a cellular phone. The connector 1961*a* additionally may provide one or more ports to the control electronics to interface the control electronics to external devices or computer systems.

The pivoting mechanism for opening the handset device provides detents for position 1945, enabling the camera 1943 to view the display screen 1931 at an angle of between 45 and 90 degrees, while at position 1946 the upper housing portion 1930*b* is open wide enough so as to be out of the field of view of the camera 1943. It is advantageous to have the camera 1943 be pivotable between two positions (illustrated by field-of-view cones 1947 and 1948) in order to optimize the angle of view or line of sight to the display screen 1931 in position 1945 while insuring that the upper housing portion 1930*b* is completely out of view otherwise.

In the case of a non-folding handset, the camera can be disposed on a miniaturized arm in a manner similar to the configuration of FIG. 39.

Figure 39E:
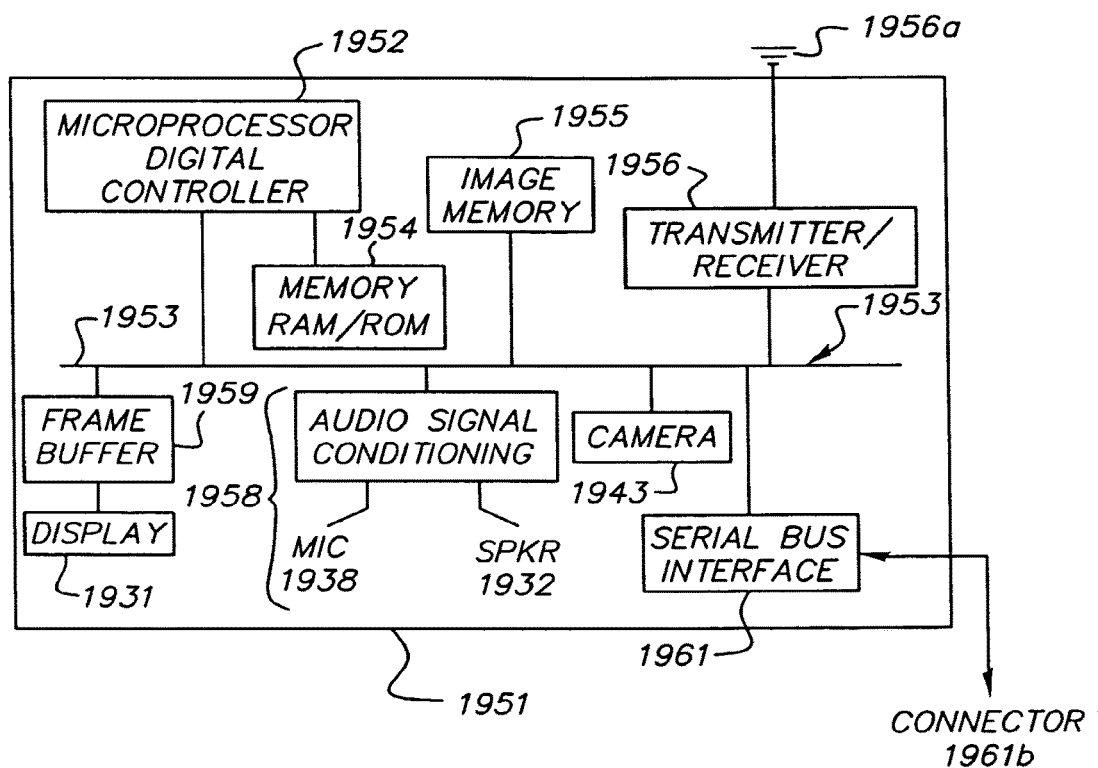
FIG. 39E is a block diagram of the electronics of the portable device of FIG. 39C.

The control electronics 1951 of the handset device 1930 is shown in the block diagram of FIG. 39E. A controller 1952 controls the operation of the handset device. Controller 1952 may be a microcontroller, microprocessor, or a conventional, programmable device which can be connected to memory 1954, at least part of which can be non-volatile memory for storing operating programs, calibration coefficients, time, date, GPS coordinates, or other data needed for operating the handset device. The controller 1951 is shown connected to peripheral modules along bus 1953, which may employ wires and/or optical fibers with suitable signal converters. The bus 1953 carries address and data signals. Image memory 1955 is general-purpose and may store text data, contact lists, appointment data, digitized audio data, extended program instructions and data (including operating system and application programs), in addition to image data in a variety of formats (e.g., JPEG, TIFF, PDF, or other formats). Image memory 1955 may include Flash memory, and/or removable memory storage, such as a memory stick, compact memory cards, or other removable storage.

A transmitter/receiver 1956 is a block comprising circuitry (e.g., signal transducers, A/D and D/A converters, modulator/demodulator or modem, or other electronics needed to send and receive voice and/or data) typical for enabling wireless (RF) communication over an antenna 1956a. It may also comprise a Network Interface Adapter enabling Ethernet communications and Voice-over-Internet-Protocol ("VoIP") when the control software is set for such a mode of operation. Serial Bus Interface 1961 is a block comprising circuitry for communicating with external devices, via one or more ports of connector 1961b, by serial communication protocols, such as one or more of Bluetooth, Firewire, Universal Serial Bus (wired or not), infrared signaling, or standards such as RS232 and the like. However, other communication means may also be used. When present in the handset device, the serial bus interface 1961 may provide alternative access to intelligent print devices (for example, EXIF-capable printers) and/or to the Internet (for VoIP and the like) by way of other computers. Camera 1943 in addition to sensor array 1944 has signal-conditioning circuitry suitable for converting raw image data captured by the sensor array into digitally useable form, preferably JPEG- or TIFF-encoded images with EXIF-compatible header fields or an equivalent. Camera 1943 has at least the same or better resolution (both spatial resolution and contrast or dynamic range) as cameras currently available in handset devices. Handset device shown is not limited to cellular phones, but may be any handheld device having a camera and communication capability, such as digital cameras with wireless communication means for data and/or voice, and personal digital assistants having a camera and such communication means.

The circuitry associated with camera 1943 may include a frame store or buffer. Alternatively, a single frame buffer 1959 may be shared by camera 1943 and display 1931. Signal conditioning for display has been discussed elsewhere throughout this disclosure and in U.S. patent application Ser. No. 09/832,553, filed Apr. 11, 2001.

Audio signal conditioning module 1958 includes microphones 1938 for transducing sound waves into electrical signals and one or more speakers 1932 for converting electrical signals into sound waves. Signal-processing software and/or hardware may be provided that enables voice and speech recognition so that a user may set the handset device into a mode in which menu choices can be made verbally rather than by traversing a sequence of keystrokes on the handset. Alternatively, controller 1952 may have a network interface enabling it to offload the tasks of speech recognition and command parsing to a suitably programmed computer of greater capability. Although control electronics 1951 is illustrated with a traditional bus architecture, other internal communication architecture may be used. For example, peripheral modules 1931, 1943, 1955, 1956, 1958, and 1961 of FIG. 39C may communicate with the controller 1952 using a serial protocol similar to that standardized in the Universal Serial Bus interface (such as described at www.usb.org).

Figure 39F:
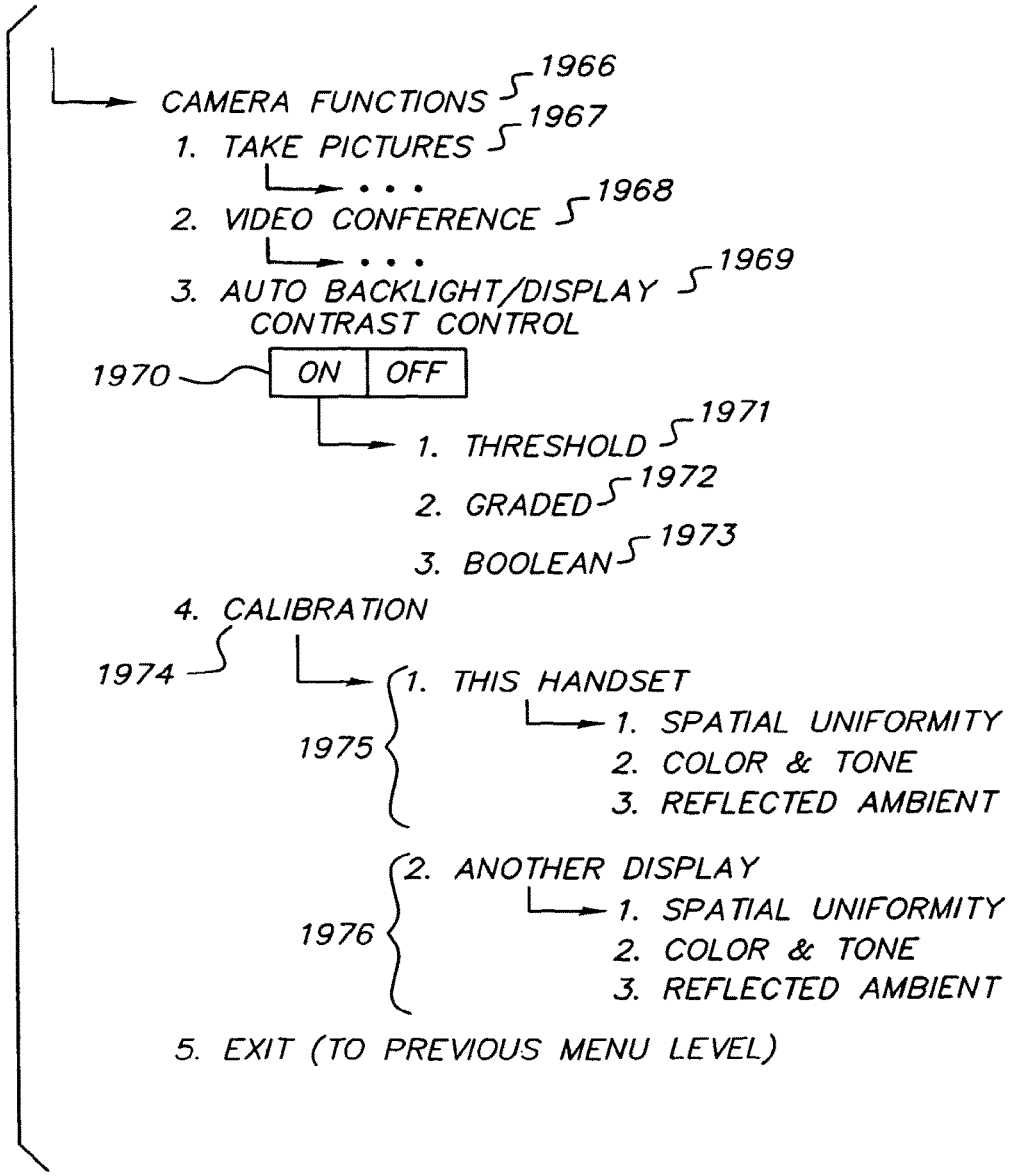
FIG. 39F illustrates the structure of menus on the user interface of the portable device of FIG. 39C enabling the user to select camera functions.

FIG. 39F illustrates a hierarchical menu structure, such structure being similar to that typically used in portable devices, such as digital cameras and cellular phones. The figure shows several, nested levels of choices in order to reveal the relationships between the levels. However, only one level of selections need be available on the display screen 1931 at a given time. The arrow at the top left indicates that Camera Functions 1966 is a submenu to a higher level in the hierarchy. For illustrative simplicity, four options/selections would appear on the display under Camera Functions: Take Pictures, Video Conference, Auto Backlight/Display Contrast Control, Calibration, and Exit (or Back) to a previous screen.

Take Pictures 1967 selection leads to another level of selections to include configuring EXIF header information (or an equivalent) and corresponding image capture settings, e.g., flash setting (if a flash is present), electronic shutter speed, resolution, or other settings typical of digital camera or cellular phone having a digital camera.

Video Conference 1968 enables the user to set up the handset device for displaying data during a telephone conversation. Such data could include images of one or both conversants (if both, a split-screen display would be optional on setup) or of other data such as a textual selection from a document or numerical data from a spreadsheet, or the like. Submenu options may be used to select the type of display, entry of addresses or phone numbers of the other party(s) device to be conferenced, or parameters for configuring the video conference.

Auto Backlight/Display Contrast Control 1969 presents a toggle, either "ON" or "OFF", which can be switched to the other state, for example, when the user employs controls 1936 and/or 1937 (FIG. 39C). When in the "ON" state, Auto Backlight operates, as elaborated below, according to either threshold 1971, graded 1972 or Boolean 1973 modes selectable by user-interface controls on the handset device. In an advantageous embodiment, the audio-signal-conditioning circuitry 1958 (FIG. 39C) of the handheld device may be used in the conversion of user manual data stored in memory of the device into computer generated speech which can be activated by the user to provide audible help on demand.

Selection of Calibration 1974 invokes a submenu that enables the user to choose to calibrate, for example, either the display of the instant handheld device 1975 (e.g., display screen 1931) or another display (or other color rendering devices) 1976. The options available for calibration will be explained further below.

In a first improvement in handset functionality, the user interface associated with the display 1931 enables a setting whereby the camera 1943, however positioned on the handset, monitors the ambient illumination whenever the user opens the handset device or otherwise indicates preparation for use. Currently, many handset devices turn on a backlight of a liquid crystal display when preparation for use is indicated whether or not the ambient illumination conditions provide contrast sufficient for reading what is displayed. This may reduce battery life unnecessarily. Then, typically, the backlight is turned off after a fixed time interval whether or not the user needs enhanced contrast. Through the interface illustrated in FIG. 39F the user is enabled to choose among, for example, three modes of conserving battery life consistent with improved display legibility when Auto Backlight Control is set to ON, as shown in more detail in the flow diagram of FIG. 39G.

Figure 39G:
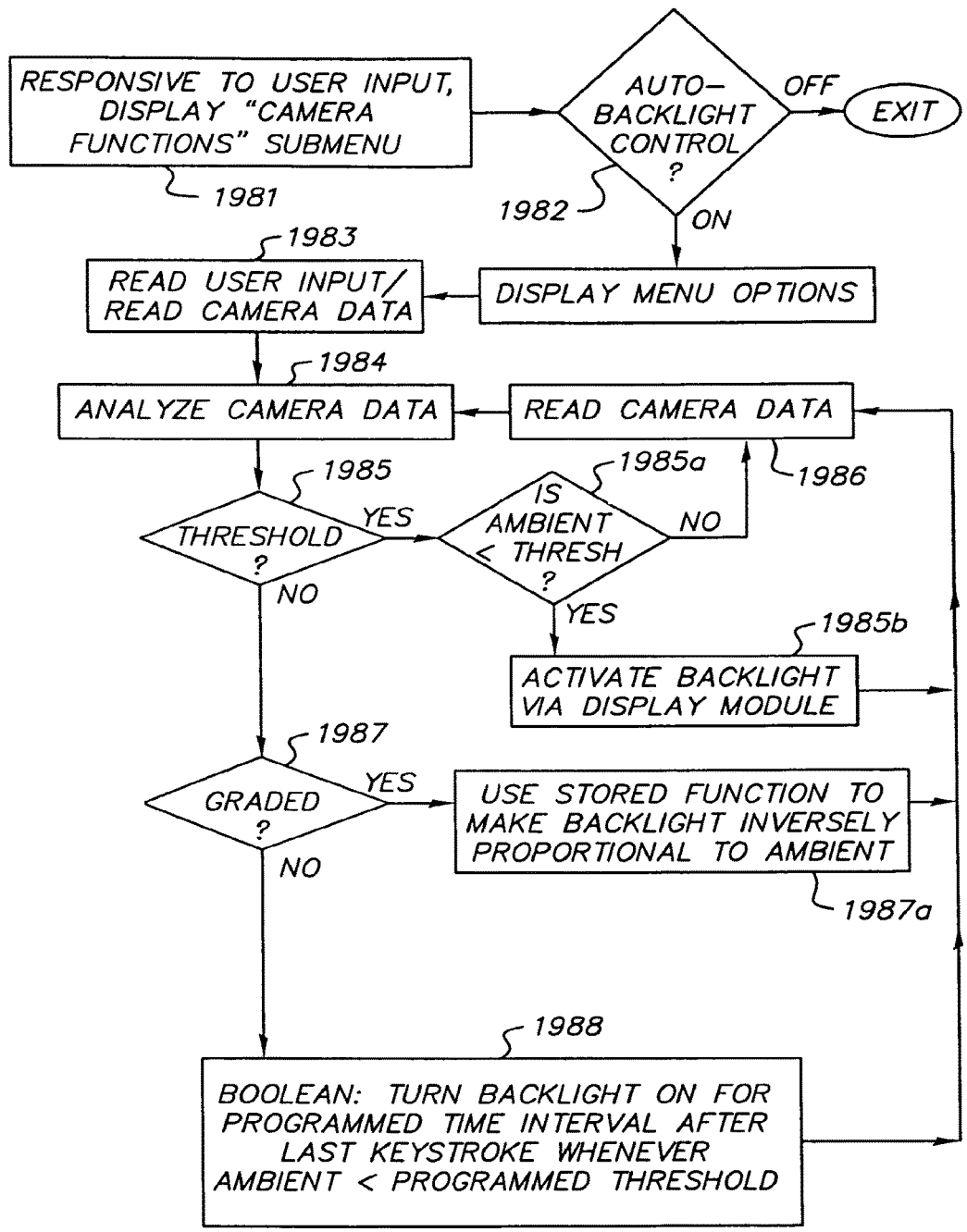
FIG. 39G is a flowchart for the process of automatically controlling the backlight of the portable device of FIG. 39C.

The flow diagram of FIG. 39G should not be viewed as one that would be translated directly into computer program source code. Rather, it is intended to illustrate the Auto Backlight functionality in terms of a few, possible implementations and in relation to handset modules, both hardware and software. Similar to FIG. 39F, flow begins at the upper left block 1981 where the user has selected Camera Functions 1966 within the menu hierarchy, and then selects at step 1982 a menu option to turn backlight control ON or OFF via keypad 1934 or controls 1936 or 1937. Optionally, controller 1952 reads at step 1982 the user input by deciphering verbal commands processed through the audio module 1958. For Auto Backlight control, the controller 1952 at step 1983 displays submenu options and receives the user selection of either a threshold, graded, or Boolean setting, initiates data collection by the camera 1943 (i.e., camera automatically captures one or more images to provide such data), and then analyzes the data at step 1984. One collection/analysis method is to average the light distribution for the values of pixels in one or more color channels in images across the camera's sensor array in time and space to produce a value. However, other methods may be used that analyze for spatial or temporal patterns in the light distribution.

A check is made to determine if the user selected a threshold setting (step 1985). If so, then the controller 1952 compares the result of analyzed camera data to a threshold value stored in memory 1954. If the ambient illumination (reflected in the results of analysis) were less than a stored value based on prior study of display legibility (step 1985*a*), then the controller would direct the electronics of display 1931 to turn on the backlight (step 1985*b*), otherwise the backlight is off. The controller 1952 may periodically read camera data (step 1986) then repeat steps 1984, 1985, 1985*a*, and 1985*b* to insure that ambient conditions continue to warrant illumination of the display. Readings may be taken so long as the threshold condition is met, the handset device continues to be open, or until the camera is put into an incompatible mode by an external event such as user choice.

Figure 39H:
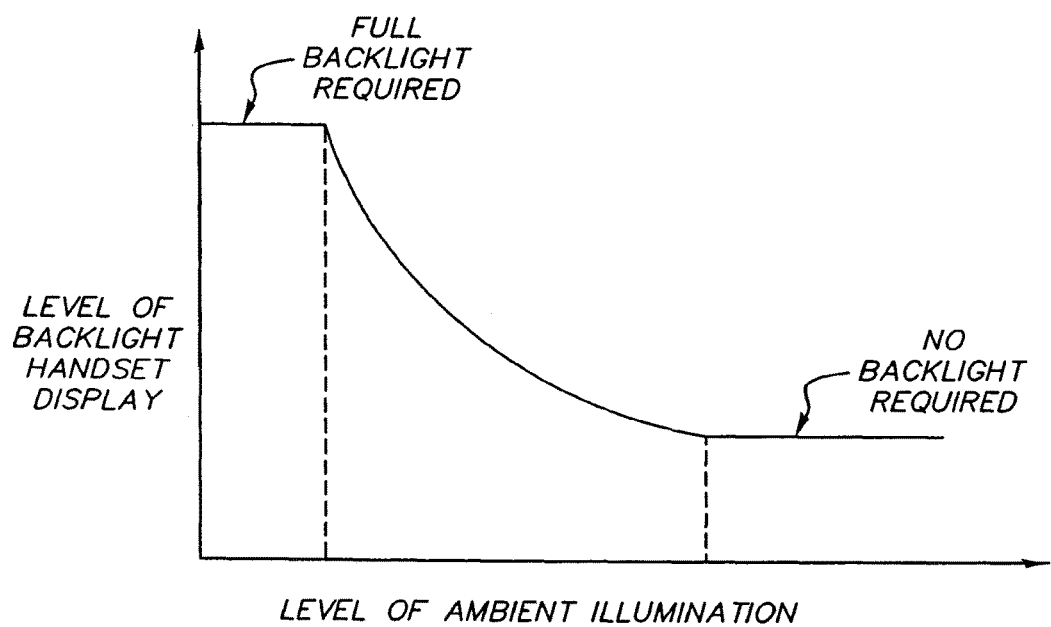
FIG. 39H is a graph illustrating an example of gradient function for determining the level of backlight illumination for the display of a portable device of FIG. 39C for different levels of ambient illumination measured by the device.

If threshold setting was not selected at step 1985, a check is made to determine if user selected a graded setting (step 1987). If so, a stored function describing luminous intensity of the backlight needed for legibility as a function of the level of ambient illumination is used to modulate the level of the backlight (step 1987*a*). For example, the level of backlight could be set to the reciprocal of the average (over space and time as discussed earlier) ambient light reading where said reading is clamped at minimum and maximum values found in prior study to represent levels at which maximum or minimum, respectively, backlight is required for readability. This clamped function is illustrated, for example, in the graph of FIG. 39H. Battery life would be enhanced consistent with display legibility if no more backlight than necessary were utilized.

If neither threshold or graded setting were selected at steps 1985 and 1987, then the Boolean setting has been selected, and at step 1988 the controller 1952 turns on the backlight only if an ambient threshold condition (similar to step 1985*a*) were met AND the time since the last keystroke via keypad (or depressing of controls 1936 and 1937) were less than a programmed value stored in memory 1954 (e.g., 15 seconds). At the expiry of the programmed interval, the handset would depart Auto Backlight mode. Boolean may not be well-suited to the situation in which the conversant needed to view variable data, such as text or images, being received for display during a conversation. Threshold, graded, and Boolean are exemplary implementations not meant to be limiting, other functions or conditions may also be used in accordance with the amount of ambient light measured by the handset camera.

Referring back to FIG. 39F, selection of Calibration 1974 of the instant handset 1975 enables the user to select one or more of three options: Spatial Uniformity, Color and Tone, or Reflected Ambient. Spatial Uniformity involves using the camera to measure non-uniformities across the display surface, preferably absent extrinsic or ambient sources of non-uniformity. Resulting data are used to homogenize display brightness regionally or spatially, preferably while maintaining a specified neutral balance. Spatial uniformity detection and correction of a display screen is described below in connection with FIGS. 40-43B. Color and Tone involves calibration for one or more of white point (neutral balance), linearization and color mixture modeling, as described earlier. Reflected Ambient refers to the estimation of the amount of light more or less diffusely reflected off the display surface of a self-luminous or emissive device.

In general, cameras of handheld devices, digital cameras, or handsets, are non-linear, colorimetrically. In other words, linear models of color mixture are not strictly applicable in the development of transformations for converting device codes into device independent color coordinates which may subsequently be converted into device-specific display codes. Digital cameras generally belong in the cell at the bottom left of FIG. 4C. Methods for preparing approximate calibration transformations for such devices are described both earlier and also later below with tools (e.g., calibration targets, etc.) for enabling a user to perform such calibration with the theatre system or on the aftermarket. With knowledge of the spectral sensitivity of the camera's color channels and the likely properties of sets of colorants and/or illuminants to be measured and characterized, a more exact, colorimetrically, calibrated transformation may be provided, as discussed below. Earlier, methods/apparatus were described for determining the spectral sensitivity of a sensor; cameras may be calibrated at the factory and calibration data (including "normalization" functions that correct for non-uniform sensitivity across the surface of an area sensor) may be stored for possible inclusion in headers to image data files. Such headers are provided for by the EXIF standard, for example. Alternatively, camera calibration may be provided as an aftermarket service.

A system similar to the Profile Server 316 discussed earlier in connection with FIG. 22 may be provided to assist in using the handset camera as a calibrator. This system, referred to hereinafter as the Calibrator Camera Server, may represent a computer server system at a network addressable site, such as via the Internet or World Wide Web. The Calibration Camera Server has memory storing a database of the sensor spectral sensitivities for different sensors, and video display color properties needed for accurate calibration for different color displays or other color rendering devices. Such Calibration Camera Server may perform the underlying computations of color transformations, as will be discussed further below. The accuracy of the color transformations desired dictates the accuracy and the methods required in preparing them. Either the handset (via a wireless network connection), or the color device to be calibrated (e.g., via a MC, modem, or other network interfacing means) may be provided with network access for enabling connection to the Calibration Camera Server to query for desired information from the database. The Calibration Camera Server may also be part of the Profile Server 316.

The use of a handset to calibrate another display 1976 has application to the calibration of digital home theatre. In connection with FIGS. 35 through 38A, several embodiments for calibration, including building sensors into projectors and associating them with wall-mounted speakers, were described. However, handsets provide viewfinders (by using real-time video images captured by the camera on handheld device's display) and, potentially, the handset's speaker(s) may convert documentary calibration procedures into audible instructions for a home user to facilitate calibration with the handset (e.g., for the user who does not care to read manuals or develop expertise in calibration procedures).

On selection of Another Display 1976 (FIG. 39F), the controller 1952 (FIG. 39E) of the handset seeks to establish communication with the control unit 1602 or 1706 (FIG. 37 or 37B) of the other display through interfaces provided by transceiver/receiver 1956 or serial interface 1961 (via cable or wireless). Unlike FIG. 37 or 37B, no CMI module 1608 may be present, but the user (or a service technician) wishes to calibrate the color of the display using a handset (which as stated earlier refers generally to a portable device having a digital camera, which preferably can be carried in one's hand). A calibration program would already have been initiated in the control unit for the other display which prompted the user to select a camera as the measurement instrument. The user would then be led through the following procedure by prompts that are either displayed on a part of the theatre display screen or "spoken" to the user by the handset speaker(s) and/or speakers of the theater system:

Step 1: Control unit 1602 or 1706 of the theatre display system acknowledges establishment of communication with handset; if a cell phone, the handset appears "busy" to incoming calls. In the case where the controller 1952 and/or memory 1955 of the handset is limited, the initial inter-device identification and "handshake" may involve a transfer of programs and reference calibration data from the theatre system to controller 1952. Alternatively, the control unit 1602 or 1706 may "take over" and treat the handheld device as a multifunction peripheral. The communication may be according to a USB or USB-like protocol, which latter has been developed to support both wireless and multifunction device interfaces (such as described at www.usb.org).

Step 2: An alignment target is displayed on the theatre display. Image data for such alignment target (e.g., crosshair(s), geometric shape(s), outlines, or the like) are stored in memory of control unit 1602 or 1706. The user is instructed to operate the handset's camera so as to capture an image of the displayed alignment target. Alternatively, on receipt of instruction from control unit 1602 or 1706, the camera enters a "free run" mode in which video images are captured regularly (e.g. real-time) and displayed on the handset display.

The user is guided in this by using the handset display as a viewfinder. A magnifier may be provided with the handset, and will be especially useful if the handset has a high-resolution, miniaturized display, as mentioned earlier. An example of such magnifier is shown in FIGS. 39M and 39N. The magnifier represents a lens 1931*a* which may be attachable for adjustment over a display of handset 1930 when such display is a miniature high-resolution display 1931*b*. The lens 1931*a* is preferably attached by a pair of arms 1931*c*, each pivotal along joints 1931*d* (e.g., about pins through arms and fixed members 1931*e*) to enable extension and retraction by the user, as needed. Each one of the arms 1931*c* is attached to one of the sides of lens 1931*a* and along display 1931*b*. Magnifier 1931*a* is advantageously removable such that display 1931*b* may be used for conventional resolution, as by clustering or averaging groups of adjacent pixels to reduce effective resolution. Alignment will be facilitated further if the proper centering of the alignment target is signaled by a comparison of features of the captured image with digital indicia of a reference image stored or loadable into handset memory 1955 from control unit 1602 or 1706. Image data may be transferred from the handset to control unit 1602 or 1706 and computations carried out there to determine when the camera array is aligned with the theatre display and then to notify by voice or visual message on the handset and/or theatre display when alignment is complete. As it may be difficult for the user to later maintain such alignment, the handset may be stabilized on a surface, such as on a table, stand, or tripod, or on a support described later in FIG. 39K.

Step 3: Once the handset's camera is properly aligned and the user has selected the kinds of calibrations 1976 (FIG. 39F) to be performed, the controller 1952 and the display unit's controller 1602 or 1706 interact to perform the calibration procedures described herein. In very brief review, this involves displaying calibration forms or images on the theatre display, capturing images of the images with the camera, analyzing said captured images and computing appropriate transformations so that colors of the digital theatre data are displayed correctly.

In order to simplify more detailed discussion of how the calibration of another display proceeds with the aid of a handset (or other handheld device, such as a digital camera), assume that a calibration program has already been initiated through user interaction with a graphical user interface (GUI) operating through controller 1602 or 1706. Assume, also, that at least one of the channels of the handset camera (e.g., the green sensor channel) has been calibrated such that differences in responses among the population of sensor elements to a flat field are normalized, and that the output of the sensors is nearly linear with the logarithm, for example, of the light intensity on the sensors. Functions other than the logarithm may be used; what is most important is that the function be known. Such calibration is performed as part of handset manufacture or through aftermarket services.

It was shown in Table Two and attendant discussion that the "lumeter" whose spectral response function approximates the human photopic luminosity function tracks a true luminance meter reasonably closely in the measurement of a gamma function. The closeness of correspondence of measurements taken through the green channel of a handset camera with those of a true Luminance meter (having the human photopic luminosity function) may depend on how closely the green channel responsivity approximates CIE Standard Observer's y-bar Color Matching Function. For the common scenario of "good enough" calibration, the correspondence is likely to be adequate for most handsets. In other words, performing a gamma calibration, such as that illustrated in Table Two, with the handset is likely to be close enough. Scenarios in which more accurate calibration of the handset is required or desired will be discussed later.

Returning, briefly, to user selection of Another Display 1976 under Calibration of FIG. 39F, it is preferred if the choices are accompanied on the displayed menu by check boxes (or other graphical selection effect) enabling the user to indicate all at once which functions are to be performed. Once selected, the calibration program stored in the handset implements the functions once the user has set up and aligned the handset camera for proper viewing of the display surface to be calibrated. It may be advantageous to perform basic Color and Tone calibrations prior to Spatial Uniformity, even if the user has requested only the latter. Likewise, measurement of Reflected Ambient, the amount of light reflected from the display surface when it would otherwise be completely dark, should precede any other calibrations. As has been mentioned previously, "dark light", "background" etc. should be factored into other calibrations and/or the user should be advised that prevailing ambient will compromise calibration and the accuracy of color reproduction.

Figure 39I:
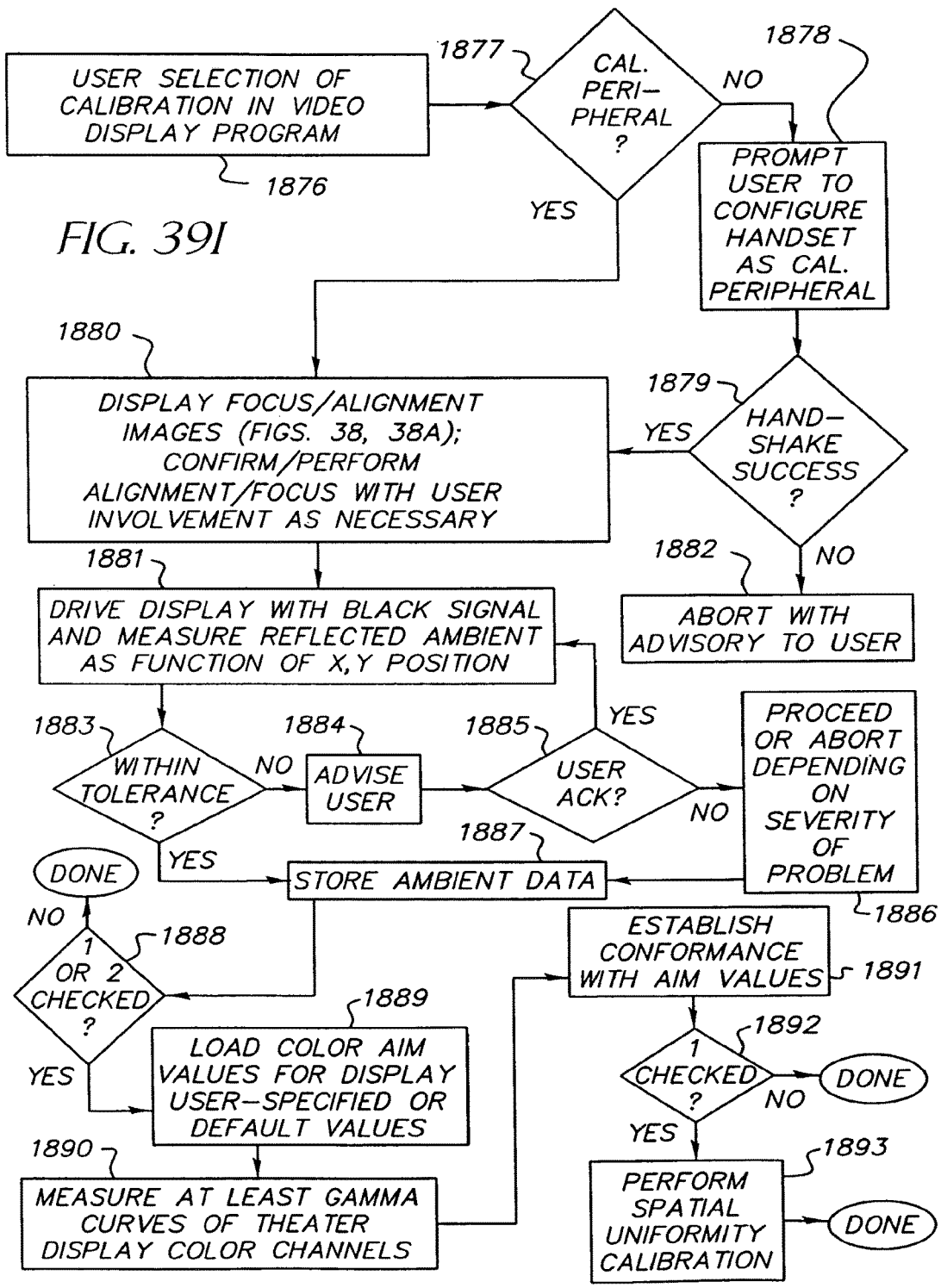
FIG. 39I is a flowchart for the process of calibrating another color display device (or system) using the portable device of FIG. 39C.

Turning now to FIG. 39I, a flowchart shows in more detail the operation of the handset in response to selection of Another Display 1976 by the user. Although the following refers to calibration of Another Display as being one associated with a theater display system, such calibration may be of other color displays or surfaces upon which rendered color images are displayed which may or may not be associated with a theater display system. Further, such calibration using a handset camera is not limited to displays, but may be of other types of rendering devices which output color images onto media, such as printers, copier, presses or the like. Such media can be fixed in a position for capture by the handset camera to enable alignment with outputted alignment target(s) and then images of other outputted media can be similarly captured for calibration processing. First, the user has initiated a calibration exercise on the home theater system, for example, as an option in a DVD-viewing program or the like (step 1876). The program operating on the theater system checks whether there is a calibration peripheral of one of the kinds described earlier (e.g., sensor 1508 or CMI module 1608) associated with the system (step 1877). If not, the program prompts the user to configure the handset camera, through a menu such as that illustrated in FIG. 39F, as a peripheral for calibration of another color display (step 1878). If communication between handset and display system is not established successfully (step 1879), then the calibration program is aborted with an error message to the user, sent via handset or the display system (step 1882).

If handshaking occurs successfully at step 1879, then alignment and focusing are verified for calibration, such as shown in FIGS. 38 and 38A (step 1880). In the case of a handset camera, the user is guided through set up of the handset for proper alignment and focus using the handset display as a viewfinder, preferably with the aid of a support base (as shown in FIG. 39K and discussed later below).

Regardless of which calibration options were selected by the user at Another Display 1976 (FIG. 39F), it is advantageous and preferred to estimate the amount of reflected ambient prior to performing other calibration functions (step 1881). Accordingly, the theater display is driven with digital codes of 0.0 (black) over its array of pixels in each color channel. The handset camera captures an image of the display when so driven to black. The captured image is then received and processed by controller 1602 or 1706; the image represents the sum of intrinsic dark light and reflected ambient as a function of spatial position. Alternatively, such processing could be carried out by the handset. It is preferred that the handset camera be configured and positioned such that specularly reflected light is not collected or, at least is minimized.

Light so measured is compared with manufacturer recommended tolerances or historical, normative data, such as may be stored in memory of the control unit 1602 or 1706 (step 1883). If ambient conditions are such that the theatre display cannot be operated in a calibrated mode due to high level of measured dark light at step 1881 or high level of spatially non-uniform dark light between highest and lowest measured values (step 1883), the user is advised that corrective action should be taken, if possible (steps 1884). For example, the user may turn off a lamp in the room or shade windows, and then repeat steps 1881 and 1883. With suitable user acknowledgement 1885 (and amelioration), a renewed cycle of ambient estimation (step 1881) is undertaken. At this point, it is more practical if the user interacts with the system via menus provided by the theatre display calibration program, rather than through the handset, that is, the handset functions only as a color measurement peripheral under the control of the display calibration program once handshaking of step 1879 has occurred. If there is no suitable user acknowledgement at step 1885, or several ameliorative attempts are fruitless, the calibration program can either abort at step 1886 (releasing the handset) or continue with a less-than-optimal calibration, depending on the severity of the ambient background problem.

If the measured reflected ambient is within tolerance at step 1883, the ambient measurement data is stored in memory of the control unit 1602 or 1706 (step 1887) for use in further calibrations, communication to other sites, etc. If other calibration options (Color & Tone and/or Spatial Uniformity) were selected (step 1888), then aim values for Color and Tonal calibration are loaded (step 1889), else the calibration program exits, releasing the handset. The aim values and profiles are stored in memory, and/or downloaded to such memory of the theater display system from the Calibrator Camera Server, which stores in its database such color aim values. As stated earlier, the theater display system and/or the handset may have accessibility to the Calibrator Camera Server to query and receive the requested aim values. Optionally, the user may specify such color aim values via a menu of a graphical user interface provided on the theater display or default values may be used. In more complex scenarios, requiring more accurate color calibration, color profiles may be computed from data collected at the site; this will be described briefly below in connection with FIG. 39J.

The aim values of step 1889 represent the color target values, such as at least one set of gamma curves and a white point that are associated with a color profile capable of converting color values into device-specific values for the theater display. Typically, this profile converts from one set of RGB coordinates to another by a multi-dimensional transformation. The profile may be formatted according to the ICC standard and/or be compatible with Virtual Proofing.

At step 1890, the handset camera measures the gamma curves of the theater display color channels. For example, successive screens may be driven to output color in accordance with programmed pixel values, and said screens are captured as images by the handset camera. Each captured image is received and stored in memory of the theatre display system, and then processed by controller 1602 or 1706 to determine the current gamma curves of the theater display. Also, the display screen is driven to the color white (i.e., each pixel in each color channel set to its highest value), and then captured as an image by the handset camera. The image is processed (e.g. averaged over all or a subset of pixels) to obtain the measured white point. The measured set of gamma curves and white point are then compared with the aim values for the gamma curves and white point stored in memory of the theater display system, and if not in conformance (within a preset tolerance) a color transformation is established to correct for the error, as described earlier, such that the color output by the theater system is substantially the same as the aim values (step 1891). The goal of the calibration at steps 1890-1891 is to make sure that the actual, operating gammas in the theater display's color channels are such that the gamma and white point "expectations" of the profile are adequately approximated.

When color calibration is verified at step 1891, the program checks to see if spatial uniformity calibration was requested (step 1892). If not, the program exits, releasing the handset. Otherwise, spatial uniformity calibration is carried out (step 1893), preferably according to procedures outlined below, especially FIGS. 40 through 43B. When such calibration is complete, the calibration program exits, releasing the handset which is re-enabled to perform other functions.

The handset is useful as a color calibrator when there is no calibration peripheral as described earlier (i.e., sensor 1508 or CMI module 1608). If at step 1877 such peripheral were present, then procedures for calibration with such peripheral are used, as described earlier or step 1880-1993 may be performed as described above using the sensor 1508 or CMI module 1608 to provide images of the theatre display rather than the handset.

In the case where the spectral response functions of the handset camera are known by virtue of factory or aftermarket calibration, more exacting calibrations may be possible. Based upon data stored in handset memory or available from the Calibrator Camera Server. If the spectral transmission/emission functions of the display-to-be-calibrated are also known, at least to a good approximation, then comprehensive color calibration (including profile and multi-dimensional transform generation) based on locally measured data are possible, especially with computational help from Calibrator Camera Server.

Briefly, the spectral response functions of both the handset camera's color channels and the CIE Standard Observer (these are referred to as cmfs or Color Matching Functions) are convolved with various levels and combinations of activation of the theater display's channels, numerically. In this way, simulated data on the responses of the handset camera and of a true colorimeter to colors of the display are accumulated. These data can be used to develop a heuristic transformation from handset camera measurement to colorimetric values in a procedure similar to the IT8 scanner calibration method referenced earlier. Other methods for conferring at least an approximately colorimetric calibration on the handset camera are also compatible.

Figure 39J:
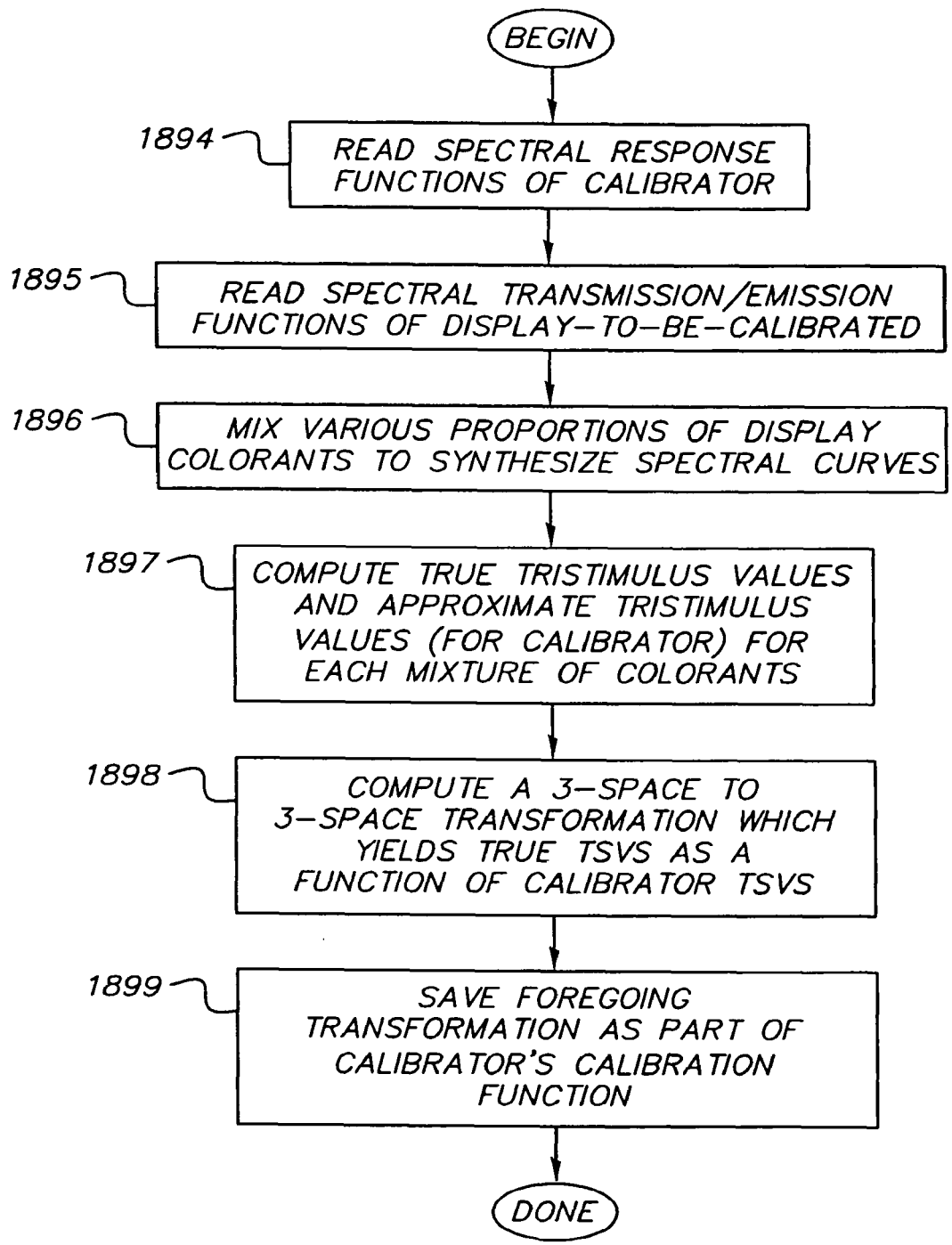
FIG. 39J is a flowchart for the process of characterizing the responses of the portable device of FIG. 39C in terms of standard color units.
Figure 39K:
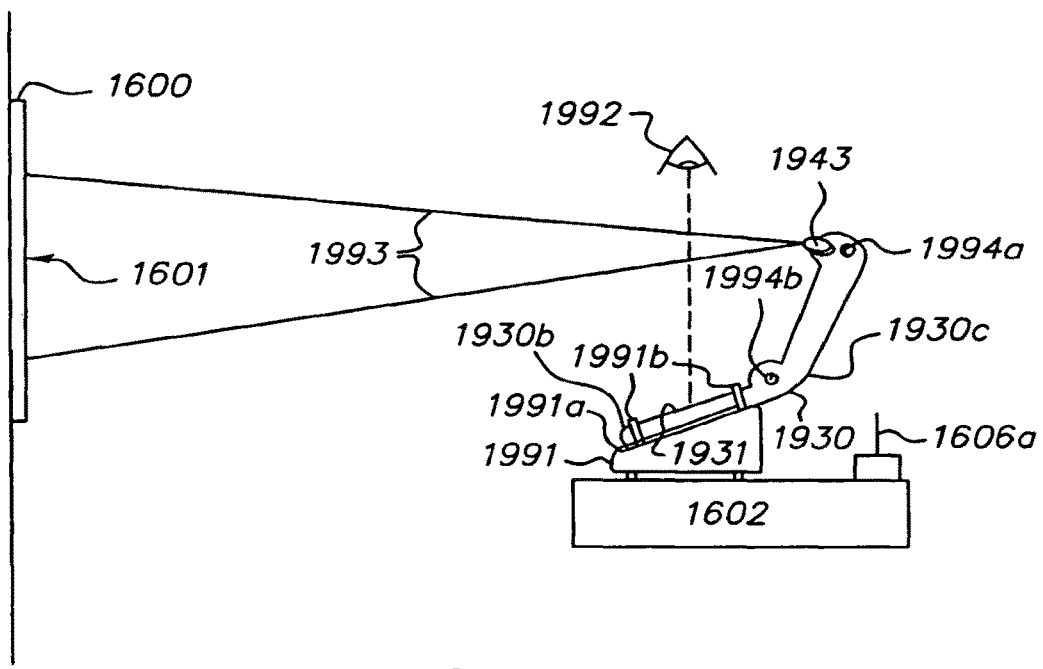
FIG. 39K is a block diagram of a support or base which may be coupled to the portable device of FIG. 39C when calibrating another color display system.

The foregoing is summarized in FIG. 39J, which is drawn with reference to processing best carried out at/by the Calibrator Camera Server. In this figure, the term "calibrator" refers to the handset camera. First, the spectral response functions of the handset camera to be used for calibration are read (step 1894). These functions could be retrieved from the database of the Calibrator Camera Server, a manufacturer's web site or from the specific handset itself, where the curves had been stored following factory calibration. In like manner, spectral transmission or emission functions of the display-to-be-calibrated are retrieved (step 1895). Then, various proportions of the display's colorants are mixed (step 1896). For a display which observes linear rules of color mixture, as discussed earlier, this amounts to scaling each of the emission curves by various constant factors and adding together the weighted curves for the respective color channels.

Next, emission curves so mixed are convolved (see earlier portions of disclosure or the referenced CIE Publication No. 15.2) with the Human Color Matching Functions to produce TriStimulus Values (TSVs) and then with the Handset Camera's spectral responsivities to produce, analogously, tsvs, where lower case indicates that they are approximate, not true relative to the Standard Observer (step 1897). Lastly, a three-dimensional space to three-dimensional space transform is determined which approximately yield true TSVs as a function of the handset display's tsvs (step 1898). This may be performed by using a least squares polynomial fitting or similar procedures to develop a mapping of tsvs to TSVs. By such methods, improved measurements of color properties, including gamma and white balance, may be provided. The transformation determined at step 1898 are stored in memory of the color display system-to-be-calibrated and/or memory of the handset (step 1899).

As stated earlier, for the calibration of "Another Displays" (1976 in FIG. 39F), it will be useful to provide a support for the handset so as to relieve the user of responsibility for holding it steadily during calibration procedures. The support could be similar in design to the battery-charging base for a handset and could even be such base when suitably adapted. FIG. 39K illustrates a possible configuration with respect to a control unit, such as control unit 1602, where no CMI module 1608 is present and calibration is desired. In this figure is shown a display screen or surface 1601, and handset 1930 with its camera 1943 and display screen 1931, as in FIGS. 39C and 39D. The camera 1943 has a field of view 1993 of screen 1601. Eye 1992 represents the eye of the user viewing handset display screen 1931 along the dashed line of sight. The upper housing 1930*b* is releasably coupled to support 1991. As such, the support 1991 mechanically latches to the upper housing 1930*b*. Such latching for example may be by locating the upper housing 1930*b* in a recessed molded cavity 1991*a* of the support 1991, and one or more adjustable and/or elastic straps or bands 1991*b* from the sides of such cavity that are adjustable to retain upper housing 1930*b* in a stable position while enabling viewing by user's eye 1992 of display 1931. Latching may also be provided by a combination of interlocking grooves, prongs, Velcro, tabs, or other feature, along the surfaces upon which the support and upper housing 1930*b* mate. Other configurations are feasible, the key factors being that the camera 1943 has a stable view of the screen 1601 and that the user be able to use viewfinder 1931 without interfering with data collection by camera 1943. If needed, the entire support 1991 may be movable by the user for aligning camera's view 1993 with features on screen 1991 during alignment (step 1881 of FIG. 39I) upon the controller unit or on another surface, such as a table or stand enabling viewing of camera 1943 of screen 1601. Although FIG. 39K shows control unit 1602, optionally control unit 1706 may used, or other projection or panel display systems which are programmed to operate in conjunction with handset to enable color calibration of their respective displays.

Additionally, intelligence may be designed into the system such that, for example, glare hotspots due to specular reflections in the camera's field of view are identified and reported. More generally, if diffuse or specular reflections from the theatre display screen are such as to significantly reduce color gamut, the user may be given an advisory that system color capability or accuracy is compromised.

Figure 39L:
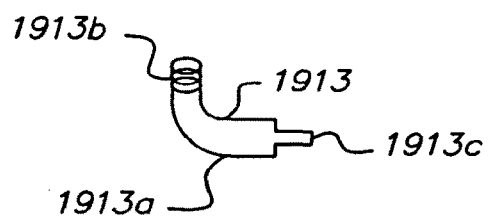
FIG. 39L is a diagram of an attachment for mounting the portable device of FIG. 39C or other digital camera in place of the camera of FIGS. 39, 39A and 39B, such that the portable device or other digital camera is coupled to the computer of FIG. 39 and the camera of the portable device can provide the same functionality as the camera of FIGS. 39, 39A and 39B.
Figure 39M:
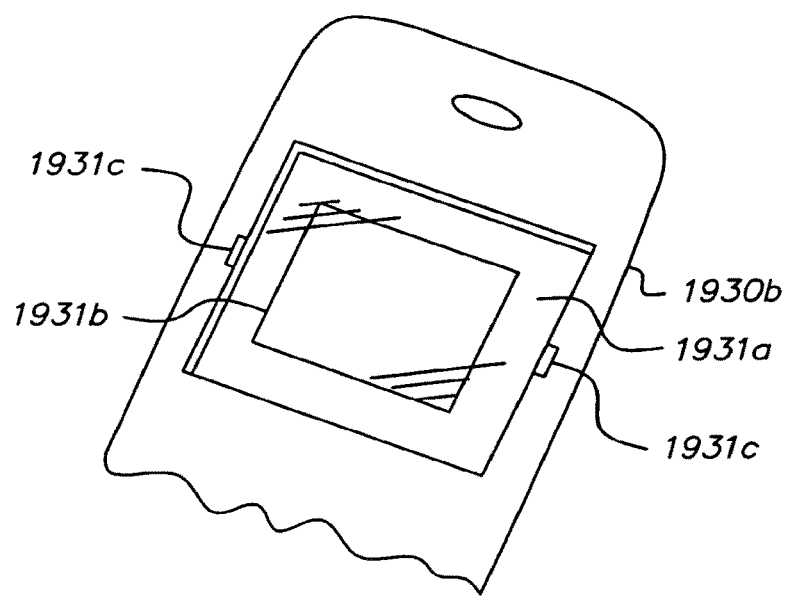
FIG. 39M is a broken partial view of the handset of FIG. 39C to show an optional magnifier attached to the handset when utilizing a miniature high resolution display.
Figure 39N:
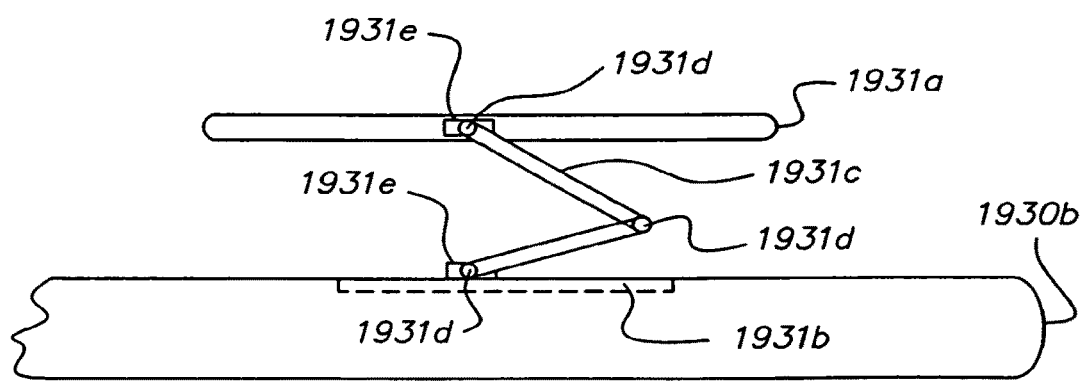
FIG. 39N is a broken side view of FIG. 39M.

Referring to FIG. 39L, an optional connector 1913 is shown for mounting handset 1930 to computer 1900 of FIG. 39 in lieu of camera 1910. Connector 1913 has a shaft 1913a having a right angular bend. The end 1913b of the shaft is threaded, such that it mates with threaded receptacle or opening 1994a or 1994b along lower housing 1930c. The other end 1913c of the shaft 1913a is coupled to arm member 1906 such as by friction fit into an hole at the end of shaft 1912 with camera 1910 removed. Use of two receptacle 1994a and 1994b provides two different placements for mounting handset 1930 in which the handset camera operates en lieu of camera 1910 so as to be able to subserve similar, multiple functionality, as described earlier. Receptable 1994a and 1994b are shown in FIG. 39K for purposes of illustration, and such handset 1930 would be removed from support 1991 when coupled via connector 1913 to computer 1900. More generally, threaded tip 1913b may be compatible with a tripod-like mounting fixture such that a user may use a compact digital camera of any sort, rather than handset 1930, if desired, for connection to arm member 1906. The handset (or such other digital camera) then transmits color images captured from its camera 1943 to computer 1900 to enable use in calibration or video conferencing, similar to camera 1910 described earlier, via communication via a cable to serial interface 1961, or wireless via receiver/transceiver 1956 of FIG. 39E, where the portable computer 1900 has an interface or port enabling communication via such interface 1961 or receiver/transceiver 1956. The mounting of a handset and/or a digital camera to a conventional or notebook computer 1900 is not limited to the use of shaft 1913 and/or arm member 1906, for example, arm member 1906 may be replaced by another shaft, which may be straight, bent, or flexible (e.g. like a snake light shaft) to extend from handset 1930 and couple to the portable computer's housing.

As shown above, the color of displays of portable handheld device, such as shown in FIGS. 39C-D, or larger portable devices such as portable laptop computer, such as shown in FIG. 39, have built-in automatic color calibration capability. In each case, the camera is a dual use camera since it is able to capture images of calibration forms on their respective displays, when the either camera (FIG. 39) or display (FIGS. 39C-D) are pivoted to enable the camera to view the display, and also for use as a typical camera for capturing images of user, objects, or screen, as the user desires. The camera of the portable handheld device, or the larger portable device of FIG. 39, may each be used as a color measuring instrument for calibrating another display once such camera is properly aligned to view such display. Portable devices with built-in camera other than those illustrated in the figures may also be used by programming of their software to enable calibration of the color of their display or another display.

Large screen display devices of FIGS. 35, 36, 37, and 37B, or small screen display of FIG. 39C, often have non-uniformities of the color displayed over their respective screens. Such non-uniformities are detected and corrected according to the improved method described below at their respective control units, or by the microprocessor-based electronics of such displays when the functionality of the control unit is provided by such electronics. The problem of non-uniformities of the color displayed may also occur on CRT display, smaller self-luminous displays and other rendering surfaces (such as paper), but may be less noticeable to users than larger display screen formats. Measurement and correction of such spatial effects was also described earlier.

Figure 40:
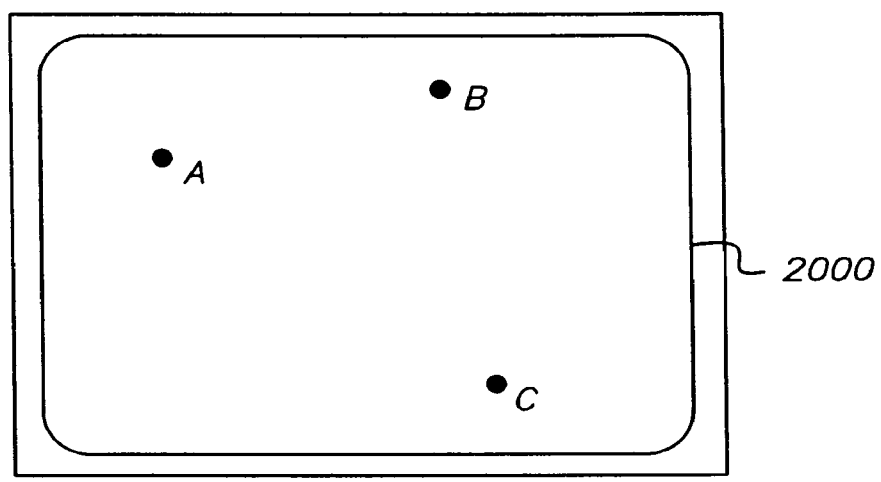
FIG. 40 illustrates an example of a display surface that is non-uniform in response to a flat field input, in which points A, B and C should have the same color, but do not.

First, consider the interaction of spatial uniformity correction with the processing and transmission of image data from a display subsystem or controller of the computer or digital system to the display device: FIG. 40 illustrates a display screen 2000 on which three points, A, B and C are identified. In the vicinity of the foregoing points, the measured luminance and color may differ, even when all correspond to pixels of identical color in the digital representation of the image. Although described in terms of a video display, spatial uniformity correction described herein also applies to hard-copy systems (e.g., printers, copiers, or presses) where, for example, phenomena such as "ink rob" or uneven charging of a photoreceptor or transfer belt may result in non-uniform reproduction of a flat-field image in lithographic or xerographic systems, respectively. Further, spatial uniformity correction also is applicable to "mosaic"-displays comprising multiple, butted panels or screens upon each of which part of the overall image is displayed.

In the course of physically rendering digital signals representative of stored page or image data, rendering devices usually impose a non-linear conversion. In other words, the modulation of light emitted by or reflected from the rendering medium (e.g., display screen or hardcopy) is not a linear function of the signal applied to the rendering device. In the case of a display that employs Cathode Ray Tube ("CRT") technology, the relationship between light output and voltage applied to the electron guns that stimulate the colored phosphors to emit light is approximately a power law. The light emitted is approximately equal to the square of the applied voltage and the exponent is called "gamma". For simplicity, spatial uniformity correction is described below for such a CRT display.

Figure 41:
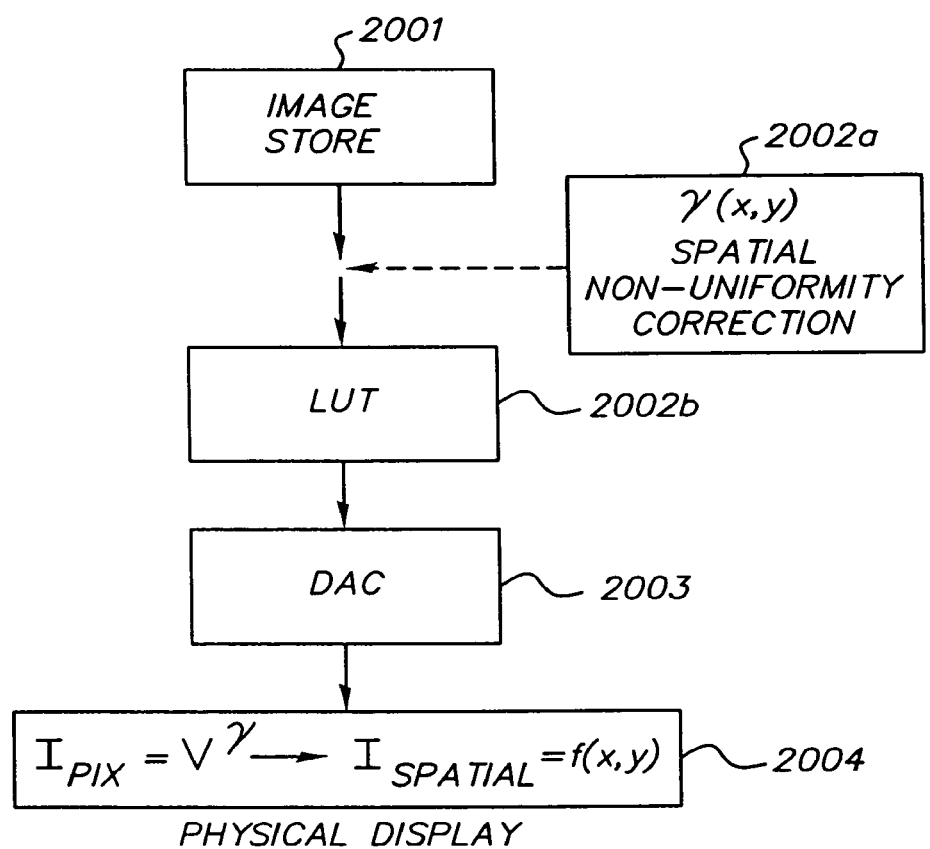
FIG. 41 is a block diagram of the flow of data through a system that drives a display having spatial non-uniformity correction.

FIG. 41 illustrates the typical flow of signals through a CRT (or CRT-like) display system which reproduces a homogeneous, flat-field input non-uniformly. In the course of rendering, two transformations occur. Light output at a pixel or small neighborhood on the screen, $I_{pix}$, grows approximately as the power (gamma or γ) of the applied voltage. For simplicity, assume that gamma is uniform across the screen, but that there are regional variations in output that scale linearly. In other words, the spatial non-uniformity function $I_{spatial}(x,y)$ is such that the ratio of the intensity measured at two different x,y coordinates on the screen (such as points A and B in FIG. 40) does not depend on the level of the uniform drive to the electron guns. Such spatial non-uniformity function of the display screen can be measured by color measuring instruments described earlier.

Additional complexity is added by the fact that image data stored in video memory is usually some form of coded RGB. Some software applications for creating image data or for apprehending it from an image capture device (e.g., scanner or digital camera) store "calibrated RGB", in which the image data may be supposed to have an exact interpretation in terms of CIE colorimetry. Whether the RGB data are calibrated or not, a typical encoding is the (approximate) inverse of the gamma transformation imposed by the physical rendering device. As a result of the foregoing pre-compensation for the display physics, the data are often referred to as being in "gamma-corrected" form.

There are two, main reasons for storing gamma-corrected data:

1) Data are represented in a more visually uniform way, so that fewer bits are required for storage. Twenty-four bits (a byte for each of Red, Green and Blue channels) are insufficient for representing linear RGB data without suffering undesirable (visually noticeable) quantization artifacts on display. However, the inverse-gamma-correction resembles the non-linear transformation of Luminance that has been found to create a perceptually uniform Lightness scale. For example, CIE Psychometric Lightness, L*, is approximately a cube-root transformation of CIE Luminance or "cap Y". Psychometric Lightness is a perceptually uniform scale.

2) Pre-compensation of stored RGB data enable them to be transferred directly into a very simple frame buffer and displayed satisfactorily with little additional processing.

Assuming that the encoding of image data in video memory is known, the problem of rendering color accurately reduces to that of insuring that discrepancies between the encoding of the digital data in memory and the actual conversion function imposed by the device are compensated, and that correction is made for the spatial non-uniformity function across the display surface, if such be needed or desired. For example, if stored image data have been "companded" according to an inverse gamma of 1/1.8, but the physical device gamma is 2.2, a harmonizing adjustment is needed to insure accurate display. The LUT $2002b$ shown in FIG. 41 may provide for such harmonization.

Linear transformations of image data, such as conversion from calibrated RGB for one set of primaries to RGB for a different set (for example, transforming "sRGB" to "Apple RGB", where the former are two common encodings) are usually accomplished, correctly, by decoding the RGB to a linear form before applying the re-mixing coefficients. Given our assumption about the nature of spatial non-uniformity, corrections are best applied to linear RGB data, but may be applied to other color channel formats.

Assume, for simplicity, that the physical conversion imposed by the rendering device is an ideal power function, with power=$\gamma$. Let P be the linear signal in one of the color channels and let nu, $v_{i,j}$, be the spatial non-uniformity correction factor for a pixel, where i,j subscripts indicate the pixel position in x,y coordinate space on the display surface. v is always a fraction (except, of course, at those pixels having $I_{min}$, where v=1) and is the ratio of the least bright pixel to the pixel-to-be-corrected (expressed as $I_{min}/I_{i,j}$).

Applying the correction factor to linear P followed by gamma compensation, and then sending the signal through the rendering device's intrinsic, physical conversion may be described by the following equation:

$$v_{i,j}*P=[(v_{i,j}*P)^{1/\gamma}]^{\gamma},$$

where the left side of the equation is the desired scaling result and the right side the signal processing or data flow just described. Inside the parentheses, the non-uniformity correction scales the linear color signal on a pixel by pixel basis; i.e., $v_{i,j}$ has subscripts but P does not. Once the pixel-dependent correction factor has been applied, then the brightest pixel (and all other pixels) will have been reduced to the brightness of the dimmest pixel and the display surface will be uniform, at least in terms of brightness.

It was mentioned earlier that it is typical to find gamma-corrected data in video memory, rather than linear RGB. Applying a spatial non-uniformity correction directly to gamma-corrected data is represented, symbolically, as:

$$[v_{i,j}*(P^{1/\gamma})]^{\gamma},$$

which simplifies to $v_{i,j}^{\gamma}*P$. Therefore, unless the non-uniformity correction factors are themselves gamma-corrected exactly as are the color coordinates in video memory, spatial uniformity will not be achieved on output and tonal distortions will be introduced. Gamma-correcting the spatial non-uniformity correction factors (as in $v_{i,j}'=v_{i,j}^{1/\gamma}$) are preferably determined prior to device rendering of user image data, such as in an "off-line" process (e.g., such as calibration setup of a rendering device performed when installed, and then periodically thereafter or as desired by the user). Although spatial non-uniformity correction may be provided at the factory, it is preferred that it is performed at the user's location.

Returning now to the FIG. 41: Spatial uniformity correction $2002a$ may be applied to image data accessed from video memory $2001$, as indicated by the dashed line labeled v(x,y). Either the image data should be decoded prior to the application of the non-uniformity correction or the correction factors should be gamma-corrected exactly as are the image data. For example, spatial uniformity correction $2002a$ may be provided by a table, such as two-dimensional look-up-table for each pixel coordinate in an image to be rendered. Alternatively, the image data themselves may be subjected to a non-uniformity- and gamma-correction prior to being written to a frame buffer or image store for display. A look-up-table ("LUT") $2002b$ is provided which can store factors that correct for departures of the physical display's transfer function from that of an ideal power function. The latter may be due to intrinsic properties of the display or, to some degree, to influences of ambient illumination. However, the ability to correct for the latter in this way may be limited. In any case, the contents of the LUT $2002b$ should generally be based on measurements of the "Voltage-Intensity transfer function" of the rendering device.

As will be described below, spatial uniformity correction table $2002a$ and LUT $2002b$ has for each pixel coordinate the correction for each of the color channels for the pixel. For example, at pixel (1,1) the spatial uniformity correction table $2002a$ for color channels R, B, and G may hold values 0.85, 0.95, and 0.92, respectively, while at pixel (1,2) the values may be 0.86, 0.94, and 0.92, respectively, and so forth for the entire two-dimensional display screen. Unlike spatial uniformity correction table $2002a$, LUT $2002b$ is not dependent on pixel location. One of the most common applications of LUT $2002b$ is compensation for differences between the assumed transfer characteristics of the physical device (that is represented in the encoding of the image data) and the actual transfer characteristic which is usually better calibrated at the user site than at the factory.

Thus, during rendering device operation in each color channel pixels of the two-dimensional (x,y) image data accessed from memory $2001$ are corrected in their value by spatial non-uniformity look-up-table $2002a$, and then by LUT $2002b$. The resulting two-dimensional (x,y) color image is converted into analog signals by the digital-to-analog converter (DAC) $2003$ for output to display $2004$. The determination of a spatial non-uniformity look-up-table $2002a$ in multiple color channels is described below.

Interactions of three or more color channels need to be accounted for in spatial non-uniformity correction. The concepts advanced in the foregoing apply to each channel individually, except that the calculation of the correction factors should be done in such a way as to be consistent with a targeted neutral (or white) balance. Given that spatial non-uniformity correction reduces the dynamic range ("contrast") and resolution (the number of displayable digital codes) of the monitor, it may be desirable to hold such effects to a minimum by calculating different non-uniformity corrections for different white points. In other words, for each neutral balance desired, a different spatial non-uniformity look-up-table $2002a$ is determined and stored in memory. Also, such different tables $2002a$ may be selected by the user (or automatically) in accordance with different ambient light situations. In a multi-channel correction, the value of $I_{min}$ used in calculating the correction factors is the least pixel response to a flat field digital input from all those across the display surface and across all color channels. Re-stated, it is the weakest channel response at the dimmest pixel.

Note that, in the course of performing spatial uniformity correction, there is a possibility of altering the white point or neutral balance away from the desired value. Indeed, the display surface is likely non-uniformly bright and non-uniformly white at the outset. Where linear rules of color mixture and superposition apply, this means that if neutral balance were the same at every pixel, then the pixel at which $I_{min}$ occurs would be the same in all three channels at the outset. White balance, in particular, is discussed in connection with the first equation presented in U.S. patent application Ser. No. 09/832,553, which is incorporated herein by reference. The essential concepts are reviewed below.

The TriStimulus Values (TSVs) X, Y and Z, can be thought of as the amounts of three lights ("additive primaries") which need to be mixed or added together in order to match another light of arbitrary wavelength composition for the Standard Observer. Consider the following set of simultaneous equations, in which we use linear combinations of the TSVs to "match" (or to provide a device independent numerical specification for) the red, green and blue lights emitted by a monitor:

$$R = a_{11}X + a_{12}Y + a_{13}Z$$

$$G = a_{21}X + a_{22}Y + a_{23}Z$$

$$B = a_{31}X + a_{32}Y + a_{33}Z$$

Normally, a display is set up, possibly at the factory or before or during calibration, so that full scale drive to R, G and B channels corresponds to a particular "white", such as Daylight 6500 ("D65") or a color temperature of 9300° Kelvin, etc. (The two colors just mentioned are both considered "white" but have very different TSVs.) The set up is often effected by adjustments to variables such as offset and gain in the control circuitry of the display. The result, ideally, is a particular relationship, R:G:B, in the light output of Red, Green and Blue channels. In order for a display screen to be truly uniform in color, not only must the overall intensity at each pixel be constant, but the ratios of R, G and B light output must also be constant. This may require adjustment (possibly iterative) in a field-flattening procedure such as that described below.

Without limiting the invention, consider, for clarity and simplicity of explanation, the determination and use of $I_{min}$ in the case of a CRT display, which approximates the model described above: to determine $L_{min}$ the screen is flooded, successively, with a relatively high level of each color, R, G and B. Locate the pixel, in x,y coordinates on the display surface, having the smallest fraction of the value of the brightest pixel. As noted, the x,y coordinates of the minima for R, G and B may not all be the same, indicating non-uniform neutral balance.

Let $I_{min}$ for the Red channel be called $R_{min}$ and let it occur at point A of FIG. 40; likewise define $G_{min}$ and $B_{min}$ and let them occur at points B and C, respectively, of FIG. 40. Suppose, for example, that $R_{min}=0.85$, $G_{min}=0.94$ and $B_{min}=0.93$. The fractions employed to "flatten" (make uniform) the G and B channels then, should be based upon G and B values that will yield the correct white balance at the x,y coordinate of $R_{min}$ (point A), unless either or both of those calculated results exceed $G_{min}$ or $B_{min}$ values observed initially (at points B and C). In the latter case, at least points B and C (and possibly many others on the display surface) can not be brought to the correct neutral balance without modification to the Red channel; the latter situation may not arise if the display surface is close to the desired white balance to begin with and/or spatial non-uniformities are not too great. If, however, the situation does arise, then the other channels are examined to find the minimum consistent with the desired white balance. That failing, the pixel is found that is as close as possible to the desired balance and then scale down the fractions in R, G and B channels, for that pixel, until the fractions are such that all pixels are correctable. In summary, once a minimum has been found in at least one of the channels such that all channels can be adjusted to achieve neutral balance, then all pixels can be scaled in each channel according to R, G and B values at that minimum pixel. A verification of uniformity and white balance may be made once the spatial non-uniformity correction table has been prepared and applied. The detection and determination of the spatial non-uniformity correction table is described in more detail later in FIGS. 43A and 43B.

Figure 42:
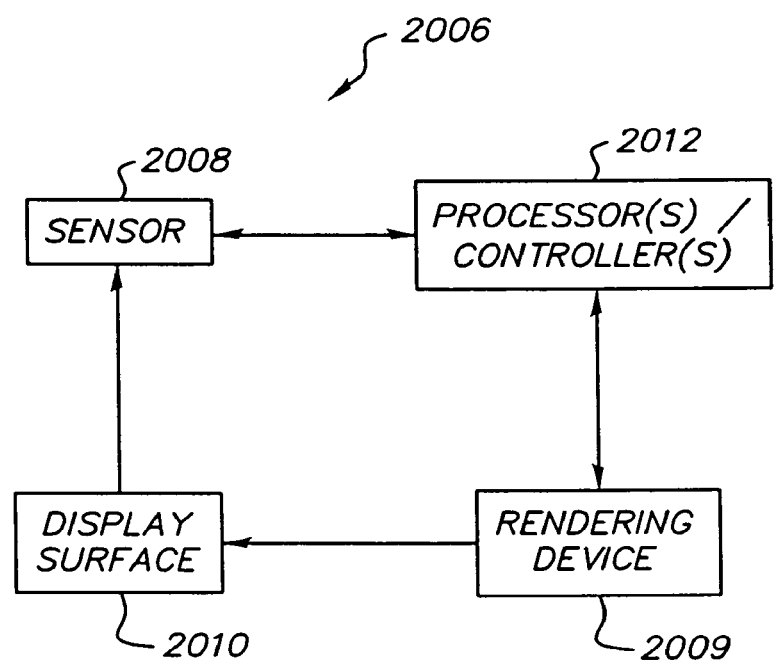
FIG. 42 is a block diagram of an apparatus for flattening the display surface by providing spatial non-uniformity correction.

Referring to FIG. 42, a system 2006 providing multi-channel spatial non-uniformity correction is shown. System 2006 has sensor 2008 as described earlier, such as an imaging sensor (CCD), a rendering device 2009 for outputting images onto a display surface 2010, and a processor(s)/controller(s) 2012 which provide image data to the rendering device and receive measurement data from sensor 2008. The processor(s)/controller(s) may represent a microprocessor-based device, such as a personal or desktop computer system, or the control units 1602 or 1706 described earlier, or a specialized display processor/controller within the host or directly with a controller within the display itself. Sensor 2008 may represent the CMI module 1608 of FIG. 37 or 37B, or sensor 1508 of FIGS. 35 and 36, or the sensor may be a "dumb" sensor controlled externally through an I/O port. The sensor 2008 may have a microcontroller that communicates with the host (general-purpose, programmable) computer providing processor(s)/controller(s) 2012.

The processor/controller operates in accordance with a software program in its memory which may be executed by one or more of the processors and at least causes test images to be displayed by rendering device 2009 on display surface 2010, causes the displayed/rendered images to be sensed utilizing sensor 2008, and analyzes the sensed image data for the purpose of creating in memory a spatial non-uniformity correction table. In reference to FIG. 41, the spatial non-uniformity correction table 2002a, image store 2001, LUT 2002b are provided for in memory of processor(s)/controllers 2012, and the processor(s)/controllers 2012 outputting via DAC 2002 images to rendering device 2009, e.g., display 2004.

Figure 43A:
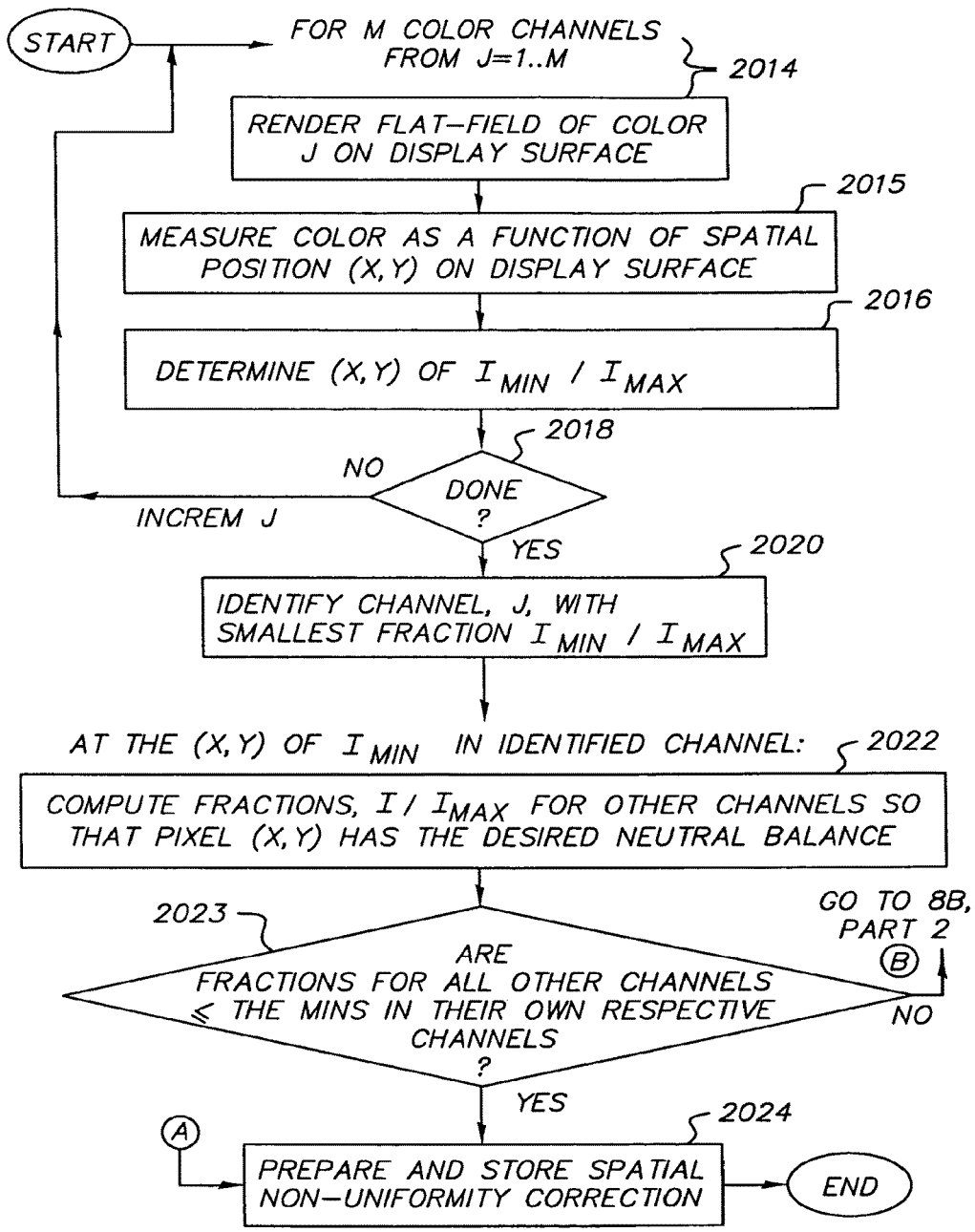
FIGS. 43A and 43B are connected flow charts of the process in the apparatus of FIG. 42 for detecting spatial non-uniformity and for preparing a table for correction thereof while preserving desired neutral or white balance.
Figure 43B:
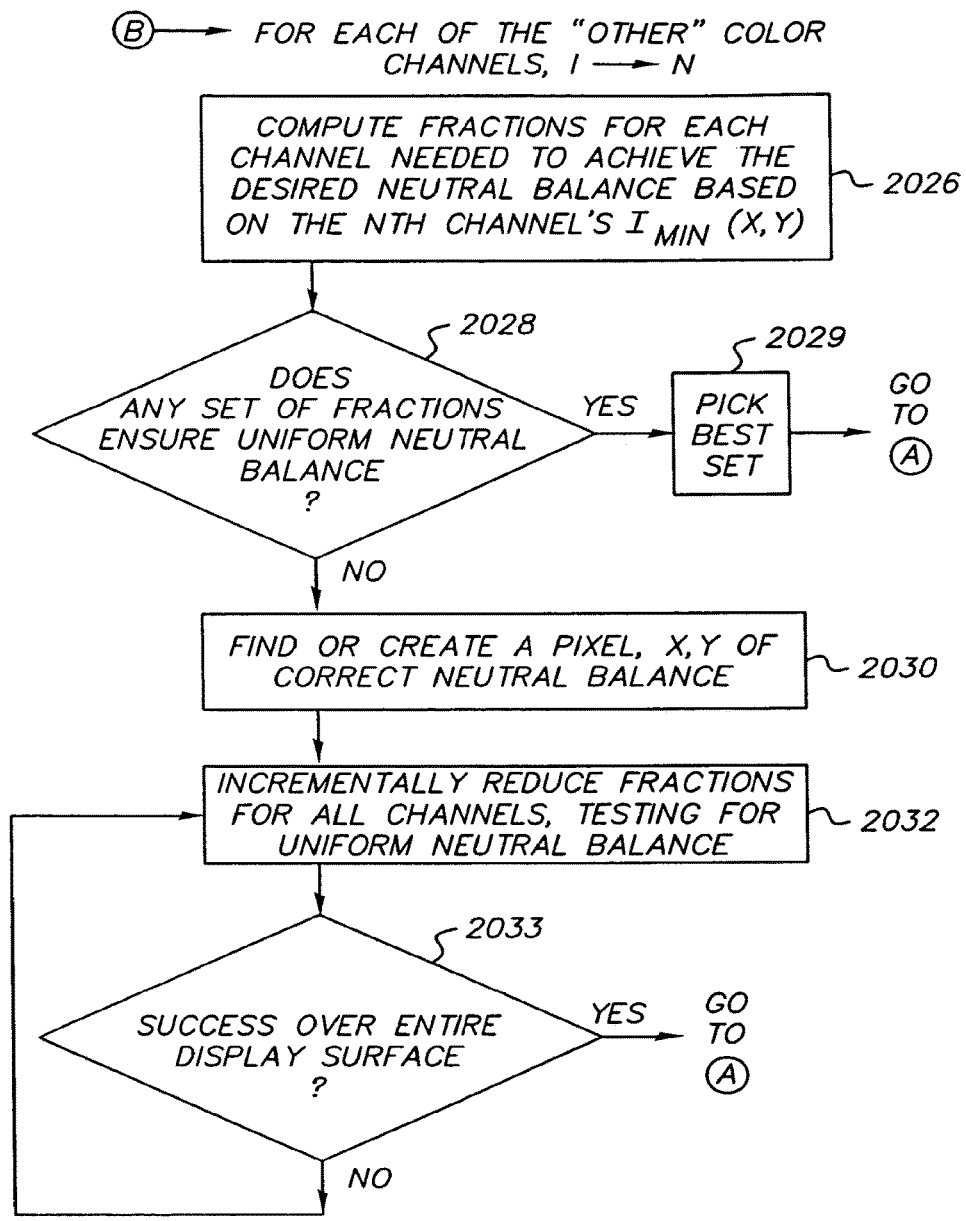

Referring to FIGS. 43A and 43B, a flow chart is shown for the program carried out by processor(s)/controllers 2012 for spatial non-uniformity correction. For each color channel j, where j=1 . . . m, a flat-field of color j is rendered 2014 on display surface 2010 by rendering device 2009 (e.g., each pixel is at or near its highest pixel value for the channel over the display surface). Sensor 2008, being earlier aligned and focused on the display surface, measures color as a function of spatial position (x,y) on the display surface 2010 (step 2015). Such measurement for each pixel of the screen is stored in memory of the processor(s)/controllers 2012. The coordinate (x,y) of the pixel on the display surface having the lowest fraction $I_{min}/I_{max}$, is determined (step 2016) and saved in memory of processor(s)/controllers 2012. $I_{min}$ represents the least pixel response to a flat field digital input from all those across the display surface for color channel j.

$I_{max}$ represents the most pixel response to a flat field digital input from all those across the display surface for the $j^{th}$ channel. In other words, for each channel $j=1 \ldots m$, $I_{min}/I_{max}$ is the ratio of the intensity of the dimmest pixel to the brightest pixel, and pixel coordinate (x,y) with the lowest $I_{min}$ is saved in memory.

After steps 2014, 2015, and 2016 are performed for each color channel (step 2018), the channel j with the smallest saved fraction $I_{min}/I_{max}$ is identified, referred to herein as channel $j_{min}$ (step 2020). For the pixel (x,y) having $I_{min}$ in channel $j_{min}$ the intensity I in the fraction $I/I_{max}$ for all other channels than $j_{min}$ are determined such that pixel (x,y) has the desired neutral or white balance (step 2022), where $I_{max}$ for the channel was determined at step 2016. In other words, the brightness of the pixel (x,y) in the other channels than channel $j_{min}$ is modified, if necessary, in order to satisfy a proportional relationship between the color channels defined by the neutral color balance preselected by the user. The resulting $I/I_{max}$ in each of the other color channels than $j_{min}$ is then compared to the saved $I_{min}/I_{max}$ for the respective channel from step 2016. If to obtain the desired neutral balance of pixel (x,y), the fraction $I/I_{max}$ for that pixel (x,y) determined at step 2020 in each of the other channels is less than or equal to fraction $I_{min}/I_{max}$ of that channel determined at step 2016 (step 2023), then the spatial non-uniformity correction table is prepared and stored (step 2024), otherwise the process proceeds to step 2026 of FIG. 43B.

For step 2023, to prepare the spatial non-uniformity correction LUT at step 2024 is as follows: the spatial non-uniformity correction v for pixel (x,y) in color channel $j_{min}$ is set to one, and for each other pixel v is set to the fraction that makes its intensity at step 2016 equal to the measured intensity of pixel (x,y). In each of the other channels than channel $j_{min}$, the spatial non-uniformity correction the pixel (x,y) has v set to fraction $I/I_{max}$ for the channel determined at step 2022, and each other pixel has v set to the fraction that makes its measured intensity at step 2016 equal to the measured intensity of pixel (x,y) for the channel when reduced by fraction $I/I_{max}$ for the channel.

If to obtain the desired neutral balance of pixel (x,y), the fraction $I/I_{max}$ for that pixel (x,y) determined at step 2022 in the other channels is greater than the fraction $I_{min}/I_{max}$ of that pixel (x,y) determined at step 2016 (step 2023), then branch to step 2026 of FIG. 43B. The pixel (a,b) is identified in the other channels than channel $j_{min}$ having lowest saved fraction $I_{min}/I_{max}$ from step 2016 (such channel is referred to herein as channel $n_{min}$), and for that pixel (a,b) one or more fractions $I/I_{max}$ are determined in each of the other color channels than $n_{min}$ to obtain the desired neutral balance. The computation at step 2026, as at step 2022, employed the calibration matrix for the display to calculate I values that ensure the correct proportions of R:B:G. The calibration matrix is that used for interconverting R, B, G codes for a particular set of colorants to phosphors and device independent units, such as XYZ TriStimulus values. One or more sets of fractions may be determined to achieved the desired neutral balance. If any set of fractions ensured uniform neutral balance (step 2028), than the best set is picked (step 2029), and the non-uniform correction table is prepared at step 2024. Step 2028 is performed the same as step 2023, where the calibration matrix is used to make sure that a minimum in one channel can ensure neutral balance in all three channels. For example, the best set may be the one which on average reduces the least the intensity of all the color channels for pixel (a,b). From step 2029, the spatial non-uniformity correction table at step 2024 is prepared as described above, except that the channel whose $I_{min}/I_{max}$ is used has changed in accord with steps 2026 to 2028.

If no set of fractions at step 2028 provides a uniform neutral balance, then one pixel is found on the display having the correct neutral balance on the basis of measurements (which may need to be interpreted in light of the calibration matrix) (step 2030). If no such pixel is found, a pixel is created with the correct neutral balance by starting with a pixel having approximately the correct balance and using the calibration matrix to calculate the correct ratios. At this "created" pixel, the fraction $I/I_{max}$ are reduced for all channels, consistent with neutral balance, until the $I_{min}$ in each of channel is the global $I_{min}$ over the display surface for that channel. When complete, the spatial non-uniformity correction table at step 2024 is prepared, in which the spatial non-uniformity correction table has v set to the fractions $I_{min}/I_{i,j}$ determined on the basis of results at step 2032 for each pixel in each channel. The term "pixel" in the foregoing discussion may be an average of a small group of pixels and the method is able to exclude "dead" pixels or other outlyers from consideration. In addition, the less-than-or-equal-to comparison at step 2023 can include a tolerance for some error, so that the computation does not get "bogged down".

The spatial non-uniformity correction table determined at step 2024 may be incorporated into the color transformations described earlier for a rendering device, and may also be useful in the case of rendering devices whose color mixture is non-linear. Also, the spatial non-uniformity correction table may be used in conjunction with the histogram method for identifying color errors of image reproduction independently of image resolution described earlier (see FIG. 20 and attendant discussion). Used alone, a determined histogram may be vulnerable depending on the display device to non-uniformities of color across a display surface which may give rise to ambiguities of interpretation of color error data. In other words, are there blurred, multiple or misplaced peaks in a measured histogram due to spatial non-uniformities of the display? Field-flattening described herein may be used either to correct the display surface prior to application of verification procedures that test for temporal drift in the rendering process, such as the histogram method. Field-flattening may also be employed to preprocess image data apprehended from a non-uniform rendering surface, so that resolution-independent methods of detecting temporal drift in color reproduction can be applied unambiguously. Alternatively, the reference histogram may be modified to reflect the spatial non-uniformities of the actual rendering process prior to cross-correlation.

Please consider, now, some additional features and advantages of the method: $I_{min}$ and the fractions stored in the spatial non-uniformity correction table may be computed with attention to allowing "headroom" or some degree of over-correction. The latter would permit changes to white balance (up to a point) without necessity of re-computing the non-uniformity correction. In the example of the CRT display device described above, it would generally be advantageous to make the digital, input, uniform-field images of relatively high brightness. However, in application of the method to a subtractive, reflection, color-reproduction medium (such as print) it will be best to make the input image one of moderate density. Indeed, for such devices having more complicated color-mixture physics, highly accurate correction of the display surface may require measuring flatness at several levels of density and computing correspondingly more complicated correction functions.

In summary, once $I_{min}$ is measured, preferably in some standard photometric or colorimetric coordinate system (such as CIE), then the values for the other channels should be chosen so as to achieve the desired white point, or balance between the channels. LUT 2002b of FIG. 41 for compensating peculiarities of the physical device may comprise a separate table for each channel. In the case of a hard copy device, the separability of "gamma" (i.e., for the non-linear relationship between digital drive and some measure of physical output) from the processes governing color mixture cannot, in general, correctly be assumed. In this case, sufficiently accurate non-uniformity correction may require that the LUT 2002b be a three-dimensional table for each color channel. Two of the address coordinates for each table represent spatial position, x,y, on the page or display surface. The third, of course, is the value of the color coordinate in that neighborhood. Methods for calculating the entries of such a table are extensions of methods for calculating the colorant values needed to realize a desired color in the reproduction that are described earlier.

For example, in the case of a CRT-type video display, the spatial non-uniformity correction functions may be fairly simple and invariant over time, provided that the magnetic fields impinging upon the display are consistent. In the case of an offset press capable of printing many different pages (of a publication, for example) in a single imposition, the situation is more complex and likely to vary from job to job. Currently, the exact color reproduced on a given page of the signature may depend markedly on where the page is situated within the signature due to phenomena such as "ink rob" mentioned earlier. The term "ink rob" refers to the relative print densities achievable at a trailing location of an impression as a function of reproduction densities required at a more leading position within the same impression (transfer of ink to paper). Today, press operators try to cope with regional dependencies within the press sheet by seeking an average optimum or by favoring particular advertisements within the signature.

Conceptually, methods disclosed herein enable more customized color control within a complex signature. By analyzing the color reproduction performance of a press in response to a variety of inputs and developing a data base of spatial dependencies, a model of press performance is created. The model informs processing of the pre-press workflow, especially at the stage where pages are imposed or laid out in a signature. Operators are given a more realistic preview of color reproduction to be expected from a given layout and press run. Additionally, they may be given a tool enabling the calculation of one or more spatial uniformity correction functions to be applied within the signature, or, alternatively, may instruct the system to compute regionally customized (for different pages within the signature) transformations from color to colorant in the interest of more accurate color reproduction. To the extent that complete compensation for the spatial non-uniformities of the reproduction process is not possible within a particular imposition, operators have the option of experimenting with different impositions which may cure the deficiency or, at the least, of informing the print buyer regarding what color tolerances can be satisfied. The methods disclosed herein are also applicable to "mosaic" video displays in which one large screen is actually comprised of an array of smaller, discrete displays.

Figure 44:
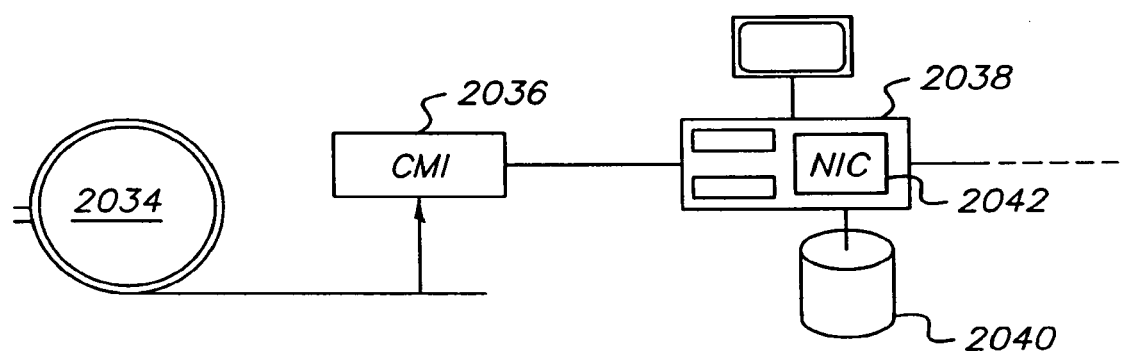
FIG. 44 is a block diagram of a system and apparatus for applying spatial uniformity correction of a printable display surface in a production printing (press) context.
Figure 45:
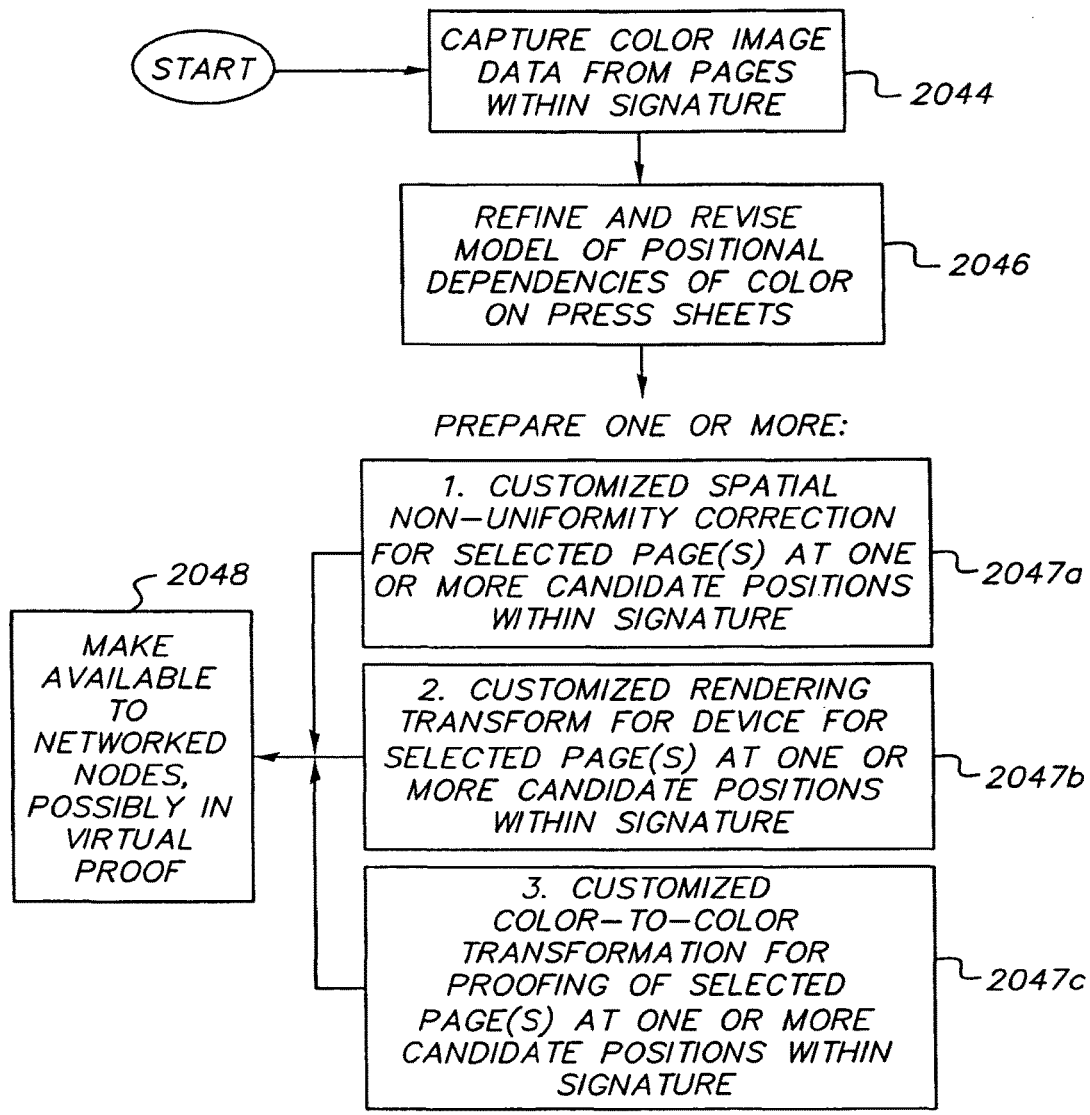
FIG. 45 is a flow diagram for the method of preparing and distributing transformations for color image data intended to enable proofing of press performance and to improve color image reproduction by the press of FIG. 44.

Referring to FIG. 44, the minimum apparatus needed to support the foregoing method and functionality is a production press 2034, a color measurement instrument 2036 (preferably an imaging colorimeter), one or more computers 2038 having memory for database storage 2040 and a network interface 2042 supporting communication with sites that perform imposition. At least part of the network communication may be wireless, to the extent that bandwidth is adequate. Minimally, the computers 2038 have a program to enable reading and analyzing color measurement data provided from color measurement instrument 2036 and refines or updates data and models of position-dependency of color reproduction within printed signatures that are stored in the database. The process is described in FIG. 45. First, color image data is captured from pages within signature (step 2044). Next, the model of positional dependences of color on press sheets is refined and revised (step 2046). Thereafter, one or more of the following at steps 2047a,b, or c is performed. Customized spatial non-uniformity correction table is prepared for selected page(s) at one or more candidate positions within the signature (step 2047a). Customized rendering transform for device for selected page(s)s at one more candidate position with the signature (step 2047b). Customized color-to-color' transformation for proofing of selected page(s) at one or more candidate position within the signature (step 2047c). The pre-press operator may select one or more of steps 2047a,b,c to be performed. The resulting table and/or transformations are made available to the one or more nodes in the network to which the computers 2038 are in communication with via network interface 2042 (step 2048).

Figure 46:
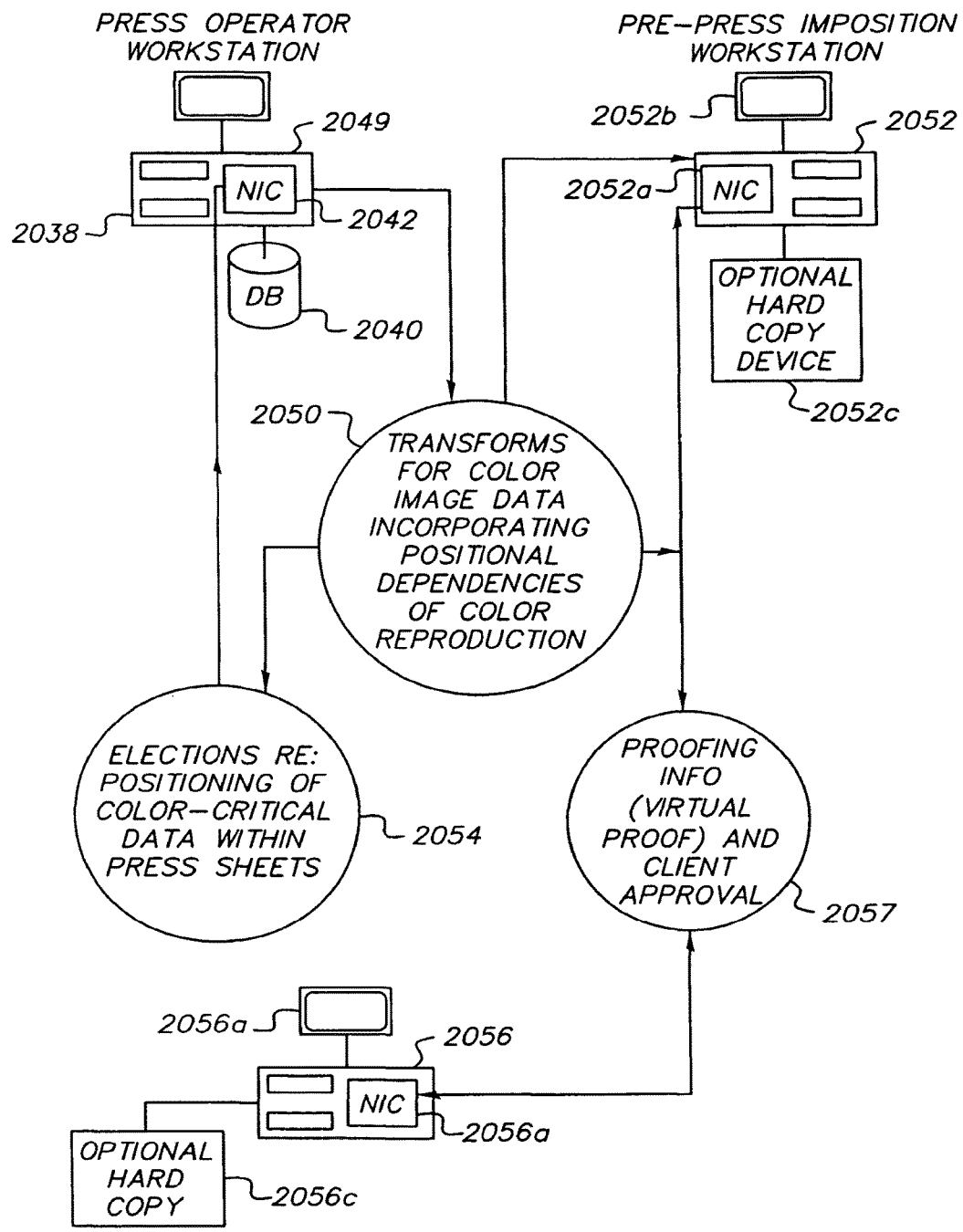
FIG. 46 is a block diagram of workstations enabling spatial non-uniformity correction in an application involving a web offset press for publication printing and the interaction with pre-press workflow, especially at the imposition stage.

Based upon foregoing data and models, customized non-uniformity corrections or rendering tables may be prepared on instruction from pre-press, most likely the imposition stage of production. Within the framework of Virtual Proofing described earlier, non-uniformity correction tables and rendering tables normally are stored locally. Information shared with node(s) upstream in production would be the color-to-color' mappings needed to represent imagery as it will be rendered in volume production along with associated information about page placements within the signature. The imposition stage may then relay the proofing representations to others, such as the print buyer or her/his agent, when satisfied with the anticipated results. The foregoing is outlined in FIG. 46. The press operator workstation 2049 (e.g., computer 2038 having database 2040) sends transforms 2050 for color image data incorporating position dependencies of color reproduction to a pre-press imposition workstation 2052. Workstation 2049 is coupled to a press 2034 (FIG. 44), such as a web offset press. Workstation 2052 may represent a computer 2052 with a network interface 2052a for receiving the transforms 2050 and may apply the transforms to image data representing page(s) for output to its display 2052b or to an optional hardcopy output device (e.g., printer) 2052c. At the pre-press operator workstation an election is made as to positions of color critical data within the press sheet(s), and such is communicated to the press operator workstation. Such election 2054 may occur prior to the generation of transforms 2050 at press operator workstation; or, if made later, such transforms 2050 may be revised at press operator workstation. One or more other workstations 2056 provide proofing information (virtual proof) and client approval 2057. One of workstations 2056 is illustrated, and may represent a computer with a network interface 2056a for receiving the transforms 2050 which may be applied to image data representing page(s) for output to its display 2056b or to an optional hardcopy output device (e.g., printer) 2056c. As such workstations 2038, 2052, and 2056 each may represent a node or site along the network of FIG. 1. It may also be expedient to share the non-uniformity corrections and/or rendering tables with sites/nodes upstream in production that are capable of computing proofing transforms (for their associated rendering devices) therefrom.

Returning, now, to the application of the spatial non-uniformity correction: The granularity (relative coarseness of spatial sampling) of the non-uniformity correction tables is a design choice reflecting a trade-off between circuit and computational complexity (often embodied in a display processor) and amount of available memory. In U.S. Pat. No. 5,510,851, a spatial interpolation method for applying non-uniformity corrections based upon Catmull-Rom splines is preferred. The spatial non-uniformity correction described herein is compatible with various trade-offs between memory and computational and hardware complexity as well as with various methods for interpolating and/or smoothing applied non-uniformity corrections.

From the foregoing description, it will be apparent that there has been provided a system, method, and apparatus for color calibration. Variations and modifications in accordance with the invention will undoubtedly suggest themselves to those skilled in the art. Accordingly, the foregoing description should be taken as illustrative and not in a limiting sense.

What is claimed is:

1. A method for detecting color differences between a source digital image and a reproduction by a rendering device of said source digital image, wherein said method is operable in a computer that communicates with said rendering device and comprises the steps of:
    providing a rendering, upon a display surface associated with said rendering device, of one or more images stored in memory of said computer, each of said one or more images comprising one or more colors present identically at a plurality of spatial positions;
    determining spatial variations of said each of said colors at said plurality of spatial positions within the rendering of each of said one or more images based upon measurements of spatial non-uniformity of the rendering upon said display surface;
    producing upon said display surface a reproduction of said source digital image;
    capturing a digital image of said reproduction of said source digital image;
    computing one or more histograms from each of said source digital image and said digital image of said reproduction of said source digital image;
    comparing corresponding ones of said one or more histograms of said each of said source digital image and said digital image of said reproduction of said source digital image from said computing step to determine color differences that are not due to said spatial non-uniformity of rendering upon said display surface by said rendering device; and
    correcting said spatial non-uniformities of rendering and said color differences that are not due to said spatial non-uniformity of rendering to provide another reproduction of said source digital image, by said rendering device, that matches the colors of said source digital image within a criterion for color error.

2. The method according to claim 1 wherein said one or more histograms enable determination of said color differences that are not due to spatial non-uniformity of rendering independently of the spatial resolution of said source digital image and said captured digital image of said reproduction of said source digital image.

3. The method according to claim 2 further comprising the step of cross-correlating said corresponding ones of said one or more histograms of each of said source digital image and said digital image of said reproduction of said source digital image to determine said color differences that are not due to spatial non-uniformity of rendering.

4. The method according to claim 1 wherein at least said source digital image and said captured digital image are in device-independent units, each of said rendering step and said producing step further comprise the step of converting each of said colors into codes for controlling image reproduction by said rendering device, and said capturing step further comprises the step of converting codes generated by an image capture device into device independent color values.

5. The method according to claim 4 wherein said converting step converts between device codes and device independent color values using a multidimensional transformation in combination with tonal transfer curves for each of a plurality of channels of said rendering device, and at least said tonal transfer curves are based upon a calibration specific to said rendering device.

6. The method according to claim 1 wherein said step that comprises correcting said spatial non-uniformity of rendering modifies at least the tonal transfer in each color channel of said rendering device for each pixel across said display surface.

7. The method according to claim 6 wherein said pixel represents an average of a group of pixels on said display surface.

8. The method according to claim 6 wherein said step that comprises correcting said spatial non-uniformity of rendering employs interpolation in providing corrections for spatial non-uniformity of rendering upon said display surface.

9. The method according to claim 1 wherein said step that comprises correcting said color differences that are not due to said spatial non-uniformity of rendering computes a color-to-color' transform to be used in combination with a multidimensional transformation that converts device-independent color values representing said source digital image into device codes for controlling rendering by said device.

10. The method according to claim 9 wherein said combination is implemented by concatenating said color-to-color' transform with said multidimensional transformation that converts device-independent color values into device codes.

11. The method according to claim 1 wherein said rendering device is one of a printer or a video monitor.

12. A method for detecting color differences between a source digital image and a reproduction by a rendering device of said source digital image, wherein said method is operable in a computer that communicates with said rendering device and comprises the steps of:
    providing a rendering, upon a display surface associated with said rendering device, of one or more images stored in memory of said computer;
    measuring spatial non-uniformity of said rendering upon said display surface by said rendering device;
    rendering upon said display surface a reproduction of said source digital image, wherein said reproduction is corrected for said spatial non-uniformity of said rendering measured by said measuring step;
    capturing a digital image of said reproduction of said source digital image;
    producing one or more histograms from each of said source digital image and said digital image of said reproduction of said source digital image;
    comparing corresponding ones of said one or more histograms of said each of said source digital image and said digital image of said reproduction of said source digital image from said producing step to determine color differences; and correcting said spatial non-uniformities of rendering and said color differences to provide another reproduction of said source digital image, by said rendering device, that matches the colors of said source digital image within a criterion for color error.

13. A method for detecting color differences between a source digital image and a reproduction by a rendering device of said source digital image, wherein said method is operable in a computer that communicates with said rendering device and comprises the steps of:

providing a rendering, upon a display surface associated with said rendering device, of one or more images stored in memory of said computer;

measuring spatial non-uniformity of said rendering upon said display surface by said rendering device;

rendering upon said display surface a reproduction of said source digital image;

capturing a digital image of said reproduction of said source digital image;

producing one or more histograms from each of said source digital image and said digital image of said reproduction of said source digital image, in which said one or more histograms produced from said source digital image are modified to account for said spatial non-uniformity of rendering measured by said measuring step;

comparing corresponding ones of said one or more histograms of said each of said source digital image and said digital image of said reproduction of said source digital image from said producing step to determine color differences; and correcting said spatial non-uniformities of rendering and said color differences to provide another reproduction of said source digital image, by said rendering device, that matches the colors of said source digital image within a criterion for color error.

14. A non-transitory, computer-readable medium encoding software executable by a computer for detecting color differences between a source digital image and a reproduction by a rendering device of said source digital image, said software comprising:

one or more programs for enabling a rendering, upon a display surface associated with said rendering device, of one or more images stored in computer memory, each of said one or more images comprising one or more colors present identically at a plurality of spatial positions;

one or more programs for determining spatial variations of each of said colors at said plurality of spatial positions across said display surface within the rendering of each of said one or more images based upon measurements of spatial non-uniformity of the rendering upon said display surface;

one or more programs for producing upon said display surface a reproduction of said source digital image;

one or more programs for capturing a digital image of said reproduction of said source digital image;

one or more programs for computing one or more histograms from each of said source digital image and said digital image of said reproduction of said source digital image;

one or more programs for comparing corresponding ones of said one or more histograms of said each of said source digital image and said digital image of said reproduction of said source digital image to determine color differences that are not due to said spatial non-uniformity of rendering upon said display surface by said rendering device; and one or more programs that correct said spatial non-uniformities of rendering and said color differences that are not due to said spatial non-uniformity of rendering to provide another reproduction of said source digital image, by said rendering device, that matches the colors of said source digital image within a criterion for color error.

15. The non-transitory, computer-readable medium according to claim 14 wherein said one or more histograms enable determination of said color differences that are not due to spatial non-uniformity of rendering independently of the spatial resolution of said source digital image and said captured digital image of said reproduction of said source digital image.

16. The non-transitory, computer-readable medium according to claim 15 wherein said determination of said color differences that are not due to spatial non-uniformity of rendering employs cross-correlation between said corresponding ones of said one or more histograms of each of said source digital image and said digital image of said reproduction of said source digital image.

17. The non-transitory, computer-readable medium according to claim 14 wherein at least said source digital image and said captured digital image are in device-independent units, said one or more programs for enabling a rendering and said one or more programs for producing perform conversion of said one or more colors into codes for controlling image reproduction by said rendering device, and wherein said one or more programs for capturing performs conversion of codes generated by an image capture device into device independent color values.

18. The non-transitory, computer-readable medium according to claim 17 wherein said conversion between device codes and device independent color values use a multidimensional transformation in combination with tonal transfer curves for each of a plurality of channels of said rendering device, in which at least said tonal transfer curves are based upon a calibration specific to said rendering device.

19. The non-transitory, computer-readable medium according to claim 14 wherein one of said one or more programs that provide color reproductions of source digital images corrects for said non-uniformity of rendering by modifying at least the tonal transfer in each color channel of said rendering device for each pixel across said display surface.

20. The non-transitory, computer-readable medium according to claim 19 wherein said pixel represents an average of a group of pixels on said display surface.

21. The non-transitory, computer-readable medium according to claim 19 wherein said program that corrects for said spatial non-uniformity of rendering employs interpolation in providing corrections for spatial non-uniformity of rendering upon said display surface.

22. The non-transitory, computer-readable medium according to claim 14 wherein one of said one or more programs that provide color reproductions of source digital images corrects said color differences that are not due to said spatial non-uniformity of rendering by computing a color-to-color' transform to be used in combination with a multidimensional transformation that converts device-independent color values representing said source digital image into device codes for controlling rendering by said device.

23. The non-transitory, computer-readable medium according to claim 22 wherein said combination is implemented by concatenating said color-to-color' transform with said multidimensional transformation that converts device-independent color values into device codes.

24. The non-transitory, computer-readable medium according to claim 14 wherein said rendering device is one of a printer or a video monitor.

25. The non-transitory, computer-readable medium according to claim 14 wherein said rendering device is a printing press and said digital image of said reproduction of said source digital image is captured by an imaging colorimeter and communicated to a computer associated with said printing press.

26. The non-transitory, computer-readable medium according to claim 25 wherein said computer associated with said printing press communicates a color-to-color' transform over a network to one or more other computers to enable matching a reproduction of said source digital image by at least one rendering device associated with each of said one or more other computers with said reproduction of said source digital image by said printing press.

27. The non-transitory, computer-readable medium according to claim 25 wherein said computer associated with said printing press stores data of press color reproduction performance for use in refining a model of spatial dependencies of rendering by said printing press.

28. The non-transitory, computer-readable medium according to claim 27 wherein said model enables an operator to preview one or more arrangements of pages within an imposition.

\* \* \* \* \*